(12) United States Patent
Masignani et al.

(10) Patent No.: US 9,987,344 B2
(45) Date of Patent: Jun. 5, 2018

(54) PSEUDOMONAS ANTIGENS AND ANTIGEN COMBINATIONS

(71) Applicants: GlaxoSmithKline Biologicals SA, Rixensart (BE); Ospedale San Raffaele Srl, Milan (IT)

(72) Inventors: Vega Masignani, Siena (IT); Maria Scarselli, Siena (IT); Roberto Petracca, Siena (IT); Irene Bianconi, Milan (IT); Alessandra Bragonzi, Milan (IT); Beatriz Alcala' Franco, Milan (IT)

(73) Assignees: GlaxoSmithKline Biologicals SA, Rixensart (BE); Ospedale San Raffaele S.R.L., Milan (IT)

( * ) Notice: Subject to any disclaimer, the term of this patent is extended or adjusted under 35 U.S.C. 154(b) by 0 days. days.

(21) Appl. No.: 14/648,198

(22) PCT Filed: Nov. 27, 2013

(86) PCT No.: PCT/EP2013/074864
§ 371 (c)(1),
(2) Date: May 28, 2015

(87) PCT Pub. No.: WO2014/083060
PCT Pub. Date: Jun. 5, 2014

(65) Prior Publication Data
US 2015/0322116 A1 Nov. 12, 2015

(30) Foreign Application Priority Data

Nov. 30, 2012 (GB) .................................. 1221638.8

(51) Int. Cl.
| | | |
|---|---|---|
| *A61K 39/104* | (2006.01) | |
| *C07K 14/21* | (2006.01) | |
| *A61K 39/39* | (2006.01) | |
| *A61K 39/385* | (2006.01) | |
| *A61K 47/61* | (2017.01) | |
| *A61K 39/00* | (2006.01) | |

(52) U.S. Cl.
CPC .......... *A61K 39/104* (2013.01); *A61K 39/385* (2013.01); *A61K 39/39* (2013.01); *A61K 47/61* (2017.08); *C07K 14/21* (2013.01); *A61K 2039/55505* (2013.01); *A61K 2039/6087* (2013.01); *A61K 2039/70* (2013.01)

(58) Field of Classification Search
None
See application file for complete search history.

(56) References Cited

U.S. PATENT DOCUMENTS

| | | |
|---|---|---|
| 5,955,090 A | 9/1999 | Knapp et al. |
| 6,551,759 B2 | 4/2003 | Daems et al. |
| 6,551,795 B1 | 4/2003 | Rubenfield et al. |

FOREIGN PATENT DOCUMENTS

| | | |
|---|---|---|
| JP | 2003-506049 A | 2/2003 |
| JP | 2005-97321 A | 4/2005 |
| JP | 2008-133206 A | 6/2008 |
| WO | 2001/09350 A3 | 8/2001 |

OTHER PUBLICATIONS

Greenspan et al (Nature Biotechnology 7: 936-937, 1999).*
Chothia et al (The EMBO Journal, 1986, 5/4:823-26).*
Rudinger et al. (Jun. 1976. Peptide Hormones. Biol.Council. pp. 5-7).*
Mikayama et al. (Nov. 1993. Proc.Natl.Acad.Sci. USA, vol. 90 : 10056-10060).*
Ellis, R.W. (Chapter 29 of "Vaccines" [Plotkin, S.A. et al. (eds) published by W. B. Saunders company (Philadelphia) in 1988.*
International Search Report and Written Opinion received for PCT Patent Application No. PCT/EP2013/074864 dated Jul. 7, 2014, 22 pages.
International Preliminary Report on Patentability received for PCT Patent Application No. PCT/EP2013/074864, dated Jun. 11, 2015, 14 pages.
Campodonico et al., "Evaluation of Flagella and Flagellin of Pseudomonas Aeruginosa as Vaccines", Infection and Immunity, vol. 78, No. 2, Feb. 2010, pp. 746-755.
Olivas et al., UniProt Accession No. H3TD87, "Putative Uncharacterized Protein", retrieved from <http://www.uniprot.org/uniprot/H3TD87.txt?version=1>, Apr. 18, 2012, 1 page.
Sawa et al., "Active and Passive Immunization with the Pseudomonas V Antigen Protects Against Type III Intoxication and Lung Injury", Nature Medicine, vol. 5, 1999, pp. 392-398.
Stover et al., UniProt Accession No. Q9HTL8, "Uncharacterized Protein", retrieved from <http://www.uniprot.org/uniprot/Q9HTL8.txt>, Mar. 1, 2001, 1 page.
Schuster et al. (2003). "Identification, Timing, and Signal Specificity of *Pseudomonas aeruginosa* Quorum-Controlled Genes: a Transcriptome Analysis," J Bact, 185(7):2066-2079.
"GenBank: AAT50448.1", Available at: <https://www.ncbi.nlm.nih.gov/protein/49082096?report=genbank&log$=protalign&blast_rank=3&RID=05UU1PV3014>, Jul. 7, 2004, 1 page.
Office Action received for Russian Patent Application No. 2015125699 dated Nov. 9, 2017, 3 pages (English Translation only).
Office Action received for Russian Patent Application No. 2015125699 dated Jun. 14, 2017, 8 pages (English Translation only).
Sharma et al., "Recent Developments for Pseudomonas Vaccines", Human Vaccines, vol. 7, Issue 10, Oct. 2011, pp. 999-1011.
Stanislavsky et al., "Pseudomonas Aeruginosa Antigens as Potential Vaccines", FEMS Microbiology Reviews, vol. 21, 1997, pp. 243-277.

* cited by examiner

*Primary Examiner* — Jennifer E Graser
(74) *Attorney, Agent, or Firm* — Morrison & Foerster LLP

(57) ABSTRACT

An effective *Pseudomonas aeruginosa* vaccine may require one or several antigenic components, and so various antigens of *P. aeruginosa* are identified for use in immunization. These polypeptides may optionally be used in combination with other nosocomial antigens.

18 Claims, No Drawings

SEQUENCE LISTING

```
<160> NUMBER OF SEQ ID NOS: 73

<210> SEQ ID NO 1
<211> LENGTH: 647
<212> TYPE: PRT
<213> ORGANISM: Pseudomonas aeruginosa

<400> SEQUENCE: 1

Met Phe Lys Pro Leu Ala Val Ala Val Gly Leu Gly Cys Ala Ala Leu
1               5                   10                  15

Ser Leu Gly Ala Asn Ala Tyr Gln Tyr Gly Glu Tyr Ala Gly Glu Thr
            20                  25                  30

Leu Glu Arg Leu Ile Thr Asp Tyr Pro Gly Arg Tyr Arg Gly Thr Ala
        35                  40                  45

Ser Phe Ala Gly Ala Ser Lys Leu Met Gln Ser Arg Leu Gly Phe Gly
    50                  55                  60

Tyr Gln Thr Ser Arg Gln Asp Phe Thr Trp Ala Gly Asn Arg Ser Ser
65                  70                  75                  80

Gln Asn Val Ile Ala Ser Ala Pro Gly Ser Ser Gly Lys Phe Leu Val
                85                  90                  95

Leu Gly Ala His Tyr Asp Thr Tyr Tyr Gly Arg Pro Thr Leu Gln Gly
            100                 105                 110

Leu Asp Asp Asn Ala Ser Gly Ala Ala Val Leu Thr Glu Ile Ala Arg
        115                 120                 125

Asn Leu Gly Gly Ile Ala Leu Glu Asn Gly Leu Glu Val Val Gly Phe
    130                 135                 140

Gly Ala Glu Glu Glu Gly Leu Arg Gly Ser Arg Ala Tyr Val Glu Ser
145                 150                 155                 160

Leu Asp Ala Ser Gln Arg Ala Asn Leu Leu Gly Met Ile Asn Leu Asp
                165                 170                 175

Ser Leu Val Thr Gly Asp Lys Met Tyr Ala His Ala Gly Ser Asn Ser
            180                 185                 190

Val Ser Asn Pro Ala Leu Gly Ala Tyr Arg Glu Gln Ile Leu Arg Ile
        195                 200                 205

Ala Arg Glu Leu Asp Ile Pro Leu Phe Thr Asn Pro Gly Leu Asn Ala
    210                 215                 220

Glu Tyr Pro Ala Gly Thr Gly Cys Cys Ser Asp Gly Glu Ser Phe Asn
225                 230                 235                 240

Gly Met Asp Ile Pro Val Leu Phe Ile Glu Ala Thr Asn Trp Glu Leu
                245                 250                 255

Gly Asp Leu Asp Gly Tyr Glu Gln Thr Asp Asn Pro Ala Ile Pro Gly
            260                 265                 270
```

Gly Ser Thr Trp His Asp Pro Ala Glu Asp Asn Lys Glu Val Leu Thr
            275                 280                 285

Asn Ala Leu Gly Gln Glu Arg Ile Glu Gln Arg Met Arg Asp Phe Ser
290                 295                 300

Arg Leu Leu Thr Arg Leu Val Leu Glu Gln Thr Asn Ala Asp Leu Leu
305                 310                 315                 320

Ala Ser Thr Ala Ser Gly Gly Ala Leu Ala Arg Gln Met Glu Asp Gln
            325                 330                 335

Leu Gln Arg Gln His Gln Ala Leu Thr Arg Leu His Asp Arg Arg Trp
            340                 345                 350

Leu Thr Leu Leu Gly Ser Asn Arg Pro Val Gly Ser Phe Asp Gly Glu
            355                 360                 365

Val Gly Ala Glu Gly Glu Val Ser Pro Asp Ser Gly Phe Asp Met Pro
370                 375                 380

Gly Asn Pro Glu Ser Arg Arg Ala Gly Val His Leu Leu Gly Asp Tyr
385                 390                 395                 400

Arg Tyr Ser Glu Ala Leu Thr Leu Gly Gly Ser Leu Ala Phe Gln Arg
                405                 410                 415

Ser Arg Asp Lys Leu Asp His Gly Gly Arg Ile Glu Gly Asp Thr Trp
                420                 425                 430

Gln Leu Gly Leu Phe Gly Leu Tyr Asn Asp Gly Gly Pro Glu Trp Leu
            435                 440                 445

Ala Gly Glu Leu Asn Leu Gly His Thr Arg Tyr Asp Ser Lys Arg Ser
450                 455                 460

Val Tyr Leu Gln Ala Ala Gly Pro Val Leu Leu Asp Gln Arg Leu
465                 470                 475                 480

Ser Gly Asp Thr Ser Ala Trp Ser Trp Gly Ala Arg Leu Glu Gly Gly
                485                 490                 495

Tyr Asp Phe Ser Phe Gly Glu Leu Arg Ser Gly Pro Leu Ala Gly Leu
                500                 505                 510

Asp Tyr Met His Tyr Arg Ile Asp Asp Phe Arg Glu Asp Glu Ala Leu
            515                 520                 525

Arg Thr Ala Leu Gly Tyr Glu Lys Gln Asp Tyr Asp Ser Leu Glu Ala
530                 535                 540

Ser Leu Gly Trp Arg Leu Arg Gly Glu Leu Ala Leu Gly Ala Arg Met
545                 550                 555                 560

Arg Leu Gln Pro Tyr Ala Ser Leu Arg Trp Val Arg Glu Leu Ala Asp
                565                 570                 575

Gly Arg Leu Asp Asp Met Asp Leu Thr Ser Arg Gly Asp Gly Arg Val
            580                 585                 590

Arg Val Ala Asp Met Gly Gly Val Asp Lys Asp Phe Gly Arg Ala Gln
            595                 600                 605

Leu Gly Ala Gln Leu Ala Ile Thr Glu Gln Leu Gly Val Phe Ala Glu
610                 615                 620

Ala Asn Ser Arg Phe Ala His Ser Glu Gly Asn Gln Ala Gly Tyr Ser
625                 630                 635                 640

Leu Gly Val Asn Trp Gln Phe
                645

<210> SEQ ID NO 2
<211> LENGTH: 200
<212> TYPE: PRT
<213> ORGANISM: Pseudomonas aeruginosa

<400> SEQUENCE: 2

-continued

```
Met Lys Ala Leu Lys Thr Leu Phe Ile Ala Thr Ala Leu Leu Gly Ser
1               5                   10                  15

Ala Ala Gly Val Gln Ala Ala Asp Asn Phe Val Gly Leu Thr Trp Gly
            20                  25                  30

Glu Thr Ser Asn Asn Ile Gln Lys Ser Lys Ser Leu Asn Arg Asn Leu
        35                  40                  45

Asn Ser Pro Asn Leu Asp Lys Val Ile Asp Asn Thr Gly Thr Trp Gly
    50                  55                  60

Ile Arg Ala Gly Gln Gln Phe Glu Gln Gly Arg Tyr Tyr Ala Thr Tyr
65                  70                  75                  80

Glu Asn Ile Ser Asp Thr Ser Ser Gly Asn Lys Leu Arg Gln Gln Asn
                85                  90                  95

Leu Leu Gly Ser Tyr Asp Ala Phe Leu Pro Ile Gly Asp Asn Asn Thr
            100                 105                 110

Lys Leu Phe Gly Gly Ala Thr Leu Gly Leu Val Lys Leu Glu Gln Asp
        115                 120                 125

Gly Lys Gly Phe Lys Arg Asp Ser Asp Val Gly Tyr Ala Ala Gly Leu
    130                 135                 140

Gln Ala Gly Ile Leu Gln Glu Leu Ser Lys Asn Ala Ser Ile Glu Gly
145                 150                 155                 160

Gly Tyr Arg Tyr Leu Arg Thr Asn Ala Ser Thr Glu Met Thr Pro His
                165                 170                 175

Gly Gly Asn Lys Leu Gly Ser Leu Asp Leu His Ser Ser Ser Gln Phe
            180                 185                 190

Tyr Leu Gly Ala Asn Tyr Lys Phe
        195                 200
```

<210> SEQ ID NO 3
<211> LENGTH: 646
<212> TYPE: PRT
<213> ORGANISM: Pseudomonas aeruginosa

<400> SEQUENCE: 3

```
Met Ile Arg Met Ala Leu Lys Pro Leu Val Ala Ala Cys Leu Leu Ala
1               5                   10                  15

Ser Leu Ser Thr Ala Pro Gln Ala Ala Pro Ser Pro Tyr Ser Thr Leu
            20                  25                  30

Val Val Phe Gly Asp Ser Leu Ser Asp Ala Gly Gln Phe Pro Asp Pro
        35                  40                  45

Ala Gly Pro Ala Gly Ser Thr Ser Arg Phe Thr Asn Arg Val Gly Pro
    50                  55                  60

Thr Tyr Gln Asn Gly Ser Gly Glu Ile Phe Gly Pro Thr Ala Pro Met
65                  70                  75                  80

Leu Leu Gly Asn Gln Leu Gly Ile Ala Pro Gly Asp Leu Ala Ala Ser
                85                  90                  95

Thr Ser Pro Val Asn Ala Gln Gln Gly Ile Ala Asp Gly Asn Asn Trp
            100                 105                 110

Ala Val Gly Gly Tyr Arg Thr Asp Gln Ile Tyr Asp Ser Ile Thr Ala
        115                 120                 125

Ala Asn Gly Ser Leu Ile Glu Arg Asp Asn Thr Leu Leu Arg Ser Arg
    130                 135                 140

Asp Gly Tyr Leu Val Asp Arg Ala Arg Gln Gly Leu Gly Ala Asp Pro
145                 150                 155                 160

Asn Ala Leu Tyr Tyr Ile Thr Gly Gly Gly Asn Asp Phe Leu Gln Gly
```

```
            165                 170                 175
Arg Ile Leu Asn Asp Val Gln Ala Gln Gln Ala Gly Arg Leu Val
            180                 185                 190

Asp Ser Val Gln Ala Leu Gln Gln Ala Gly Ala Arg Tyr Ile Val Val
            195                 200                 205

Trp Leu Leu Pro Asp Leu Gly Leu Thr Pro Ala Thr Phe Gly Gly Pro
            210                 215                 220

Leu Gln Pro Phe Ala Ser Gln Leu Ser Gly Thr Phe Asn Ala Glu Leu
225                 230                 235                 240

Thr Ala Gln Leu Ser Gln Ala Gly Ala Asn Val Ile Pro Leu Asn Ile
                    245                 250                 255

Pro Leu Leu Lys Glu Gly Met Ala Asn Pro Ala Ser Phe Gly Leu
            260                 265                 270

Ala Ala Asp Gln Asn Leu Ile Gly Thr Cys Phe Ser Gly Asn Gly Cys
            275                 280                 285

Thr Met Asn Pro Thr Tyr Gly Ile Asn Gly Ser Thr Pro Asp Pro Ser
            290                 295                 300

Lys Leu Leu Phe Asn Asp Ser Val His Pro Thr Ile Thr Gly Gln Arg
305                 310                 315                 320

Leu Ile Ala Asp Tyr Thr Tyr Ser Leu Leu Ser Ala Pro Trp Glu Leu
                    325                 330                 335

Thr Leu Leu Pro Glu Met Ala His Gly Thr Leu Arg Ala Tyr Gln Asp
            340                 345                 350

Glu Leu Arg Ser Gln Trp Gln Ala Asp Trp Glu Asn Trp Gln Asn Val
            355                 360                 365

Gly Gln Trp Arg Gly Phe Val Gly Gly Gly Gln Arg Leu Asp Phe
            370                 375                 380

Asp Ser Gln Asp Ser Ala Ala Ser Gly Asp Gly Asn Gly Tyr Asn Leu
385                 390                 395                 400

Thr Leu Gly Gly Ser Tyr Arg Ile Asp Glu Ala Trp Arg Ala Gly Val
                    405                 410                 415

Ala Ala Gly Phe Tyr Arg Gln Lys Leu Glu Gly Ala Lys Asp Ser
            420                 425                 430

Asp Tyr Arg Met Asn Ser Tyr Met Ala Ser Ala Phe Val Gln Tyr Gln
            435                 440                 445

Glu Asn Arg Trp Trp Ala Asp Ala Ala Leu Thr Gly Gly Tyr Leu Asp
            450                 455                 460

Tyr Asp Asp Leu Lys Arg Lys Phe Ala Leu Gly Gly Gly Glu Arg Ser
465                 470                 475                 480

Glu Lys Gly Asp Thr Asn Gly His Leu Trp Ala Phe Ser Ala Arg Leu
                    485                 490                 495

Gly Tyr Asp Ile Ala Gln Gln Ala Asp Ser Pro Trp His Leu Ser Pro
            500                 505                 510

Phe Val Ser Ala Asp Tyr Ala Arg Val Glu Val Asp Gly Tyr Ser Glu
            515                 520                 525

Lys Gly Ala Ser Ala Thr Ala Leu Asp Tyr Asp Asp Gln Lys Arg Ser
            530                 535                 540

Ser Lys Arg Leu Gly Ala Gly Leu Gln Gly Lys Tyr Ala Phe Gly Ser
545                 550                 555                 560

Asp Thr Gln Leu Phe Ala Glu Tyr Ala His Glu Arg Glu Tyr Glu Asp
                    565                 570                 575

Asp Thr Gln Asp Leu Thr Met Ser Leu Asn Ser Leu Pro Gly Asn Arg
            580                 585                 590
```

-continued

```
Phe Thr Leu Glu Gly Tyr Thr Pro Gln Asp His Leu Asn Arg Val Ser
            595                 600                 605

Leu Gly Phe Ser Gln Lys Leu Ala Pro Glu Leu Ser Leu Arg Gly Gly
        610                 615                 620

Tyr Asn Trp Arg Lys Gly Glu Asp Thr Gln Gln Ser Val Ser Leu
625                 630                 635                 640

Ala Leu Ser Leu Asp Phe
            645

<210> SEQ ID NO 4
<211> LENGTH: 481
<212> TYPE: PRT
<213> ORGANISM: Pseudomonas aeruginosa

<400> SEQUENCE: 4

Met Thr Met Arg Arg Leu Met Thr Trp Leu Phe Gly Ala Phe Leu Leu
1               5                   10                  15

Leu Leu Arg Glu Asp Ala Phe Ala Leu Gly Leu Leu Asp Gly Tyr His
            20                  25                  30

Leu Ala Leu Glu Asn Asp Pro Gln Phe Gln Ala Ala Ile Gln Glu His
        35                  40                  45

Glu Ala Gly Arg Gln Tyr Arg Ala Leu Gly Arg Ala Ala Leu Leu Pro
    50                  55                  60

Arg Leu Val Tyr Ser Tyr Asn Arg Gly Arg Ser Trp Ser Asp Val Thr
65                  70                  75                  80

Gln Thr Thr Thr Arg Gly Asp Phe Lys Glu Asp Arg Asp Tyr Asp Ser
                85                  90                  95

Tyr Val Ser Thr Leu Ser Leu Gln Gln Pro Leu Phe Asp Tyr Glu Ala
            100                 105                 110

Phe Ser Arg Tyr Arg Lys Gly Val Ala Gln Ala Leu Leu Ser Asp Glu
        115                 120                 125

Arg Phe Arg Ser Gln Ser Gln Glu Leu Leu Val Arg Val Leu Glu Ala
    130                 135                 140

Tyr Thr Gly Ala Leu Leu Ala Gln Asp Gln Ile Glu Leu Ala Arg Ala
145                 150                 155                 160

Gln Lys Arg Ser Tyr Arg Glu Gln Phe Gln Leu Asn Gln Arg Gln Phe
                165                 170                 175

Glu Arg Gly Asn Gly Thr Arg Thr Asp Thr Leu Glu Thr Gln Ala Arg
            180                 185                 190

Phe Asn Leu Ala Gln Ala Gln Glu Ile Glu Ala Arg Asp Ser Gln Asp
        195                 200                 205

Ala Ala Leu Arg Glu Leu Glu Arg Leu Val Gly Ala Pro Leu Glu Ile
    210                 215                 220

Ala Asp Leu Ala Pro Leu Gly Glu Arg Phe Gln Val Arg Pro Leu Ser
225                 230                 235                 240

Pro Ala Ser Tyr Thr Ala Trp Arg Asp Leu Ala Leu Ala Glu Asn Pro
                245                 250                 255

Glu Leu Ala Ser Leu Arg His Ala Val Asp Val Ala Arg Tyr Glu Val
            260                 265                 270

Glu Gln Asn Arg Ala Asp Phe Leu Pro Arg Leu Gly Leu Tyr Ala Ser
        275                 280                 285

Thr Gly Lys Ser Lys Ser Gly Ser Glu Asn Thr Tyr Asn Gln Arg Tyr
    290                 295                 300

Glu Thr Asp Ser Val Gly Ile Gln Leu Ser Val Pro Leu Phe Ser Gly
```

-continued

```
              305                 310                 315                 320
Gly Glu Thr Leu Ala Ala Thr Arg Gln Ala Thr His Arg Met Glu Lys
                    325                 330                 335
Ser His Tyr Asp Leu Asp Asp Lys Val Arg Glu Thr Leu Asn Gln Val
                    340                 345                 350
Arg Lys Met Tyr Asn Gln Ser Ser Ser Ala Ala Lys Ile Arg Ala
                    355                 360                 365
Tyr Glu Met Thr Val Asp Ser Arg Thr Leu Val Met Ala Thr Arg
        370                 375                 380
Lys Ser Ile Ala Ala Gly Val Arg Val Asn Leu Asp Leu Leu Asn Ala
385                 390                 395                 400
Glu Gln Ala Leu Tyr Ser Ala Met Asn Glu Leu Ser Lys Ala Lys Tyr
                    405                 410                 415
Asp Tyr Leu Thr Ala Trp Ala Arg Leu Arg Phe Tyr Ala Gly Val Leu
                    420                 425                 430
Asp Glu Ala Asp Leu Glu Leu Val Ala Ala Asn Phe Val Ser Gly Glu
                    435                 440                 445
Thr Pro Ala Arg Arg Asp Cys Ala Thr Thr Asp Cys Pro Ala Pro
        450                 455                 460
Leu His Thr Leu Ser Lys Thr Asp Thr Glu Glu Asn Arg Ser Ala Leu
465                 470                 475                 480
Asn

<210> SEQ ID NO 5
<211> LENGTH: 317
<212> TYPE: PRT
<213> ORGANISM: Pseudomonas aeruginosa

<400> SEQUENCE: 5

Met Leu Phe Ser Arg Arg Ser Arg Pro Arg Gly Leu Ala Ala Leu
1               5                   10                  15
Leu Pro Gly Arg Ala Leu Leu Ala Ala Leu Leu Ala Leu Leu Ala
                    20                  25                  30
Pro Leu Ala Gln Ala Glu Asp Gly Lys Arg Leu Arg Ile Gly Ile Thr
                    35                  40                  45
Leu His Pro Tyr Tyr Ser Tyr Val Ser Asn Ile Val Gly Asp Lys Ala
            50                  55                  60
Glu Val Val Pro Leu Ile Pro Ala Gly Phe Asn Pro His Ala Tyr Glu
65                  70                  75                  80
Pro Arg Ala Glu Asp Ile Lys Arg Ile Gly Thr Leu Asp Val Val
                    85                  90                  95
Leu Asn Gly Val Gly His Asp Asp Phe Ala Glu Arg Met Ile Ala Ser
                    100                 105                 110
Ser Glu Lys Pro Gly Ile Pro Val Ile Glu Ala Asn Ala Lys Val Pro
                    115                 120                 125
Leu Leu Ala Ala Thr Gly Met Ala Ala Arg Gly Ala Gly Lys Val Val
                    130                 135                 140
Asn Pro His Thr Phe Leu Ser Ile Ser Ala Ser Ile Thr Gln Val Asn
145                 150                 155                 160
Thr Ile Ala Arg Glu Leu Gly Lys Leu Asp Pro Ala Asn Ala Lys Ala
                    165                 170                 175
Tyr Thr Arg Asn Ala Arg Ala Tyr Ala Lys Arg Leu Arg Ala Leu Arg
                    180                 185                 190
Ala Asp Ala Leu Ala Arg Leu Asn Lys Ala Pro Ala Ala Asp Phe Arg
```

```
            195                 200                 205
Val Ala Thr Ile His Gly Ala Tyr Asp Tyr Leu Leu Arg Glu Phe Gly
210                 215                 220

Leu Glu Val Thr Ala Val Val Glu Pro Ala His Gly Ile Glu Pro Ser
225                 230                 235                 240

Pro Ser Gln Leu Lys Lys Thr Ile Asp Gln Leu Lys Ala Leu Asp Val
                245                 250                 255

Lys Val Ile Phe Ser Glu Ile Asp Phe Pro Ser Thr Tyr Val Glu Thr
                260                 265                 270

Ile Gln Arg Glu Ser Gly Val Lys Leu Tyr Ser Leu Ser His Ile Ser
            275                 280                 285

Tyr Gly Asp Tyr Ser Ala Gly Lys Tyr Glu Glu Met Ala Arg Asn
        290                 295                 300

Leu Asp Thr Val Val Arg Ala Ile Gln Glu Ser Gly Ala
305                 310                 315

<210> SEQ ID NO 6
<211> LENGTH: 321
<212> TYPE: PRT
<213> ORGANISM: Pseudomonas aeruginosa

<400> SEQUENCE: 6

Met Gln Pro Arg Leu Leu Leu Pro Phe Leu Leu Ser Ser Leu Pro
1               5                   10                  15

Ala Leu Ala Val Thr Phe Gln Thr Arg Leu Glu Ser Val Glu Trp Lys
                20                  25                  30

Val Glu Gly Asp Gln Phe Glu Cys Arg Leu Ser Gln Pro Val Ala Asn
            35                  40                  45

Phe Gly Val Gly Glu Phe Val Arg Arg Ala Gly Glu Gln Ala Thr Phe
        50                  55                  60

Arg Leu Lys Pro Glu Ala Gln Trp Leu Gly Arg Gly Ser Ala Thr Leu
65                  70                  75                  80

Leu Ala Ala Pro Pro Trp Arg Pro Gly Gln Gly Asp Ile Asn Leu
                85                  90                  95

Gly Gln Val Ser Ile Gly Ser Gly Glu Val Pro Phe Asn Ser Ser Gln
                100                 105                 110

Gln Gln Ala Gly Arg Leu Leu Thr Gly Leu Leu Glu Gly Arg Ser Pro
            115                 120                 125

Leu Val Arg His Arg Thr Trp Gln Gly Asp Arg Leu Glu Val Arg Leu
        130                 135                 140

Leu Pro Ala Arg Phe Ala Ser Val Tyr Ser Gln Tyr Gln Ala Cys Ile
145                 150                 155                 160

Ala Lys Leu Leu Pro Val Asn Phe Asp Gln Val Lys Leu Ala Gln Val
                165                 170                 175

Gly Phe Pro Asp Gly Gly Thr Ala Leu Asn Asp Val Ala Arg Ala Lys
            180                 185                 190

Leu Asp Ile Ile Leu Gln Leu Leu Lys Ala Asp Pro Ser Ile Asn Arg
        195                 200                 205

Ile Glu Leu Asp Gly His Ser Asp Asn Ser Gly Asn Arg Leu Thr Asn
        210                 215                 220

Arg Asp Leu Ser Arg Arg Ala Leu Ala Val Gln Glu Tyr Leu Lys
225                 230                 235                 240

Ser Asn Gly Val Pro Glu Ser Gln Ile Asn Val Arg Phe Tyr Gly Glu
                245                 250                 255
```

```
Arg Tyr Pro Leu Val Ala Asn Asn Ser Ala Ala Asn Arg Ala Arg Asn
            260                 265                 270

Arg Arg Val Thr Val His Leu Ser Arg Glu Ala Val Val Glu Pro Ala
        275                 280                 285

Thr Glu Ala Pro Lys Ala Glu Asp Lys Pro Ala Pro Pro Ala Ala Glu
    290                 295                 300

Pro Ala Ala Pro Lys Pro Pro Ala Ala Ser Leu Gln Gly Lys Pro Thr
305                 310                 315                 320

Val

<210> SEQ ID NO 7
<211> LENGTH: 1018
<212> TYPE: PRT
<213> ORGANISM: Pseudomonas aeruginosa

<400> SEQUENCE: 7

Met Asn Lys Cys Tyr Ala Leu Val Trp Asn Val Ser Gln Gly Cys Trp
1               5                   10                  15

Asn Val Val Ser Glu Gly Ser Arg Arg Gly Lys Pro Ala Gly Ala
                20                  25                  30

Lys Ala Ala Ile Ala Ser Val Leu Ala Leu Gly Ala Thr Ala Leu
            35                  40                  45

Ala Pro Ala Tyr Ala Leu Pro Ser Gly Gly Thr Val Val Gly Ser
50                  55                  60

Ala Asn Gly Glu Ile His Leu Ser Gly Gly Asn Ser Leu Ser Val Asn
65                  70                  75                  80

Gln Lys Val Asp Lys Leu Ile Ala Asn Trp Asp Ser Phe Ser Val Ala
                85                  90                  95

Ala Gly Glu Arg Val Ile Phe Asn Gln Pro Ser Ser Ser Ser Ile Ala
            100                 105                 110

Leu Asn Arg Val Ile Gly Thr Lys Ala Ser Asp Ile Gln Gly Arg Ile
        115                 120                 125

Asp Ala Asn Gly Gln Val Phe Leu Val Asn Pro Asn Gly Val Leu Phe
130                 135                 140

Gly Arg Gly Ala Gln Val Asn Val Gly Gly Leu Val Ala Ser Thr Leu
145                 150                 155                 160

Asp Ile Thr Asp Ala Glu Phe Asn Gly Asn Ser Ser Arg Tyr Arg Phe
                165                 170                 175

Thr Gly Pro Ser Thr Asn Gly Val Leu Asn His Gly Gly Ala Ile Thr
            180                 185                 190

Ala Ala Glu Gly Gly Ser Ile Ala Leu Leu Gly Ala Gln Val Asp Asn
        195                 200                 205

Arg Gly Thr Val Leu Ala Gln Met Gly Gly Val Gly Leu Gly Ala Gly
210                 215                 220

Ser Asp Leu Thr Leu Asn Phe Asp Gly Asn Lys Leu Leu Asp Ile Arg
225                 230                 235                 240

Val Asp Ala Gly Val Ala Asn Ala Leu Ala Ser Asn Gly Gly Leu Leu
                245                 250                 255

Lys Ala Asp Gly Gly Arg Val Leu Met Ala Ala Arg Thr Ala Asn Ala
            260                 265                 270

Leu Leu Asn Thr Val Val Asn Ser Gln Gly Ala Ile Glu Ala Arg Ser
        275                 280                 285

Leu Arg Gly Lys Asn Gly Arg Ile Val Leu Asp Gly Gly Pro Asp Gly
290                 295                 300
```

-continued

```
Lys Val Met Val Gly Gly Ala Leu Ser Ala Asn Ala Leu Asn Gly Pro
305                 310                 315                 320
Gly His Gly Gly Thr Val Glu Val Arg Gly Gln Ala Val Glu Val Ala
            325                 330                 335
Leu Gly Thr Gln Val Asn Thr Leu Ala Ser Asn Gly Leu Asn Gly Thr
        340                 345                 350
Trp Lys Ile Ala Ala Asp Lys Ile Asp Val Arg Pro Ser Ala Val Ser
            355                 360                 365
Asp Gly Val Thr Val His Ala Asp Thr Leu Ser Arg Asn Leu Ala Ser
370                 375                 380
Thr Asn Ile Glu Leu Val Ser Thr Lys Gly Asp Leu Asp Leu Asp Gly
385                 390                 395                 400
Ser Val Asn Trp Ala Ser Gly Asn Arg Leu Gly Leu Gly Ser Ala Ala
                405                 410                 415
Asp Leu Thr Leu Asn Gly Arg Leu Asn Ala Ser Gly Ala Lys Ala Gly
            420                 425                 430
Leu Glu Leu Lys Ala Glu Gly Ala Ile Asp Ile Asn Asp Lys Ile Val
        435                 440                 445
Leu Gly Gly Ala Gly Ser Ala Leu Ala Met Asp Ala Gly Glu Gly His
    450                 455                 460
Arg Val Asn Gly Thr Ala Ser Val Ser Leu Ala Gly Ala Asn Ala Thr
465                 470                 475                 480
Tyr Val Ser Gly Gly Tyr Tyr Tyr Thr Val Gln Asn Leu Ala Gln
                485                 490                 495
Leu Gln Ala Ile Asn Lys Asn Leu Asp Gly Leu Tyr Val Leu Gly Gly
            500                 505                 510
Asn Ile Leu Gly Gly Ser Tyr Tyr Cys Thr Ala Leu Gln Ser Ile Gly
        515                 520                 525
Gly Pro Ala Gly Val Phe Ser Gly Thr Leu Asp Gly Leu Gly Asn Ser
    530                 535                 540
Ile Gly Asn Leu Ser Ile Ser Asn Thr Gly Pro Asn Val Gly Leu Phe
545                 550                 555                 560
Ala Arg Ser Ser Gly Thr Leu Ser Asn Leu Lys Leu Asn Asn Leu Arg
                565                 570                 575
Val Ser Asp Asn Thr Tyr Gly Ser Gly Pro Ser Ser Leu Gly Ala Leu
            580                 585                 590
Val Gly Ile Asn Ser Gly Arg Ile Ala Asn Val Ser Ala Ser Gly Val
        595                 600                 605
Ser Val Val Gly Ser Arg Leu Arg Ser Asn Ala Leu Gly Gly Leu Val
    610                 615                 620
Gly Arg Asn Ile Ser Gly Gln Ile Ala Asn Ala Ser Val Ser Gly Gly
625                 630                 635                 640
Val Thr Gly Tyr Ala Ala Ser Thr Ala Val Gly Gly Leu Val Gly Glu
                645                 650                 655
Asn Phe Thr Ala Trp Gly Pro Glu Ala Val Ile Glu Asn Ala His
            660                 665                 670
Ser Asn Val His Val Ala Ala Gln Ser Thr Glu Arg Asn Ser Leu Gly
        675                 680                 685
Gly Val Gly Gly Leu Val Gly Leu Asn Ala Lys Gly Met Ile Arg Ala
    690                 695                 700
Ser Gly Ser Gln Gly Lys Val Glu Thr Tyr Arg Pro Gly Leu Asn Val
705                 710                 715                 720
Gly Gly Leu Val Gly Tyr Asn Met Phe Gly His Val Ser Asp Ser Ser
```

```
                725                 730                 735
Ala Ser Gly Gln Val Glu Ala Gly Gly Ala Gly Asn Thr Gly Gly Leu
            740                 745                 750

Val Gly Leu Ser Ser Gly Gly Glu Ile Phe Arg Ser Gln Ala Ser Gly
        755                 760                 765

Ser Val Tyr Ser Lys Gly Gly Leu Ala Thr Gly Gly Leu Ile Gly Lys
    770                 775                 780

Ala Glu Gly Asn Gly Met Leu Gly Asn Leu Lys Ala Ser Gly Ser Val
785                 790                 795                 800

Thr Asp Gln Gly Gly Ala Asp Leu Gly Gly Leu Val Gly Asn Asn Ser
                805                 810                 815

Gln Ser Ala Ile Glu Thr Ala Glu Ala Thr Gly Lys Val Ser Gly Gly
            820                 825                 830

Ser Asn Ser Arg Val Gly Leu Ile Gly His Asn Leu Gly Gly Ser
        835                 840                 845

Val Ala His Ala Ile Ser Arg Gly Asp Val Ser Gly Gly Phe Asn Ser
    850                 855                 860

Leu Val Gly Gly Leu Val Gly His Asn Gly Gly Glu Leu Val Asn Val
865                 870                 875                 880

Asp Ala Ser Gly Arg Val Ser Ala Ala Ser Ala Ser Val Gly Gly
                885                 890                 895

Leu Val Gly Ser Asn Ala Gly Ser Ile Leu Ser Ala Arg Ser Ser
            900                 905                 910

Thr Val Asn Gly Ser Gly Arg Ser Arg Ile Gly Gly Leu Val Gly Glu
        915                 920                 925

Asn Gln Ile Gln Gly Arg Ile Val Ser Ser Met Ser Glu Gly Thr Val
    930                 935                 940

Ser Gly Asp Tyr Tyr Val Ser Met Gly Gly Leu Ala Gly Leu Asn Leu
945                 950                 955                 960

Gly Ser Ile Glu Tyr Ser Gly Val Ser Gly Lys Ile Asp Phe Lys Pro
                965                 970                 975

Gln Ser His Tyr Gly Gln Ile Tyr Gly Ala Gln Val Gly Glu Asn His
            980                 985                 990

Gly Val Leu Gly Gly Asn Tyr Val Ile Gly Glu Ala Ala Leu Leu Pro
        995                 1000                1005

Pro Ala Gly Ile Asp Tyr Gly Asn Ile Trp
    1010                1015

<210> SEQ ID NO 8
<211> LENGTH: 176
<212> TYPE: PRT
<213> ORGANISM: Pseudomonas aeruginosa

<400> SEQUENCE: 8

Met Gln Asn Ala Lys Leu Met Leu Thr Cys Leu Ala Phe Ala Gly Leu
1               5                   10                  15

Ala Ala Leu Ala Gly Cys Ser Phe Pro Gly Val Tyr Lys Ile Asp Ile
            20                  25                  30

Gln Gln Gly Asn Val Val Thr Gln Asp Met Ile Asp Gln Leu Arg Pro
        35                  40                  45

Gly Met Thr Arg Arg Gln Val Arg Phe Ile Met Gly Asn Pro Leu Ile
    50                  55                  60

Val Asp Thr Phe His Ala Asn Arg Trp Asp Tyr Leu Tyr Ser Ile Gln
65                  70                  75                  80
```

Pro Gly Gly Gly Arg Gln Gln Glu Arg Val Ser Leu Phe Phe Asn
            85                  90                  95

Asp Ser Asp Gln Leu Ala Gly Leu Asn Gly Asp Phe Met Pro Gly Val
        100                 105                 110

Ser Arg Asp Glu Ala Ile Leu Gly Lys Glu Gly Ser Thr Thr Val Thr
        115                 120                 125

Gln Pro Ala Asp Gln Gln Lys Pro Glu Ala Gln Lys Glu Glu Pro Pro
        130                 135                 140

Lys Pro Gly Ser Thr Leu Glu Gln Leu Gln Arg Glu Val Asp Glu Ala
145                 150                 155                 160

Gln Pro Val Pro Val Pro Thr Pro Glu Pro Leu Asp Pro Ser Pro Gln
                165                 170                 175

<210> SEQ ID NO 9
<211> LENGTH: 479
<212> TYPE: PRT
<213> ORGANISM: Pseudomonas aeruginosa

<400> SEQUENCE: 9

Met Lys Thr Ala Trp Leu Leu Leu Leu Leu Gly Val Gly Ala Leu
1               5                   10                  15

Gly Gly Cys Ala Val Asn Pro Ala Thr Gly Lys Ser Asp Phe Val Met
            20                  25                  30

Met Ser Glu Gln Gln Glu Leu Gly Met Gly Ala Arg Tyr Asn Gln Glu
        35                  40                  45

Ile Leu Lys Gln Phe Pro Arg Tyr Asn Asp Glu Lys Leu Gln Ala Tyr
    50                  55                  60

Val Gln Arg Val Gly Glu Arg Val Ala Arg Ser Ser His Arg Ser Asn
65                  70                  75                  80

Leu Gln Tyr His Phe Thr Val Ile Asp Ser Pro Asp Ile Asn Ala Phe
                85                  90                  95

Ala Leu Pro Gly Gly Tyr Ile Tyr Ile His Arg Gly Leu Ile Ala Tyr
            100                 105                 110

Leu Gly Ser Glu Ala Glu Leu Ala Ala Val Leu Gly His Glu Val Gly
        115                 120                 125

His Val Thr Ala Arg His Ser Val Arg Gln Gln Ser Gln Ala Ser Ala
    130                 135                 140

Trp Asn Ile Leu Gly Gln Ala Val Ala Ile Gly Thr Gly Val Gly Ala
145                 150                 155                 160

Ala Gly Asp Leu Ala Asn Val Leu Gly Thr Ala Phe Val Arg Gly Tyr
                165                 170                 175

Gly Arg Asp Met Glu Leu Glu Ala Asp Gly Leu Gly Ala Gln Tyr Leu
            180                 185                 190

Ala Arg Ala Gly Tyr Asp Pro Thr Ala Met Ile Gln Val Val Arg Val
        195                 200                 205

Leu Lys Asn Gln Glu Asp Phe Ala Arg Glu Ala Ala Arg Asn Gly
    210                 215                 220

Gln Ala Val Gln Ala Gly Gly Tyr His Gly Leu Phe Asp Thr His Pro
225                 230                 235                 240

Asp Asn Asp Arg Arg Leu Gln Glu Val Val Gly Pro Ala Arg Gln Leu
                245                 250                 255

Ala Asn Gly Gln Gln Glu Val Gly Arg Glu Val Phe Leu Arg His Leu
            260                 265                 270

Glu Gly Met Pro Phe Gly Asp Ser Ala Ser Ala Gly Val Arg Arg Gly
        275                 280                 285

```
Gln Asn Phe Tyr His Ala Glu Leu Asp Phe Thr Leu Ser Tyr Pro Ala
    290                 295                 300

Gly Trp Lys Ile Leu Asn Gln Pro Ser Ala Leu Leu Gly Tyr Pro Ala
305                 310                 315                 320

Asp Glu Gln Ser Phe Ile Gly Met Lys Leu Val Pro His Asp Ser Arg
                325                 330                 335

Leu Thr Pro Ala Glu Phe Leu Arg Lys Asn Ala Gly Gln Arg Leu Ala
            340                 345                 350

Gln Glu Glu Ser Leu Lys Gln Ala Gly Leu Asn Gly Tyr Thr Ala Val
        355                 360                 365

Val Pro Gly Asn Pro Ala Arg Arg Val Ala Val Ile Tyr Gln Gly Asp
    370                 375                 380

Arg Ala Tyr Leu Phe Val Gly Val Val Lys Val Gly Ser Leu Glu Thr
385                 390                 395                 400

Gln Asp Asp Arg Phe Leu Ser Val Ile Arg Ser Phe Arg Pro Leu Arg
                405                 410                 415

Asp Lys Glu Arg Ala Leu Ala Gln Pro Arg Arg Leu His Leu Val Gln
            420                 425                 430

Val Lys Ala Gly Gln Thr Leu Glu Gln Leu Ala Ala Gly Gly Glu Gly
        435                 440                 445

Ser Leu Ser Asp Ser Val Ala Arg Leu Arg Leu Leu Asn Asp Leu Tyr
    450                 455                 460

Pro Ser Gly Glu Pro Arg Pro Gly Asp Trp Leu Lys Val Val Arg
465                 470                 475

<210> SEQ ID NO 10
<211> LENGTH: 243
<212> TYPE: PRT
<213> ORGANISM: Pseudomonas aeruginosa

<400> SEQUENCE: 10

Met Arg Arg Val Ile Phe Leu Ala Ala Ala Ala Thr Leu Leu Ala Gly
  1               5                  10                  15

Cys Ala Gly Thr Ala Asp Pro Ser Gly Thr Trp Ile Asn Gln Ala Ala
                20                  25                  30

Ile Asp Ala Ala Ser Lys Asp Gly Lys Leu Arg Glu Ala Leu Leu Ala
            35                  40                  45

Tyr Gly Pro Asn Leu Glu Trp Lys Leu Asp Ser Lys Ala Gly Glu Ala
        50                  55                  60

Thr Phe Ser Asn Gly Phe Glu Leu Gly Glu Gly Thr Leu Ser Lys Ser
 65                  70                  75                  80

Asp Asp Glu His Trp Lys Val Ala Phe Tyr Gly Asp Asp Asn Gln Glu
                85                  90                  95

Ser Leu Glu Leu Asp Gly Lys Glu Leu Ile Gln Gln Ala Ser Ala Asn
            100                 105                 110

Gly Pro Glu Gln Arg Phe Arg Arg Leu Asp Pro Gln Pro Ala Ala Ser
        115                 120                 125

Ser Pro Ala Gly Ser Gly Phe Glu Arg Ala Leu Tyr Gly Ser Tyr Leu
    130                 135                 140

Lys Gly Ser Trp Lys Ile Arg Glu Gly Gln Gly Gln Gly Lys Val
145                 150                 155                 160

Glu Phe Gln Ala Asn Gly Leu Val Ser Gly Leu Pro Gly Ala Glu Arg
                165                 170                 175

Tyr Ala Leu Cys Leu Ala Gly Asp Cys Ala Ala Met Ser Gly Asp Asn
```

```
                   180                 185                 190
Asp Ser Ile Trp Leu Gln Gln Gly Asn Arg Gly Arg Glu Leu Leu Phe
            195                 200                 205

Ser Leu Asp Asp Glu Leu Gln Leu Phe Glu Ala Val Asn Thr Ala
        210                 215                 220

Gly Ala Asn Glu Met Pro Ser Tyr Val Pro Gly Lys Arg Val Trp Leu
225                 230                 235                 240

Leu Glu Arg

<210> SEQ ID NO 11
<211> LENGTH: 924
<212> TYPE: PRT
<213> ORGANISM: Pseudomonas aeruginosa

<400> SEQUENCE: 11

Met Ala Val Lys Ser Leu Val Phe Arg Arg Lys Phe Pro Leu Leu Val
1               5                   10                  15

Thr Gly Ser Leu Leu Ala Leu Gln Pro Val Ala Ala Leu Thr Val Gln
            20                  25                  30

Ala Ala Asp Gln Phe Asp Cys Lys Val Ser Ala Thr Gly Gly Trp Asp
        35                  40                  45

Cys Ser Pro Leu Gln Asn Ala Asn Ala Asn Leu Pro Pro Arg Pro Ala
    50                  55                  60

His Thr Ala Thr Ser Val Ser Thr Ala Ala Ala Gly Ser Ser Val Ser
65                  70                  75                  80

Gly Ser Gly Gly Glu Thr Val Glu Ala Glu Pro Thr Gln Arg Leu Val
                85                  90                  95

Thr Glu Ser Gly Gly Arg Ala Leu Lys Ser Arg Ser Ala Asp Tyr Ser
            100                 105                 110

His Leu Asp Trp Ile Pro Arg Glu Lys Leu Thr Ala Ala Gln Leu Ala
        115                 120                 125

Glu Ile Gly Pro Tyr Cys Gly Gly Ser Tyr Ile Glu Pro Val Arg Pro
    130                 135                 140

Gly Met Asp Asp Gly Ala Pro Ser Asp Glu Ser Pro Thr Tyr Val Ser
145                 150                 155                 160

Ala Lys Ala Ser Arg Tyr Glu Gln Glu Lys Gln Ile Ala Thr Leu Ala
                165                 170                 175

Gly Asp Val Val Leu Arg Gln Gly Ser Met Gln Val Glu Gly Asp Glu
            180                 185                 190

Ala Asn Leu His Gln Leu Glu Asn Arg Gly Leu Val Gly Asn Val
        195                 200                 205

Lys Leu Arg Asp Lys Gly Met Leu Val Val Gly Asp His Ala Gln Val
    210                 215                 220

Gln Leu Asp Asn Gly Glu Ala Gln Val Asp Asn Ala Glu Tyr Val Ile
225                 230                 235                 240

His Lys Ala His Ala Arg Gly Ser Ala Leu Tyr Ala Lys Arg Ser Glu
                245                 250                 255

Asn Ala Ile Ile Met Leu Lys Asp Gly Thr Tyr Thr Arg Cys Glu Pro
            260                 265                 270

Ser Ser Asn Ala Trp Thr Leu Lys Gly Asn Asn Val Lys Leu Asn Pro
        275                 280                 285

Ala Thr Gly Phe Gly Thr Ala Thr Asn Ala Thr Leu Arg Val Lys Asp
    290                 295                 300

Phe Pro Val Phe Tyr Thr Pro Tyr Ile Tyr Phe Pro Ile Asp Asp Arg
```

-continued

|     | 305 |     |     |     | 310 |     |     |     | 315 |     |     |     | 320 |
| --- | --- | --- | --- | --- | --- | --- | --- | --- | --- | --- | --- | --- | --- |

Arg Gln Ser Gly Phe Leu Pro Pro Ser Phe Ser Thr Ser Asp Thr
            325                 330                 335

Gly Phe Thr Leu Val Thr Pro Tyr Tyr Phe Asn Leu Ala Pro Asn Tyr
            340                 345                 350

Asp Ala Thr Leu Tyr Pro Arg Tyr Met Ala Lys Arg Gly Met Met Leu
            355                 360                 365

Glu Gly Glu Phe Arg Tyr Leu Thr His Ser Ser Glu Gly Ile Val Asn
    370                 375                 380

Ala Ala Tyr Leu Asn Asp Lys Asp His Arg Glu Gly Phe Pro Asp
385                 390                 395                 400

Tyr Ser Lys Asp Arg Trp Leu Tyr Gly Leu Lys Asn Thr Thr Gly Leu
            405                 410                 415

Asp Ser Arg Trp Leu Ala Glu Val Asp Tyr Thr Arg Ile Ser Asp Pro
            420                 425                 430

Tyr Tyr Phe Gln Asp Leu Asp Thr Asp Leu Gly Val Gly Ser Thr Thr
            435                 440                 445

Tyr Val Asn Gln Arg Gly Thr Leu Thr Tyr Arg Gly Asp Thr Phe Thr
    450                 455                 460

Gly Arg Leu Asn Ala Gln Ala Tyr Gln Leu Ala Thr Thr Thr Asp Val
465                 470                 475                 480

Thr Pro Tyr Asp Arg Leu Pro Gln Ile Thr Phe Asp Gly Phe Leu Pro
            485                 490                 495

Tyr Asn Pro Gly Gly Met Gln Phe Thr Tyr Gly Thr Glu Phe Val Arg
            500                 505                 510

Phe Asp Arg Asp Leu Asp Glu Asn Ile Tyr Phe Asn Asp Asp Gly Ser
            515                 520                 525

Ile Arg Gly Lys Arg Pro Asp Ala Ser Leu Gln Gly Leu Ala Arg Ala
    530                 535                 540

Thr Gly Asp Arg Met His Leu Glu Pro Gly Met Ser Leu Pro Met Thr
545                 550                 555                 560

Arg Ser Trp Gly Tyr Val Thr Pro Thr Leu Lys Tyr Leu Tyr Thr Lys
            565                 570                 575

Tyr Asp Leu Asp Leu Asp Ser Gln Gly Lys Thr Asp Leu Asn Lys Arg
            580                 585                 590

Asp Glu Ser Phe Asp Ser Asn Gln Asp Arg Ser Leu Pro Leu Val Lys
            595                 600                 605

Val Asp Ser Gly Leu Tyr Phe Asp Arg Asp Thr Thr Phe Ala Gly Thr
    610                 615                 620

Pro Phe Arg Gln Thr Leu Glu Pro Arg Ala Met Tyr Leu Tyr Val Pro
625                 630                 635                 640

Tyr Lys Asp Gln Asp Ser Leu Pro Val Phe Asp Thr Ser Glu Pro Ser
            645                 650                 655

Phe Ser Tyr Asp Ser Leu Trp Arg Glu Asn Arg Phe Thr Gly Lys Asp
            660                 665                 670

Arg Ile Gly Asp Ala Asn Gln Leu Ser Leu Gly Val Thr Ser Arg Phe
            675                 680                 685

Ile Glu Glu Asn Gly Phe Glu Arg Ala Ser Ile Ser Ala Gly Gln Ile
    690                 695                 700

Tyr Tyr Phe Arg Asp Arg Arg Val Gln Leu Pro Gly Leu Thr Glu Lys
705                 710                 715                 720

Asp Leu Lys Arg Leu Asn Leu Asp Pro Ser Gly Leu Asp Asn Asp Ser
            725                 730                 735

Trp Arg Ser Pro Tyr Ala Phe Ala Gly Gln Tyr Arg Phe Asn Arg Asp
                740                 745                 750

Trp Arg Ile Asn Ser Asp Phe Asn Trp Asn Pro Asn Thr Ser Arg Thr
            755                 760                 765

Glu Ser Gly Ser Ala Ile Phe His Tyr Gln Pro Glu Val Asp Pro Gly
770                 775                 780

Lys Val Val Asn Val Gly Tyr Arg Tyr Ala Asp Ala Arg Arg Phe
785                 790                 795                 800

Asp Ser Ser Arg Gly Thr Phe Arg Tyr Gly Asn Glu Asn Asp Ile Ile
                805                 810                 815

Lys Gln His Asp Phe Ser Val Ile Trp Pro Leu Val Pro Gln Trp Ser
            820                 825                 830

Val Leu Ala Arg Trp Gln Tyr Asp Tyr Asn Lys Asn Arg Thr Leu Glu
        835                 840                 845

Ala Phe Gly Gly Phe Glu Tyr Asp Ser Cys Cys Trp Lys Leu Arg Leu
    850                 855                 860

Ile Asn Arg Tyr Trp Leu Asp Val Asp Asp Ala Phe Leu Val Gln
865                 870                 875                 880

Ser Glu Lys Ala Asp Arg Gly Ile Phe Leu Gln Ile Val Leu Lys Gly
                885                 890                 895

Leu Gly Gly Ile Val Gly Asn Lys Thr Glu Met Phe Leu Asp Lys Gly
            900                 905                 910

Ile Gln Gly Tyr Arg Gln Arg Glu Asp Gln Ala Met
        915                 920

<210> SEQ ID NO 12
<211> LENGTH: 340
<212> TYPE: PRT
<213> ORGANISM: Pseudomonas aeruginosa

<400> SEQUENCE: 12

Met Lys Ala Thr Met Val Leu Thr Pro Leu Ala Leu Ala Met Ala Ala
1               5                   10                  15

Val Leu Ser Val Ser Ala Tyr Ala Gly Asn Glu Gly Gly Trp His Pro
            20                  25                  30

Pro Lys Pro Asn Pro Gln Ser Asn Asn Lys Gly Gly Ala Thr Ala Leu
        35                  40                  45

Val Val Asp Thr Gln Gln Asn Tyr Asn Asn Lys Val Ser Asn Phe Gly
    50                  55                  60

Thr Leu Asn Asn Ala Ser Val Ser Gly Ser Ile Lys Asp Ala Ser Gly
65                  70                  75                  80

Asn Val Gly Val Asn Val Ala Ala Gly Asp Asn Asn Gln Gln Ala Asn
                85                  90                  95

Ala Ala Ala Leu Ala Ser Ala Asp Ala Ser Phe Val Phe Gly Thr Ala
            100                 105                 110

Thr Ala Ser Thr Ser Val Leu Gln Ser Gly Tyr Gly Asn Thr Leu Asn
        115                 120                 125

Asn Tyr Ser Asn Pro Asn Thr Ala Ser Leu Ser Asn Ser Ala Asn Asn
    130                 135                 140

Val Ser Gly Asn Leu Gly Val Asn Val Ala Gly Asn Phe Asn Gln
145                 150                 155                 160

Gln Lys Asn Asp Leu Ala Ala Ala Val Ser Asn Gly Gln Tyr Ser Thr
                165                 170                 175

Ala Gly Ser Ala Ala Ser Gln Thr Ser Thr Gly Asn Thr Thr Val Asn

```
            180                 185                 190
Ser Ala Asn Tyr Ala Tyr Gly Gly Thr Tyr Val Ser Leu Lys Leu Asn
                195                 200                 205

Ala Asp Gly Ser Tyr Lys Gly Thr Ser Asp Gln Ile Gly Asp Val Tyr
210                 215                 220

Leu Asp Thr Trp Glu Gly Gln Thr His Pro Gly Ser Asn Thr Gly
225                 230                 235                 240

His Ile Asp Val Asp Ser Gln Ala Gln Gly Lys Asp Leu Asn His
                245                 250                 255

Asp Gly Gly Ala Phe Ala Phe Lys Glu Lys Gly Asp Val Asp Leu Lys
                260                 265                 270

Gly Thr Val Ser Gly Phe Ile Pro Ala Ile Val Gly Phe Lys Thr Pro
                275                 280                 285

Val Thr Asn Asn Ala Ser Leu Ser Asn Ser Leu Gln Asn Val Ser Gly
                290                 295                 300

Asn Val Gly Val Asn Ile Ala Ala Gly Gly Gly Asn Gln Gln Ser Asn
305                 310                 315                 320

Ser Leu Ser Ile Ala Ala Gly Cys Ser Ser Cys Pro Ala Gly Gly Glu
                325                 330                 335

Ser Leu Gly Phe
                340

<210> SEQ ID NO 13
<211> LENGTH: 261
<212> TYPE: PRT
<213> ORGANISM: Pseudomonas aeruginosa

<400> SEQUENCE: 13

Met Arg Lys Tyr Ile Ala Leu Pro Ala Val Ser Leu Leu Ala Leu Ala
1               5                   10                  15

Leu Ala Ala Cys Ser Thr Pro Pro Asn Ala Asn Leu Glu Gln Ala Arg
                20                  25                  30

Ser Asn Phe Ser Ala Leu Gln Ser Gln Pro Asp Ala Thr Lys Val Ala
            35                  40                  45

Ala Leu Glu Thr Lys Asp Ala Gly Asp Trp Leu Ala Lys Ala Asp Lys
        50                  55                  60

Ala Tyr Gln Asp Gly Glu Asp Gln Arg Asp Val Asp Gln Leu Ala Tyr
65                  70                  75                  80

Leu Thr Asn Gln Arg Ile Glu Leu Ala Lys Gln Thr Ile Val Leu Arg
                85                  90                  95

Asn Ala Glu Ala Gln Leu Gln Asn Ala Ser Ala Gln Arg Ala Gln Ala
                100                 105                 110

Arg Leu Asp Ala Arg Thr Ala Gln Leu Asp Lys Leu Arg Ser Gln Leu
            115                 120                 125

Asn Ala Lys Gln Thr Ser Arg Gly Thr Met Val Thr Phe Gly Asp Val
130                 135                 140

Leu Phe Asp Leu Asp Lys Ser Asp Leu Lys Pro Gly Ala Met Arg Asn
145                 150                 155                 160

Ile Gln Gln Leu Ala Glu Phe Leu Gln Gln Asn Pro Glu Arg Gln Val
                165                 170                 175

Ile Val Glu Gly Tyr Thr Asp Ser Thr Gly Ser Ala Asn Tyr Asn Gln
            180                 185                 190

Arg Leu Ser Glu Arg Arg Ala Asp Ser Val Arg Met Ala Leu Leu Ser
            195                 200                 205
```

```
Arg Gly Ile Ser Pro Glu Arg Val Ala Thr Arg Gly Tyr Gly Lys Glu
    210                 215                 220

Tyr Pro Val Ala Ser Asn Gly Thr Ser Gly Arg Ala Met Asn Arg
225                 230                 235                 240

Arg Val Glu Val Thr Ile Ser Asn Asp Ala Lys Pro Val Ala Pro Arg
                    245                 250                 255

Ser Ser Val Ser Gly
            260

<210> SEQ ID NO 14
<211> LENGTH: 446
<212> TYPE: PRT
<213> ORGANISM: Pseudomonas aeruginosa

<400> SEQUENCE: 14

Met Thr Arg Met Pro Leu Ala Thr Ala Ser Leu Leu Ala Leu Ala Ile
1               5                   10                  15

Ser Leu Ala Gly Cys Gly Asp Asp Lys Lys Ala Glu Ala Pro Ala Thr
            20                  25                  30

Pro Ala Ala Ser Thr Gln Pro Ala Pro Ala Ala Pro Ala Ala
                35                  40                  45

Lys Val Asp Glu Ala Ala Ala Lys Ala Val Ile Lys Asn Tyr Ala Asp
50                  55                  60

Leu Ala Glu Ala Thr Phe Ala Asp Ala Leu Ser Thr Ala Lys Asp Leu
65                  70                  75                  80

Gln Lys Ala Ile Asp Ala Phe Leu Ala Lys Pro Asp Ala Glu Thr Leu
                85                  90                  95

Lys Ala Ala Lys Glu Ala Trp Phe Ala Ala Arg Thr Pro Tyr Ser Gln
                100                 105                 110

Ser Glu Ala Phe Arg Phe Gly Asn Ala Ile Ile Asp Asp Trp Glu Gly
                115                 120                 125

Gln Val Asn Ala Trp Pro Leu Asp Glu Gly Leu Ile Asp Tyr Val Ala
            130                 135                 140

Lys Asp Tyr Gln His Ala Leu Gly Asn Pro Gly Ala Thr Ala Asn Ile
145                 150                 155                 160

Val Ala Asn Thr Glu Ile Gln Val Gly Glu Asp Lys Ile Asp Val Lys
                    165                 170                 175

Glu Ile Thr Gly Glu Lys Leu Ala Ser Leu Asn Glu Leu Gly Gly Ser
                180                 185                 190

Glu Ala Asn Val Ala Thr Gly Tyr His Ala Ile Glu Phe Leu Leu Trp
            195                 200                 205

Gly Gln Asp Leu Asn Gly Thr Gly Pro Gly Ala Gly Asn Arg Pro Ala
210                 215                 220

Thr Asp Tyr Ala Gln Gly Lys Asp Cys Thr Gly His Cys Asp Arg
225                 230                 235                 240

Arg Ala Ala Tyr Leu Lys Ala Val Thr Asp Leu Leu Val Ser Asp Leu
                245                 250                 255

Glu Tyr Met Ala Gly Gln Trp Lys Ala Gly Val Ala Asp Asn Tyr Arg
                260                 265                 270

Ala Lys Leu Glu Ala Glu Pro Val Asp Thr Gly Leu Arg Lys Met Phe
            275                 280                 285

Phe Gly Met Gly Ser Leu Ser Leu Gly Glu Leu Ala Gly Glu Arg Met
290                 295                 300

Lys Val Ala Leu Glu Ala Asn Ser Thr Glu Asp Glu His Asp Cys Phe
305                 310                 315                 320
```

```
Ser Asp Asp Thr His His Thr Leu Phe Phe Asn Gly Lys Ser Ile Arg
            325                 330                 335

Asn Ile Tyr Leu Gly Glu Tyr Lys Arg Ile Asp Gly Ser Val Val Lys
            340                 345                 350

Gly Pro Ser Leu Ala Asp Leu Val Ala Lys Ala Asp Ala Ala Ala Asn
            355                 360                 365

Asp Thr Leu Lys Ala Asp Leu Ala Asp Thr Glu Ala Lys Leu Gln Ala
            370                 375                 380

Ile Val Asp Ser Ala Glu Lys Asp Gly Val His Phe Asp Gln Met Ile
385                 390                 395                 400

Ala Pro Asp Asn Lys Asp Gly Gln Gln Lys Ile Arg Asp Ala Ile Ala
            405                 410                 415

Ala Leu Val Lys Gln Thr Gly Ala Ile Glu Gln Ala Ala Gly Lys Leu
            420                 425                 430

Gly Ile Gln Asp Leu Lys Pro Asp Asn Ala Asp His Glu Phe
            435                 440                 445

<210> SEQ ID NO 15
<211> LENGTH: 764
<212> TYPE: PRT
<213> ORGANISM: Pseudomonas aeruginosa

<400> SEQUENCE: 15

Met Pro Leu Ser Pro Pro Phe Ala Leu Arg Pro Cys Leu Ala Leu Leu
  1               5                  10                  15

Leu Leu Ser Pro Ser Leu Ala Leu Ala Gly Asn Ala Val Pro Leu Thr
             20                  25                  30

Pro Thr Thr Ile Thr Ala Thr Arg Thr Glu Gln Ala Val Asp Ser Val
         35                  40                  45

Pro Ser Thr Val Ser Val Gln Thr Arg Glu Gln Leu Asp Arg Gln Asn
     50                  55                  60

Val Asn Asn Ile Lys Glu Leu Val Arg Tyr Glu Pro Gly Val Ser Val
 65                  70                  75                  80

Gly Gly Ala Gly Gln Arg Ala Gly Ile Thr Gly Tyr Asn Ile Arg Gly
             85                  90                  95

Ile Asp Gly Asn Arg Ile Leu Thr Gln Ile Asp Gly Val Glu Leu Pro
            100                 105                 110

Asn Asp Phe Phe Ser Gly Pro Tyr Ala Gln Thr His Arg Asn Tyr Val
            115                 120                 125

Asp Pro Asp Ile Val Lys Arg Val Glu Ile Leu Arg Gly Pro Ala Ser
            130                 135                 140

Ala Leu Tyr Gly Ser Asn Ala Ile Gly Gly Ala Val Ser Tyr Phe Thr
145                 150                 155                 160

Leu Asp Pro Ser Asp Ile Ile Lys Asp Gly Lys Asp Val Gly Ala Arg
            165                 170                 175

Leu Lys Ala Gly Tyr Glu Ser Ala Ser His Ser Trp Leu Thr Ser Ala
            180                 185                 190

Thr Val Ala Gly Arg Ala Asp Asp Phe Asp Gly Leu Leu His Tyr Gly
            195                 200                 205

Tyr Arg Gln Gly His Glu Thr Glu Ser Asn Gly His Gly Gly Thr
            210                 215                 220

Gly Leu Ser Arg Ser Glu Ala Asn Pro Glu Asp Ala Asp Ser Tyr Ser
225                 230                 235                 240

Leu Leu Gly Lys Leu Gly Trp Asn Tyr Ala Glu Gly Ser Arg Phe Gly
```

```
            245                 250                 255
Leu Val Phe Glu Lys Tyr Lys Ser Asp Val Asp Thr Asp Gln Lys Ser
            260                 265                 270

Ala Tyr Gly Gly Pro Tyr Asp Lys Gly Lys Pro Ala Ile Pro Pro Ser
            275                 280                 285

Met Leu Pro Gly Gly Met Tyr Gln Trp Arg Lys Gly Asn Asp Thr Leu
            290                 295                 300

Thr Arg Glu Arg Tyr Gly Leu Glu His His Phe Leu Leu Asp Ser Gln
305                 310                 315                 320

Val Ala Asp Arg Ile Gln Trp Ser Leu Asn Tyr Gln Leu Ala Lys Thr
            325                 330                 335

Asp Gln Ala Thr Arg Glu Phe Tyr Tyr Pro Ile Thr Arg Lys Val Leu
            340                 345                 350

Arg Thr Arg Asp Thr Thr Tyr Lys Glu Arg Leu Trp Val Phe Asp Ser
            355                 360                 365

Gln Leu Asp Lys Ser Phe Ala Ile Gly Glu Thr Glu His Leu Leu Ser
            370                 375                 380

Tyr Gly Ile Asn Leu Lys His Gln Lys Val Thr Gly Met Arg Ser Gly
385                 390                 395                 400

Thr Gly Thr Asn Leu Asp Thr Gly Ala Asp Ser Pro Arg Asp Ala Leu
                405                 410                 415

Glu Arg Ser Ser Asp Phe Pro Asp Pro Thr Val Lys Thr Tyr Ala Leu
                420                 425                 430

Phe Ala Gln Asp Ser Ile Ser Trp Asn Asp Trp Thr Phe Thr Pro Gly
                435                 440                 445

Leu Arg Tyr Asp Tyr Thr Arg Met Glu Pro His Ile Thr Asp Glu Phe
            450                 455                 460

Leu Arg Thr Met Lys Gln Ser Gln Asn Thr Ala Val Asp Glu Ser Asp
465                 470                 475                 480

Lys Lys Trp His Arg Val Ser Pro Lys Phe Gly Val Thr Tyr Asp Phe
                485                 490                 495

Ala Gln His Tyr Thr Trp Tyr Gly Gln Tyr Ala Gln Gly Phe Arg Thr
                500                 505                 510

Pro Thr Ala Lys Ala Leu Tyr Gly Arg Phe Glu Asn Leu Gln Ala Gly
            515                 520                 525

Tyr His Ile Glu Pro Asn Pro Asn Leu Lys Pro Glu Lys Ser Gln Ser
            530                 535                 540

Phe Glu Thr Gly Leu Arg Gly Lys Phe Asp Glu Gly Ser Phe Gly Val
545                 550                 555                 560

Ala Val Phe Tyr Asn Lys Tyr Arg Asp Phe Ile Asp Glu Asp Ala Leu
                565                 570                 575

Asn Thr Asp Ser Thr Gly Gly Asn Gly Gln Thr Phe Gln Ser Asn Asn
            580                 585                 590

Ile Glu Arg Ala Val Ile Lys Gly Val Glu Leu Lys Gly Arg Leu Glu
            595                 600                 605

Leu Gly Ala Phe Gly Ala Pro Gln Gly Leu Tyr Thr Gln Gly Ser Val
    610                 615                 620

Ala Tyr Ala Tyr Gly Arg Asn Lys Asp Asn Gly Glu Pro Ile Asn Ser
625                 630                 635                 640

Val Asn Pro Leu Thr Gly Val Phe Gly Leu Gly Tyr Asp Glu Ala Asp
                645                 650                 655

Gly Asn Tyr Gly Gly Leu Leu Ser Trp Thr Leu Val Lys Arg Lys Asp
            660                 665                 670
```

```
Arg Val Asp Asp Ser Thr Phe His Thr Pro Asp Gly Thr Ala Ser Gln
            675                 680                 685

Phe Lys Thr Pro Gly Phe Gly Val Leu Asp Leu Ser Ala Tyr Tyr Arg
    690                 695                 700

Leu Ser Lys Asp Leu Thr Leu Asn Ala Gly Leu Tyr Asn Leu Thr Asp
705                 710                 715                 720

Lys Lys Tyr Trp Leu Trp Asp Asp Val Arg Gly Tyr Asp Ser Val Gly
                725                 730                 735

Glu Ala Ser Ala Leu Ala Pro Ala Asn Ile Asp Arg Leu Ser Gln Pro
            740                 745                 750

Gly Arg Asn Phe Ala Val Asn Leu Val Trp Asp Ile
            755                 760

<210> SEQ ID NO 16
<211> LENGTH: 1088
<212> TYPE: PRT
<213> ORGANISM: Pseudomonas aeruginosa

<400> SEQUENCE: 16

Met Pro Lys Gly Leu Lys Arg Ala Val Ser Ala Leu Leu Ile Thr Phe
1               5                   10                  15

Leu Val Tyr Cys Leu Leu Gly Phe Leu Ile Pro Gly Ile Gly Leu
            20                  25                  30

Arg Val Ala Asn Gln Gln Leu Ala Gln Tyr Ala Thr Val Pro Ala Arg
            35                  40                  45

Leu Glu Arg Ile Glu Phe Asn Pro Phe Ser Leu Glu Leu Thr Leu Trp
 50                 55                  60

Gly Leu Arg Leu Gly Glu Glu Lys Asn Pro Gln Leu Ala Phe Arg Arg
65                  70                  75                  80

Leu Tyr Ala Asn Leu Gln Leu Asp Ser Leu Trp Lys Arg Gln Leu His
                85                  90                  95

Leu Ala Asp Val Glu Leu Glu Gly Pro His Thr Glu Leu Leu Phe Gly
            100                 105                 110

Glu Lys Gly Gln Leu Asn Leu Ala Ser Leu Phe Arg Ile Pro Pro Ser
        115                 120                 125

Glu Ser Pro Glu Pro Glu Gln Pro Ser Asp Pro Phe Pro Leu Arg Ile
    130                 135                 140

Asp Arg Ile Gln Leu Ala Glu Gly Ser Leu His Phe Gln Asp Leu Arg
145                 150                 155                 160

Pro Ser Glu Pro Val Asp Phe Ser Phe Asp Pro Leu Gly Phe Glu Leu
                165                 170                 175

His Asn Leu Ser Thr Leu Pro Asp Asp Gly Ala Lys Met Thr Leu Val
            180                 185                 190

Ala Thr Gly Pro Asn Gly Gly Arg Leu Asp Trp Glu Gly Asp Leu Thr
        195                 200                 205

Leu Val Pro Ile Thr Ser Arg Gly His Leu Ser Val Lys Asp Ile Gln
    210                 215                 220

Leu Lys Ala Trp Trp Pro Tyr Val Arg Asp Asn Ala Pro Leu Val Leu
225                 230                 235                 240

Glu Asn Gly Val Val Ser Leu Ser Ser Asp Tyr Arg Leu Asp Leu Ser
                245                 250                 255

Lys Asp Thr Gln Leu Leu Leu Asp Lys Ala Leu Lys Leu Ala Asp
            260                 265                 270

Phe Ser Ile Asn Ser Pro Gln Gly Lys Pro Leu Ala Lys Leu Ala Ser
```

-continued

```
            275                 280                 285
Leu Asp Val Ala Ala Thr Thr Leu Asp Leu Ala Lys Gln Glu Val Val
            290                 295                 300
Leu Gly Glu Val Arg Ser Gln Gly Leu Glu Ala Trp Ala Ala Arg Glu
305                 310                 315                 320
Lys Asp Gly Gln Leu Asp Trp Gln Lys Leu Phe Ala Asp Phe Thr Pro
            325                 330                 335
Pro Pro Arg Lys Ala Pro Ala Pro Lys Pro Ala Glu Asn Thr Asp Pro
            340                 345                 350
Ala Ala Ala Pro Thr Asp Ala Ala Lys Thr Thr Ser Glu Pro Ala Thr
            355                 360                 365
Asp Gly Ala Ala Lys Ala Ala Ala Ile Ala Ser Gly Glu Ala Ser Lys
            370                 375                 380
Asp Arg Pro Ala Glu Lys Asp Ala Ser Val Ala Glu Thr Glu Arg Ala
385                 390                 395                 400
Thr Asp Asp Lys Glu Ser Ala Lys Ala Ala Glu Gly Ala Ala Asp Lys
            405                 410                 415
Val Ala Lys Gln Glu Thr Ser Lys Ala Pro Lys Thr Gly Lys Ala Thr
            420                 425                 430
Gly Gln Glu Thr Ala Lys Thr Ala Glu Ile Asp Lys Ala Ala Ser Asp
            435                 440                 445
Ser Pro Gln Gln Leu Ala Asp Thr Ala Lys Thr Pro Pro Glu Ser
            450                 455                 460
Thr Lys Ala Ser Ala Glu Thr Pro Ala Lys Pro Trp Asn Ile Val Leu
465                 470                 475                 480
Arg Asp Ala Gln Leu Arg Gly Tyr Lys Ala His Leu Val Asp Arg Gln
            485                 490                 495
Pro Ala Thr Glu Val Pro Leu Glu Val Gly Pro Leu Asp Leu Asp Leu
            500                 505                 510
Gln Asn Val Asp Ser Leu Gly Lys Thr Pro Phe Asp Leu Lys Leu Lys
            515                 520                 525
Thr Gly Leu Gly Asn Arg Gly Gln Val Gln Ala Ser Gly Gln Val Val
            530                 535                 540
Leu Asp Pro Val Ser Ala Arg Leu Lys Val Ser Thr Arg Asp Ile Asp
545                 550                 555                 560
Leu Arg Val Ala Gln Ala Tyr Ile Ser Pro Phe Ile Arg Leu Glu Leu
            565                 570                 575
Arg Ser Gly Phe Leu Gly Ser Glu Leu Ala Val Asp Leu Lys Ser Val
            580                 585                 590
Glu Pro Leu Ala Phe Ser Val Asp Gly Ser Ala Glu Val Ser Gln Leu
            595                 600                 605
His Thr Leu Asp Thr Ile Lys Asp Arg Asp Phe Val Lys Trp Thr Lys
            610                 615                 620
Leu Thr Leu Asn Gly Leu Ala Tyr Arg His Glu Asp Ser Leu Ser Ile
625                 630                 635                 640
Gln Ser Val Ser Phe Glu Glu Pro Tyr Ala Arg Phe Ile Ile Asn Glu
            645                 650                 655
Asp Arg Ser Thr Asn Val Ser Glu Leu Ile Ile Pro Gln Pro Ala Ser
            660                 665                 670
Ser Ser Gly Lys Thr Ala Ala Glu Ser Lys Asn Ala Pro Ala Ser Lys
            675                 680                 685
Pro Leu Gly Ile His Ile Gly Gly Val Arg Ile Asn Asn Gly Ser Ala
            690                 695                 700
```

```
Asn Phe Ala Asp Leu Thr Leu Met Pro Pro Phe Gly Thr Ala Ile Gln
705                 710                 715                 720

Gln Leu Ser Gly Glu Val Gly Thr Leu Asp Thr Arg Asn Ser Gln Pro
            725                 730                 735

Ala Lys Val Asp Ile Lys Gly Lys Val Asp Lys Tyr Ala Pro Val Thr
            740                 745                 750

Ile Ala Gly Glu Leu Asp Pro Phe Asp Pro Leu Lys Lys Leu Asp Ile
            755                 760                 765

Thr Thr Ser Phe Lys Arg Val Glu Leu Thr Thr Leu Thr Pro Tyr Ser
770                 775                 780

Gly Lys Phe Ala Gly Tyr Arg Ile Arg Lys Gly Arg Leu Asn Leu Asp
785                 790                 795                 800

Leu His Tyr Gln Ile Glu Arg Ser Gln Leu Lys Ala Glu Asn Lys Val
                805                 810                 815

Leu Leu Glu Gly Leu Gln Leu Gly Glu Lys Val Asp Ser Pro Asp Ala
            820                 825                 830

Val Asp Leu Pro Val Lys Leu Ala Val Ala Leu Leu Lys Asp Thr Lys
            835                 840                 845

Gly Asn Ile Asp Ile Gln Leu Pro Val Ala Gly Asp Leu Asn Asn Pro
850                 855                 860

Glu Phe Ser Val Met Pro Ile Val Trp Gln Thr Leu Arg Asn Leu Val
865                 870                 875                 880

Leu Arg Ala Val Gln Ala Pro Phe Lys Phe Ile Ala Gly Leu Ala Ala
                885                 890                 895

Gly Gly Asn Glu Asp Leu Gly Thr Val Pro Phe Ala Ala Gly Ser Asp
            900                 905                 910

Glu Leu Thr Pro Glu Ala Gln Ala Asn Leu Asp Lys Leu Ala Asp Ala
            915                 920                 925

Leu Lys Glu Arg Pro Ala Leu Arg Leu Glu Val Glu Gly Val Ala Ser
930                 935                 940

Ala Ala Ala Asp Gly Pro Ser Ile Gly Ala Lys Arg Leu Glu Leu Glu
945                 950                 955                 960

Tyr Gln Asn Thr Tyr Tyr Arg Met Leu Gln Arg Arg Gly Asp Lys Val
                965                 970                 975

Pro Ser Asp Ala Lys Gln Leu Glu Val Pro Glu Asn Met Gln Ala Pro
            980                 985                 990

Leu Leu Glu Gly Ile Tyr Arg Thr Arg Leu Lys Gln Gln Pro Pro Ala
            995                 1000                1005

Glu Trp Lys Glu Leu Asp Ser Asp Glu Arg Thr Ala Lys Met Arg Glu
            1010                1015                1020

Ala Val Ile Ala Ser Trp Ala Lys Ser Gln Val Leu Leu Arg Gln Ile
1025                1030                1035                1040

Gly Gln Ala Arg Ala Thr Arg Ile Lys Asp Tyr Leu Val Glu Lys Gly
                1045                1050                1055

Gln Leu Pro Asp Asp Arg Ile Tyr Leu Ile Asp Val Ser Phe Ala Glu
            1060                1065                1070

Gly Glu Asp Lys Gly Asn Val Asp Thr Gln Leu His Leu Asp Ser Glu
            1075                1080                1085

<210> SEQ ID NO 17
<211> LENGTH: 168
<212> TYPE: PRT
<213> ORGANISM: Pseudomonas aeruginosa
```

<400> SEQUENCE: 17

Met Arg Lys Phe Thr Gln Phe Val Leu Ile Thr Ala Ala Ile Met Ala
1               5                   10                  15

Ala Pro Ser Ala Phe Ala Glu Met Lys Ile Ala Val Leu Asn Tyr Gln
            20                  25                  30

Met Ala Leu Leu Glu Ser Asp Ala Ala Lys Gln Tyr Ala Val Asp Ala
        35                  40                  45

Glu Lys Lys Phe Gly Pro Gln Leu Asn Lys Leu Lys Asn Leu Glu Arg
    50                  55                  60

Asp Ala Lys Ala Leu Gln Asp Lys Leu Val Ser Asn Gly Ser Lys Met
65                  70                  75                  80

Ser Gln Gly Asp Arg Glu Lys Ala Glu Leu Asp Phe Lys Gln Lys Ala
                85                  90                  95

Arg Asp Phe Gln Phe Gln Ser Lys Glu Leu Asn Glu Ser Lys Ala Ala
            100                 105                 110

Ala Asp Arg Asp Met Leu Lys Lys Leu Lys Pro Lys Leu Asp Gln Ala
        115                 120                 125

Val Glu Glu Thr Ile Lys Lys Gly Gly Tyr Asp Met Val Ile Glu Arg
    130                 135                 140

Gly Ala Val Val Asp Val Lys Pro Gln Tyr Asp Ile Thr Arg Gln Val
145                 150                 155                 160

Ile Glu Arg Met Asn Gln Leu Arg
                165

<210> SEQ ID NO 18
<211> LENGTH: 206
<212> TYPE: PRT
<213> ORGANISM: Pseudomonas aeruginosa

<400> SEQUENCE: 18

Met Pro Thr Arg Val Leu Arg Gly Leu Val Ala Ala Leu Pro Leu Phe
1               5                   10                  15

Leu Ala Ala Cys Ser Asp Ser Ala Pro Ser Ser Glu Glu Ile Ala Arg
            20                  25                  30

Leu Leu Ala Glu Arg Gly Phe Asp Lys Pro Ala Cys Ala Ser Ser Thr
        35                  40                  45

Leu Phe Lys Thr Phe Pro Val Thr Leu Ser Asp Ser Phe Ser Gly Pro
    50                  55                  60

Gly Pro Ala Lys Gly Asn Ala Ala Val Tyr Asp Ala Leu Val Gly Val
65                  70                  75                  80

Gly Leu Leu Arg Arg Asp Gly Asp Ser Tyr Asp Leu Thr Pro Ala Gly
                85                  90                  95

Arg Glu Asp Tyr Lys Pro Glu Ser Lys Ala Phe Cys Tyr Ser Ser Gly
            100                 105                 110

Phe Asp Val Ser Val Arg Ser Val Asp Pro Ala Lys Pro Asp Asp Tyr
        115                 120                 125

Gly Pro Ala Val Glu Lys Gly Trp Leu Val Thr Val Glu Val Lys Pro
    130                 135                 140

Arg Glu Val Lys Asp Trp Ala Lys Asn Pro Glu Val Leu Lys Gln Ala
145                 150                 155                 160

Ser Leu Thr Thr Leu Gln Gln Ile Thr Gln Pro Gln Val Gly Gln Val
                165                 170                 175

Ser Leu Val Lys Pro Arg Gly Glu Glu Gly Tyr Lys Leu Val Asn Thr
            180                 185                 190

Arg Phe Ser Pro Arg Gln Gly Phe His Phe Asn Gln Ala Trp
            195                 200                 205

<210> SEQ ID NO 19
<211> LENGTH: 452
<212> TYPE: PRT
<213> ORGANISM: Pseudomonas aeruginosa

<400> SEQUENCE: 19

Met Gln Asn Leu Arg Arg Ala Val Phe Ala Gly Leu Val Ala Gly Thr
 1               5                  10                  15

Leu Ser Glu Gly Ala Ala Ala Thr Ala Gly Asp Gly Gly Phe Val Glu
            20                  25                  30

Asp Ser Glu Leu Gln Phe Leu Ala Arg Thr Tyr Tyr Phe Asn Arg Asp
            35                  40                  45

Tyr Arg Asp Ser Pro Asn Asn Ala Gly Arg Asn Arg Phe Lys Pro Arg
        50                  55                  60

Ser Glu Arg Asn Gly Tyr Arg Glu Glu Ala Thr Gln Gly Leu Arg Leu
 65                  70                  75                  80

Gln Phe Ala Ser Gly Tyr Thr Pro Gly Ser Leu Gly Phe Gly Leu Asp
                85                  90                  95

Ala His Ala Met Leu Gly Leu Gln Leu Asp Ser Gly Gly Arg Thr
                100                 105                 110

Gly Thr Gly Asn Leu Pro Val Gly Ala Asp Gly His Pro Asp His Arg
            115                 120                 125

Tyr Gly Lys Val Gly Gly Ala Leu Arg Leu Arg His Gly Glu Thr Arg
        130                 135                 140

Leu Lys Tyr Gly Gln Thr Thr Thr Ser Ala Pro Val Phe Ala Ala Ser
145                 150                 155                 160

Ser Asn Arg Thr Leu Ala Gly Met Ala Tyr Gly Leu Leu Leu Glu Asp
                165                 170                 175

Arg Ser Phe Asp Gly Leu Leu Leu Glu Gly Gly Arg Phe Thr Ala Ala
            180                 185                 190

Ser Gly Pro Gly Glu Ser Lys Val Arg Gly Asp Ile Ser Thr Val Tyr
            195                 200                 205

Gly Arg Leu Gly Ala Tyr Pro Val Arg Leu Asp Ala Val Gly Phe Leu
        210                 215                 220

Gly Gly Gln Trp Gln Ala Thr Glu Arg Leu Gln Leu Ser Leu Tyr Ala
225                 230                 235                 240

Ser Arg Phe Asp Asp Ile Trp Gln Gln Ala Tyr Phe Gly Ala Ser His
                245                 250                 255

Arg Gln Pro Leu Gly Gly Glu Arg Ala Leu Arg Val Asp Leu Asp Ala
            260                 265                 270

Tyr Arg Thr Arg Asp Ser Gly Gln Ser Arg Phe Gly Arg Ile Asp Thr
        275                 280                 285

Leu Thr Ser Ser Leu Ala Leu Gly Tyr Glu His Gly Pro Gln Arg Ile
        290                 295                 300

Thr Leu Ala Tyr Gln Arg Val His Gly Glu Gln Pro Phe Asp Tyr Met
305                 310                 315                 320

Ala Phe Gly Asp Gly Arg Ser Ala Ser Met Val Leu Ala Asn Ser
                325                 330                 335

Val Gly Tyr Ser Asp Phe Asn Gly Pro Gly Glu Arg Ser Trp Gln Leu
            340                 345                 350

Arg Tyr Asp Leu Asp Leu Gly Ala Leu Gly Leu Pro Gly Leu Ser Leu
        355                 360                 365

```
His Ala Leu His Ala Arg Gly Arg Ala Gly Ala Ser Ala Ser Ser Ala
        370                 375                 380

Ala Glu Ser Ile Tyr Ala Gly Leu Tyr Gly Arg Asp Gly Arg His Arg
385                 390                 395                 400

Glu Asn Asp Leu Gly Phe Ala Tyr Arg Val Lys Ala Gly Pro Leu Ala
                405                 410                 415

Gly Leu Ala Leu Arg Ala Ser Gln Ala Trp His Arg Gly Asn Ala Ser
            420                 425                 430

Tyr Leu Asp Gly Asp Ile Asp Glu Thr Arg Leu Val Val Asp Tyr Ser
        435                 440                 445

Arg Ser Ile Trp
    450

<210> SEQ ID NO 20
<211> LENGTH: 256
<212> TYPE: PRT
<213> ORGANISM: Pseudomonas aeruginosa

<400> SEQUENCE: 20

Met Leu Arg Pro Ala Leu Pro Ala Val Leu Cys Leu Tyr Cys Leu Leu
  1               5                  10                  15

Leu Ala Leu Pro Ala Arg Ala Ala Leu Asp Asp Gln Gln Arg Ala Leu
                20                  25                  30

Gln Gln Leu Gln Val Gln Ala Cys Arg Ala Val Gly Ser Leu Leu Leu
            35                  40                  45

Leu Arg Gly Glu Gly Phe Gln Glu Gln His Ala Ala Gln Leu Glu Lys
        50                  55                  60

Asp Leu Ala Ser Leu Asp Arg Ala Leu Ala Ala Pro Glu Gly Val
 65                 70                  75                  80

Leu Leu Arg Gln Gly Glu Lys Thr Leu Val Ala Arg Ile Arg Glu Gly
                85                  90                  95

Ala Ala Tyr Gly Pro Arg Glu Glu Asp Leu Pro Trp Arg Tyr Pro Gln
            100                 105                 110

Gln Leu Ser Arg Ala Leu Arg Asp Phe Leu Asn Leu Val Glu Arg Gln
        115                 120                 125

Val Pro Pro Pro Pro Gly Gln Pro Leu Pro Leu Trp Gln Leu Pro
130                 135                 140

Val Arg Val Glu Tyr Leu Ser Leu Gln Tyr Leu Ala Arg Ala Tyr Leu
145                 150                 155                 160

Gly Gly Leu Glu Thr Ala Arg Glu Gln Pro Arg Asp Tyr Leu Gly Gln
                165                 170                 175

Asp Glu Ser Val Leu Val Pro Leu Ile Asp Arg Arg Ile Ala Leu Leu
            180                 185                 190

Val Ala Gln Ser Ala Asn Pro Ala Gly Leu Lys Lys Leu Glu Asn Arg
        195                 200                 205

Trp Glu Tyr Leu Ser Gln Ala Leu Arg Asp Leu Asn Ser Lys Ser Ser
    210                 215                 220

Ala Leu Val Ser Ala Ser Gly Arg Pro Trp Ala Pro Ile Ile Val Asp
225                 230                 235                 240

Arg His Ala Arg Ala Leu Ser Glu Ser Leu Met Arg Leu Ser Ala Glu
                245                 250                 255

<210> SEQ ID NO 21
<211> LENGTH: 202
<212> TYPE: PRT
```

<213> ORGANISM: Pseudomonas aeruginosa

<400> SEQUENCE: 21

Met Pro Arg Phe Leu Arg Asn Ala Leu Leu Pro Val Leu Ala Leu Leu
1               5                   10                  15

Leu Ser Gly Cys Gly Tyr Asn Ala Met Gln Ala Gly Asp Glu Gln Val
            20                  25                  30

Lys Ala Ala Trp Ser Glu Val Leu Asn Gln Tyr Gln Arg Arg Ala Asp
        35                  40                  45

Leu Val Pro Asn Leu Val Ser Thr Val Lys Gly Tyr Ala Ser His Glu
    50                  55                  60

Ala Ser Val Leu Thr Gln Val Thr Glu Ala Arg Ala Lys Val Gly Ser
65                  70                  75                  80

Val Gln Leu Asn Ala Asp Gln Leu Asp Asp Glu Gln Ala Val Gln Arg
                85                  90                  95

Phe Gln Lys Ala Gln Gly Glu Leu Ser Ser Ala Leu Ser Arg Leu Leu
            100                 105                 110

Val Val Thr Glu Asn Tyr Pro Gln Leu Lys Ala Asp Gly Leu Phe Lys
        115                 120                 125

Asp Leu Leu Thr Gln Leu Glu Gly Thr Glu Asn Arg Ile Ala Val Ala
    130                 135                 140

Arg Gly Arg Tyr Val Lys Ser Val Gln Glu Tyr Asn Val Leu Leu Arg
145                 150                 155                 160

Gln Phe Pro Gly Val Ile Thr Ala Lys Leu Phe Gly Tyr Lys Pro Lys
                165                 170                 175

Ala Asn Phe Ser Val Glu Asn Glu Ala Ala Ile Ser Thr Ala Pro Lys
            180                 185                 190

Val Asp Phe Gly Asn Pro Gln Pro Ala Gln
        195                 200

<210> SEQ ID NO 22
<211> LENGTH: 151
<212> TYPE: PRT
<213> ORGANISM: Pseudomonas aeruginosa

<400> SEQUENCE: 22

Met Trp Arg Thr Phe Leu Arg Val Pro Leu Leu Leu Leu Ala Ser
1               5                   10                  15

Leu Gly Gly Cys Ala Val Tyr Asp Tyr Asp Tyr Asp Gly Asp Trp
            20                  25                  30

Arg His Tyr Arg Gly Gln Pro Tyr Gly Tyr Ala Tyr Glu Val Pro Arg
        35                  40                  45

Tyr Arg Val Tyr Asp Asp Gly Trp Arg Ser Glu Arg Arg Tyr Tyr Ser
    50                  55                  60

Thr Arg Tyr Tyr Asp Gln Arg Tyr Pro Ala Pro Arg Arg Tyr Asp
65                  70                  75                  80

Gly His Arg Asp Tyr Arg Arg Glu Gln Tyr Arg Tyr Gln Gln Arg Tyr
                85                  90                  95

His Glu Ser Arg Pro Ala His Arg Gly Glu Arg His Pro Gly Asn Trp
            100                 105                 110

Gln Arg Gly Gly Gln Pro Gln Trp Arg Gly His Ser Pro Gln Arg Trp
        115                 120                 125

Gln Gln His Gly Arg Gln Asp Arg Pro Gly His Gln Gly Gln Gln Gly
    130                 135                 140

Gly Thr Pro Arg Trp Arg Asn

```
                        145                 150

<210> SEQ ID NO 23
<211> LENGTH: 683
<212> TYPE: PRT
<213> ORGANISM: Pseudomonas aeruginosa

<400> SEQUENCE: 23

Met Ser Asp Leu Leu Ser Ile Gly Leu Ser Gly Leu Gly Thr Ser Gln
 1               5                  10                  15

Thr Trp Leu Thr Val Thr Gly His Asn Ile Thr Asn Val Lys Thr Pro
            20                  25                  30

Gly Tyr Ser Arg Gln Asp Ala Ile Gln Gln Thr Arg Ile Pro Gln Phe
        35                  40                  45

Ser Gly Ala Gly Tyr Met Gly Ser Gly Ser Gln Ile Val Asp Val Arg
    50                  55                  60

Arg Leu Ala Ser Asp Phe Leu Thr Gly Gln Leu Arg Asn Ala Thr Ser
65                  70                  75                  80

Gln Asn Ser Glu Leu Asn Ala Phe Leu Gly Gln Ile Asp Gln Leu Asn
                85                  90                  95

Ser Leu Leu Ala Asp Asn Thr Thr Gly Val Ser Pro Ala Met Gln Arg
            100                 105                 110

Phe Phe Ser Ala Leu Gln Thr Ala Ala Gln Asn Pro Ser Ser Thr Glu
        115                 120                 125

Ala Arg Glu Ala Val Leu Ala Gln Ala Gln Gly Leu Ser Lys Thr Phe
    130                 135                 140

Asn Thr Leu Tyr Asp Gln Leu Asp Lys Gln Asn Ser Leu Ile Asn Gln
145                 150                 155                 160

Gln Leu Gly Ala Leu Thr Ser Gln Val Asn Asn Leu Ser Gln Ser Val
                165                 170                 175

Ala Glu Tyr Asn Asp Ala Ile Ala Lys Ala Lys Ser Ala Gly Ala Val
            180                 185                 190

Pro Asn Asp Leu Leu Asp Ala Arg Asp Glu Ala Val Arg Lys Leu Ser
        195                 200                 205

Glu Met Val Gly Val Thr Ala Val Thr Gln Asp Asn Ser Val Ser
    210                 215                 220

Leu Phe Ile Gly Ser Gly Gln Pro Leu Val Val Gly Asn Thr Val Ser
225                 230                 235                 240

Thr Leu Ser Val Val Pro Gly Leu Asp Asp Pro Thr Arg Tyr Gln Val
                245                 250                 255

Gln Leu Thr Leu Gly Asp Ser Thr Gln Asn Val Thr Arg Leu Val Ser
            260                 265                 270

Gly Gly Gln Met Gly Gly Leu Leu Ala Tyr Arg Asp Thr Val Leu Asp
        275                 280                 285

Ser Ser Tyr Asn Lys Leu Gly Gln Leu Ala Leu Thr Phe Ala Asp Thr
    290                 295                 300

Val Asn Lys Gln Leu Gly Gln Gly Leu Asp Leu Ala Gly Lys Ala Gly
305                 310                 315                 320

Ala Asn Leu Phe Gly Asp Ile Asn Asp Pro Asp Ile Thr Ala Leu Arg
                325                 330                 335

Val Leu Ala Lys Asn Gly Asn Thr Gly Asn Val His Ala Asn Leu Asn
            340                 345                 350

Ile Thr Asp Thr Ser Lys Leu Asn Ser Ser Asp Phe Arg Leu Asp Phe
        355                 360                 365
```

-continued

```
Asp Gly Thr Asn Phe Thr Ala Arg Arg Leu Gly Asp Asp Ala Ser Met
    370                 375                 380
Gln Val Thr Val Ser Gly Thr Gly Pro Tyr Thr Leu Ser Phe Lys Asp
385                 390                 395                 400
Ala Asn Gly Val Asp Gln Gly Phe Ser Val Thr Leu Asp Gln Leu Pro
                405                 410                 415
Ala Ala Gly Asp Arg Phe Thr Leu Gln Pro Thr Arg Arg Gly Ala Ser
            420                 425                 430
Asp Ile Glu Thr Thr Leu Lys Asn Ala Ser Gln Leu Ala Phe Ala Gly
        435                 440                 445
Ser Ala Arg Ala Glu Ala Thr Thr Asn Arg Gly Ser Gly Ala Ile
    450                 455                 460
Gly Gln Pro Asn Leu Val Asp Gly Pro Ser Ile Asp Pro Ala Val
465                 470                 475                 480
Leu Gln Asn Ala Phe Gly Ala Asn Gly Leu Pro Leu Ser Ala Thr Val
                485                 490                 495
Ser Ala Asp Gly Lys Thr Tyr Thr Met Thr Ser Pro Leu Pro Ala Gly
            500                 505                 510
Trp Ser Tyr Val Asp Lys Asp Gly Asn Ala Leu Pro Gly Ser Pro Thr
        515                 520                 525
Leu Asn Ser Gly Thr Ser Asn Ser Val Arg Met Ala Tyr Thr Asp Pro
    530                 535                 540
Gly Ser Gly Gln Thr Tyr Thr Tyr Glu Phe Asn Leu Ser Asn Val Pro
545                 550                 555                 560
Gln Thr Gly Asp Ser Phe Thr Leu Ser Phe Asn Lys Asp Gly Ile Ala
                565                 570                 575
Asp Asn Arg Asn Ala Leu Asn Leu Asn Ala Leu Gln Thr Lys Pro Thr
            580                 585                 590
Val Gly Gly Thr Asp Ser Thr Gly Ser Thr Tyr Asn Asp Ala Tyr Gly
        595                 600                 605
Gly Leu Val Glu Arg Val Gly Thr Leu Thr Ala Gln Ala Arg Ala Ser
    610                 615                 620
Ala Asp Ala Ser Gln Thr Val Leu Lys Gln Ala Gln Asp Ser Arg Asp
625                 630                 635                 640
Ser Leu Ser Gly Val Ser Leu Asp Glu Glu Ala Ala Asn Leu Ile Gln
                645                 650                 655
Phe Gln Gln Tyr Tyr Ser Ala Ser Ala Gln Val Ile Gln Val Ala Arg
            660                 665                 670
Ser Leu Phe Asp Thr Leu Ile Gly Ala Phe Arg
        675                 680

<210> SEQ ID NO 24
<211> LENGTH: 237
<212> TYPE: PRT
<213> ORGANISM: Pseudomonas aeruginosa

<400> SEQUENCE: 24

Met Leu Lys His Leu Leu Val Leu Thr Cys Ala Leu Leu Ala Ser Ser
  1               5                  10                  15
Ser Ala Leu Ala Gln Val Met Ala Arg Asp Leu Gly Asp Phe Glu Leu
                20                  25                  30
Lys Leu Ala Thr Ser Pro Thr Arg Ser Met Ala Gln Gly Leu Val Thr
            35                  40                  45
Pro Gly Ser Ser Gly Ser Phe His Gly Gly Leu Asp Leu Ser His Glu
        50                  55                  60
```

```
Ser Gly Trp Tyr Ile Gly Asn Trp Thr Ser Asn Leu Asp Pro Gly Lys
 65                  70                  75                  80

Pro Thr Glu Ile Asp Ser Tyr Ala Gly Phe Lys Arg Pro Leu Asn Asn
                 85                  90                  95

Arg Leu Gly Tyr Glu Met Gly Leu Ile Arg Tyr Ser Arg Pro Glu Gln
            100                 105                 110

Pro Ala Asn Asp Ala Ala Glu Leu Tyr Gly Gly Leu Ser Ile Phe Gly
        115                 120                 125

Ser Arg Leu Gly Ala Ala Leu Ser Ser Asp Pro Gly Arg Asn Asp Thr
130                 135                 140

Thr Leu Phe Ala Asp Leu Gly Val Asn Pro Pro Phe Gly Phe Asp Val
145                 150                 155                 160

Thr Leu Lys Tyr Gly Asn His Arg Leu Asp Asn Pro Ala Ser Leu Ser
                165                 170                 175

Gly Gly Gly Tyr Val Ser Val Phe Asn Asp Trp Ser Val Asn Leu Ser
            180                 185                 190

Arg Pro Trp Leu Gly Ile Asp Leu Asn Leu Ser Tyr Ser Gly Thr Ser
        195                 200                 205

Leu Thr Gly Ser Asp Cys Ser Ala Tyr Ser Gly His Asn Ser Tyr Cys
210                 215                 220

Asp Thr Thr Phe Met Leu Lys Ala Ser Arg Pro Phe Phe
225                 230                 235

<210> SEQ ID NO 25
<211> LENGTH: 170
<212> TYPE: PRT
<213> ORGANISM: Pseudomonas aeruginosa

<400> SEQUENCE: 25

Met Leu Ser Ile Lys Lys Asn Leu Gly Leu Leu Ala Met Thr Ala Ala
 1               5                  10                  15

Leu Ala Ala Cys Ala Ser Asn Pro Asn Asp Leu Pro Asp Phe Pro Glu
                 20                  25                  30

His Glu Tyr Ala Ala Thr Gln Gln Val Gly Glu Gly Val Ile Asn Gly
            35                  40                  45

Asp Leu Tyr Leu Thr Ser Ala Ser Gly Ala Ile Gln Lys Gly Thr Asn
 50                  55                  60

Thr Lys Val Ala Leu Glu Pro Ala Thr Ser Tyr Met Lys Ala Tyr Tyr
 65                  70                  75                  80

Ala Lys Phe Gly Asn Leu Asp Ala Lys Arg Asp Pro Asp Val Gln
                 85                  90                  95

Pro Pro Val Leu Asp Pro Arg Arg Ala Thr Tyr Val Arg Glu Ala Thr
            100                 105                 110

Thr Asp Gln Asn Gly Arg Phe Asp Phe Asp His Ile Pro Asn Gly Thr
        115                 120                 125

Tyr Tyr Ile Ser Ser Glu Leu Thr Trp Ser Ala Gln Ser Asp Gly Lys
130                 135                 140

Thr Ile Thr Glu Gly Gly Thr Val Thr Lys Leu Val Thr Val Ser Gly
145                 150                 155                 160

Ser Gln Pro Gln Lys Val Leu Leu Thr Arg
                165                 170

<210> SEQ ID NO 26
<211> LENGTH: 350
<212> TYPE: PRT
```

<213> ORGANISM: Pseudomonas aeruginosa

<400> SEQUENCE: 26

```
Met Lys Leu Lys Asn Thr Leu Gly Val Val Ile Gly Ser Leu Val Ala
 1               5                  10                  15
Ala Ser Ala Met Asn Ala Phe Ala Gln Gly Gln Asn Ser Val Glu Ile
            20                  25                  30
Glu Ala Phe Gly Lys Arg Tyr Phe Thr Asp Ser Val Arg Asn Met Lys
        35                  40                  45
Asn Ala Asp Leu Tyr Gly Gly Ser Ile Gly Tyr Phe Leu Thr Asp Asp
    50                  55                  60
Val Glu Leu Ala Leu Ser Tyr Gly Glu Tyr His Asp Val Arg Gly Thr
65                  70                  75                  80
Tyr Glu Thr Gly Asn Lys Lys Val His Gly Asn Leu Thr Ser Leu Asp
                85                  90                  95
Ala Ile Tyr His Phe Gly Thr Pro Gly Val Gly Leu Arg Pro Tyr Val
            100                 105                 110
Ser Ala Gly Leu Ala His Gln Asn Ile Thr Asn Ile Asn Ser Asp Ser
        115                 120                 125
Gln Gly Arg Gln Met Thr Met Ala Asn Ile Gly Ala Gly Leu Lys
    130                 135                 140
Tyr Tyr Phe Thr Glu Asn Phe Phe Ala Lys Ala Ser Leu Asp Gly Gln
145                 150                 155                 160
Tyr Gly Leu Glu Lys Arg Asp Asn Gly His Gln Gly Glu Trp Met Ala
                165                 170                 175
Gly Leu Gly Val Gly Phe Asn Phe Gly Gly Ser Lys Ala Ala Pro Ala
            180                 185                 190
Pro Glu Pro Val Ala Asp Val Cys Ser Asp Ser Asp Asn Asp Gly Val
        195                 200                 205
Cys Asp Asn Val Asp Lys Cys Pro Asp Thr Pro Ala Asn Val Thr Val
    210                 215                 220
Asp Ala Asn Gly Cys Pro Ala Val Ala Glu Val Val Arg Val Gln Leu
225                 230                 235                 240
Asp Val Lys Phe Asp Phe Asp Lys Ser Lys Val Lys Glu Asn Ser Tyr
                245                 250                 255
Ala Asp Ile Lys Asn Leu Ala Asp Phe Met Lys Gln Tyr Pro Ser Thr
            260                 265                 270
Ser Thr Thr Val Glu Gly His Thr Asp Ser Val Gly Thr Asp Ala Tyr
        275                 280                 285
Asn Gln Lys Leu Ser Glu Arg Arg Ala Asn Ala Val Arg Asp Val Leu
    290                 295                 300
Val Asn Glu Tyr Gly Val Glu Gly Gly Arg Val Asn Ala Val Gly Tyr
305                 310                 315                 320
Gly Glu Ser Arg Pro Val Ala Asp Asn Ala Thr Ala Glu Gly Arg Ala
                325                 330                 335
Ile Asn Arg Arg Val Glu Ala Glu Val Glu Ala Glu Ala Lys
            340                 345                 350
```

<210> SEQ ID NO 27
<211> LENGTH: 344
<212> TYPE: PRT
<213> ORGANISM: Pseudomonas aeruginosa

<400> SEQUENCE: 27

Met Arg Leu Pro Arg Pro Arg Phe Ala Leu Ser Ala Ala Leu Leu Leu

```
            1               5                   10                  15
        Cys Leu Ser Gly Cys Val Ser Glu Leu Asp Ser Gly Ala Tyr Gly Ser
                    20                  25                  30

Met Asp Asp Pro Arg Asn Ala Gln Met Leu Asp Leu Val Asp Gln Ala
                    35                  40                  45

Leu Lys Gly Asn Met Ala Val Leu Val Ala Asp Val Met Pro His
                    50                  55                  60

Lys Ser Leu Ser Asp Ala Leu Thr Met Thr Gln Trp Thr Pro Thr Ala
        65                  70                  75                  80

Ile Trp Glu Tyr Glu Lys Asp Pro Lys Val Thr Phe Gly Arg Lys Phe
                        85                  90                  95

Gln Thr Asn Ala Leu Gln Arg Lys Pro Asp Glu Thr Tyr Leu Phe Lys
                    100                 105                 110

Ala Phe Glu Val His Ile Leu Pro Pro Gly Lys Tyr Leu Leu Thr Gly
                    115                 120                 125

Gly Asp Asp Tyr Gln Ile His Gly Leu Leu Asp Gln Val Gly Ala Arg
                    130                 135                 140

Ser Gly Pro Pro Gly Ser Gly His Gly Ala Asn Gly Thr Ala Tyr Leu
        145                 150                 155                 160

Ser Pro Glu Leu Tyr Arg Glu Tyr Tyr Arg Glu Val Trp Lys Asp
                        165                 170                 175

Ala Thr Tyr Gly Ser Glu Ile Lys Thr Glu Lys Val Cys Thr Ala Val
                    180                 185                 190

His Val Ala Ser Gly Ala Cys Val Ser Trp Gly Glu Gln Gln Tyr Thr
                    195                 200                 205

Gln Thr Thr Gln Gly Ser Gln Ala Gly Tyr Tyr Gln Gln Thr Asp Ser
                    210                 215                 220

Arg Asp Val Pro Ser Ile Lys Val Gln Ala Arg Leu Pro Val Asp Lys
        225                 230                 235                 240

Ala Leu Ala Ser Phe Thr Val Gln Gly Gly Gln Leu Leu Ala Pro
                        245                 250                 255

Arg Met His Leu Lys Thr Pro Gly Tyr Lys Tyr Gln Gln Ser Lys Cys
                    260                 265                 270

Arg Ala Ile Asp Pro Lys Lys Ile Glu Cys Pro Leu Glu Asn Leu Thr
                    275                 280                 285

Val Tyr Thr Trp Pro Ala Pro Met Asp Phe Ser Gln Ser Leu Ile Ala
                    290                 295                 300

Gln Arg Ala Leu Ser Asp Lys His Arg Gln Leu Leu Ser Arg Leu Gln
        305                 310                 315                 320

Pro Leu Gln Ile Thr Pro Leu Arg Lys Gln Gly Met Glu Asp Pro Val
                        325                 330                 335

Trp Gly Val Pro Leu Ser Leu Lys
                    340

<210> SEQ ID NO 28
<211> LENGTH: 995
<212> TYPE: PRT
<213> ORGANISM: Pseudomonas aeruginosa

<400> SEQUENCE: 28

Met Thr Asp Asp His Ser Phe Arg Pro Arg Pro Thr Ser Leu Ser Ala
        1               5                   10                  15

Ala Leu Leu Leu Gly Ala Trp Ile Ala Gln Pro Ala Thr Ala Ala Tyr
                    20                  25                  30
```

```
Val Glu Ala Gly Arg Pro Gly Asp Pro Ala Ser Trp Arg Ser Ala Glu
         35                  40                  45

Tyr Gln Gln Asp Trp Gly Leu Glu Arg Met Arg Ala Asp Gln Ala Tyr
 50                  55                  60

Ala Ala Gly Ile Asp Gly Gln Gly Val Lys Ile Gly Glu Met Asp Ser
 65                  70                  75                  80

Gly Phe Asp Pro Ser His Pro Asp Thr Pro Ala Ser Arg Tyr Gln Pro
                 85                  90                  95

Val Thr Ala Ser Gly Thr Tyr Val Asp Gly Thr Pro Phe Ser Val Ser
             100                 105                 110

Gly Ala Met Asn Gly Asn Asn Asp Ser His Gly Thr His Val Gly Gly
             115                 120                 125

Thr Leu Gly Ala Ser Arg Asp Gly Val Gly Met His Gly Val Ala Tyr
         130                 135                 140

Ala Ala Gln Val Tyr Val Ala Asn Thr Asn Gln Asn Asp Ser Phe Leu
145                 150                 155                 160

Phe Gly Pro Thr Pro Asp Pro Asn Tyr Phe Lys Ala Ala Tyr Gln Ala
                 165                 170                 175

Leu Ala Asp Ala Gly Val Arg Ala Ile Asn Asn Ser Trp Gly Ser Gln
             180                 185                 190

Pro Lys Asp Val Ser Tyr Glu Thr Leu Asp Gly Leu His Ala Ala Tyr
             195                 200                 205

Ala Gln His Tyr Gly Arg Ser Thr Trp Leu Asp Ala Ala Ala Gly Val
         210                 215                 220

Ser Arg Gln Gly Val Ile Asn Val Phe Ser Ala Gly Asn Ser Gly Tyr
225                 230                 235                 240

Ala Asn Ala Ser Val Arg Ser Ala Leu Pro Tyr Phe Gln Pro Asp Leu
                 245                 250                 255

Glu Gly His Trp Leu Ala Val Ser Gly Leu Asp Gln Gln Asn Gly Gln
             260                 265                 270

Arg Tyr Asn Arg Cys Gly Ile Ala Lys Tyr Trp Cys Ile Thr Thr Pro
         275                 280                 285

Gly Arg Leu Ile Asn Ser Thr Met Pro Gly Gly Gly Tyr Ala Asn Lys
         290                 295                 300

Ser Gly Thr Ser Met Ala Ala Pro His Ala Thr Gly Ala Leu Ala Leu
305                 310                 315                 320

Val Met Gln Arg Tyr Pro Tyr Leu Asn Asn Glu Gln Ala Leu Gln Val
                 325                 330                 335

Leu Leu Thr Thr Ala Thr Gln Leu Asp Gly Thr Pro Thr Gly Ala Pro
             340                 345                 350

Thr Asp Thr Val Gly Trp Gly Val Pro Asp Leu Gly Arg Ala Met His
             355                 360                 365

Gly Pro Gly Gln Leu Leu Gly Arg Phe Glu Ala Asn Leu Pro Ala Gly
         370                 375                 380

Leu Arg Asp Glu Trp Ser Asn Pro Ile Ser Asp Ser Ala Leu Leu Gln
385                 390                 395                 400

Arg Gln Ala Glu Asp Ala Ala Glu His Ala Ala Trp Gln Arg Thr Leu
                 405                 410                 415

Lys Asp Lys Gly Trp Glu Asn Gly Leu Pro Ala Gly Ala Ser Gln Gln
             420                 425                 430

Glu Arg Thr Asp Tyr Ala Ile Gly Met Ala Arg Asp Gln Ala Ala Ala
             435                 440                 445

Gln Arg Gln Tyr Gln Gly Ser Leu Val Lys Ala Gly Ala Gly Ser Leu
```

-continued

```
            450                 455                 460
Val Leu Ser Gly Asp Ser Thr Tyr Arg Gly Pro Thr Leu Val Asp Gly
465                 470                 475                 480

Gly Leu Leu Ser Val Asp Gly Ser Leu Leu Ser Ala Val Glu Val Asn
                485                 490                 495

Ala Gly Gly Thr Leu Gly Gly Ser Gly Arg Ile Gly Gly Leu Leu Ala
                500                 505                 510

Arg Ser Gly Gly Thr Val Ala Ala Gly Asn Ser Ile Gly Thr Leu Glu
                515                 520                 525

Val Ala Gly Asp Leu Arg Phe Glu Ser Gly Ser Thr Tyr Ala Val Glu
                530                 535                 540

Leu Ser Glu Ser Ala Ser Asp Arg Ile Val Ala Ser Gly Lys Ala Ser
545                 550                 555                 560

Ile Ala Gly Gly Asn Val Thr Leu Ala Met Glu Asn Ser Pro Asp Leu
                565                 570                 575

Leu Ser Gln Ser Gln Val Glu Ser Leu Val Gly Arg Arg Tyr Asp Ile
                580                 585                 590

Leu Asp Ala Ala Gly Gly Ile Asp Gly Arg Phe Asp Ala Val Leu Pro
                595                 600                 605

Asn Tyr Leu Phe Leu Gly Gly Thr Leu Asp Tyr Ala Ala Asn Ala Ile
                610                 615                 620

Arg Leu Asp Ile Gly Arg Asn Gly Thr Thr Leu Ala Ser Val Ala Gln
625                 630                 635                 640

Thr Pro Asn Gln Ala Ala Val Ala Gly Ala Val Glu Thr Leu Gly Ala
                645                 650                 655

Gly Asn Pro Val Tyr Glu Ser Leu Leu Leu Ser Glu Asn Ala Ala Thr
                660                 665                 670

Ala Gln Arg Ala Phe Gln Leu Ser Gly Glu Ile Tyr Pro Ala Leu
                675                 680                 685

Ala Gly Leu Leu Leu Asn Asp Ser Arg Tyr Leu Arg Asp Ser Val Gly
                690                 695                 700

Glu Arg Leu Arg Gln Thr Ser Asp Gly Glu Ala Gly Gly Glu Ala Pro
705                 710                 715                 720

Glu Gly Trp Phe Lys Ala Leu Gly Ser Trp Gly Lys Ser Ala Asp Gly
                725                 730                 735

Ser His Gly Ser Glu Gly Tyr Arg His Ser Val Gly Gly Phe Leu Leu
                740                 745                 750

Gly Val Asp Ser Gln Val Ala Ser Asp Thr Arg Leu Gly Leu Val Ala
                755                 760                 765

Gly Tyr Ser Asn Ser Ser Leu Asn Met Asp Ser Ser Leu Gln Ser Ser
770                 775                 780

Ala Ser Ile Asp Ser Tyr His Leu Gly Ala Tyr Leu Gly Arg Gln Leu
785                 790                 795                 800

Gln Gln Trp Arg Leu Ser Leu Gly Ala Ala His Ala Trp His Arg Ala
                805                 810                 815

Glu Val Lys Arg Asp Leu Gln Tyr Gly Ala Val Ala Gly Lys Gln Lys
                820                 825                 830

Ala Lys Leu Asp Ala Gln Ser Ser Gln Leu Phe Ala Glu Ala Ala Tyr
                835                 840                 845

Ala Leu Gly Trp Arg Ser Leu Glu Leu Glu Pro Phe Ala Gly Leu Ala
                850                 855                 860

Tyr Val His Val Ala Ser Asp Asp Phe Arg Glu Arg Gly Ser Ala Ala
865                 870                 875                 880
```

```
Ala Leu Glu Gly Gly Asp Asp Asn Leu Asp Ala Ala Phe Thr Thr Leu
                885                 890                 895

Gly Leu Arg Ala Lys Arg His Phe Glu Leu Asp Ala Gly Arg Arg Leu
            900                 905                 910

Ala Leu Ser Gly Thr Leu Gly Trp Arg His Asn Leu Ser Asp Thr Thr
        915                 920                 925

Pro Gln Arg His Leu Ala Phe Ala Ser Gly Ser Gln Pro Phe Ser Val
    930                 935                 940

Glu Ser Val Ala Leu Ser Arg Asp Ala Ala Leu Leu Gly Val Asp Ala
945                 950                 955                 960

Ser Leu Ala Val Asn Arg Glu Val Ser Val Arg Leu Gly Tyr Asn Gly
                965                 970                 975

Leu Leu Gly Ser Arg Glu Lys Asp His Gly Val Gly Leu Ala Val Asp
            980                 985                 990

Trp Arg Phe
        995
```

```
<210> SEQ ID NO 29
<211> LENGTH: 162
<212> TYPE: PRT
<213> ORGANISM: Pseudomonas aeruginosa

<400> SEQUENCE: 29
```

```
Met Lys Arg Ile Leu Leu Gly Thr Leu Phe Ala Ala Ala Ser Phe Asn
1               5                   10                  15

Ala Phe Ala Asp Ala Pro Gly Gly Ala Gly Cys Gly Trp Gly Asn Met
            20                  25                  30

Leu Phe Lys Gly Gln Arg Gly Val Ala Thr His Val Val Ala Ala Thr
        35                  40                  45

Thr Asn Gly Thr Ser Gly Asn Asn Thr Phe Gly Met Thr Thr Gly Thr
    50                  55                  60

Asn Gly Cys His Thr Asn Gly Ala Leu Ser Tyr Gly Gly Lys Pro Leu
65                  70                  75                  80

Leu Val Leu Gly Ser Met Met Asp Glu Leu Ser Glu Asp Met Ala Lys
                85                  90                  95

Gly Asn Gly Glu Ala Leu Thr Thr Tyr Ala Val Val Leu Gly Val Gln
            100                 105                 110

Pro Gln Asp Arg Glu His Phe Ala Ala Val Thr His Glu His Phe Ser
        115                 120                 125

Glu Ile Phe Asn Lys Ser Asp Ala Thr Ala Ala Asp Val Tyr Ala Asn
    130                 135                 140

Thr Gln Ala Ile Leu Lys Gln Asp Ala Arg Leu Ala Lys Tyr Ala Glu
145                 150                 155                 160

Gln Ala
```

```
<210> SEQ ID NO 30
<211> LENGTH: 590
<212> TYPE: PRT
<213> ORGANISM: Pseudomonas aeruginosa

<400> SEQUENCE: 30
```

```
Met Met Ala Pro Pro Ser Gln Val Gln Gly Arg Leu Ser Ser Ser Met
1               5                   10                  15

Asn Lys Ser Leu Ala Leu Leu Thr Val Thr Leu Leu Leu Gly Gly Cys
            20                  25                  30
```

Gln Ser Leu Ile His Lys Thr Pro Asp Gly Thr Pro Pro Val Glu Asp
                35                  40                  45

Thr Ala Val Glu Thr Lys Ala Lys Pro Glu Lys Tyr Gly Ser Phe Ser
 50                  55                  60

Glu Asp Ser Leu Tyr Ser Leu Leu Val Ala Glu Leu Ala Gly Gln Arg
 65                  70                  75                  80

Asn Arg Phe Asp Ile Ala Leu Ser Asn Tyr Val Val Gln Ala Gln Lys
                85                  90                  95

Thr Arg Asp Pro Gly Val Ser Glu Arg Ala Phe Arg Ile Ala Glu Tyr
                100                 105                 110

Leu Gly Ala Asp Gln Glu Ala Leu Asp Thr Ser Leu Leu Trp Ala Arg
                115                 120                 125

Ser Ala Pro Asp Asn Leu Asp Ala Gln Arg Ala Ala Ile Gln Leu
 130                 135                 140

Ala Arg Ala Gly Arg Tyr Glu Glu Ser Met Val Tyr Met Glu Lys Val
145                  150                 155                 160

Leu Asn Gly Gln Gly Asp Thr His Phe Asp Phe Leu Ala Leu Ser Ala
                165                 170                 175

Ala Glu Thr Asp Pro Asp Thr Arg Ala Gly Leu Leu Gln Ser Phe Asp
                180                 185                 190

His Leu Leu Lys Lys Tyr Pro Asn Asn Gly Gln Leu Leu Phe Gly Lys
                195                 200                 205

Ala Leu Leu Leu Gln Gln Asp Gly Arg Pro Asp Glu Ala Leu Thr Leu
                210                 215                 220

Leu Glu Asp Asn Ser Ala Ser Arg His Glu Val Ala Pro Leu Leu Leu
225                 230                 235                 240

Arg Ser Arg Leu Leu Gln Ser Met Lys Arg Ser Asp Glu Ala Leu Pro
                245                 250                 255

Leu Leu Lys Ala Gly Ile Lys Glu His Pro Asp Asp Lys Arg Val Arg
                260                 265                 270

Leu Ala Tyr Ala Arg Leu Leu Val Glu Gln Asn Arg Leu Asp Asp Ala
                275                 280                 285

Lys Ala Glu Phe Ala Gly Leu Val Gln Gln Phe Pro Asp Asp Asp
                290                 295                 300

Leu Arg Phe Ser Leu Ala Leu Val Cys Leu Glu Ala Gln Ala Trp Asp
305                 310                 315                 320

Glu Ala Arg Ile Tyr Leu Glu Glu Leu Val Glu Arg Asp Ser His Val
                325                 330                 335

Asp Ala Ala His Phe Asn Leu Gly Arg Leu Ala Glu Glu Gln Lys Asp
                340                 345                 350

Thr Ala Arg Ala Leu Asp Glu Tyr Ala Gln Val Gly Pro Gly Asn Asp
                355                 360                 365

Phe Leu Pro Ala Gln Leu Arg Gln Thr Asp Val Leu Leu Lys Ala Gly
370                 375                 380

Arg Val Asp Glu Ala Ala Gln Arg Leu Asp Lys Ala Arg Ser Glu Gln
385                 390                 395                 400

Pro Asp Tyr Ala Ile Gln Leu Tyr Leu Ile Glu Ala Glu Ala Leu Ser
                405                 410                 415

Asn Asn Asp Gln Gln Glu Lys Ala Trp Gln Ala Ile Gln Glu Gly Leu
                420                 425                 430

Lys Gln Tyr Pro Glu Asp Leu Asn Leu Leu Tyr Thr Arg Ser Met Leu
                435                 440                 445

Ala Glu Lys Arg Asn Asp Leu Ala Gln Met Glu Lys Asp Leu Arg Phe

```
                     450                 455                 460

Val Ile Ala Arg Glu Pro Asp Asn Ala Met Ala Leu Asn Ala Leu Gly
465                 470                 475                 480

Tyr Thr Leu Ala Asp Arg Thr Thr Arg Tyr Gly Glu Ala Arg Glu Leu
                485                 490                 495

Ile Leu Lys Ala His Lys Leu Asn Pro Asp Asp Pro Ala Ile Leu Asp
            500                 505                 510

Ser Met Gly Trp Ile Asn Tyr Arg Gln Gly Lys Leu Ala Asp Ala Glu
        515                 520                 525

Arg Tyr Leu Arg Gln Ala Leu Gln Arg Tyr Pro Asp His Glu Val Ala
    530                 535                 540

Ala His Leu Gly Glu Val Leu Trp Ala Gln Gly Arg Gln Gly Asp Ala
545                 550                 555                 560

Arg Ala Ile Trp Arg Glu Tyr Leu Asp Lys Gln Pro Asp Ser Asp Val
                565                 570                 575

Leu Arg Arg Thr Ile Lys Arg Leu Thr Gly Ala Glu Thr Pro
                580                 585                 590

<210> SEQ ID NO 31
<211> LENGTH: 149
<212> TYPE: PRT
<213> ORGANISM: Pseudomonas aeruginosa

<400> SEQUENCE: 31

Met Lys Ala Gln Lys Gly Phe Thr Leu Ile Glu Leu Met Ile Val Val
1               5                   10                  15

Ala Ile Ile Gly Ile Leu Ala Ala Ile Ala Ile Pro Gln Tyr Gln Asn
            20                  25                  30

Tyr Val Ala Arg Ser Glu Gly Ala Ser Ala Leu Ala Thr Ile Asn Pro
        35                  40                  45

Leu Lys Thr Thr Val Glu Glu Ser Leu Ser Arg Gly Ile Ala Gly Ser
    50                  55                  60

Lys Ile Lys Ile Gly Thr Thr Ala Ser Thr Ala Thr Glu Thr Tyr Val
65                  70                  75                  80

Gly Val Glu Pro Asp Ala Asn Lys Leu Gly Val Ile Ala Val Ala Ile
                85                  90                  95

Glu Asp Ser Gly Ala Gly Asp Ile Thr Phe Thr Phe Gln Thr Gly Thr
            100                 105                 110

Ser Ser Pro Lys Asn Ala Thr Lys Val Ile Thr Leu Asn Arg Thr Ala
        115                 120                 125

Asp Gly Val Trp Ala Cys Lys Ser Thr Gln Asp Pro Met Phe Thr Pro
    130                 135                 140

Lys Gly Cys Asp Asn
145

<210> SEQ ID NO 32
<211> LENGTH: 224
<212> TYPE: PRT
<213> ORGANISM: Artificial Sequence
<220> FEATURE:
<223> OTHER INFORMATION: Synthetic polypeptide

<400> SEQUENCE: 32

Met Ala His His His His His His Ala Pro Ala Pro Glu Pro Val Ala
1               5                   10                  15

Asp Val Cys Ser Asp Ser Asp Asn Asp Gly Val Cys Asp Asn Val Asp
            20                  25                  30
```

```
Lys Cys Pro Asp Thr Pro Ala Asn Val Thr Val Asp Ala Asn Gly Cys
             35                  40                  45

Pro Ala Val Ala Glu Val Val Arg Val Gln Leu Asp Val Lys Phe Asp
         50                  55                  60

Phe Asp Lys Ser Lys Val Lys Glu Asn Ser Tyr Ala Asp Ile Lys Asn
 65                  70                  75                  80

Leu Ala Asp Phe Met Lys Gln Tyr Pro Ser Thr Ser Thr Val Glu
                 85                  90                  95

Gly His Thr Asp Ser Val Gly Thr Asp Ala Tyr Asn Gln Lys Leu Ser
                100                 105                 110

Glu Arg Arg Ala Asn Ala Val Arg Asp Val Leu Val Asn Glu Tyr Gly
             115                 120                 125

Val Glu Gly Gly Arg Val Asn Ala Val Gly Tyr Gly Glu Ser Arg Pro
         130                 135                 140

Val Ala Asp Asn Ala Thr Ala Glu Gly Arg Ala Ile Asn Arg Arg Val
145                 150                 155                 160

Glu Ser Ser His Ser Lys Glu Thr Glu Ala Arg Leu Thr Ala Thr Glu
                165                 170                 175

Asp Ala Ala Ala Arg Ala Gln Ala Arg Ala Asp Glu Ala Tyr Arg Lys
                180                 185                 190

Ala Asp Glu Ala Leu Gly Ala Ala Gln Lys Ala Gln Gln Thr Ala Asp
             195                 200                 205

Glu Ala Asn Glu Arg Ala Leu Arg Met Leu Glu Lys Ala Ser Arg Lys
         210                 215                 220

<210> SEQ ID NO 33
<211> LENGTH: 488
<212> TYPE: PRT
<213> ORGANISM: Pseudomonas aeruginosa

<400> SEQUENCE: 33

Met Ala Leu Thr Val Asn Thr Asn Ile Ala Ser Leu Asn Thr Gln Arg
  1               5                  10                  15

Asn Leu Asn Ala Ser Ser Asn Asp Leu Asn Thr Ser Leu Gln Arg Leu
             20                  25                  30

Thr Thr Gly Tyr Arg Ile Asn Ser Ala Lys Asp Asp Ala Ala Gly Leu
         35                  40                  45

Gln Ile Ser Asn Arg Leu Ser Asn Gln Ile Ser Gly Leu Asn Val Ala
     50                  55                  60

Thr Arg Asn Ala Asn Asp Gly Ile Ser Leu Ala Gln Thr Ala Glu Gly
 65                  70                  75                  80

Ala Leu Gln Gln Ser Thr Asn Ile Leu Gln Arg Ile Arg Asp Leu Ala
                 85                  90                  95

Leu Gln Ser Ala Asn Gly Ser Asn Ser Asp Ala Asp Arg Ala Ala Leu
            100                 105                 110

Gln Lys Glu Val Ala Ala Gln Ala Glu Leu Thr Arg Ile Ser Asp
             115                 120                 125

Thr Thr Thr Phe Gly Gly Arg Lys Leu Leu Asp Gly Ser Phe Gly Thr
        130                 135                 140

Thr Ser Phe Gln Val Gly Ser Asn Ala Tyr Glu Thr Ile Asp Ile Ser
145                 150                 155                 160

Leu Gln Asn Ala Ser Ala Ser Ala Ile Gly Ser Tyr Gln Val Gly Ser
                165                 170                 175

Asn Gly Ala Gly Thr Val Ala Ser Val Ala Gly Thr Ala Thr Ala Ser
```

-continued

```
                180                 185                 190
Gly Ile Ala Ser Gly Thr Val Asn Leu Val Gly Gly Gln Val Lys
            195                 200                 205
Asn Ile Ala Ile Ala Ala Gly Asp Ser Ala Lys Ala Ile Ala Glu Lys
        210                 215                 220
Met Asp Gly Ala Ile Pro Asn Leu Ser Ala Arg Ala Arg Thr Val Phe
225                 230                 235                 240
Thr Ala Asp Val Ser Gly Val Thr Gly Gly Ser Leu Asn Phe Asp Val
                245                 250                 255
Thr Val Gly Ser Asn Thr Val Ser Leu Ala Gly Val Thr Ser Thr Gln
            260                 265                 270
Asp Leu Ala Asp Gln Leu Asn Ser Asn Ser Ser Lys Leu Gly Ile Thr
        275                 280                 285
Ala Ser Ile Asn Asp Lys Gly Val Leu Thr Ile Thr Ser Ala Thr Gly
    290                 295                 300
Glu Asn Val Lys Phe Gly Ala Gln Thr Gly Thr Ala Thr Ala Gly Gln
305                 310                 315                 320
Val Ala Val Lys Val Gln Gly Ser Asp Gly Lys Phe Glu Ala Ala Ala
                325                 330                 335
Lys Asn Val Val Ala Ala Gly Thr Ala Ala Thr Thr Ile Val Thr
            340                 345                 350
Gly Tyr Val Gln Leu Asn Ser Pro Thr Ala Tyr Ser Val Ser Gly Thr
        355                 360                 365
Gly Thr Gln Ala Ser Gln Val Phe Gly Asn Ala Ser Ala Ala Gln Lys
    370                 375                 380
Ser Ser Val Ala Ser Val Asp Ile Ser Thr Ala Asp Gly Ala Gln Asn
385                 390                 395                 400
Ala Ile Ala Val Val Asp Asn Ala Leu Ala Ala Ile Asp Ala Gln Arg
                405                 410                 415
Ala Asp Leu Gly Ala Val Gln Asn Arg Phe Lys Asn Thr Ile Asp Asn
            420                 425                 430
Leu Thr Asn Ile Ser Glu Asn Ala Thr Asn Ala Arg Ser Arg Ile Lys
        435                 440                 445
Asp Thr Asp Phe Ala Ala Glu Thr Ala Ala Leu Ser Lys Asn Gln Val
    450                 455                 460
Leu Gln Gln Ala Gly Thr Ala Ile Leu Ala Gln Ala Asn Gln Leu Pro
465                 470                 475                 480
Gln Ala Val Leu Ser Leu Leu Arg
                485
```

<210> SEQ ID NO 34
<211> LENGTH: 474
<212> TYPE: PRT
<213> ORGANISM: Pseudomonas aeruginosa

<400> SEQUENCE: 34

```
Met Ala Gly Ile Ser Ile Gly Val Gly Ser Thr Asp Tyr Thr Asp Leu
1               5                   10                  15
Val Asn Lys Met Val Asn Leu Glu Gly Ala Ala Lys Thr Asn Gln Leu
            20                  25                  30
Ala Thr Leu Glu Lys Thr Thr Thr Arg Leu Thr Ala Leu Gly Gln
        35                  40                  45
Phe Lys Ser Ala Ile Ser Ala Phe Gln Thr Ala Leu Thr Ala Leu Asn
    50                  55                  60
```

-continued

```
Ser Asn Ala Val Phe Met Ala Arg Thr Ala Lys Ser Ser Asn Glu Asp
 65                  70                  75                  80

Ile Leu Lys Ala Ser Ala Thr Gln Ser Ala Val Ala Gly Thr Tyr Gln
                 85                  90                  95

Ile Gln Val Asn Ser Leu Ala Thr Ser Ser Lys Ile Ala Leu Gln Ala
            100                 105                 110

Ile Ala Asp Pro Ala Asn Ala Lys Phe Asn Ser Gly Thr Leu Asn Ile
        115                 120                 125

Ser Val Gly Asp Thr Lys Leu Pro Ala Ile Thr Val Asp Ser Ser Asn
    130                 135                 140

Asn Thr Leu Ala Gly Met Arg Asp Ala Ile Asn Gln Ala Gly Lys Glu
145                 150                 155                 160

Ala Gly Val Ser Ala Thr Ile Ile Thr Asp Asn Ser Gly Ser Arg Leu
                165                 170                 175

Val Leu Ser Ser Thr Lys Thr Gly Asp Gly Lys Asp Ile Lys Val Glu
            180                 185                 190

Val Ser Asp Asp Gly Ser Gly Gly Asn Thr Ser Leu Ser Gln Leu Ala
        195                 200                 205

Phe Asp Pro Ala Thr Ala Pro Lys Leu Ser Asp Gly Ala Ala Ala Gly
    210                 215                 220

Tyr Val Thr Lys Ala Ala Asn Gly Glu Ile Thr Val Asp Gly Leu Lys
225                 230                 235                 240

Arg Ser Ile Ala Ser Asn Ser Val Ser Asp Val Ile Asp Gly Val Ser
                245                 250                 255

Phe Asp Val Lys Ala Val Thr Glu Ala Gly Lys Pro Ile Thr Leu Thr
            260                 265                 270

Val Ser Arg Asp Asp Ala Gly Val Lys Asp Asn Val Lys Lys Phe Val
        275                 280                 285

Glu Ala Tyr Asn Thr Leu Thr Lys Phe Ile Asn Glu Gln Thr Val Val
    290                 295                 300

Thr Lys Val Gly Glu Asp Lys Asn Pro Val Thr Gly Ala Leu Leu Gly
305                 310                 315                 320

Asp Ala Ser Val Arg Ala Leu Val Asn Thr Met Arg Ser Glu Leu Ile
                325                 330                 335

Ala Ser Asn Glu Asn Gly Ser Val Arg Asn Leu Ala Ala Leu Gly Ile
            340                 345                 350

Thr Thr Thr Lys Asp Gly Thr Leu Glu Ile Asp Glu Lys Lys Leu Asp
        355                 360                 365

Lys Ala Ile Ser Ala Asp Phe Glu Gly Val Ala Ser Tyr Phe Thr Gly
    370                 375                 380

Asp Thr Gly Leu Ala Lys Arg Leu Gly Asp Lys Met Lys Pro Tyr Thr
385                 390                 395                 400

Asp Ala Gln Gly Ile Leu Asp Gln Arg Thr Thr Leu Gln Lys Thr
                405                 410                 415

Leu Ser Asn Val Asp Thr Gln Lys Ala Asp Leu Ala Lys Arg Leu Ala
            420                 425                 430

Ala Leu Gln Glu Lys Leu Thr Thr Gln Phe Asn Leu Leu Ser Ala Met
        435                 440                 445

Gln Asp Glu Met Thr Lys Arg Gln Lys Ser Ile Thr Asp Asn Leu Ala
    450                 455                 460

Ser Leu Pro Tyr Gly Ser Gly Lys Lys Thr
465                 470
```

```
<210> SEQ ID NO 35
<211> LENGTH: 638
<212> TYPE: PRT
<213> ORGANISM: Pseudomonas aeruginosa

<400> SEQUENCE: 35

Met His Leu Thr Pro His Trp Ile Pro Leu Val Ala Ser Leu Gly Leu
  1               5                  10                  15

Leu Ala Gly Gly Ser Phe Ala Ser Ala Ala Glu Glu Ala Phe Asp Leu
             20                  25                  30

Trp Asn Glu Cys Ala Lys Ala Cys Val Leu Asp Leu Lys Asp Gly Val
         35                  40                  45

Arg Ser Ser Arg Met Ser Val Asp Pro Ala Ile Ala Asp Thr Asn Gly
 50                  55                  60

Gln Gly Val Leu His Tyr Ser Met Val Leu Glu Gly Gly Asn Asp Ala
 65                  70                  75                  80

Leu Lys Leu Ala Ile Asp Asn Ala Leu Ser Ile Thr Ser Asp Gly Leu
                 85                  90                  95

Thr Ile Arg Leu Glu Gly Gly Val Glu Pro Asn Lys Pro Val Arg Tyr
            100                 105                 110

Ser Tyr Thr Arg Gln Ala Arg Gly Ser Trp Ser Leu Asn Trp Leu Val
        115                 120                 125

Pro Ile Gly His Glu Lys Pro Ser Asn Ile Lys Val Phe Ile His Glu
130                 135                 140

Leu Asn Ala Gly Asn Gln Leu Ser His Met Ser Pro Ile Tyr Thr Ile
145                 150                 155                 160

Glu Met Gly Asp Glu Leu Leu Ala Lys Leu Ala Arg Asp Ala Thr Phe
                165                 170                 175

Phe Val Arg Ala His Glu Ser Asn Glu Met Gln Pro Thr Leu Ala Ile
            180                 185                 190

Ser His Ala Gly Val Ser Val Met Ala Gln Ala Gln Pro Arg Arg
        195                 200                 205

Glu Lys Arg Trp Ser Glu Trp Ala Ser Gly Lys Val Leu Cys Leu Leu
210                 215                 220

Asp Pro Leu Asp Gly Val Tyr Asn Tyr Leu Ala Gln Gln Arg Cys Asn
225                 230                 235                 240

Leu Asp Asp Thr Trp Glu Gly Lys Ile Tyr Arg Val Leu Ala Gly Asn
                245                 250                 255

Pro Ala Lys His Asp Leu Asp Ile Lys Pro Thr Val Ile Ser His Arg
            260                 265                 270

Leu His Phe Pro Glu Gly Gly Ser Leu Ala Ala Leu Thr Ala His Gln
        275                 280                 285

Ala Cys His Leu Pro Leu Glu Thr Phe Thr Arg His Arg Gln Pro Arg
290                 295                 300

Gly Trp Glu Gln Leu Glu Gln Cys Gly Tyr Pro Val Gln Arg Leu Val
305                 310                 315                 320

Ala Leu Tyr Leu Ala Ala Arg Leu Ser Trp Asn Gln Val Asp Gln Val
                325                 330                 335

Ile Arg Asn Ala Leu Ala Ser Pro Gly Ser Gly Gly Asp Leu Gly Glu
            340                 345                 350

Ala Ile Arg Glu Gln Pro Glu Gln Ala Arg Leu Ala Leu Thr Leu Ala
        355                 360                 365

Ala Ala Glu Ser Glu Arg Phe Val Arg Gln Gly Thr Gly Asn Asp Glu
370                 375                 380
```

```
Ala Gly Ala Ala Ser Ala Asp Val Val Ser Leu Thr Cys Pro Val Ala
385                 390                 395                 400

Ala Gly Glu Cys Ala Gly Pro Ala Asp Ser Gly Asp Ala Leu Leu Glu
            405                 410                 415

Arg Asn Tyr Pro Thr Gly Ala Glu Phe Leu Gly Asp Gly Gly Asp Ile
        420                 425                 430

Ser Phe Ser Thr Arg Gly Thr Gln Asn Trp Thr Val Glu Arg Leu Leu
    435                 440                 445

Gln Ala His Arg Gln Leu Glu Arg Gly Tyr Val Phe Val Gly Tyr
450                 455                 460

His Gly Thr Phe Leu Glu Ala Ala Gln Ser Ile Val Phe Gly Gly Val
465                 470                 475                 480

Arg Ala Arg Ser Gln Asp Leu Asp Ala Ile Trp Arg Gly Phe Tyr Ile
            485                 490                 495

Ala Gly Asp Pro Ala Leu Ala Tyr Gly Tyr Ala Gln Asp Gln Glu Pro
        500                 505                 510

Asp Ala Arg Gly Arg Ile Arg Asn Gly Ala Leu Leu Arg Val Tyr Val
    515                 520                 525

Pro Arg Ser Ser Leu Pro Gly Phe Tyr Arg Thr Gly Leu Thr Leu Ala
530                 535                 540

Ala Pro Glu Ala Ala Gly Glu Val Glu Arg Leu Ile Gly His Pro Leu
545                 550                 555                 560

Pro Leu Arg Leu Asp Ala Ile Thr Gly Pro Glu Glu Gly Gly Arg
            565                 570                 575

Leu Glu Thr Ile Leu Gly Trp Pro Leu Ala Glu Arg Thr Val Val Ile
        580                 585                 590

Pro Ser Ala Ile Pro Thr Asp Pro Arg Asn Val Gly Gly Asp Leu Asp
    595                 600                 605

Pro Ser Ser Ile Pro Asp Lys Glu Gln Ala Ile Ser Ala Leu Pro Asp
610                 615                 620

Tyr Ala Ser Gln Pro Gly Lys Pro Pro Arg Glu Asp Leu Lys
625                 630                 635

<210> SEQ ID NO 36
<211> LENGTH: 625
<212> TYPE: PRT
<213> ORGANISM: Pseudomonas aeruginosa

<400> SEQUENCE: 36

Tyr Gln Tyr Gly Glu Tyr Ala Gly Glu Thr Leu Glu Arg Leu Ile Thr
1               5                   10                  15

Asp Tyr Pro Gly Arg Tyr Arg Gly Thr Ala Ser Phe Ala Gly Ala Ser
            20                  25                  30

Lys Leu Met Gln Ser Arg Leu Gly Phe Gly Tyr Gln Thr Ser Arg Gln
        35                  40                  45

Asp Phe Thr Trp Ala Gly Asn Arg Ser Ser Gln Asn Val Ile Ala Ser
    50                  55                  60

Ala Pro Gly Ser Ser Gly Lys Phe Leu Val Leu Gly Ala His Tyr Asp
65                  70                  75                  80

Thr Tyr Tyr Gly Arg Pro Thr Leu Gln Gly Leu Asp Asp Asn Ala Ser
            85                  90                  95

Gly Ala Ala Val Leu Thr Glu Ile Ala Arg Asn Leu Gly Gly Ile Ala
        100                 105                 110

Leu Glu Asn Gly Leu Glu Val Val Gly Phe Gly Ala Glu Glu Glu Gly
    115                 120                 125
```

```
Leu Arg Gly Ser Arg Ala Tyr Val Glu Ser Leu Asp Ala Ser Gln Arg
130                 135                 140

Ala Asn Leu Leu Gly Met Ile Asn Leu Asp Ser Leu Val Thr Gly Asp
145                 150                 155                 160

Lys Met Tyr Ala His Ala Gly Ser Asn Ser Val Ser Asn Pro Ala Leu
                165                 170                 175

Gly Ala Tyr Arg Glu Gln Ile Leu Arg Ile Ala Arg Glu Leu Asp Ile
                180                 185                 190

Pro Leu Phe Thr Asn Pro Gly Leu Asn Ala Glu Tyr Pro Ala Gly Thr
            195                 200                 205

Gly Cys Cys Ser Asp Gly Glu Ser Phe Asn Gly Met Asp Ile Pro Val
210                 215                 220

Leu Phe Ile Glu Ala Thr Asn Trp Glu Leu Gly Asp Leu Asp Gly Tyr
225                 230                 235                 240

Glu Gln Thr Asp Asn Pro Ala Ile Pro Gly Gly Ser Thr Trp His Asp
                245                 250                 255

Pro Ala Glu Asp Asn Lys Glu Val Leu Thr Asn Ala Leu Gly Gln Glu
            260                 265                 270

Arg Ile Glu Gln Arg Met Arg Asp Phe Ser Arg Leu Leu Thr Arg Leu
        275                 280                 285

Val Leu Glu Gln Thr Asn Ala Asp Leu Leu Ala Ser Thr Ala Ser Gly
290                 295                 300

Gly Ala Leu Ala Arg Gln Met Glu Asp Gln Leu Gln Arg Gln His Gln
305                 310                 315                 320

Ala Leu Thr Arg Leu His Asp Arg Arg Trp Leu Thr Leu Leu Gly Ser
                325                 330                 335

Asn Arg Pro Val Gly Ser Phe Asp Gly Glu Val Gly Ala Glu Gly Glu
            340                 345                 350

Val Ser Pro Asp Ser Gly Phe Asp Met Pro Gly Asn Pro Glu Ser Arg
            355                 360                 365

Arg Ala Gly Val His Leu Leu Gly Asp Tyr Arg Tyr Ser Glu Ala Leu
370                 375                 380

Thr Leu Gly Gly Ser Leu Ala Phe Gln Arg Ser Arg Asp Lys Leu Asp
385                 390                 395                 400

His Gly Gly Arg Ile Glu Gly Asp Thr Trp Gln Leu Gly Leu Phe Gly
                405                 410                 415

Leu Tyr Asn Asp Gly Gly Pro Glu Trp Leu Ala Gly Glu Leu Asn Leu
                420                 425                 430

Gly His Thr Arg Tyr Asp Ser Lys Arg Ser Val Tyr Leu Gln Ala Ala
            435                 440                 445

Gly Gly Pro Val Leu Leu Asp Gln Arg Leu Ser Gly Asp Thr Ser Ala
450                 455                 460

Trp Ser Trp Gly Ala Arg Leu Glu Gly Gly Tyr Asp Phe Ser Phe Gly
465                 470                 475                 480

Glu Leu Arg Ser Gly Pro Leu Ala Gly Leu Asp Tyr Met His Tyr Arg
                485                 490                 495

Ile Asp Asp Phe Arg Glu Asp Glu Ala Leu Arg Thr Ala Leu Gly Tyr
            500                 505                 510

Glu Lys Gln Asp Tyr Asp Ser Leu Glu Ala Ser Leu Gly Trp Arg Leu
        515                 520                 525

Arg Gly Glu Leu Ala Leu Gly Ala Arg Met Arg Leu Gln Pro Tyr Ala
530                 535                 540
```

```
Ser Leu Arg Trp Val Arg Glu Leu Ala Asp Gly Arg Leu Asp Asp Met
545                 550                 555                 560

Asp Leu Thr Ser Arg Gly Asp Gly Arg Val Arg Val Ala Asp Met Gly
            565                 570                 575

Gly Val Asp Lys Asp Phe Gly Arg Ala Gln Leu Gly Ala Gln Leu Ala
        580                 585                 590

Ile Thr Glu Gln Leu Gly Val Phe Ala Glu Ala Asn Ser Arg Phe Ala
    595                 600                 605

His Ser Glu Gly Asn Gln Ala Gly Tyr Ser Leu Gly Val Asn Trp Gln
610                 615                 620

Phe
625

<210> SEQ ID NO 37
<211> LENGTH: 178
<212> TYPE: PRT
<213> ORGANISM: Pseudomonas aeruginosa

<400> SEQUENCE: 37

Ala Asp Asn Phe Val Gly Leu Thr Trp Gly Glu Thr Ser Asn Asn Ile
1               5                   10                  15

Gln Lys Ser Lys Ser Leu Asn Arg Asn Leu Asn Ser Pro Asn Leu Asp
            20                  25                  30

Lys Val Ile Asp Asn Thr Gly Thr Trp Gly Ile Arg Ala Gly Gln Gln
        35                  40                  45

Phe Glu Gln Gly Arg Tyr Tyr Ala Thr Tyr Glu Asn Ile Ser Asp Thr
    50                  55                  60

Ser Ser Gly Asn Lys Leu Arg Gln Gln Asn Leu Leu Gly Ser Tyr Asp
65                  70                  75                  80

Ala Phe Leu Pro Ile Gly Asp Asn Asn Thr Lys Leu Phe Gly Gly Ala
                85                  90                  95

Thr Leu Gly Leu Val Lys Leu Glu Gln Asp Gly Lys Gly Phe Lys Arg
            100                 105                 110

Asp Ser Asp Val Gly Tyr Ala Ala Gly Leu Gln Ala Gly Ile Leu Gln
        115                 120                 125

Glu Leu Ser Lys Asn Ala Ser Ile Glu Gly Gly Tyr Arg Tyr Leu Arg
    130                 135                 140

Thr Asn Ala Ser Thr Glu Met Thr Pro His Gly Gly Asn Lys Leu Gly
145                 150                 155                 160

Ser Leu Asp Leu His Ser Ser Ser Gln Phe Tyr Leu Gly Ala Asn Tyr
                165                 170                 175

Lys Phe

<210> SEQ ID NO 38
<211> LENGTH: 622
<212> TYPE: PRT
<213> ORGANISM: Pseudomonas aeruginosa

<400> SEQUENCE: 38

Ala Pro Ser Pro Tyr Ser Thr Leu Val Val Phe Gly Asp Ser Leu Ser
1               5                   10                  15

Asp Ala Gly Gln Phe Pro Asp Pro Ala Gly Pro Ala Gly Ser Thr Ser
            20                  25                  30

Arg Phe Thr Asn Arg Val Gly Pro Thr Tyr Gln Asn Gly Ser Gly Glu
        35                  40                  45

Ile Phe Gly Pro Thr Ala Pro Met Leu Leu Gly Asn Gln Leu Gly Ile
```

```
            50                  55                  60
Ala Pro Gly Asp Leu Ala Ala Ser Thr Ser Pro Val Asn Ala Gln Gln
 65                  70                  75                  80

Gly Ile Ala Asp Gly Asn Asn Trp Ala Val Gly Gly Tyr Arg Thr Asp
                     85                  90                  95

Gln Ile Tyr Asp Ser Ile Thr Ala Ala Asn Gly Ser Leu Ile Glu Arg
                    100                 105                 110

Asp Asn Thr Leu Leu Arg Ser Arg Asp Gly Tyr Leu Val Asp Arg Ala
                115                 120                 125

Arg Gln Gly Leu Gly Ala Asp Pro Asn Ala Leu Tyr Tyr Ile Thr Gly
            130                 135                 140

Gly Gly Asn Asp Phe Leu Gln Gly Arg Ile Leu Asn Asp Val Gln Ala
145                 150                 155                 160

Gln Gln Ala Ala Gly Arg Leu Val Asp Ser Val Gln Ala Leu Gln Gln
                    165                 170                 175

Ala Gly Ala Arg Tyr Ile Val Val Trp Leu Leu Pro Asp Leu Gly Leu
                180                 185                 190

Thr Pro Ala Thr Phe Gly Gly Pro Leu Gln Pro Phe Ala Ser Gln Leu
                195                 200                 205

Ser Gly Thr Phe Asn Ala Glu Leu Thr Ala Gln Leu Ser Gln Ala Gly
            210                 215                 220

Ala Asn Val Ile Pro Leu Asn Ile Pro Leu Leu Leu Lys Glu Gly Met
225                 230                 235                 240

Ala Asn Pro Ala Ser Phe Gly Leu Ala Ala Asp Gln Asn Leu Ile Gly
                    245                 250                 255

Thr Cys Phe Ser Gly Asn Gly Cys Thr Met Asn Pro Thr Tyr Gly Ile
                260                 265                 270

Asn Gly Ser Thr Pro Asp Pro Ser Lys Leu Leu Phe Asn Asp Ser Val
            275                 280                 285

His Pro Thr Ile Thr Gly Gln Arg Leu Ile Ala Asp Tyr Thr Tyr Ser
            290                 295                 300

Leu Leu Ser Ala Pro Trp Glu Leu Thr Leu Leu Pro Glu Met Ala His
305                 310                 315                 320

Gly Thr Leu Arg Ala Tyr Gln Asp Glu Leu Arg Ser Gln Trp Gln Ala
                    325                 330                 335

Asp Trp Glu Asn Trp Gln Asn Val Gly Gln Trp Arg Gly Phe Val Gly
                340                 345                 350

Gly Gly Gly Gln Arg Leu Asp Phe Asp Ser Gln Asp Ser Ala Ala Ser
            355                 360                 365

Gly Asp Gly Asn Gly Tyr Asn Leu Thr Leu Gly Gly Ser Tyr Arg Ile
            370                 375                 380

Asp Glu Ala Trp Arg Ala Gly Val Ala Ala Gly Phe Tyr Arg Gln Lys
385                 390                 395                 400

Leu Glu Ala Gly Ala Lys Asp Ser Asp Tyr Arg Met Asn Ser Tyr Met
                    405                 410                 415

Ala Ser Ala Phe Val Gln Tyr Gln Glu Asn Arg Trp Trp Ala Asp Ala
                420                 425                 430

Ala Leu Thr Gly Gly Tyr Leu Asp Tyr Asp Leu Lys Arg Lys Phe
            435                 440                 445

Ala Leu Gly Gly Gly Glu Arg Ser Glu Lys Gly Asp Thr Asn Gly His
            450                 455                 460

Leu Trp Ala Phe Ser Ala Arg Leu Gly Tyr Asp Ile Ala Gln Gln Ala
465                 470                 475                 480
```

```
Asp Ser Pro Trp His Leu Ser Pro Phe Val Ala Asp Tyr Ala Arg
            485                 490                 495

Val Glu Val Asp Gly Tyr Ser Glu Lys Gly Ala Ser Ala Thr Ala Leu
                500                 505                 510

Asp Tyr Asp Asp Gln Lys Arg Ser Ser Lys Arg Leu Gly Ala Gly Leu
            515                 520                 525

Gln Gly Lys Tyr Ala Phe Gly Ser Asp Thr Gln Leu Phe Ala Glu Tyr
        530                 535                 540

Ala His Glu Arg Glu Tyr Glu Asp Asp Thr Gln Asp Leu Thr Met Ser
545                 550                 555                 560

Leu Asn Ser Leu Pro Gly Asn Arg Phe Thr Leu Glu Gly Tyr Thr Pro
                565                 570                 575

Gln Asp His Leu Asn Arg Val Ser Leu Gly Phe Ser Gln Lys Leu Ala
            580                 585                 590

Pro Glu Leu Ser Leu Arg Gly Gly Tyr Asn Trp Arg Lys Gly Glu Asp
        595                 600                 605

Asp Thr Gln Gln Ser Val Ser Leu Ala Leu Ser Leu Asp Phe
    610                 615                 620

<210> SEQ ID NO 39
<211> LENGTH: 463
<212> TYPE: PRT
<213> ORGANISM: Pseudomonas aeruginosa

<400> SEQUENCE: 39

Arg Glu Asp Ala Phe Ala Leu Gly Leu Leu Asp Gly Tyr His Leu Ala
1               5                   10                  15

Leu Glu Asn Asp Pro Gln Phe Gln Ala Ala Ile Gln Glu His Glu Ala
                20                  25                  30

Gly Arg Gln Tyr Arg Ala Leu Gly Arg Ala Ala Leu Leu Pro Arg Leu
            35                  40                  45

Val Tyr Ser Tyr Asn Arg Gly Arg Ser Trp Ser Asp Val Thr Gln Thr
    50                  55                  60

Thr Thr Arg Gly Asp Phe Lys Glu Asp Arg Asp Tyr Asp Ser Tyr Val
65                  70                  75                  80

Ser Thr Leu Ser Leu Gln Gln Pro Leu Phe Asp Tyr Glu Ala Phe Ser
                85                  90                  95

Arg Tyr Arg Lys Gly Val Ala Gln Ala Leu Leu Ser Asp Glu Arg Phe
            100                 105                 110

Arg Ser Gln Ser Gln Glu Leu Leu Val Arg Val Leu Glu Ala Tyr Thr
        115                 120                 125

Gly Ala Leu Leu Ala Gln Asp Gln Ile Glu Leu Ala Arg Ala Gln Lys
    130                 135                 140

Arg Ser Tyr Arg Glu Gln Phe Gln Leu Asn Gln Arg Gln Phe Glu Arg
145                 150                 155                 160

Gly Asn Gly Thr Arg Thr Asp Thr Leu Glu Thr Gln Ala Arg Phe Asn
                165                 170                 175

Leu Ala Gln Ala Gln Glu Ile Glu Ala Arg Asp Ser Gln Asp Ala Ala
            180                 185                 190

Leu Arg Glu Leu Glu Arg Leu Val Gly Ala Pro Leu Glu Ile Ala Asp
        195                 200                 205

Leu Ala Pro Leu Gly Glu Arg Phe Gln Val Arg Pro Leu Ser Pro Ala
    210                 215                 220

Ser Tyr Thr Ala Trp Arg Asp Leu Ala Leu Ala Glu Asn Pro Glu Leu
```

```
                225                 230                 235                 240
Ala Ser Leu Arg His Ala Val Asp Val Ala Arg Tyr Glu Val Glu Gln
                245                 250                 255

Asn Arg Ala Asp Phe Leu Pro Arg Leu Gly Leu Tyr Ala Ser Thr Gly
                260                 265                 270

Lys Ser Lys Ser Gly Ser Glu Asn Thr Tyr Asn Gln Arg Tyr Glu Thr
                275                 280                 285

Asp Ser Val Gly Ile Gln Leu Ser Val Pro Leu Phe Ser Gly Gly Glu
                290                 295                 300

Thr Leu Ala Ala Thr Arg Gln Ala Thr His Arg Met Glu Lys Ser His
305                 310                 315                 320

Tyr Asp Leu Asp Asp Lys Val Arg Glu Thr Leu Asn Gln Val Arg Lys
                325                 330                 335

Met Tyr Asn Gln Ser Ser Ser Ala Ala Lys Ile Arg Ala Tyr Glu
                340                 345                 350

Met Thr Val Asp Ser Ala Arg Thr Leu Val Met Ala Thr Arg Lys Ser
                355                 360                 365

Ile Ala Ala Gly Val Arg Val Asn Leu Asp Leu Leu Asn Ala Glu Gln
370                 375                 380

Ala Leu Tyr Ser Ala Met Asn Glu Leu Ser Lys Ala Lys Tyr Asp Tyr
385                 390                 395                 400

Leu Thr Ala Trp Ala Arg Leu Arg Phe Tyr Ala Gly Val Leu Asp Glu
                405                 410                 415

Ala Asp Leu Glu Leu Val Ala Ala Asn Phe Val Ser Gly Thr Pro
                420                 425                 430

Ala Arg Arg Arg Asp Cys Ala Thr Thr Asp Cys Pro Ala Pro Leu His
                435                 440                 445

Thr Leu Ser Lys Thr Asp Thr Glu Glu Asn Arg Ser Ala Leu Asn
                450                 455                 460

<210> SEQ ID NO 40
<211> LENGTH: 280
<212> TYPE: PRT
<213> ORGANISM: Pseudomonas aeruginosa

<400> SEQUENCE: 40

Glu Asp Gly Lys Arg Leu Arg Ile Gly Ile Thr Leu His Pro Tyr Tyr
1               5                   10                  15

Ser Tyr Val Ser Asn Ile Val Gly Asp Lys Ala Glu Val Val Pro Leu
                20                  25                  30

Ile Pro Ala Gly Phe Asn Pro His Ala Tyr Glu Pro Arg Ala Glu Asp
                35                  40                  45

Ile Lys Arg Ile Gly Thr Leu Asp Val Val Leu Asn Gly Val Gly
                50                  55                  60

His Asp Asp Phe Ala Glu Arg Met Ile Ala Ser Ser Glu Lys Pro Gly
65                  70                  75                  80

Ile Pro Val Ile Glu Ala Asn Ala Lys Val Pro Leu Leu Ala Ala Thr
                85                  90                  95

Gly Met Ala Ala Arg Gly Ala Gly Lys Val Val Asn Pro His Thr Phe
                100                 105                 110

Leu Ser Ile Ser Ala Ser Ile Thr Gln Val Asn Thr Ile Ala Arg Glu
                115                 120                 125

Leu Gly Lys Leu Asp Pro Ala Asn Ala Lys Ala Tyr Thr Arg Asn Ala
                130                 135                 140
```

```
Arg Ala Tyr Ala Lys Arg Leu Arg Ala Leu Ala Asp Ala Leu Ala
145                 150                 155                 160

Arg Leu Asn Lys Ala Pro Ala Ala Asp Phe Arg Val Ala Thr Ile His
                165                 170                 175

Gly Ala Tyr Asp Tyr Leu Leu Arg Glu Phe Gly Leu Glu Val Thr Ala
            180                 185                 190

Val Val Glu Pro Ala His Gly Ile Glu Pro Ser Pro Ser Gln Leu Lys
        195                 200                 205

Lys Thr Ile Asp Gln Leu Lys Ala Leu Asp Val Lys Val Ile Phe Ser
    210                 215                 220

Glu Ile Asp Phe Pro Ser Thr Tyr Val Glu Thr Ile Gln Arg Glu Ser
225                 230                 235                 240

Gly Val Lys Leu Tyr Ser Leu Ser His Ile Ser Tyr Gly Asp Tyr Ser
                245                 250                 255

Ala Gly Lys Tyr Glu Glu Glu Met Ala Arg Asn Leu Asp Thr Val Val
            260                 265                 270

Arg Ala Ile Gln Glu Ser Gly Ala
        275                 280

<210> SEQ ID NO 41
<211> LENGTH: 302
<212> TYPE: PRT
<213> ORGANISM: Pseudomonas aeruginosa

<400> SEQUENCE: 41

Val Thr Phe Gln Thr Arg Leu Glu Ser Val Glu Trp Lys Val Glu Gly
1               5                   10                  15

Asp Gln Phe Glu Cys Arg Leu Ser Gln Pro Val Ala Asn Phe Gly Val
                20                  25                  30

Gly Glu Phe Val Arg Arg Ala Gly Glu Gln Ala Thr Phe Arg Leu Lys
            35                  40                  45

Pro Glu Ala Gln Trp Leu Gly Arg Gly Ser Ala Thr Leu Leu Ala Ala
        50                  55                  60

Ala Pro Pro Trp Arg Pro Gly Gln Gly Asp Ile Asn Leu Gly Gln Val
65                  70                  75                  80

Ser Ile Gly Ser Gly Glu Val Pro Phe Asn Ser Ser Gln Gln Gln Ala
                85                  90                  95

Gly Arg Leu Leu Thr Gly Leu Leu Glu Gly Arg Ser Pro Leu Val Arg
            100                 105                 110

His Arg Thr Trp Gln Gly Asp Arg Leu Glu Val Arg Leu Leu Pro Ala
        115                 120                 125

Arg Phe Ala Ser Val Tyr Ser Gln Tyr Gln Ala Cys Ile Ala Lys Leu
    130                 135                 140

Leu Pro Val Asn Phe Asp Gln Val Lys Leu Ala Gln Val Gly Phe Pro
145                 150                 155                 160

Asp Gly Gly Thr Ala Leu Asn Asp Val Ala Arg Ala Lys Leu Asp Ile
                165                 170                 175

Ile Leu Gln Leu Leu Lys Ala Asp Pro Ser Ile Asn Arg Ile Glu Leu
            180                 185                 190

Asp Gly His Ser Asp Asn Ser Gly Asn Arg Leu Thr Asn Arg Asp Leu
        195                 200                 205

Ser Arg Arg Arg Ala Leu Ala Val Gln Glu Tyr Leu Lys Ser Asn Gly
    210                 215                 220

Val Pro Glu Ser Gln Ile Asn Val Arg Phe Tyr Gly Glu Arg Tyr Pro
225                 230                 235                 240
```

-continued

Leu Val Ala Asn Asn Ser Ala Ala Asn Arg Ala Arg Asn Arg Arg Val
                245                 250                 255

Thr Val His Leu Ser Arg Glu Ala Val Val Glu Pro Ala Thr Glu Ala
            260                 265                 270

Pro Lys Ala Glu Asp Lys Pro Ala Pro Pro Ala Glu Pro Ala Ala
        275                 280                 285

Pro Lys Pro Pro Ala Ala Ser Leu Gln Gly Lys Pro Thr Val
        290                 295                 300

<210> SEQ ID NO 42
<211> LENGTH: 530
<212> TYPE: PRT
<213> ORGANISM: Pseudomonas aeruginosa

<400> SEQUENCE: 42

Leu Pro Ser Gly Gly Thr Val Val Gly Gly Ser Ala Asn Gly Glu Ile
  1               5                  10                  15

His Leu Ser Gly Gly Asn Ser Leu Ser Val Asn Gln Lys Val Asp Lys
             20                  25                  30

Leu Ile Ala Asn Trp Asp Ser Phe Ser Val Ala Ala Gly Glu Arg Val
         35                  40                  45

Ile Phe Asn Gln Pro Ser Ser Ser Ile Ala Leu Asn Arg Val Ile
 50                  55                  60

Gly Thr Lys Ala Ser Asp Ile Gln Gly Arg Ile Asp Ala Asn Gly Gln
 65                  70                  75                  80

Val Phe Leu Val Asn Pro Asn Gly Val Leu Phe Gly Arg Gly Ala Gln
                 85                  90                  95

Val Asn Val Gly Gly Leu Val Ala Ser Thr Leu Asp Ile Thr Asp Ala
            100                 105                 110

Glu Phe Asn Gly Asn Ser Ser Arg Tyr Arg Phe Thr Gly Pro Ser Thr
        115                 120                 125

Asn Gly Val Leu Asn His Gly Gly Ala Ile Thr Ala Ala Glu Gly Gly
    130                 135                 140

Ser Ile Ala Leu Leu Gly Ala Gln Val Asp Asn Arg Gly Thr Val Leu
145                 150                 155                 160

Ala Gln Met Gly Gly Val Gly Leu Gly Ala Gly Ser Asp Leu Thr Leu
                165                 170                 175

Asn Phe Asp Gly Asn Lys Leu Leu Asp Ile Arg Val Asp Ala Gly Val
            180                 185                 190

Ala Asn Ala Leu Ala Ser Asn Gly Gly Leu Leu Lys Ala Asp Gly Gly
        195                 200                 205

Arg Val Leu Met Ala Ala Arg Thr Ala Asn Ala Leu Leu Asn Thr Val
    210                 215                 220

Val Asn Ser Gln Gly Ala Ile Glu Ala Arg Ser Leu Arg Gly Lys Asn
225                 230                 235                 240

Gly Arg Ile Val Leu Asp Gly Pro Asp Gly Lys Val Met Val Gly
                245                 250                 255

Gly Ala Leu Ser Ala Asn Ala Leu Asn Gly Pro Gly His Gly Gly Thr
            260                 265                 270

Val Glu Val Arg Gly Gln Ala Val Glu Val Ala Leu Gly Thr Gln Val
        275                 280                 285

Asn Thr Leu Ala Ser Asn Gly Leu Asn Gly Thr Trp Lys Ile Ala Ala
    290                 295                 300

Asp Lys Ile Asp Val Arg Pro Ser Ala Val Ser Asp Gly Val Thr Val

His Ala Asp Thr Leu Ser Arg Asn Leu Ala Ser Thr Asn Ile Glu Leu
305                 310                 315                 320

Val Ser Thr Lys Gly Asp Leu Asp Leu Asp Gly Ser Val Asn Trp Ala
            325                 330                 335

Ser Gly Asn Arg Leu Gly Leu Gly Ser Ala Ala Asp Leu Thr Leu Asn
                355                 360                 365

Gly Arg Leu Asn Ala Ser Gly Ala Lys Ala Gly Leu Glu Leu Lys Ala
370                 375                 380

Glu Gly Ala Ile Asp Ile Asn Asp Lys Ile Val Leu Gly Gly Ala Gly
385                 390                 395                 400

Ser Ala Leu Ala Met Asp Ala Gly Glu Gly His Arg Val Asn Gly Thr
                405                 410                 415

Ala Ser Val Ser Leu Ala Gly Ala Asn Ala Thr Tyr Val Ser Gly Gly
                420                 425                 430

Tyr Tyr Tyr Thr Val Val Gln Asn Leu Ala Gln Leu Gln Ala Ile Asn
            435                 440                 445

Lys Asn Leu Asp Gly Leu Tyr Val Leu Gly Gly Asn Ile Leu Gly Gly
450                 455                 460

Ser Tyr Tyr Cys Thr Ala Leu Gln Ser Ile Gly Gly Pro Ala Gly Val
465                 470                 475                 480

Phe Ser Gly Thr Leu Asp Gly Leu Gly Asn Ser Ile Gly Asn Leu Ser
                485                 490                 495

Ile Ser Asn Thr Gly Pro Asn Val Gly Leu Phe Ala Arg Ser Ser Gly
                500                 505                 510

Thr Leu Ser Asn Leu Lys Leu Asn Asn Leu Arg Val Ser Asp Asn Thr
            515                 520                 525

Tyr Gly
    530

<210> SEQ ID NO 43
<211> LENGTH: 155
<212> TYPE: PRT
<213> ORGANISM: Pseudomonas aeruginosa

<400> SEQUENCE: 43

Cys Ser Phe Pro Gly Val Tyr Lys Ile Asp Ile Gln Gln Gly Asn Val
1               5                   10                  15

Val Thr Gln Asp Met Ile Asp Gln Leu Arg Pro Gly Met Thr Arg Arg
            20                  25                  30

Gln Val Arg Phe Ile Met Gly Asn Pro Leu Ile Val Asp Thr Phe His
        35                  40                  45

Ala Asn Arg Trp Asp Tyr Leu Tyr Ser Ile Gln Pro Gly Gly Gly Arg
50                  55                  60

Arg Gln Gln Glu Arg Val Ser Leu Phe Phe Asn Asp Ser Asp Gln Leu
65                  70                  75                  80

Ala Gly Leu Asn Gly Asp Phe Met Pro Gly Val Ser Arg Asp Glu Ala
                85                  90                  95

Ile Leu Gly Lys Glu Gly Ser Thr Thr Val Thr Gln Pro Ala Asp Gln
            100                 105                 110

Gln Lys Pro Glu Ala Gln Lys Glu Glu Pro Lys Pro Gly Ser Thr
        115                 120                 125

Leu Glu Gln Leu Gln Arg Glu Val Asp Glu Ala Gln Pro Val Pro Val
    130                 135                 140

```
Pro Thr Pro Glu Pro Leu Asp Pro Ser Pro Gln
145                 150                 155

<210> SEQ ID NO 44
<211> LENGTH: 461
<212> TYPE: PRT
<213> ORGANISM: Pseudomonas aeruginosa

<400> SEQUENCE: 44

Cys Ala Val Asn Pro Ala Thr Gly Lys Ser Asp Phe Val Met Met Ser
1               5                   10                  15

Glu Gln Gln Glu Leu Gly Met Gly Ala Arg Tyr Asn Gln Glu Ile Leu
            20                  25                  30

Lys Gln Phe Pro Arg Tyr Asn Asp Glu Lys Leu Gln Ala Tyr Val Gln
        35                  40                  45

Arg Val Gly Glu Arg Val Ala Arg Ser Ser His Arg Ser Asn Leu Gln
    50                  55                  60

Tyr His Phe Thr Val Ile Asp Ser Pro Asp Ile Asn Ala Phe Ala Leu
65                  70                  75                  80

Pro Gly Gly Tyr Ile Tyr Ile His Arg Gly Leu Ile Ala Tyr Leu Gly
                85                  90                  95

Ser Glu Ala Glu Leu Ala Ala Val Leu Gly His Glu Val Gly His Val
            100                 105                 110

Thr Ala Arg His Ser Val Arg Gln Gln Ser Gln Ala Ser Ala Trp Asn
        115                 120                 125

Ile Leu Gly Gln Ala Val Ala Ile Gly Thr Gly Val Gly Ala Ala Gly
    130                 135                 140

Asp Leu Ala Asn Val Leu Gly Thr Ala Phe Val Arg Gly Tyr Gly Arg
145                 150                 155                 160

Asp Met Glu Leu Glu Ala Asp Gly Leu Gly Ala Gln Tyr Leu Ala Arg
                165                 170                 175

Ala Gly Tyr Asp Pro Thr Ala Met Ile Gln Val Val Arg Val Leu Lys
            180                 185                 190

Asn Gln Glu Asp Phe Ala Arg Glu Glu Ala Ala Arg Asn Gly Gln Ala
        195                 200                 205

Val Gln Ala Gly Gly Tyr His Gly Leu Phe Asp Thr His Pro Asp Asn
    210                 215                 220

Asp Arg Arg Leu Gln Glu Val Val Gly Pro Ala Arg Gln Leu Ala Asn
225                 230                 235                 240

Gly Gln Gln Glu Val Gly Arg Glu Val Phe Leu Arg His Leu Glu Gly
                245                 250                 255

Met Pro Phe Gly Asp Ser Ala Ser Ala Gly Val Arg Arg Gly Gln Asn
            260                 265                 270

Phe Tyr His Ala Glu Leu Asp Phe Thr Leu Ser Tyr Pro Ala Gly Trp
        275                 280                 285

Lys Ile Leu Asn Gln Pro Ser Ala Leu Leu Gly Tyr Pro Ala Asp Glu
    290                 295                 300

Gln Ser Phe Ile Gly Met Lys Leu Val Pro His Asp Ser Arg Leu Thr
305                 310                 315                 320

Pro Ala Glu Phe Leu Arg Lys Asn Ala Gly Gln Arg Leu Ala Gln Glu
                325                 330                 335

Glu Ser Leu Lys Gln Ala Gly Leu Asn Gly Tyr Thr Ala Val Val Pro
            340                 345                 350

Gly Asn Pro Ala Arg Arg Val Ala Val Ile Tyr Gln Gly Asp Arg Ala
        355                 360                 365
```

```
Tyr Leu Phe Val Gly Val Val Lys Val Gly Ser Leu Glu Thr Gln Asp
        370             375                 380

Asp Arg Phe Leu Ser Val Ile Arg Ser Phe Arg Pro Leu Arg Asp Lys
385                 390                 395                 400

Glu Arg Ala Leu Ala Gln Pro Arg Arg Leu His Leu Val Gln Val Lys
                405                 410                 415

Ala Gly Gln Thr Leu Glu Gln Leu Ala Ala Gly Gly Glu Gly Ser Leu
                420                 425                 430

Ser Asp Ser Val Ala Arg Leu Arg Leu Leu Asn Asp Leu Tyr Pro Ser
            435                 440                 445

Gly Glu Pro Arg Pro Gly Asp Trp Leu Lys Val Val Arg
        450                 455                 460

<210> SEQ ID NO 45
<211> LENGTH: 227
<212> TYPE: PRT
<213> ORGANISM: Pseudomonas aeruginosa

<400> SEQUENCE: 45

Cys Ala Gly Thr Ala Asp Pro Ser Gly Thr Trp Ile Asn Gln Ala Ala
1               5                   10                  15

Ile Asp Ala Ala Ser Lys Asp Gly Lys Leu Arg Glu Ala Leu Leu Ala
                20                  25                  30

Tyr Gly Pro Asn Leu Glu Trp Lys Leu Asp Ser Lys Ala Gly Glu Ala
            35                  40                  45

Thr Phe Ser Asn Gly Phe Glu Leu Gly Glu Gly Thr Leu Ser Lys Ser
    50                  55                  60

Asp Asp Glu His Trp Lys Val Ala Phe Tyr Gly Asp Asn Gln Glu
65                  70                  75                  80

Ser Leu Glu Leu Asp Gly Lys Glu Leu Ile Gln Ala Ser Ala Asn
                85                  90                  95

Gly Pro Glu Gln Arg Phe Arg Arg Leu Asp Pro Gln Pro Ala Ala Ser
            100                 105                 110

Ser Pro Ala Gly Ser Gly Phe Glu Arg Ala Leu Tyr Gly Ser Tyr Leu
        115                 120                 125

Lys Gly Ser Trp Lys Ile Arg Glu Gly Gln Gly Gln Gly Gly Lys Val
    130                 135                 140

Glu Phe Gln Ala Asn Gly Leu Val Ser Gly Leu Pro Gly Ala Glu Arg
145                 150                 155                 160

Tyr Ala Leu Cys Leu Ala Gly Asp Cys Ala Ala Met Ser Gly Asp Asn
                165                 170                 175

Asp Ser Ile Trp Leu Gln Gln Gly Asn Arg Gly Arg Glu Leu Leu Phe
            180                 185                 190

Ser Leu Asp Asp Glu Leu Gln Leu Phe Glu Ala Val Asn Thr Ala
        195                 200                 205

Gly Ala Asn Glu Met Pro Ser Tyr Val Pro Gly Lys Arg Val Trp Leu
    210                 215                 220

Leu Glu Arg
225

<210> SEQ ID NO 46
<211> LENGTH: 891
<212> TYPE: PRT
<213> ORGANISM: Pseudomonas aeruginosa

<400> SEQUENCE: 46
```

```
Ala Asp Gln Phe Asp Cys Lys Val Ser Ala Thr Gly Gly Trp Asp Cys
 1               5                  10                  15

Ser Pro Leu Gln Asn Ala Asn Ala Asn Leu Pro Pro Arg Pro Ala His
             20                  25                  30

Thr Ala Thr Ser Val Ser Thr Ala Ala Gly Ser Ser Val Ser Gly
             35                  40                  45

Ser Gly Gly Glu Thr Val Glu Ala Glu Pro Thr Gln Arg Leu Val Thr
 50                  55                  60

Glu Ser Gly Gly Arg Ala Leu Lys Ser Arg Ser Ala Asp Tyr Ser His
 65                  70                  75                  80

Leu Asp Trp Ile Pro Arg Glu Lys Leu Thr Ala Ala Gln Leu Ala Glu
                 85                  90                  95

Ile Gly Pro Tyr Cys Gly Gly Ser Tyr Ile Glu Pro Val Arg Pro Gly
                100                 105                 110

Met Asp Asp Gly Ala Pro Ser Asp Glu Ser Pro Thr Tyr Val Ser Ala
             115                 120                 125

Lys Ala Ser Arg Tyr Glu Gln Glu Lys Gln Ile Ala Thr Leu Ala Gly
            130                 135                 140

Asp Val Val Leu Arg Gln Gly Ser Met Gln Val Glu Gly Asp Glu Ala
145                 150                 155                 160

Asn Leu His Gln Leu Glu Asn Arg Gly Glu Leu Val Gly Asn Val Lys
                165                 170                 175

Leu Arg Asp Lys Gly Met Leu Val Val Gly Asp His Ala Gln Val Gln
                180                 185                 190

Leu Asp Asn Gly Glu Ala Gln Val Asp Asn Ala Glu Tyr Val Ile His
            195                 200                 205

Lys Ala His Ala Arg Gly Ser Ala Leu Tyr Ala Lys Arg Ser Glu Asn
210                 215                 220

Ala Ile Ile Met Leu Lys Asp Gly Thr Tyr Thr Arg Cys Glu Pro Ser
225                 230                 235                 240

Ser Asn Ala Trp Thr Leu Lys Gly Asn Asn Val Lys Leu Asn Pro Ala
                245                 250                 255

Thr Gly Phe Gly Thr Ala Thr Asn Ala Thr Leu Arg Val Lys Asp Phe
            260                 265                 270

Pro Val Phe Tyr Thr Pro Tyr Ile Tyr Phe Pro Ile Asp Asp Arg Arg
            275                 280                 285

Gln Ser Gly Phe Leu Pro Pro Ser Phe Ser Thr Ser Asp Thr Gly
290                 295                 300

Phe Thr Leu Val Thr Pro Tyr Phe Asn Leu Ala Pro Asn Tyr Asp
305                 310                 315                 320

Ala Thr Leu Tyr Pro Arg Tyr Met Ala Lys Arg Gly Met Met Leu Glu
            325                 330                 335

Gly Glu Phe Arg Tyr Leu Thr His Ser Ser Glu Gly Ile Val Asn Ala
            340                 345                 350

Ala Tyr Leu Asn Asp Lys Asp His Arg Glu Gly Phe Pro Asp Tyr
            355                 360                 365

Ser Lys Asp Arg Trp Leu Tyr Gly Leu Lys Asn Thr Thr Gly Leu Asp
370                 375                 380

Ser Arg Trp Leu Ala Glu Val Asp Tyr Thr Arg Ile Ser Asp Pro Tyr
385                 390                 395                 400

Tyr Phe Gln Asp Leu Asp Thr Asp Leu Gly Val Gly Ser Thr Thr Tyr
                405                 410                 415
```

```
Val Asn Gln Arg Gly Thr Leu Thr Tyr Arg Gly Asp Thr Phe Thr Gly
                420                 425                 430

Arg Leu Asn Ala Gln Ala Tyr Gln Leu Ala Thr Thr Thr Asp Val Thr
                435                 440                 445

Pro Tyr Asp Arg Leu Pro Gln Ile Thr Phe Asp Gly Phe Leu Pro Tyr
                450                 455                 460

Asn Pro Gly Gly Met Gln Phe Thr Tyr Gly Thr Glu Phe Val Arg Phe
465                 470                 475                 480

Asp Arg Asp Leu Asp Glu Asn Ile Tyr Phe Asn Asp Gly Ser Ile
                485                 490                 495

Arg Gly Lys Arg Pro Asp Ala Ser Leu Gln Gly Leu Ala Arg Ala Thr
                500                 505                 510

Gly Asp Arg Met His Leu Glu Pro Gly Met Ser Leu Pro Met Thr Arg
                515                 520                 525

Ser Trp Gly Tyr Val Thr Pro Thr Leu Lys Tyr Leu Tyr Thr Lys Tyr
                530                 535                 540

Asp Leu Asp Leu Asp Ser Gln Gly Lys Thr Asp Leu Asn Lys Arg Asp
545                 550                 555                 560

Glu Ser Phe Asp Ser Asn Gln Asp Arg Ser Leu Pro Leu Val Lys Val
                565                 570                 575

Asp Ser Gly Leu Tyr Phe Asp Arg Asp Thr Thr Phe Ala Gly Thr Pro
                580                 585                 590

Phe Arg Gln Thr Leu Glu Pro Arg Ala Met Tyr Leu Tyr Val Pro Tyr
                595                 600                 605

Lys Asp Gln Asp Ser Leu Pro Val Phe Asp Thr Ser Glu Pro Ser Phe
610                 615                 620

Ser Tyr Asp Ser Leu Trp Arg Glu Asn Arg Phe Thr Gly Lys Asp Arg
625                 630                 635                 640

Ile Gly Asp Ala Asn Gln Leu Ser Leu Gly Val Thr Ser Arg Phe Ile
                645                 650                 655

Glu Glu Asn Gly Phe Glu Arg Ala Ser Ile Ser Ala Gly Gln Ile Tyr
                660                 665                 670

Tyr Phe Arg Asp Arg Arg Val Gln Leu Pro Gly Leu Thr Glu Lys Asp
                675                 680                 685

Leu Lys Arg Leu Asn Leu Asp Pro Ser Gly Leu Asp Asn Asp Ser Trp
                690                 695                 700

Arg Ser Pro Tyr Ala Phe Ala Gly Gln Tyr Arg Phe Asn Arg Asp Trp
705                 710                 715                 720

Arg Ile Asn Ser Asp Phe Asn Trp Asn Pro Asn Thr Ser Arg Thr Glu
                725                 730                 735

Ser Gly Ser Ala Ile Phe His Tyr Gln Pro Glu Val Asp Pro Gly Lys
                740                 745                 750

Val Val Asn Val Gly Tyr Arg Tyr Arg Ala Asp Ala Arg Arg Phe Asp
                755                 760                 765

Ser Ser Arg Gly Thr Phe Arg Tyr Gly Asn Glu Asn Asp Ile Ile Lys
                770                 775                 780

Gln His Asp Phe Ser Val Ile Trp Pro Leu Val Pro Gln Trp Ser Val
785                 790                 795                 800

Leu Ala Arg Trp Gln Tyr Asp Tyr Asn Lys Asn Arg Thr Leu Glu Ala
                805                 810                 815

Phe Gly Gly Phe Glu Tyr Asp Ser Cys Cys Trp Lys Leu Arg Leu Ile
                820                 825                 830

Asn Arg Tyr Trp Leu Asp Val Asp Asp Ala Phe Leu Val Gln Ser
```

```
            835                 840                 845
Glu Lys Ala Asp Arg Gly Ile Phe Leu Gln Ile Val Leu Lys Gly Leu
    850                 855                 860

Gly Gly Ile Val Gly Asn Lys Thr Glu Met Phe Leu Asp Lys Gly Ile
865                 870                 875                 880

Gln Gly Tyr Arg Gln Arg Glu Asp Gln Ala Met
            885                 890

<210> SEQ ID NO 47
<211> LENGTH: 316
<212> TYPE: PRT
<213> ORGANISM: Pseudomonas aeruginosa

<400> SEQUENCE: 47

Gly Asn Glu Gly Gly Trp His Pro Pro Lys Pro Asn Pro Gln Ser Asn
1               5                   10                  15

Asn Lys Gly Gly Ala Thr Ala Leu Val Val Asp Thr Gln Gln Asn Tyr
            20                  25                  30

Asn Asn Lys Val Ser Asn Phe Gly Thr Leu Asn Asn Ala Ser Val Ser
        35                  40                  45

Gly Ser Ile Lys Asp Ala Ser Gly Asn Val Gly Val Asn Val Ala Ala
    50                  55                  60

Gly Asp Asn Gln Gln Ala Asn Ala Ala Leu Ala Ser Ala Asp
65                  70                  75                  80

Ala Ser Phe Val Phe Gly Thr Ala Thr Ala Ser Thr Ser Val Leu Gln
                85                  90                  95

Ser Gly Tyr Gly Asn Thr Leu Asn Asn Tyr Ser Asn Pro Asn Thr Ala
            100                 105                 110

Ser Leu Ser Asn Ser Ala Asn Asn Val Ser Gly Asn Leu Gly Val Asn
        115                 120                 125

Val Ala Ala Gly Asn Phe Asn Gln Gln Lys Asn Asp Leu Ala Ala Ala
    130                 135                 140

Val Ser Asn Gly Gln Tyr Ser Thr Ala Gly Ser Ala Ala Ser Gln Thr
145                 150                 155                 160

Ser Thr Gly Asn Thr Thr Val Asn Ser Ala Asn Tyr Ala Tyr Gly Gly
                165                 170                 175

Thr Tyr Val Ser Leu Lys Leu Asn Ala Asp Gly Ser Tyr Lys Gly Thr
            180                 185                 190

Ser Asp Gln Ile Gly Asp Val Tyr Leu Asp Thr Trp Glu Gly Gln Thr
        195                 200                 205

His Pro Gly Gly Ser Asn Thr Gly His Ile Asp Val Asp Ser Gln Ala
    210                 215                 220

Gln Gly Ala Lys Asp Leu Asn His Asp Gly Gly Ala Phe Ala Phe Lys
225                 230                 235                 240

Glu Lys Gly Asp Val Asp Leu Lys Gly Thr Val Ser Gly Phe Ile Pro
                245                 250                 255

Ala Ile Val Gly Phe Lys Thr Pro Val Thr Asn Asn Ala Ser Leu Ser
            260                 265                 270

Asn Ser Leu Gln Asn Val Ser Gly Asn Val Gly Val Asn Ile Ala Ala
        275                 280                 285

Gly Gly Gly Asn Gln Gln Ser Asn Ser Leu Ser Ile Ala Ala Gly Cys
    290                 295                 300

Ser Ser Cys Pro Ala Gly Gly Glu Ser Leu Gly Phe
305                 310                 315
```

<210> SEQ ID NO 48
<211> LENGTH: 242
<212> TYPE: PRT
<213> ORGANISM: Pseudomonas aeruginosa

<400> SEQUENCE: 48

Cys Ser Thr Pro Pro Asn Ala Asn Leu Glu Gln Ala Arg Ser Asn Phe
1               5                   10                  15

Ser Ala Leu Gln Ser Gln Pro Asp Ala Thr Lys Val Ala Ala Leu Glu
            20                  25                  30

Thr Lys Asp Ala Gly Asp Trp Leu Ala Lys Ala Asp Lys Ala Tyr Gln
        35                  40                  45

Asp Gly Glu Asp Gln Arg Asp Val Asp Gln Leu Ala Tyr Leu Thr Asn
    50                  55                  60

Gln Arg Ile Glu Leu Ala Lys Gln Thr Ile Val Leu Arg Asn Ala Glu
65                  70                  75                  80

Ala Gln Leu Gln Asn Ala Ser Ala Gln Arg Ala Gln Ala Arg Leu Asp
                85                  90                  95

Ala Arg Thr Ala Gln Leu Asp Lys Leu Arg Ser Gln Leu Asn Ala Lys
            100                 105                 110

Gln Thr Ser Arg Gly Thr Met Val Thr Phe Gly Asp Val Leu Phe Asp
        115                 120                 125

Leu Asp Lys Ser Asp Leu Lys Pro Gly Ala Met Arg Asn Ile Gln Gln
    130                 135                 140

Leu Ala Glu Phe Leu Gln Gln Asn Pro Glu Arg Gln Val Ile Val Glu
145                 150                 155                 160

Gly Tyr Thr Asp Ser Thr Gly Ser Ala Asn Tyr Asn Gln Arg Leu Ser
                165                 170                 175

Glu Arg Arg Ala Asp Ser Val Arg Met Ala Leu Leu Ser Arg Gly Ile
            180                 185                 190

Ser Pro Glu Arg Val Ala Thr Arg Gly Tyr Gly Lys Glu Tyr Pro Val
        195                 200                 205

Ala Ser Asn Gly Thr Ser Ser Gly Arg Ala Met Asn Arg Arg Val Glu
    210                 215                 220

Val Thr Ile Ser Asn Asp Ala Lys Pro Val Ala Pro Arg Ser Ser Val
225                 230                 235                 240

Ser Gly

<210> SEQ ID NO 49
<211> LENGTH: 426
<212> TYPE: PRT
<213> ORGANISM: Pseudomonas aeruginosa

<400> SEQUENCE: 49

Cys Gly Asp Asp Lys Lys Ala Glu Ala Pro Ala Thr Pro Ala Ala Ser
1               5                   10                  15

Thr Gln Pro Ala Ala Pro Ala Ala Pro Ala Ala Lys Val Asp Glu
            20                  25                  30

Ala Ala Ala Lys Ala Val Ile Lys Asn Tyr Ala Asp Leu Ala Glu Ala
            35                  40                  45

Thr Phe Ala Asp Ala Leu Ser Thr Ala Lys Asp Leu Gln Lys Ala Ile
        50                  55                  60

Asp Ala Phe Leu Ala Lys Pro Asp Ala Glu Thr Leu Lys Ala Ala Lys
65                  70                  75                  80

Glu Ala Trp Phe Ala Ala Arg Thr Pro Tyr Ser Gln Ser Glu Ala Phe

```
                85                  90                  95
Arg Phe Gly Asn Ala Ile Ile Asp Asp Trp Glu Gly Gln Val Asn Ala
            100                 105                 110

Trp Pro Leu Asp Glu Gly Leu Ile Asp Tyr Val Ala Lys Asp Tyr Gln
        115                 120                 125

His Ala Leu Gly Asn Pro Gly Ala Thr Ala Asn Ile Val Ala Asn Thr
    130                 135                 140

Glu Ile Gln Val Gly Glu Asp Lys Ile Asp Val Lys Glu Ile Thr Gly
145                 150                 155                 160

Glu Lys Leu Ala Ser Leu Asn Glu Leu Gly Gly Ser Glu Ala Asn Val
                165                 170                 175

Ala Thr Gly Tyr His Ala Ile Glu Phe Leu Leu Trp Gly Gln Asp Leu
            180                 185                 190

Asn Gly Thr Gly Pro Gly Ala Gly Asn Arg Pro Ala Thr Asp Tyr Ala
        195                 200                 205

Gln Gly Lys Asp Cys Thr Gly Gly His Cys Asp Arg Arg Ala Ala Tyr
    210                 215                 220

Leu Lys Ala Val Thr Asp Leu Leu Val Ser Asp Leu Glu Tyr Met Ala
225                 230                 235                 240

Gly Gln Trp Lys Ala Gly Val Ala Asp Asn Tyr Arg Ala Lys Leu Glu
                245                 250                 255

Ala Glu Pro Val Asp Thr Gly Leu Arg Lys Met Phe Phe Gly Met Gly
            260                 265                 270

Ser Leu Ser Leu Gly Glu Leu Ala Gly Glu Arg Met Lys Val Ala Leu
        275                 280                 285

Glu Ala Asn Ser Thr Glu Asp Glu His Asp Cys Phe Ser Asp Asp Thr
    290                 295                 300

His His Thr Leu Phe Phe Asn Gly Lys Ser Ile Arg Asn Ile Tyr Leu
305                 310                 315                 320

Gly Glu Tyr Lys Arg Ile Asp Gly Ser Val Val Lys Gly Pro Ser Leu
                325                 330                 335

Ala Asp Leu Val Ala Lys Ala Asp Ala Ala Asn Asp Thr Leu Lys
            340                 345                 350

Ala Asp Leu Ala Asp Thr Glu Ala Lys Leu Gln Ala Ile Val Asp Ser
        355                 360                 365

Ala Glu Lys Asp Gly Val His Phe Asp Gln Met Ile Ala Pro Asp Asn
    370                 375                 380

Lys Asp Gly Gln Gln Lys Ile Arg Asp Ala Ile Ala Ala Leu Val Lys
385                 390                 395                 400

Gln Thr Gly Ala Ile Glu Gln Ala Ala Gly Lys Leu Gly Ile Gln Asp
                405                 410                 415

Leu Lys Pro Asp Asn Ala Asp His Glu Phe
            420                 425

<210> SEQ ID NO 50
<211> LENGTH: 739
<212> TYPE: PRT
<213> ORGANISM: Pseudomonas aeruginosa

<400> SEQUENCE: 50

Gly Asn Ala Val Pro Leu Thr Pro Thr Thr Ile Thr Ala Thr Arg Thr
1               5                   10                  15

Glu Gln Ala Val Asp Ser Val Pro Ser Thr Val Ser Val Gln Thr Arg
            20                  25                  30
```

```
Glu Gln Leu Asp Arg Gln Asn Val Asn Asn Ile Lys Glu Leu Val Arg
         35                  40                  45
Tyr Glu Pro Gly Val Ser Val Gly Gly Ala Gly Gln Arg Ala Gly Ile
 50                  55                  60
Thr Gly Tyr Asn Ile Arg Gly Ile Asp Gly Asn Arg Ile Leu Thr Gln
 65                  70                  75                  80
Ile Asp Gly Val Glu Leu Pro Asn Asp Phe Phe Ser Gly Pro Tyr Ala
                 85                  90                  95
Gln Thr His Arg Asn Tyr Val Asp Pro Asp Ile Val Lys Arg Val Glu
             100                 105                 110
Ile Leu Arg Gly Pro Ala Ser Ala Leu Tyr Gly Ser Asn Ala Ile Gly
         115                 120                 125
Gly Ala Val Ser Tyr Phe Thr Leu Asp Pro Ser Asp Ile Ile Lys Asp
130                 135                 140
Gly Lys Asp Val Gly Ala Arg Leu Lys Ala Gly Tyr Glu Ser Ala Ser
145                 150                 155                 160
His Ser Trp Leu Thr Ser Ala Thr Val Ala Gly Arg Ala Asp Asp Phe
                 165                 170                 175
Asp Gly Leu Leu His Tyr Gly Tyr Arg Gln Gly His Glu Thr Glu Ser
             180                 185                 190
Asn Gly Gly His Gly Gly Thr Gly Leu Ser Arg Ser Glu Ala Asn Pro
         195                 200                 205
Glu Asp Ala Asp Ser Tyr Ser Leu Leu Gly Lys Leu Gly Trp Asn Tyr
210                 215                 220
Ala Glu Gly Ser Arg Phe Gly Leu Val Phe Glu Lys Tyr Lys Ser Asp
225                 230                 235                 240
Val Asp Thr Asp Gln Lys Ser Ala Tyr Gly Gly Pro Tyr Asp Lys Gly
                 245                 250                 255
Lys Pro Ala Ile Pro Pro Ser Met Leu Pro Gly Gly Met Tyr Gln Trp
             260                 265                 270
Arg Lys Gly Asn Asp Thr Leu Thr Arg Glu Arg Tyr Gly Leu Glu His
         275                 280                 285
His Phe Leu Leu Asp Ser Gln Val Ala Asp Arg Ile Gln Trp Ser Leu
290                 295                 300
Asn Tyr Gln Leu Ala Lys Thr Asp Gln Ala Thr Arg Glu Phe Tyr Tyr
305                 310                 315                 320
Pro Ile Thr Arg Lys Val Leu Arg Thr Arg Asp Thr Thr Tyr Lys Glu
                 325                 330                 335
Arg Leu Trp Val Phe Asp Ser Gln Leu Asp Lys Ser Phe Ala Ile Gly
             340                 345                 350
Glu Thr Glu His Leu Leu Ser Tyr Gly Ile Asn Leu Lys His Gln Lys
         355                 360                 365
Val Thr Gly Met Arg Ser Gly Thr Gly Thr Asn Leu Asp Thr Gly Ala
370                 375                 380
Asp Ser Pro Arg Asp Ala Leu Glu Arg Ser Ser Asp Phe Pro Asp Pro
385                 390                 395                 400
Thr Val Lys Thr Tyr Ala Leu Phe Ala Gln Asp Ser Ile Ser Trp Asn
                 405                 410                 415
Asp Trp Thr Phe Thr Pro Gly Leu Arg Tyr Asp Tyr Thr Arg Met Glu
             420                 425                 430
Pro His Ile Thr Asp Glu Phe Leu Arg Thr Met Lys Gln Ser Gln Asn
         435                 440                 445
Thr Ala Val Asp Glu Ser Asp Lys Lys Trp His Arg Val Ser Pro Lys
```

```
                450                 455                 460
Phe Gly Val Thr Tyr Asp Phe Ala Gln His Tyr Thr Trp Tyr Gly Gln
465                 470                 475                 480

Tyr Ala Gln Gly Phe Arg Thr Pro Thr Ala Lys Ala Leu Tyr Gly Arg
                485                 490                 495

Phe Glu Asn Leu Gln Ala Gly Tyr His Ile Glu Pro Asn Pro Asn Leu
            500                 505                 510

Lys Pro Glu Lys Ser Gln Ser Phe Glu Thr Gly Leu Arg Gly Lys Phe
        515                 520                 525

Asp Glu Gly Ser Phe Gly Val Ala Val Phe Tyr Asn Lys Tyr Arg Asp
    530                 535                 540

Phe Ile Asp Glu Asp Ala Leu Asn Thr Asp Ser Thr Gly Gly Asn Gly
545                 550                 555                 560

Gln Thr Phe Gln Ser Asn Asn Ile Glu Arg Ala Val Ile Lys Gly Val
                565                 570                 575

Glu Leu Lys Gly Arg Leu Glu Leu Gly Ala Phe Gly Ala Pro Gln Gly
            580                 585                 590

Leu Tyr Thr Gln Gly Ser Val Ala Tyr Ala Tyr Gly Arg Asn Lys Asp
        595                 600                 605

Asn Gly Glu Pro Ile Asn Ser Val Asn Pro Leu Thr Gly Val Phe Gly
    610                 615                 620

Leu Gly Tyr Asp Glu Ala Asp Gly Asn Tyr Gly Gly Leu Leu Ser Trp
625                 630                 635                 640

Thr Leu Val Lys Arg Lys Asp Arg Val Asp Asp Ser Thr Phe His Thr
                645                 650                 655

Pro Asp Gly Thr Ala Ser Gln Phe Lys Thr Pro Gly Phe Gly Val Leu
            660                 665                 670

Asp Leu Ser Ala Tyr Tyr Arg Leu Ser Lys Asp Leu Thr Leu Asn Ala
        675                 680                 685

Gly Leu Tyr Asn Leu Thr Asp Lys Lys Tyr Trp Leu Trp Asp Asp Val
    690                 695                 700

Arg Gly Tyr Asp Ser Val Gly Glu Ala Ser Ala Leu Ala Pro Ala Asn
705                 710                 715                 720

Ile Asp Arg Leu Ser Gln Pro Gly Arg Asn Phe Ala Val Asn Leu Val
                725                 730                 735

Trp Asp Ile

<210> SEQ ID NO 51
<211> LENGTH: 1069
<212> TYPE: PRT
<213> ORGANISM: Pseudomonas aeruginosa

<400> SEQUENCE: 51

Cys Leu Leu Gly Phe Leu Leu Ile Pro Gly Ile Gly Leu Arg Val Ala
1               5                   10                  15

Asn Gln Gln Leu Ala Gln Tyr Ala Thr Val Pro Ala Arg Leu Glu Arg
            20                  25                  30

Ile Glu Phe Asn Pro Phe Ser Leu Glu Leu Thr Leu Trp Gly Leu Arg
        35                  40                  45

Leu Gly Glu Glu Lys Asn Pro Gln Leu Ala Phe Arg Arg Leu Tyr Ala
    50                  55                  60

Asn Leu Gln Leu Asp Ser Leu Trp Lys Arg Gln Leu His Leu Ala Asp
65                  70                  75                  80

Val Glu Leu Glu Gly Pro His Thr Glu Leu Leu Phe Gly Glu Lys Gly
```

```
                    85                  90                  95
Gln Leu Asn Leu Ala Ser Leu Phe Arg Ile Pro Ser Glu Ser Pro
                100                 105                 110

Glu Pro Glu Gln Pro Ser Asp Pro Phe Pro Leu Arg Ile Asp Arg Ile
            115                 120                 125

Gln Leu Ala Glu Gly Ser Leu His Phe Gln Asp Leu Arg Pro Ser Glu
        130                 135                 140

Pro Val Asp Phe Ser Phe Asp Pro Leu Gly Phe Glu Leu His Asn Leu
145                 150                 155                 160

Ser Thr Leu Pro Asp Asp Gly Ala Lys Met Thr Leu Val Ala Thr Gly
                165                 170                 175

Pro Asn Gly Gly Arg Leu Asp Trp Glu Gly Asp Leu Thr Leu Val Pro
            180                 185                 190

Ile Thr Ser Arg Gly His Leu Ser Val Lys Asp Ile Gln Leu Lys Ala
        195                 200                 205

Trp Trp Pro Tyr Val Arg Asp Asn Ala Pro Leu Val Leu Glu Asn Gly
    210                 215                 220

Val Val Ser Leu Ser Ser Asp Tyr Arg Leu Asp Leu Ser Lys Asp Thr
225                 230                 235                 240

Gln Leu Leu Leu Asp Lys Ala Ala Leu Lys Leu Ala Asp Phe Ser Ile
                245                 250                 255

Asn Ser Pro Gln Gly Lys Pro Leu Ala Lys Leu Ala Ser Leu Asp Val
            260                 265                 270

Ala Ala Thr Thr Leu Asp Leu Ala Lys Gln Glu Val Val Leu Gly Glu
        275                 280                 285

Val Arg Ser Gln Gly Leu Glu Ala Trp Ala Ala Arg Glu Lys Asp Gly
    290                 295                 300

Gln Leu Asp Trp Gln Lys Leu Phe Ala Asp Phe Thr Pro Pro Pro Arg
305                 310                 315                 320

Lys Ala Pro Ala Pro Lys Pro Ala Glu Asn Thr Asp Pro Ala Ala Ala
                325                 330                 335

Pro Thr Asp Ala Ala Lys Thr Thr Ser Glu Pro Ala Thr Asp Gly Ala
            340                 345                 350

Ala Lys Ala Ala Ala Ile Ala Ser Gly Glu Ala Ser Lys Asp Arg Pro
        355                 360                 365

Ala Glu Lys Asp Ala Ser Val Ala Glu Thr Glu Arg Ala Thr Asp Asp
    370                 375                 380

Lys Glu Ser Ala Lys Ala Ala Glu Gly Ala Ala Asp Lys Val Ala Lys
385                 390                 395                 400

Gln Glu Thr Ser Lys Ala Pro Lys Thr Gly Lys Ala Thr Gly Gln Glu
                405                 410                 415

Thr Ala Lys Thr Ala Glu Ile Asp Lys Ala Ala Ser Asp Ser Pro Gln
            420                 425                 430

Gln Leu Ala Asp Thr Ala Lys Thr Pro Pro Glu Ser Thr Lys Ala
        435                 440                 445

Ser Ala Glu Thr Pro Ala Lys Pro Trp Asn Ile Val Leu Arg Asp Ala
    450                 455                 460

Gln Leu Arg Gly Tyr Lys Ala His Leu Val Asp Arg Gln Pro Ala Thr
465                 470                 475                 480

Glu Val Pro Leu Glu Val Gly Pro Leu Asp Leu Asp Leu Gln Asn Val
                485                 490                 495

Asp Ser Leu Gly Lys Thr Pro Phe Asp Leu Lys Leu Lys Thr Gly Leu
            500                 505                 510
```

```
Gly Asn Arg Gly Gln Val Gln Ala Ser Gly Gln Val Val Leu Asp Pro
            515                 520                 525

Val Ser Ala Arg Leu Lys Val Ser Thr Arg Asp Ile Asp Leu Arg Val
530                 535                 540

Ala Gln Ala Tyr Ile Ser Pro Phe Ile Arg Leu Glu Leu Arg Ser Gly
545                 550                 555                 560

Phe Leu Gly Ser Glu Leu Ala Val Asp Leu Lys Ser Val Glu Pro Leu
                565                 570                 575

Ala Phe Ser Val Asp Gly Ser Ala Glu Val Ser Gln Leu His Thr Leu
            580                 585                 590

Asp Thr Ile Lys Asp Arg Asp Phe Val Lys Trp Thr Lys Leu Thr Leu
            595                 600                 605

Asn Gly Leu Ala Tyr Arg His Glu Asp Ser Leu Ser Ile Gln Ser Val
            610                 615                 620

Ser Phe Glu Glu Pro Tyr Ala Arg Phe Ile Ile Asn Glu Asp Arg Ser
625                 630                 635                 640

Thr Asn Val Ser Glu Leu Ile Ile Pro Gln Pro Ala Ser Ser Ser Gly
                645                 650                 655

Lys Thr Ala Ala Glu Ser Lys Asn Ala Pro Ala Ser Lys Pro Leu Gly
            660                 665                 670

Ile His Ile Gly Gly Val Arg Ile Asn Asn Gly Ser Ala Asn Phe Ala
            675                 680                 685

Asp Leu Thr Leu Met Pro Pro Phe Gly Thr Ala Ile Gln Gln Leu Ser
            690                 695                 700

Gly Glu Val Gly Thr Leu Asp Thr Arg Asn Ser Gln Pro Ala Lys Val
705                 710                 715                 720

Asp Ile Lys Gly Lys Val Asp Lys Tyr Ala Pro Val Thr Ile Ala Gly
                725                 730                 735

Glu Leu Asp Pro Phe Asp Pro Leu Lys Lys Leu Asp Ile Thr Thr Ser
            740                 745                 750

Phe Lys Arg Val Glu Leu Thr Thr Leu Thr Pro Tyr Ser Gly Lys Phe
            755                 760                 765

Ala Gly Tyr Arg Ile Arg Lys Gly Arg Leu Asn Leu Asp Leu His Tyr
            770                 775                 780

Gln Ile Glu Arg Ser Gln Leu Lys Ala Glu Asn Lys Val Leu Leu Glu
785                 790                 795                 800

Gly Leu Gln Leu Gly Glu Lys Val Asp Ser Pro Asp Ala Val Asp Leu
                805                 810                 815

Pro Val Lys Leu Ala Val Ala Leu Leu Lys Asp Thr Lys Gly Asn Ile
            820                 825                 830

Asp Ile Gln Leu Pro Val Ala Gly Asp Leu Asn Pro Glu Phe Ser
            835                 840                 845

Val Met Pro Ile Val Trp Gln Thr Leu Arg Asn Leu Val Leu Arg Ala
850                 855                 860

Val Gln Ala Pro Phe Lys Phe Ile Ala Gly Leu Ala Ala Gly Gly Asn
865                 870                 875                 880

Glu Asp Leu Gly Thr Val Pro Phe Ala Ala Gly Ser Asp Glu Leu Thr
                885                 890                 895

Pro Glu Ala Gln Ala Asn Leu Asp Lys Leu Ala Asp Ala Leu Lys Glu
            900                 905                 910

Arg Pro Ala Leu Arg Leu Glu Val Glu Gly Val Ala Ser Ala Ala Ala
            915                 920                 925
```

```
Asp Gly Pro Ser Ile Gly Ala Lys Arg Leu Glu Leu Glu Tyr Gln Asn
        930                 935                 940

Thr Tyr Tyr Arg Met Leu Gln Arg Arg Gly Asp Lys Val Pro Ser Asp
945                 950                 955                 960

Ala Lys Gln Leu Glu Val Pro Glu Asn Met Gln Ala Pro Leu Leu Glu
                965                 970                 975

Gly Ile Tyr Arg Thr Arg Leu Lys Gln Gln Pro Pro Ala Glu Trp Lys
            980                 985                 990

Glu Leu Asp Ser Asp Glu Arg Thr Ala Lys Met Arg Glu Ala Val Ile
        995                 1000                1005

Ala Ser Trp Ala Lys Ser Gln Val Leu Leu Arg Gln Ile Gly Gln Ala
    1010                1015                1020

Arg Ala Thr Arg Ile Lys Asp Tyr Leu Val Glu Lys Gly Gln Leu Pro
1025                1030                1035                1040

Asp Asp Arg Ile Tyr Leu Ile Asp Val Ser Phe Ala Glu Gly Glu Asp
                1045                1050                1055

Lys Gly Asn Val Asp Thr Gln Leu His Leu Asp Ser Glu
            1060                1065

<210> SEQ ID NO 52
<211> LENGTH: 146
<212> TYPE: PRT
<213> ORGANISM: Pseudomonas aeruginosa

<400> SEQUENCE: 52

Glu Met Lys Ile Ala Val Leu Asn Tyr Gln Met Ala Leu Leu Glu Ser
1               5                   10                  15

Asp Ala Ala Lys Gln Tyr Ala Val Asp Ala Glu Lys Lys Phe Gly Pro
            20                  25                  30

Gln Leu Asn Lys Leu Lys Asn Leu Glu Arg Asp Ala Lys Ala Leu Gln
        35                  40                  45

Asp Lys Leu Val Ser Asn Gly Ser Lys Met Ser Gln Gly Asp Arg Glu
    50                  55                  60

Lys Ala Glu Leu Asp Phe Lys Gln Lys Ala Arg Asp Phe Gln Phe Gln
65                  70                  75                  80

Ser Lys Glu Leu Asn Glu Ser Lys Ala Ala Ala Asp Arg Asp Met Leu
                85                  90                  95

Lys Lys Leu Lys Pro Lys Leu Asp Gln Ala Val Glu Glu Thr Ile Lys
            100                 105                 110

Lys Gly Gly Tyr Asp Met Val Ile Glu Arg Gly Ala Val Val Asp Val
        115                 120                 125

Lys Pro Gln Tyr Asp Ile Thr Arg Gln Val Ile Glu Arg Met Asn Gln
    130                 135                 140

Leu Arg
145

<210> SEQ ID NO 53
<211> LENGTH: 187
<212> TYPE: PRT
<213> ORGANISM: Pseudomonas aeruginosa

<400> SEQUENCE: 53

Cys Ser Asp Ser Ala Pro Ser Ser Glu Glu Ile Ala Arg Leu Leu Ala
1               5                   10                  15

Glu Arg Gly Phe Asp Lys Pro Ala Cys Ala Ser Ser Thr Leu Phe Lys
            20                  25                  30
```

```
Thr Phe Pro Val Thr Leu Ser Asp Ser Phe Ser Gly Pro Gly Pro Ala
            35                  40                  45

Lys Gly Asn Ala Ala Val Tyr Asp Ala Leu Val Gly Val Gly Leu Leu
 50                  55                  60

Arg Arg Asp Gly Asp Ser Tyr Asp Leu Thr Pro Ala Gly Arg Glu Asp
 65                  70                  75                  80

Tyr Lys Pro Glu Ser Lys Ala Phe Cys Tyr Ser Ser Gly Phe Asp Val
                 85                  90                  95

Ser Val Arg Ser Val Asp Pro Ala Lys Pro Asp Tyr Gly Pro Ala
            100                 105                 110

Val Glu Lys Gly Trp Leu Val Thr Val Glu Val Lys Pro Arg Glu Val
            115                 120                 125

Lys Asp Trp Ala Lys Asn Pro Glu Val Leu Lys Gln Ala Ser Leu Thr
130                 135                 140

Thr Leu Gln Gln Ile Thr Gln Pro Gln Val Gly Gln Val Ser Leu Val
145                 150                 155                 160

Lys Pro Arg Gly Glu Glu Gly Tyr Lys Leu Val Asn Thr Arg Phe Ser
                 165                 170                 175

Pro Arg Gln Gly Phe His Phe Asn Gln Ala Trp
            180                 185

<210> SEQ ID NO 54
<211> LENGTH: 427
<212> TYPE: PRT
<213> ORGANISM: Pseudomonas aeruginosa

<400> SEQUENCE: 54

Gly Asp Gly Gly Phe Val Glu Asp Ser Glu Leu Gln Phe Leu Ala Arg
 1               5                  10                  15

Thr Tyr Tyr Phe Asn Arg Asp Tyr Arg Asp Ser Pro Asn Asn Ala Gly
                 20                  25                  30

Arg Asn Arg Phe Lys Pro Arg Ser Glu Arg Asn Gly Tyr Arg Glu Glu
             35                  40                  45

Ala Thr Gln Gly Leu Arg Leu Gln Phe Ala Ser Gly Tyr Thr Pro Gly
 50                  55                  60

Ser Leu Gly Phe Gly Leu Asp Ala His Ala Met Leu Gly Leu Gln Leu
 65                  70                  75                  80

Asp Ser Gly Gly Arg Thr Thr Gly Asn Leu Pro Val Gly Ala
             85                  90                  95

Asp Gly His Pro Asp His Arg Tyr Gly Lys Val Gly Gly Ala Leu Arg
            100                 105                 110

Leu Arg His Gly Glu Thr Arg Leu Lys Tyr Gly Gln Thr Thr Thr Ser
            115                 120                 125

Ala Pro Val Phe Ala Ala Ser Asn Arg Thr Leu Ala Gly Met Ala
130                 135                 140

Tyr Gly Leu Leu Leu Glu Asp Arg Ser Phe Asp Gly Leu Leu Leu Glu
145                 150                 155                 160

Gly Gly Arg Phe Thr Ala Ala Ser Gly Pro Gly Glu Ser Lys Val Arg
                 165                 170                 175

Gly Asp Ile Ser Thr Val Tyr Gly Arg Leu Gly Ala Tyr Pro Val Arg
            180                 185                 190

Leu Asp Ala Val Gly Phe Leu Gly Gly Gln Trp Gln Ala Thr Glu Arg
            195                 200                 205

Leu Gln Leu Ser Leu Tyr Ala Ser Arg Phe Asp Asp Ile Trp Gln Gln
210                 215                 220
```

Ala Tyr Phe Gly Ala Ser His Arg Gln Pro Leu Gly Gly Glu Arg Ala
225                 230                 235                 240

Leu Arg Val Asp Leu Asp Ala Tyr Arg Thr Arg Asp Ser Gly Gln Ser
            245                 250                 255

Arg Phe Gly Arg Ile Asp Thr Leu Thr Ser Ser Leu Ala Leu Gly Tyr
            260                 265                 270

Glu His Gly Pro Gln Arg Ile Thr Leu Ala Tyr Gln Arg Val His Gly
            275                 280                 285

Glu Gln Pro Phe Asp Tyr Met Ala Phe Gly Asp Gly Arg Ser Ser Ala
            290                 295                 300

Ser Met Val Leu Ala Asn Ser Val Gly Tyr Ser Asp Phe Asn Gly Pro
305                 310                 315                 320

Gly Glu Arg Ser Trp Gln Leu Arg Tyr Asp Leu Asp Leu Gly Ala Leu
            325                 330                 335

Gly Leu Pro Gly Leu Ser Leu His Ala Leu His Ala Arg Gly Arg Ala
            340                 345                 350

Gly Ala Ser Ala Ser Ser Ala Ala Glu Ser Ile Tyr Ala Gly Leu Tyr
            355                 360                 365

Gly Arg Asp Gly Arg His Arg Glu Asn Asp Leu Gly Phe Ala Tyr Arg
370                 375                 380

Val Lys Ala Gly Pro Leu Ala Gly Leu Ala Leu Arg Ala Ser Gln Ala
385                 390                 395                 400

Trp His Arg Gly Asn Ala Ser Tyr Leu Asp Gly Asp Ile Asp Glu Thr
            405                 410                 415

Arg Leu Val Val Asp Tyr Ser Arg Ser Ile Trp
            420                 425

<210> SEQ ID NO 55
<211> LENGTH: 233
<212> TYPE: PRT
<213> ORGANISM: Pseudomonas aeruginosa

<400> SEQUENCE: 55

Ala Leu Asp Asp Gln Gln Arg Ala Leu Gln Gln Leu Gln Val Gln Ala
1               5                   10                  15

Cys Arg Ala Val Gly Ser Leu Leu Leu Arg Gly Glu Gly Phe Gln
            20                  25                  30

Glu Gln His Ala Ala Gln Leu Glu Lys Asp Leu Ala Ser Leu Asp Arg
            35                  40                  45

Ala Leu Ala Ala Ala Pro Glu Gly Val Leu Leu Arg Gln Gly Glu Lys
50                  55                  60

Thr Leu Val Ala Arg Ile Arg Glu Gly Ala Ala Tyr Gly Pro Arg Glu
65                  70                  75                  80

Glu Asp Leu Pro Trp Arg Tyr Pro Gln Gln Leu Ser Arg Ala Leu Arg
            85                  90                  95

Asp Phe Leu Asn Leu Val Glu Arg Gln Val Pro Pro Pro Pro Gly
            100                 105                 110

Gln Pro Leu Pro Leu Trp Gln Leu Pro Val Arg Val Glu Tyr Leu Ser
            115                 120                 125

Leu Gln Tyr Leu Ala Arg Ala Tyr Leu Gly Gly Leu Glu Thr Ala Arg
            130                 135                 140

Glu Gln Pro Arg Asp Tyr Leu Gly Gln Asp Glu Ser Val Leu Val Pro
145                 150                 155                 160

Leu Ile Asp Arg Arg Ile Ala Leu Leu Val Ala Gln Ser Ala Asn Pro

```
              165                 170                 175

Ala Gly Leu Lys Lys Leu Glu Asn Arg Trp Glu Tyr Leu Ser Gln Ala
            180                 185                 190

Leu Arg Asp Leu Asn Ser Lys Ser Ala Leu Val Ser Ala Ser Gly
        195                 200                 205

Arg Pro Trp Ala Pro Ile Ile Val Asp Arg His Ala Arg Ala Leu Ser
        210                 215                 220

Glu Ser Leu Met Arg Leu Ser Ala Glu
225                 230

<210> SEQ ID NO 56
<211> LENGTH: 183
<212> TYPE: PRT
<213> ORGANISM: Pseudomonas aeruginosa

<400> SEQUENCE: 56

Cys Gly Tyr Asn Ala Met Gln Ala Gly Asp Glu Gln Val Lys Ala Ala
1               5                   10                  15

Trp Ser Glu Val Leu Asn Gln Tyr Gln Arg Arg Ala Asp Leu Val Pro
            20                  25                  30

Asn Leu Val Ser Thr Val Lys Gly Tyr Ala Ser His Glu Ala Ser Val
        35                  40                  45

Leu Thr Gln Val Thr Glu Ala Arg Ala Lys Val Gly Ser Val Gln Leu
    50                  55                  60

Asn Ala Asp Gln Leu Asp Asp Glu Gln Ala Val Gln Arg Phe Gln Lys
65                  70                  75                  80

Ala Gln Gly Glu Leu Ser Ser Ala Leu Ser Arg Leu Leu Val Val Thr
                85                  90                  95

Glu Asn Tyr Pro Gln Leu Lys Ala Asp Gly Leu Phe Lys Asp Leu Leu
            100                 105                 110

Thr Gln Leu Glu Gly Thr Glu Asn Arg Ile Ala Val Ala Arg Gly Arg
        115                 120                 125

Tyr Val Lys Ser Val Gln Glu Tyr Asn Val Leu Leu Arg Gln Phe Pro
    130                 135                 140

Gly Val Ile Thr Ala Lys Leu Phe Gly Tyr Lys Pro Lys Ala Asn Phe
145                 150                 155                 160

Ser Val Glu Asn Glu Ala Ala Ile Ser Thr Ala Pro Lys Val Asp Phe
                165                 170                 175

Gly Asn Pro Gln Pro Ala Gln
            180

<210> SEQ ID NO 57
<211> LENGTH: 132
<212> TYPE: PRT
<213> ORGANISM: Pseudomonas aeruginosa

<400> SEQUENCE: 57

Cys Ala Val Tyr Asp Tyr Asp Tyr Asp Asp Gly Asp Trp Arg His Tyr
1               5                   10                  15

Arg Gly Gln Pro Tyr Gly Tyr Ala Tyr Glu Val Pro Arg Tyr Arg Val
            20                  25                  30

Tyr Asp Asp Gly Trp Arg Ser Glu Arg Arg Tyr Tyr Ser Thr Arg Tyr
        35                  40                  45

Tyr Asp Gln Arg Tyr Tyr Pro Ala Pro Arg Arg Tyr Asp Gly His Arg
    50                  55                  60

Asp Tyr Arg Arg Glu Gln Tyr Arg Tyr Gln Gln Arg Tyr His Glu Ser
```

```
                65                  70                  75                  80
Arg Pro Ala His Arg Gly Glu Arg His Pro Gly Asn Trp Gln Arg Gly
                    85                  90                  95

Gly Gln Pro Gln Trp Arg Gly His Ser Pro Gln Arg Trp Gln Gln His
                100                 105                 110

Gly Arg Gln Asp Arg Pro Gly His Gln Gly Gln Gln Gly Gly Thr Pro
                115                 120                 125

Arg Trp Arg Asn
    130

<210> SEQ ID NO 58
<211> LENGTH: 682
<212> TYPE: PRT
<213> ORGANISM: Pseudomonas aeruginosa

<400> SEQUENCE: 58

Ser Asp Leu Leu Ser Ile Gly Leu Ser Gly Leu Gly Thr Ser Gln Thr
1               5                   10                  15

Trp Leu Thr Val Thr Gly His Asn Ile Thr Asn Val Lys Thr Pro Gly
                20                  25                  30

Tyr Ser Arg Gln Asp Ala Ile Gln Gln Thr Arg Ile Pro Gln Phe Ser
            35                  40                  45

Gly Ala Gly Tyr Met Gly Ser Gly Ser Gln Ile Val Asp Val Arg Arg
        50                  55                  60

Leu Ala Ser Asp Phe Leu Thr Gly Gln Leu Arg Asn Ala Thr Ser Gln
65                  70                  75                  80

Asn Ser Glu Leu Asn Ala Phe Leu Gly Gln Ile Asp Gln Leu Asn Ser
                85                  90                  95

Leu Leu Ala Asp Asn Thr Thr Gly Val Ser Pro Ala Met Gln Arg Phe
                100                 105                 110

Phe Ser Ala Leu Gln Thr Ala Ala Gln Asn Pro Ser Ser Thr Glu Ala
            115                 120                 125

Arg Glu Ala Val Leu Ala Gln Ala Gln Gly Leu Ser Lys Thr Phe Asn
        130                 135                 140

Thr Leu Tyr Asp Gln Leu Asp Lys Gln Asn Ser Leu Ile Asn Gln Gln
145                 150                 155                 160

Leu Gly Ala Leu Thr Ser Gln Val Asn Asn Leu Ser Gln Ser Val Ala
                165                 170                 175

Glu Tyr Asn Asp Ala Ile Ala Lys Ala Lys Ser Ala Gly Ala Val Pro
                180                 185                 190

Asn Asp Leu Leu Asp Ala Arg Asp Glu Ala Val Arg Lys Leu Ser Glu
            195                 200                 205

Met Val Gly Val Thr Ala Val Thr Gln Asp Asp Asn Ser Val Ser Leu
        210                 215                 220

Phe Ile Gly Ser Gly Gln Pro Leu Val Val Gly Asn Thr Val Ser Thr
225                 230                 235                 240

Leu Ser Val Val Pro Gly Leu Asp Asp Pro Thr Arg Tyr Gln Val Gln
                245                 250                 255

Leu Thr Leu Gly Asp Ser Thr Gln Asn Val Thr Arg Leu Val Ser Gly
                260                 265                 270

Gly Gln Met Gly Gly Leu Leu Ala Tyr Arg Asp Thr Val Leu Asp Ser
            275                 280                 285

Ser Tyr Asn Lys Leu Gly Gln Leu Ala Leu Thr Phe Ala Asp Thr Val
        290                 295                 300
```

```
Asn Lys Gln Leu Gly Gln Gly Leu Asp Leu Ala Gly Lys Ala Gly Ala
305                 310                 315                 320

Asn Leu Phe Gly Asp Ile Asn Asp Pro Asp Ile Thr Ala Leu Arg Val
            325                 330                 335

Leu Ala Lys Asn Gly Asn Thr Gly Asn Val His Ala Asn Leu Asn Ile
        340                 345                 350

Thr Asp Thr Ser Lys Leu Asn Ser Ser Asp Phe Arg Leu Asp Phe Asp
    355                 360                 365

Gly Thr Asn Phe Thr Ala Arg Arg Leu Gly Asp Asp Ala Ser Met Gln
370                 375                 380

Val Thr Val Ser Gly Thr Gly Pro Tyr Thr Leu Ser Phe Lys Asp Ala
385                 390                 395                 400

Asn Gly Val Asp Gln Gly Phe Ser Val Thr Leu Asp Gln Leu Pro Ala
            405                 410                 415

Ala Gly Asp Arg Phe Thr Leu Gln Pro Thr Arg Arg Gly Ala Ser Asp
        420                 425                 430

Ile Glu Thr Thr Leu Lys Asn Ala Ser Gln Leu Ala Phe Ala Gly Ser
    435                 440                 445

Ala Arg Ala Glu Ala Thr Thr Asn Asn Arg Gly Ser Gly Ala Ile Gly
450                 455                 460

Gln Pro Asn Leu Val Asp Gly Pro Ser Pro Ile Asp Pro Ala Val Leu
465                 470                 475                 480

Gln Asn Ala Phe Gly Ala Asn Gly Leu Pro Leu Ser Ala Thr Val Ser
            485                 490                 495

Ala Asp Gly Lys Thr Tyr Thr Met Thr Ser Pro Leu Pro Ala Gly Trp
        500                 505                 510

Ser Tyr Val Asp Lys Asp Gly Asn Ala Leu Pro Gly Ser Pro Thr Leu
    515                 520                 525

Asn Ser Gly Thr Ser Asn Ser Val Arg Met Ala Tyr Thr Asp Pro Gly
530                 535                 540

Ser Gly Gln Thr Tyr Thr Tyr Glu Phe Asn Leu Ser Asn Val Pro Gln
545                 550                 555                 560

Thr Gly Asp Ser Phe Thr Leu Ser Phe Asn Lys Asp Gly Ile Ala Asp
            565                 570                 575

Asn Arg Asn Ala Leu Asn Leu Asn Ala Leu Gln Thr Lys Pro Thr Val
        580                 585                 590

Gly Gly Thr Asp Ser Thr Gly Ser Thr Tyr Asn Asp Ala Tyr Gly Gly
    595                 600                 605

Leu Val Glu Arg Val Gly Thr Leu Thr Ala Gln Ala Arg Ala Ser Ala
610                 615                 620

Asp Ala Ser Gln Thr Val Leu Lys Gln Ala Gln Asp Ser Arg Asp Ser
625                 630                 635                 640

Leu Ser Gly Val Ser Leu Asp Glu Glu Ala Ala Asn Leu Ile Gln Phe
            645                 650                 655

Gln Gln Tyr Tyr Ser Ala Ser Ala Gln Val Ile Gln Val Ala Arg Ser
        660                 665                 670

Leu Phe Asp Thr Leu Ile Gly Ala Phe Arg
    675                 680

<210> SEQ ID NO 59
<211> LENGTH: 217
<212> TYPE: PRT
<213> ORGANISM: Pseudomonas aeruginosa

<400> SEQUENCE: 59
```

```
Gln Val Met Ala Arg Asp Leu Gly Asp Phe Glu Leu Lys Leu Ala Thr
 1               5                  10                  15

Ser Pro Thr Arg Ser Met Ala Gln Gly Leu Val Thr Pro Gly Ser Ser
             20                  25                  30

Gly Ser Phe His Gly Gly Leu Asp Leu Ser His Glu Ser Gly Trp Tyr
         35                  40                  45

Ile Gly Asn Trp Thr Ser Asn Leu Asp Pro Gly Lys Pro Thr Glu Ile
 50                  55                  60

Asp Ser Tyr Ala Gly Phe Lys Arg Pro Leu Asn Asn Arg Leu Gly Tyr
 65                  70                  75                  80

Glu Met Gly Leu Ile Arg Tyr Ser Arg Pro Gln Pro Ala Asn Asp
                 85                  90                  95

Ala Ala Glu Leu Tyr Gly Gly Leu Ser Ile Phe Gly Ser Arg Leu Gly
             100                 105                 110

Ala Ala Leu Ser Ser Asp Pro Gly Arg Asn Asp Thr Thr Leu Phe Ala
             115                 120                 125

Asp Leu Gly Val Asn Pro Pro Phe Gly Phe Asp Val Thr Leu Lys Tyr
         130                 135                 140

Gly Asn His Arg Leu Asp Asn Pro Ala Ser Leu Ser Gly Gly Gly Tyr
145                 150                 155                 160

Val Ser Val Phe Asn Asp Trp Ser Val Asn Leu Ser Arg Pro Trp Leu
                 165                 170                 175

Gly Ile Asp Leu Asn Leu Ser Tyr Ser Gly Thr Ser Leu Thr Gly Ser
             180                 185                 190

Asp Cys Ser Ala Tyr Ser Gly His Asn Ser Tyr Cys Asp Thr Thr Phe
             195                 200                 205

Met Leu Lys Ala Ser Arg Pro Phe Phe
         210                 215

<210> SEQ ID NO 60
<211> LENGTH: 151
<212> TYPE: PRT
<213> ORGANISM: Pseudomonas aeruginosa

<400> SEQUENCE: 60

Cys Ala Ser Asn Pro Asn Asp Leu Pro Asp Phe Pro Glu His Glu Tyr
 1               5                  10                  15

Ala Ala Thr Gln Gln Val Gly Glu Gly Val Ile Asn Gly Asp Leu Tyr
             20                  25                  30

Leu Thr Ser Ala Ser Gly Ala Ile Gln Lys Gly Thr Asn Thr Lys Val
         35                  40                  45

Ala Leu Glu Pro Ala Thr Ser Tyr Met Lys Ala Tyr Tyr Ala Lys Phe
 50                  55                  60

Gly Asn Leu Asp Ala Ala Lys Arg Asp Pro Asp Val Gln Pro Pro Val
 65                  70                  75                  80

Leu Asp Pro Arg Arg Ala Thr Tyr Val Arg Glu Ala Thr Thr Asp Gln
                 85                  90                  95

Asn Gly Arg Phe Asp Phe Asp His Ile Pro Asn Gly Thr Tyr Tyr Ile
             100                 105                 110

Ser Ser Glu Leu Thr Trp Ser Ala Gln Ser Asp Gly Lys Thr Ile Thr
             115                 120                 125

Glu Gly Gly Thr Val Thr Lys Leu Val Thr Val Ser Gly Ser Gln Pro
         130                 135                 140

Gln Lys Val Leu Leu Thr Arg
```

```
                    145                 150

<210> SEQ ID NO 61
<211> LENGTH: 326
<212> TYPE: PRT
<213> ORGANISM: Pseudomonas aeruginosa

<400> SEQUENCE: 61

Gln Gly Gln Asn Ser Val Glu Ile Glu Ala Phe Gly Lys Arg Tyr Phe
  1               5                  10                  15

Thr Asp Ser Val Arg Asn Met Lys Asn Ala Asp Leu Tyr Gly Gly Ser
             20                  25                  30

Ile Gly Tyr Phe Leu Thr Asp Val Glu Leu Ala Leu Ser Tyr Gly
         35                  40                  45

Glu Tyr His Asp Val Arg Gly Thr Tyr Glu Thr Gly Asn Lys Lys Val
 50                  55                  60

His Gly Asn Leu Thr Ser Leu Asp Ala Ile Tyr His Phe Gly Thr Pro
 65                  70                  75                  80

Gly Val Gly Leu Arg Pro Tyr Val Ser Ala Gly Leu Ala His Gln Asn
                 85                  90                  95

Ile Thr Asn Ile Asn Ser Asp Ser Gln Gly Arg Gln Gln Met Thr Met
            100                 105                 110

Ala Asn Ile Gly Ala Gly Leu Lys Tyr Tyr Phe Thr Glu Asn Phe Phe
        115                 120                 125

Ala Lys Ala Ser Leu Asp Gly Gln Tyr Gly Leu Glu Lys Arg Asp Asn
130                 135                 140

Gly His Gln Gly Glu Trp Met Ala Gly Leu Gly Val Gly Phe Asn Phe
145                 150                 155                 160

Gly Gly Ser Lys Ala Ala Pro Ala Pro Glu Pro Val Ala Asp Val Cys
                165                 170                 175

Ser Asp Ser Asp Asn Asp Gly Val Cys Asp Asn Val Asp Lys Cys Pro
            180                 185                 190

Asp Thr Pro Ala Asn Val Thr Val Asp Ala Asn Gly Cys Pro Ala Val
        195                 200                 205

Ala Glu Val Val Arg Val Gln Leu Asp Val Lys Phe Asp Phe Asp Lys
    210                 215                 220

Ser Lys Val Lys Glu Asn Ser Tyr Ala Asp Ile Lys Asn Leu Ala Asp
225                 230                 235                 240

Phe Met Lys Gln Tyr Pro Ser Thr Ser Thr Val Glu Gly His Thr
                245                 250                 255

Asp Ser Val Gly Thr Asp Ala Tyr Asn Gln Lys Leu Ser Glu Arg Arg
            260                 265                 270

Ala Asn Ala Val Arg Asp Val Leu Val Asn Glu Tyr Gly Val Glu Gly
        275                 280                 285

Gly Arg Val Asn Ala Val Gly Tyr Gly Glu Ser Arg Pro Val Ala Asp
    290                 295                 300

Asn Ala Thr Ala Glu Gly Arg Ala Ile Asn Arg Val Glu Ala Glu
305                 310                 315                 320

Val Glu Ala Glu Ala Lys
                325

<210> SEQ ID NO 62
<211> LENGTH: 324
<212> TYPE: PRT
<213> ORGANISM: Pseudomonas aeruginosa
```

<400> SEQUENCE: 62

Cys Val Ser Glu Leu Asp Ser Gly Ala Tyr Gly Ser Met Asp Pro
1               5                   10                  15

Arg Asn Ala Gln Met Leu Asp Leu Val Asp Gln Ala Leu Lys Gly Asn
                20                  25                  30

Met Ala Val Val Leu Val Ala Asp Val Met Pro His Lys Ser Leu Ser
            35                  40                  45

Asp Ala Leu Thr Met Thr Gln Trp Thr Pro Thr Ala Ile Trp Glu Tyr
        50                  55                  60

Glu Lys Asp Pro Lys Val Thr Phe Gly Arg Lys Phe Gln Thr Asn Ala
65                  70                  75                  80

Leu Gln Arg Lys Pro Asp Glu Thr Tyr Leu Phe Lys Ala Phe Glu Val
                85                  90                  95

His Ile Leu Pro Pro Gly Lys Tyr Leu Leu Thr Gly Gly Asp Asp Tyr
                100                 105                 110

Gln Ile His Gly Leu Leu Asp Gln Val Gly Ala Arg Ser Gly Pro Pro
            115                 120                 125

Gly Ser Gly His Gly Ala Asn Gly Thr Ala Tyr Leu Ser Pro Glu Leu
        130                 135                 140

Tyr Arg Glu Tyr Tyr Arg Glu Glu Val Trp Lys Asp Ala Thr Tyr Gly
145                 150                 155                 160

Ser Glu Ile Lys Thr Glu Lys Val Cys Thr Ala Val His Val Ala Ser
                165                 170                 175

Gly Ala Cys Val Ser Trp Gly Glu Gln Gln Tyr Thr Gln Thr Thr Gln
            180                 185                 190

Gly Ser Gln Ala Gly Tyr Tyr Gln Gln Thr Asp Ser Arg Asp Val Pro
        195                 200                 205

Ser Ile Lys Val Gln Ala Arg Leu Pro Val Asp Lys Ala Leu Ala Ser
210                 215                 220

Phe Thr Val Gln Gly Gly Gln Leu Leu Leu Ala Pro Arg Met His Leu
225                 230                 235                 240

Lys Thr Pro Gly Tyr Lys Tyr Gln Gln Ser Lys Cys Arg Ala Ile Asp
                245                 250                 255

Pro Lys Lys Ile Glu Cys Pro Leu Glu Asn Leu Thr Val Tyr Thr Trp
            260                 265                 270

Pro Ala Pro Met Asp Phe Ser Gln Ser Leu Ile Ala Gln Arg Ala Leu
        275                 280                 285

Ser Asp Lys His Arg Gln Leu Leu Ser Arg Leu Gln Pro Leu Gln Ile
290                 295                 300

Thr Pro Leu Arg Lys Gln Gly Met Glu Asp Pro Val Trp Gly Val Pro
305                 310                 315                 320

Leu Ser Leu Lys

<210> SEQ ID NO 63
<211> LENGTH: 965
<212> TYPE: PRT
<213> ORGANISM: Pseudomonas aeruginosa

<400> SEQUENCE: 63

Ala Tyr Val Glu Ala Gly Arg Pro Gly Asp Pro Ala Ser Trp Arg Ser
1               5                   10                  15

Ala Glu Tyr Gln Gln Asp Trp Gly Leu Glu Arg Met Arg Ala Asp Gln
                20                  25                  30

Ala Tyr Ala Ala Gly Ile Asp Gly Gln Gly Val Lys Ile Gly Glu Met

```
                35                  40                  45
Asp Ser Gly Phe Asp Pro Ser His Pro Asp Thr Pro Ala Ser Arg Tyr
 50                  55                  60
Gln Pro Val Thr Ala Ser Gly Thr Tyr Val Asp Gly Thr Pro Phe Ser
 65                  70                  75                  80
Val Ser Gly Ala Met Asn Gly Asn Asn Asp Ser His Gly Thr His Val
                 85                  90                  95
Gly Gly Thr Leu Gly Ala Ser Arg Asp Gly Val Gly Met His Gly Val
                100                 105                 110
Ala Tyr Ala Ala Gln Val Tyr Val Ala Asn Thr Asn Gln Asn Asp Ser
                115                 120                 125
Phe Leu Phe Gly Pro Thr Pro Asp Pro Asn Tyr Phe Lys Ala Ala Tyr
130                 135                 140
Gln Ala Leu Ala Asp Ala Gly Val Arg Ala Ile Asn Asn Ser Trp Gly
145                 150                 155                 160
Ser Gln Pro Lys Asp Val Ser Tyr Glu Thr Leu Asp Gly Leu His Ala
                165                 170                 175
Ala Tyr Ala Gln His Tyr Gly Arg Ser Thr Trp Leu Asp Ala Ala Ala
                180                 185                 190
Gly Val Ser Arg Gln Gly Val Ile Asn Val Phe Ser Ala Gly Asn Ser
                195                 200                 205
Gly Tyr Ala Asn Ala Ser Val Arg Ser Ala Leu Pro Tyr Phe Gln Pro
                210                 215                 220
Asp Leu Glu Gly His Trp Leu Ala Val Ser Gly Leu Asp Gln Asn
225                 230                 235                 240
Gly Gln Arg Tyr Asn Arg Cys Gly Ile Ala Lys Tyr Trp Cys Ile Thr
                245                 250                 255
Thr Pro Gly Arg Leu Ile Asn Ser Thr Met Pro Gly Gly Gly Tyr Ala
                260                 265                 270
Asn Lys Ser Gly Thr Ser Met Ala Ala Pro His Ala Thr Gly Ala Leu
                275                 280                 285
Ala Leu Val Met Gln Arg Tyr Pro Tyr Leu Asn Asn Glu Gln Ala Leu
                290                 295                 300
Gln Val Leu Leu Thr Thr Ala Thr Gln Leu Asp Gly Thr Pro Thr Gly
305                 310                 315                 320
Ala Pro Thr Asp Thr Val Gly Trp Gly Val Pro Asp Leu Gly Arg Ala
                325                 330                 335
Met His Gly Pro Gly Gln Leu Leu Gly Arg Phe Glu Ala Asn Leu Pro
                340                 345                 350
Ala Gly Leu Arg Asp Glu Trp Ser Asn Pro Ile Ser Asp Ser Ala Leu
                355                 360                 365
Leu Gln Arg Gln Ala Glu Asp Ala Ala Glu His Ala Ala Trp Gln Arg
                370                 375                 380
Thr Leu Lys Asp Lys Gly Trp Glu Asn Gly Leu Pro Ala Gly Ala Ser
385                 390                 395                 400
Gln Gln Glu Arg Thr Asp Tyr Ala Ile Gly Met Ala Arg Asp Gln Ala
                405                 410                 415
Ala Ala Gln Arg Gln Tyr Gln Ser Leu Val Lys Ala Gly Ala Gly
                420                 425                 430
Ser Leu Val Leu Ser Gly Asp Ser Thr Tyr Arg Gly Pro Thr Leu Val
                435                 440                 445
Asp Gly Gly Leu Leu Ser Val Asp Gly Ser Leu Leu Ser Ala Val Glu
                450                 455                 460
```

```
Val Asn Ala Gly Gly Thr Leu Gly Gly Ser Gly Arg Ile Gly Gly Leu
465                 470                 475                 480

Leu Ala Arg Ser Gly Gly Thr Val Ala Ala Gly Asn Ser Ile Gly Thr
                485                 490                 495

Leu Glu Val Ala Gly Asp Leu Arg Phe Glu Ser Gly Ser Thr Tyr Ala
            500                 505                 510

Val Glu Leu Ser Glu Ser Ala Ser Asp Arg Ile Val Ala Ser Gly Lys
            515                 520                 525

Ala Ser Ile Ala Gly Gly Asn Val Thr Leu Ala Met Glu Asn Ser Pro
            530                 535                 540

Asp Leu Leu Ser Gln Ser Gln Val Glu Ser Leu Val Gly Arg Arg Tyr
545                 550                 555                 560

Asp Ile Leu Asp Ala Ala Gly Ile Asp Gly Arg Phe Asp Ala Val
                565                 570                 575

Leu Pro Asn Tyr Leu Phe Leu Gly Gly Thr Leu Asp Tyr Ala Ala Asn
                580                 585                 590

Ala Ile Arg Leu Asp Ile Gly Arg Asn Gly Thr Thr Leu Ala Ser Val
                595                 600                 605

Ala Gln Thr Pro Asn Gln Ala Ala Val Ala Gly Ala Val Glu Thr Leu
                610                 615                 620

Gly Ala Gly Asn Pro Val Tyr Glu Ser Leu Leu Leu Ser Glu Asn Ala
625                 630                 635                 640

Ala Thr Ala Gln Arg Ala Phe Gln Gln Leu Ser Gly Glu Ile Tyr Pro
                645                 650                 655

Ala Leu Ala Gly Leu Leu Leu Asn Asp Ser Arg Tyr Leu Arg Asp Ser
                660                 665                 670

Val Gly Glu Arg Leu Arg Gln Thr Ser Asp Gly Glu Ala Gly Gly Glu
                675                 680                 685

Ala Pro Glu Gly Trp Phe Lys Ala Leu Gly Ser Trp Gly Lys Ser Ala
                690                 695                 700

Asp Gly Ser His Gly Ser Glu Gly Tyr Arg His Ser Val Gly Gly Phe
705                 710                 715                 720

Leu Leu Gly Val Asp Ser Gln Val Ala Ser Asp Thr Arg Leu Gly Leu
                725                 730                 735

Val Ala Gly Tyr Ser Asn Ser Ser Leu Asn Met Asp Ser Ser Leu Gln
                740                 745                 750

Ser Ser Ala Ser Ile Asp Ser Tyr His Leu Gly Ala Tyr Leu Gly Arg
                755                 760                 765

Gln Leu Gln Gln Trp Arg Leu Ser Leu Gly Ala Ala His Ala Trp His
                770                 775                 780

Arg Ala Glu Val Lys Arg Asp Leu Gln Tyr Gly Ala Val Ala Gly Lys
785                 790                 795                 800

Gln Lys Ala Lys Leu Asp Ala Gln Ser Ser Gln Leu Phe Ala Glu Ala
                805                 810                 815

Ala Tyr Ala Leu Gly Trp Arg Ser Leu Glu Leu Glu Pro Phe Ala Gly
                820                 825                 830

Leu Ala Tyr Val His Val Ala Ser Asp Asp Phe Arg Glu Arg Gly Ser
                835                 840                 845

Ala Ala Ala Leu Glu Gly Gly Asp Asp Asn Leu Asp Ala Ala Phe Thr
                850                 855                 860

Thr Leu Gly Leu Arg Ala Lys Arg His Phe Glu Leu Asp Ala Gly Arg
865                 870                 875                 880
```

```
Arg Leu Ala Leu Ser Gly Thr Leu Gly Trp Arg His Asn Leu Ser Asp
                885                 890                 895

Thr Thr Pro Gln Arg His Leu Ala Phe Ala Ser Gly Ser Gln Pro Phe
            900                 905                 910

Ser Val Glu Ser Val Ala Leu Ser Arg Asp Ala Ala Leu Leu Gly Val
        915                 920                 925

Asp Ala Ser Leu Ala Val Asn Arg Glu Val Ser Val Arg Leu Gly Tyr
    930                 935                 940

Asn Gly Leu Leu Gly Ser Arg Glu Lys Asp His Gly Val Gly Leu Ala
945                 950                 955                 960

Val Asp Trp Arg Phe
                965

<210> SEQ ID NO 64
<211> LENGTH: 143
<212> TYPE: PRT
<213> ORGANISM: Pseudomonas aeruginosa

<400> SEQUENCE: 64

Asp Ala Pro Gly Gly Ala Gly Cys Gly Trp Gly Asn Met Leu Phe Lys
1               5                   10                  15

Gly Gln Arg Gly Val Ala Thr His Val Val Ala Ala Thr Thr Asn Gly
            20                  25                  30

Thr Ser Gly Asn Asn Thr Phe Gly Met Thr Thr Gly Thr Asn Gly Cys
        35                  40                  45

His Thr Asn Gly Ala Leu Ser Tyr Gly Gly Lys Pro Leu Leu Val Leu
    50                  55                  60

Gly Ser Met Met Asp Glu Leu Ser Glu Asp Met Ala Lys Gly Asn Gly
65                  70                  75                  80

Glu Ala Leu Thr Thr Tyr Ala Val Val Leu Gly Val Gln Pro Gln Asp
                85                  90                  95

Arg Glu His Phe Ala Ala Val Thr His Glu His Phe Ser Glu Ile Phe
            100                 105                 110

Asn Lys Ser Asp Ala Thr Ala Ala Asp Val Tyr Ala Asn Thr Gln Ala
        115                 120                 125

Ile Leu Lys Gln Asp Ala Arg Leu Ala Lys Tyr Ala Glu Gln Ala
    130                 135                 140

<210> SEQ ID NO 65
<211> LENGTH: 559
<212> TYPE: PRT
<213> ORGANISM: Pseudomonas aeruginosa

<400> SEQUENCE: 65

Cys Gln Ser Leu Ile His Lys Thr Pro Asp Gly Thr Pro Pro Val Glu
1               5                   10                  15

Asp Thr Ala Val Glu Thr Lys Ala Lys Pro Glu Lys Tyr Gly Ser Phe
            20                  25                  30

Ser Glu Asp Ser Leu Tyr Ser Leu Val Ala Glu Leu Ala Gly Gln
        35                  40                  45

Arg Asn Arg Phe Asp Ile Ala Leu Ser Asn Tyr Val Val Gln Ala Gln
    50                  55                  60

Lys Thr Arg Asp Pro Gly Val Ser Glu Arg Ala Phe Arg Ile Ala Glu
65                  70                  75                  80

Tyr Leu Gly Ala Asp Gln Glu Ala Leu Asp Thr Ser Leu Leu Trp Ala
                85                  90                  95
```

```
Arg Ser Ala Pro Asp Asn Leu Asp Ala Gln Arg Ala Ala Ile Gln
                100                 105                 110

Leu Ala Arg Ala Gly Arg Tyr Glu Glu Ser Met Val Tyr Met Glu Lys
            115                 120                 125

Val Leu Asn Gly Gln Gly Asp Thr His Phe Asp Phe Leu Ala Leu Ser
        130                 135                 140

Ala Ala Glu Thr Asp Pro Asp Thr Arg Ala Gly Leu Leu Gln Ser Phe
145                 150                 155                 160

Asp His Leu Leu Lys Lys Tyr Pro Asn Asn Gly Gln Leu Leu Phe Gly
                165                 170                 175

Lys Ala Leu Leu Leu Gln Gln Asp Gly Arg Pro Asp Glu Ala Leu Thr
            180                 185                 190

Leu Leu Glu Asp Asn Ser Ala Ser Arg His Glu Val Ala Pro Leu Leu
        195                 200                 205

Leu Arg Ser Arg Leu Leu Gln Ser Met Lys Arg Ser Asp Glu Ala Leu
    210                 215                 220

Pro Leu Leu Lys Ala Gly Ile Lys Glu His Pro Asp Asp Lys Arg Val
225                 230                 235                 240

Arg Leu Ala Tyr Ala Arg Leu Leu Val Glu Gln Asn Arg Leu Asp Asp
                245                 250                 255

Ala Lys Ala Glu Phe Ala Gly Leu Val Gln Gln Phe Pro Asp Asp Asp
            260                 265                 270

Asp Leu Arg Phe Ser Leu Ala Leu Val Cys Leu Glu Ala Gln Ala Trp
        275                 280                 285

Asp Glu Ala Arg Ile Tyr Leu Glu Glu Leu Val Glu Arg Asp Ser His
    290                 295                 300

Val Asp Ala Ala His Phe Asn Leu Gly Arg Leu Ala Glu Glu Gln Lys
305                 310                 315                 320

Asp Thr Ala Arg Ala Leu Asp Glu Tyr Ala Gln Val Gly Pro Gly Asn
                325                 330                 335

Asp Phe Leu Pro Ala Gln Leu Arg Gln Thr Asp Val Leu Leu Lys Ala
            340                 345                 350

Gly Arg Val Asp Glu Ala Ala Gln Arg Leu Asp Lys Ala Arg Ser Glu
        355                 360                 365

Gln Pro Asp Tyr Ala Ile Gln Leu Tyr Leu Ile Glu Ala Glu Ala Leu
    370                 375                 380

Ser Asn Asn Asp Gln Gln Gly Lys Ala Trp Gln Ala Ile Gln Glu Gly
385                 390                 395                 400

Leu Lys Gln Tyr Pro Glu Asp Leu Asn Leu Leu Tyr Thr Arg Ser Met
                405                 410                 415

Leu Ala Glu Lys Arg Asn Asp Leu Ala Gln Met Glu Lys Asp Leu Arg
            420                 425                 430

Phe Val Ile Ala Arg Glu Pro Asp Asn Ala Met Ala Leu Asn Ala Leu
        435                 440                 445

Gly Tyr Thr Leu Ala Asp Arg Thr Thr Arg Tyr Gly Glu Ala Arg Glu
    450                 455                 460

Leu Ile Leu Lys Ala His Lys Leu Asn Pro Asp Asp Pro Ala Ile Leu
465                 470                 475                 480

Asp Ser Met Gly Trp Ile Asn Tyr Arg Gln Gly Lys Leu Ala Asp Ala
                485                 490                 495

Glu Arg Tyr Leu Arg Gln Ala Leu Gln Arg Tyr Pro Asp His Glu Val
            500                 505                 510

Ala Ala His Leu Gly Glu Val Leu Trp Ala Gln Gly Arg Gln Gly Asp
```

```
            515                 520                 525
Ala Arg Ala Ile Trp Arg Glu Tyr Leu Asp Lys Gln Pro Asp Ser Asp
        530                 535                 540

Val Leu Arg Arg Thr Ile Lys Arg Leu Thr Gly Ala Glu Thr Pro
545                 550                 555
```

<210> SEQ ID NO 66
<211> LENGTH: 8
<212> TYPE: PRT
<213> ORGANISM: Artificial Sequence
<220> FEATURE:
<223> OTHER INFORMATION: Synthetic peptide

<400> SEQUENCE: 66

```
Met Ala His His His His His His
 1               5
```

<210> SEQ ID NO 67
<211> LENGTH: 6
<212> TYPE: PRT
<213> ORGANISM: Artificial Sequence
<220> FEATURE:
<223> OTHER INFORMATION: Synthetic peptide

<400> SEQUENCE: 67

```
Gly Ser Gly Gly Gly Gly
 1               5
```

<210> SEQ ID NO 68
<211> LENGTH: 8
<212> TYPE: PRT
<213> ORGANISM: Artificial Sequence
<220> FEATURE:
<223> OTHER INFORMATION: Synthetic peptide

<400> SEQUENCE: 68

```
Gly Ser Gly Ser Gly Gly Gly Gly
 1               5
```

<210> SEQ ID NO 69
<211> LENGTH: 6
<212> TYPE: PRT
<213> ORGANISM: Artificial Sequence
<220> FEATURE:
<223> OTHER INFORMATION: Synthetic peptide

<400> SEQUENCE: 69

```
Ala Ser Gly Gly Gly Ser
 1               5
```

<210> SEQ ID NO 70
<211> LENGTH: 6
<212> TYPE: PRT
<213> ORGANISM: Artificial Sequence
<220> FEATURE:
<223> OTHER INFORMATION: Synthetic 6xHis tag

<400> SEQUENCE: 70

```
His His His His His His
 1               5
```

<210> SEQ ID NO 71
<211> LENGTH: 10
<212> TYPE: PRT
<213> ORGANISM: Artificial Sequence
<220> FEATURE:

```
<223> OTHER INFORMATION: Synthetic peptide
<220> FEATURE:
<221> NAME/KEY: VARIANT
<222> LOCATION: (1)...(10)
<223> OTHER INFORMATION: This sequence may encompass 2 to 10 residues,
      wherein some positions may be absent
<220> FEATURE:
<221> NAME/KEY: VARIANT
<222> LOCATION: (1)...(10)
<223> OTHER INFORMATION: Variant residues given in the sequence have no
      preference with respect to those in the
      annotations for variant positions

<400> SEQUENCE: 71

Gly Gly Gly Gly Gly Gly Gly Gly Gly Gly
  1               5                  10

<210> SEQ ID NO 72
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)...(10)
<223> OTHER INFORMATION: This sequence may encompass 3 to 10 residues,
      wherein some positions may be absent
<220> FEATURE:
<221> NAME/KEY: VARIANT
<222> LOCATION: (1)...(10)
<223> OTHER INFORMATION: Variant residues given in the sequence have no
      preference with respect to those in the
      annotations for variant positions

<400> SEQUENCE: 72

His His His His His His His His His His
  1               5                  10

<210> SEQ ID NO 73
<211> LENGTH: 4
<212> TYPE: PRT
<213> ORGANISM: Artificial Sequence
<220> FEATURE:
<223> OTHER INFORMATION: Synthetic peptide

<400> SEQUENCE: 73

Gly Gly Gly Gly
  1
```

PSEUDOMONAS ANTIGENS AND ANTIGEN COMBINATIONS

CROSS REFERENCE TO RELATED APPLICATIONS

This application is a U.S. National Phase patent application of PCT/EP2013/074846, filed Nov. 27, 2013, which claims priority to United Kingdom provisional application 1221638.8, filed Nov. 30, 2012, all of which are hereby incorporated by reference in the present disclosure in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 529552005200SEQLIST.txt, date recorded: May 26, 2015, size: 228 KB).

TECHNICAL FIELD

This invention relates to antigens derived from *P. aeruginosa* and to their use in immunisation.

BACKGROUND ART

*Pseudomonas aeruginosa*, an opportunistic gram-negative bacterial pathogen found in most environments including water reservoirs and soil, is one of the leading nosocomial pathogen worldwide. This Gram-negative bacterium is best known for being the leading cause of morbidity and mortality in cystic fibrosis (CF) patients, with 80% of adult CF patients carrying *P. aeruginosa* in their lungs [1], and has recently gained notoriety by being classified as a 'superbug' by the media. The latter emanates from the intrinsic resistance that this opportunistic pathogen has against antibiotics [2], and its prominence as a cause of nosocomial infections (i.e. there are an estimated 10.000 cases each year in UK hospitals) [3].

Despite considerable advances in antimicrobial therapy, effective treatment and control of *P. aeruginosa* infections remains a persistent problem, primarily because of the natural resistance of the organism and its remarkable ability to acquire resistance to multiple antimicrobial agents by various mechanisms.

A vaccine against *P. aeruginosa* has long been sought after, but is so far not available. Several vaccine candidates have been assessed in experimental animals and humans, which include sub-cellular fractions, capsule components, purified and recombinant proteins.

Unique characteristics of the host and the pathogen have complicated the vaccine development.

Reference 4 reports a recombinant protein based vaccine approach on a single fusion polypeptide obtained by the fusion of two fragments of two outer membrane derived proteins, namely OprF and OprI. This vaccine is undergoing clinical trials [5], and further details are disclosed in ref 6.

Thus there remains a need to identify further and improved antigens for use as single antigens or in combinations in *P. aeruginosa* vaccines, and in particular for vaccines which are useful against multiple *P. aeruginosa* pathologies, comprising e.g. cystic fibrosis. Summing up, there is still the need to obtain an effective vaccine against *P. aeruginosa*.

DISCLOSURE OF THE INVENTION

The inventors have identified various *P. aeruginosa* polypeptides that are useful for immunisation, either alone or in combination. These polypeptides may be combined with *P. aeruginosa* saccharides or other *P. aeruginosa* polypeptides or antigens derived from other pathogens (i.e. *S. aureus, E. coli*, etc). The antigens are useful in *P. aeruginosa* vaccines but may also be used as components in vaccines for immunising against multiple pathogens.

The inventors have identified in total the following polypeptides:

a PSE54 (PA5340) antigen; a PSE44-4 (PA3526) antigen; a PSE10-1 (PA1178) antigen; a PSE21-5 (PA5112) antigen; a PSE27-1 (PA0328) antigen; a PSE52-1 (PA4765) antigen; a PSE53-1 (PA5047) antigen; PSE11-3 (PA1248) antigen; a PSE41-5 (PA2407) antigen; a PSE47A-2 (PA4082); PSE5-1 (PA0595); PSE13-2 (PA1954); PSE17-1 (PA3692); PSE18-2 (PA4370); PSE20-1 (PA4735); PSE23-1 (PA3647); PSE24-1 (PA0126); PSE25-1 (PA0189); PSE26-1 (PA0274); PSE28-2 (PA0537); PSE31-2 (PA0737); PSE33-2 (PA1086); PSE42-1 (PA2793); PSE45-2 (PA3535); PSE50-1 (PA4578); PSE51-4 (PA4667); PSE19-1 (PA4710); PSE34-1 (PA1106); PSE36-3 (PA1324); PSE38-1 (PA1777).

Amongst the total set of selected antigens it can be distinguished a 'first antigen group' which is described as a group of antigens for which no prior attempts have been made to test them as vaccine antigens. The "first antigen group" comprises 25 out of the 30 selected antigens.

In particular the "first antigen group" comprises the following antigens: a PSE54 (PA5340) antigen; a PSE44-4 (PA3526) antigen; a PSE21-5 (PA5112) antigen; a PSE27-1 (PA0328) antigen; a PSE53-1 (PA5047) antigen; a PSE41-5 (PA2407) antigen; a PSE47A-2 (PA4082) antigen; a PSE5-1 (PA0595) antigen; a PSE13-2 (PA1954) antigen; a PSE17-1 (PA3692) antigen; a PSE18-2 (PA4370) antigen; a PSE20-1 (PA4735) antigen; a PSE23-1 (PA3647) antigen; a PSE24-1 (PA0126) antigen; a PSE25-1 (PA0189) antigen; a PSE26-1 (PA0274) antigen; a PSE28-2 (PA0537) antigen; a PSE31-2 (PA0737) antigen; a PSE33-2 (PA1086) antigen; a PSE42-1 (PA2793) antigen; a PSE45-2 (PA3535) antigen; a PSE50-1 (PA4578) antigen; a PSE51-4 (PA4667) antigen; a PSE34-1 (PA1106) antigen; and a PSE36-3 antigen (PA1324).

Thus the invention provides an immunogenic composition comprising one or more (i.e. 1, 2, 3, 4, 5 or more) antigens selected from the first antigen group.

Within the first antigen group, antigens are preferably selected from the list of a PSE54 (PA5340) antigen, PSE21-5 (PA5112) antigen; a PSE27-1 (PA0328) antigen; a PSE41-5 (PA2407) antigen; a PSE44-4 (PA3526) antigen; a PSE47A-2 (PA4082) antigen; and/or a PSE53-1 (PA5047) antigen.

Within the 'first antigen group', antigens are preferably selected from a subset of 5 polypeptides, and particularly useful in producing a protective immunogenic response in vivo if used as single antigens or in combinations are: a PSE54 (PA5340) antigen; a PSE44-4 (PA3526) antigen; a PSE21-5 (PA5112) antigen; a PSE53-1 (PA5047) antigen; PSE42-1 (PA2793).

Within the first antigen group, all the listed antigens can be selected as single antigens for use against *P. aeruginosa*, with the proviso that the PSE27-1 (PA0328) antigen can be usefully omitted from this list ('first antigen group').

A "second antigen group" is defined as a group of identified antigens which has already been proposed as possible immunogenic stand-alone vaccine antigen but never considered in combination of at least two (i.e. 2, 3, 4, 5, 6 or more) antigens in in vivo experiments. A subset of the "second antigen group" is defined as the "further antigenic polypeptides" group and comprises those antigenic polypeptides that have been extensively tested as vaccine antigens in vivo.

The second antigen group comprises the following list of antigens: PSE10-1 (PA1178) antigen; PSE11-3 (PA1248) antigen; PSE52-1 (PA4765) antigen; PSE19-1 (PA4710) antigen; and PSE38-1 (PA1777) antigen.

The subset of the second antigen group defined as "further antigenic polypetides" group comprises the following list of antigens: PilA (PA4524), OprF-OprI, FliC (PA1092), FliD (PA1094) and/or Exoprotein A (PA1148). Hence, the "second antigen group" comprises 10 polypeptides in total.

Thus the invention provides an immunogenic composition comprising a combination of antigens, said combination comprising two or more (i.e. 2, 3, 4, 5, 6 or more) antigens selected from the group consisting of: a PSE54 (PA5340) antigen; a PSE44-4 (PA3526) antigen; a PSE10-1 (PA1178) antigen; a PSE21-5 (PA5112) antigen; a PSE27-1 (PA0328) antigen; a PSE52-1 (PA4765) antigen; a PSE53-1 (PA5047) antigen; PSE11-3 (PA1248) antigen; a PSE41 (PA2407) antigen; a PSE47A-2 (PA4082); PSE5-1 (PA0595); PSE13-2 (PA1954); PSE17-1 (PA3692); PSE18-2 (PA4370); PSE20-1 (PA4735); PSE23-1 (PA3647); PSE24-1 (PA0126); PSE25-1 (PA0189); PSE26-1 (PA0274); PSE28-2 (PA0537); PSE31-2 (PA0737); PSE33-2 (PA1086); PSE42-1 (PA2793); PSE45-2 (PA3535); PSE50-1 (PA4578); PSE51-4 (PA4667); PSE19-1 (PA4710); PSE34-1 (PA1106); PSE36-3 (PA1324); PSE38-1 (PA1777).

Within the first antigen group, antigens are preferably selected from a subset of 7 of 30 polypeptides, namely: PSE54 (PA5340), PSE47A-2 (PA4082), PSE41-5 (PA2407), PSE53-1 (PA5047), PSE21-5 (PA5112), PSE27-1 (PA0328) or PSE44-4 (PA3526) antigens and a subset of the "second antigen group", namely: PSE52-1 (PA4765), PSE10-1 (PA1178), PSE11-3 (PA1248) and the OprF-OprI which is selected from the subset of the 'second antigen group' defined as "further antigenic polypeptides" group. Thus the invention provides an immunogenic composition comprising a combination of antigens, said combination comprising two or more (i.e. 2, 3, 4, 5, 6 or more) antigens selected from the group consisting of these eleven antigens.

Within the 11 antigens selected from the first, the second and the further antigenic polypeptides group there are 55 possible pairs of antigen combinations.

Within the 'second antigen group', comprising the subset of 5 polypeptides referred to herein as 'the further antigenic polypeptides", there are in total 10 polypeptides. The invention provides an immunogenic composition comprising a combination of antigens, said combination comprising a mixture of two or more (i.e. 2, 3, 4, 5, 6 or more) antigens selected from any of the preferred antigens of the "first antigen group" with anyone of the "second antigen group" or "further antigenic polypeptides" group.

The invention provides an immunogenic composition comprising a combination of antigens, said combination comprising a mixture of two or more (i.e. 2, 3, 4, 5, 6 or more) antigens selected from any antigens from the first antigen group and the second antigen group.

Within the 30 antigens of the mixture of the first antigen group and second antigen group there are 435 possible pairs of different antigens. All such pairs are disclosed herein and are part of the invention. Thus the invention provides an immunogenic composition comprising a pair of antigens, wherein said pair is one of said 435 pairs.

Within the 35 antigens of the mixture of the first antigen group and second antigen group there are 595 possible pairs of different antigens. All such pairs are disclosed herein and are part of the invention. Thus the invention provides an immunogenic composition comprising a pair of antigens, wherein said pair is one of said 595 pairs.

In one embodiment, a composition includes at least one antigen (i.e. 1, 2, 3, 4, 5, 6 or more) selected from the first antigen group and at least one antigen (i.e. 1, 2, 3, 4, 5, 6 or more) selected from the second antigen group. Antigens from the first antigen group may be selected from the preferred subset of PSE54 (PA5340), PSE47A-2 (PA4082), PSE41-5 (PA2407), PSE53-1 (PA5047), PSE21-5 (PA5112), or PSE44-4 (PA3526) antigens, and antigens from the second antigen group can be selected from PSE52-1 (PA4765), PSE10-1 (PA1178) or from any of the further antigenic polypeptide sub-set of the second antigen group, preferring the fusion OprF-OprI.

The invention also provides an immunogenic composition comprising a combination of antigens, said combination comprising two or more (i.e. 2, 3, 4 or 5) antigens selected from the group consisting of: (1) a PSE54 antigen; (2) a PSE10-1 antigen; (3) a PSE44-4 antigen; (4) a PSE52-1 antigen; (5) a PSE53-1 antigen; (6) a PSE21-5 antigen; (7) a PSE27-1 antigen; (8) a PSE47A-2 antigen; and/or (9) an OprF-OprI antigen.

Within the preferred 9 antigens selected from the first antigen group, the second antigen group and/or the further antigen group there are 36 possible pairs of different antigens. All such pairs are disclosed herein and are part of the invention. Thus the invention provides an immunogenic composition comprising a pair of antigens, wherein said pair is one of said 36 pairs.

The composition may also include an adjuvant e.g. an aluminium hydroxide adjuvant.

Advantageous combinations of the invention are those in which two or more antigens act synergistically. Thus the protection against *P. aeruginosa* disease achieved by their combined administration exceeds that expected by mere addition of their individual protective efficacy.

Specific combinations of interest include, but are not limited to:

(1) An immunogenic composition comprising a PSE54 antigen, a PSE27 antigen (2) An immunogenic composition comprising a PSE54 antigen and OprF-OprI antigen (3) An immunogenic composition comprising a PSE54 antigen, a PSE27 antigen and/or a OprF-OprI antigen (4) An immunogenic composition comprising PSE54 antigen and/or a PSE44 antigen (5) An immunogenic composition comprising PSE54 antigen and/or PSE21-5 antigen (6) An immunogenic composition comprising PSE54 antigen and/or PSE52-1 antigen (7) An immunogenic composition comprising PSE47A-2 antigen and/or PSE53-1 antigen (8) An immunogenic composition comprising PSE54 antigen and/or PSE10-1 antigen (9) An immunogenic composition comprising PSE54 and PSE53-1 antigen

(10) An immunogenic composition comprising PSE47A-2 and PSE52-1 antigen

(11) An immunogenic composition comprising PSE54 antigen and/or PSE44-4 antigen and/or PSE47A-2 antigen

(12) An immunogenic composition comprising a PSE47A-2 antigen, a PSE53-1 antigen, or a PSE54 antigen and/or a PSE27 antigen.

(13) An immunogenic composition comprising (a) a PSE47A-2 antigen combined with a PSE53-1 antigen, or (b) a PSE54 antigen combined with a PSE21-5 antigen.

(14) An immunogenic composition comprising a PSE47A-2 antigen and/or PSE52 antigen.

In some embodiments, any of these immunogenic and protective compositions may include additional *pseudomonas* antigens, and these further antigens can be polypeptides and/or saccharides. For example, they can useful also include one or more *Pseudomonas antigens* belonging to the "second antigen group" which includes the "further antigenic polypeptides" group, which include the fusion polypeptide OprF-OprI in a synergistic manner.

The immunogenic composition may also include an adjuvant.

Further Polypeptide Antigens Group

In additions to antigens from the various antigen groups of the invention, immunogenic compositions may include one or more of the following *P. aeruginosa* antigens (or antigens comprising immunogenic fragment(s) thereof to enhance the efficacy against *P. aeruginosa* of an immune response elicited by the composition:

OprF-OprI [4]
PA4525, known also as PilA
PA1092, known also as FliC
PA1094, known also as FliD
PA1148, Exoprotein A or Exotoxin A The "further antigenic polypeptides" group is defined as a subgroup of the second antigen group. This group of known antigens can be useful used in combination with 1, 2 or more other useful antigens of the first antigen group or the second antigen group.

Combinations with Other *P. aeruginosa* Derived Antigens

The individual antigens identified in the antigen groups of the invention may be used in combination with other antigens from *P. aeruginosa*. In some embodiments the other antigens from *P. aeruginosa* can be in the form of saccharides conjugated with a carrier protein. Thus the invention provides an immunogenic composition comprising a combination of:

(1) one or more antigen(s) selected from the first, second, or further antigen groups (as defined above); and/or their combination or admixture and (2) one or more conjugates of a saccharide moiety, and a carrier protein.

A conjugate used in component (2) of this combination includes a saccharide moiety and a carrier moiety.

In embodiments of the invention, the composition further comprises the *P. aeruginosa* 5-hexose Psl polysaccharide, which can be present as free polysaccharide and/or conjugated to a carrier protein. Optionally, one or more flagellin adjuvants and/or fusion proteins of the invention act as the carrier protein and have Psl polysaccharide conjugated thereto. For example, monomers and/or dimers of the *P. aeruginosa* polysaccharide can be conjugated to one or more of the flagellin adjuvants and/or fusion proteins. See reference 7.

A conjugate used in component (2) of this combination includes a saccharide moiety and a carrier moiety. The saccharide moiety is from the exopolysaccharide of a *P. aeruginosa*. The saccharide may be a polysaccharide having the size that arises during purification from bacteria, or it may be an oligosaccharide achieved by fragmentation of such a polysaccharide.

The invention also provides an immunogenic composition comprising a combination of:

(1) one or more antigen(s) selected from the first, second, or further antigen groups;

(2) one or more conjugates of a *P. aeruginosa* exopolysaccharide and a carrier protein.

The carrier moiety in these conjugates will usually be a protein, but usually not one of the antigens of (1).

Typical carrier proteins are bacterial toxins, such as diphtheria or tetanus toxins, or toxoids or mutants or fragments thereof. The CRM197 diphtheria toxin mutant [8] is useful. Other suitable carrier proteins include the *N. meningitidis* outer membrane protein complex [9], synthetic peptides [10], heat shock proteins [11], pertussis proteins [12], cytokines [13], lymphokines [13], growth factors [13], artificial proteins comprising multiple human CD4$^+$ T cell epitopes from various pathogen-derived antigens [14] such as N19 [15], protein D from *H. influenzae* 16, pneumolysin [17] or its non-toxic derivatives [18], pneumococcal surface protein PspA [19], iron-uptake proteins [20], toxin A or B from *C. difficile* [21], recombinant *P. aeruginosa* exoprotein A (rEPA) [22], etc. In some embodiments the carrier protein is a *P. aeruginosa* protein, such as an antigen selected from the first, second, or further antigen groups.

Where a composition includes more than one conjugate, each conjugate may use the same carrier protein or a different carrier protein.

Conjugates may have excess carrier (w/w) or excess saccharide (w/w). In some embodiments, a conjugate may include substantially equal weights of each.

The carrier molecule may be covalently conjugated to the carrier directly or via a linker. Direct linkages to the protein may be achieved by, for instance, reductive amination between the saccharide and the carrier, as described in, for example, references 23 and 24. The saccharide may first need to be activated e.g. by oxidation. Linkages via a linker group may be made using any known procedure, for example, the procedures described in references 25 and 26. A preferred type of linkage is an adipic acid linker, which may be formed by coupling a free —NH$_2$ group (e.g. introduced to a glucan by amination) with adipic acid (using, for example, diimide activation), and then coupling a protein to the resulting saccharide-adipic acid intermediate [27]. Another preferred type of linkage is a carbonyl linker, which may be formed by reaction of a free hydroxyl group of a saccharide CDI [28] followed by reaction with a protein to form a carbamate linkage. Other linkers include β-propionamido [29], nitrophenyl-ethylamine [30], haloacyl halides [31], glycosidic linkages [32], 6-aminocaproic acid [33], ADH [34], $C_4$ to $C_{12}$ moieties [35], etc. Carbodiimide condensation can also be used [36].

The individual antigens identified in the antigen groups of the invention may be used as carrier proteins for exopolysaccharides, to form a covalent conjugate. Thus the invention provides an immunogenic composition comprising a conjugate of (1) an antigen selected from the first, second, and further antigen groups and (2) a *P. aeruginosa* exopolysaccharide. These conjugates may be combined with any of the antigens disclosed herein.

Combinations with Other Pathogens Derived (Non-*Pseudomonas*) Antigens

The individual antigens identified in the antigen groups of the invention may be used also in combination with other pathogens derived antigens, i.e. non-*pseudomonas* antigens, and in particular with antigens from bacteria associated with nosocomial infections. Thus the invention provides an immunogenic composition comprising a combination of:

(1) one or more antigen(s) selected from the first, second, and further antigen groups (as defined above); and
(2) one or more antigen(s) selected from the pathogen group consisting of: *S. aureus* (including one or more conjugates of (i) a *S. aureus* exopolysaccharide; and/or one or more protein antigens of *S. aureus*); *Burkholderia cenocepacia* (e.g. O antigen lipopolysaccharide), *Clostridium difficile*; *Candida albicans*; and/or extraintestinal pathogenic *Escherichia coli*.

First Antigen Group
PA0328 or PSE27-1

The 'PA0328' antigen is annotated as 'outer membrane autotransporter'. In the PAO1 strain is annotated as 'hypothetical protein' and has amino acid sequence SEQ ID NO: 1 and described as PA0328 in reference 37. This sequence is annotated in NCBI as GI: 15595525. It has been recently demonstrated to be an autotransporter protein relevant in the virulence strategy adopted by *Pseudomonas aeruginosa* through its arginine-specific aminopeptidase activity, as in reference 38. Sometimes, PA0328 is referred to herein as 'PSE27-1' or as 'PSE27'.

Useful PA0328 antigens can elicit an antibody (e.g. when administered to a human) that recognises SEQ ID NO: 1 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 1; and/or (b) comprising a fragment of at least 'n' consecutive amino acids of SEQ ID NO: 1, wherein 'n' is 7 or more (e.g. 8, 10, 12, 14, 16, 18, 20, 25, 30, 35, 40, 50, 60, 70, 80, 90, 100, 150, 200, 250 or more). These PA0328 proteins include variants of SEQ ID NO: 1. Preferred fragments of (b) comprise an epitope from SEQ ID NO: 1. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25, 27, 28, 29, 30, 35, 40, 45, 49, 50 or more) from the N-terminus of SEQ ID NO: 1 while retaining at least one epitope of SEQ ID NO: 1. The final 40-50 C-terminal amino acids of SEQ ID NO: 1 can usefully be omitted. The first 22 N-terminal amino acids of SEQ ID NO: 1 can usefully be omitted. Other fragments omit one or more protein domains.

SEQ ID NO: 36 is a useful fragment of SEQ ID NO: 1 ('PA0328$_{22-647}$'). This fragment omits the leader peptide at the N-terminal portion to enable expression and purification.

PA5112 or PSE21-5

The 'PSE21-5' antigen is annotated as 'Esterase or EstA' in the PAO1 strain. In the PAO1 strain PSE21-5 is described as 'PA5112' and has amino acid sequence SEQ ID NO: 3. In the PAO1 strain its identifier in NCBI is GI: 15600305 See Ref. 37. Sometimes, PA5112 is referred to herein as 'PSE21-5' or 'PSE21'.

Useful PSE21-5 antigens can elicit an antibody (e.g. when administered to a human) that recognises SEQ ID NO: 3 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 3; and/or (b) comprising a fragment of at least 'n' consecutive amino acids of SEQ ID NO: 3, wherein 'n' is 7 or more (e.g. 8, 10, 12, 14, 16, 18, 20, 25, 30, 35, 40, 50, 60, 70, 80, 90, 100, 150, 200, 250 or more). These PSE21-5 proteins include variants of SEQ ID NO: 3. Preferred fragments of (b) comprise an epitope from SEQ ID NO: 3. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 3 while retaining at least one epitope of SEQ ID NO: 3. The final 40 C-terminal amino acids of SEQ ID NO: 3 can usefully be omitted. The first 24 N-terminal amino acids of SEQ ID NO: 3 can usefully be omitted. Other fragments omit one or more protein domains. PSE21-5 is naturally a long protein and so the use of fragments is helpful e.g. for purification, handling, fusion, expression, etc.

SEQ ID NO: 38 is a useful fragment of SEQ ID NO: 3 ('PSE21-5$_{25-646}$'). This fragment includes the most exposed domain of PSE21-5 and is more easily used at an industrial scale.

PA2407 or PSE41-5

The 'PSE41-5' antigen is annotated as 'probable adhesion protein'. In the PAO1 strain PSE41-5 is named PA2407 and has amino acid sequence SEQ ID NO: 5 (GI: 15597603). See Ref. 37. Sometimes, PA2407 is referred to herein as 'PSE41-5' or 'PSE41'. Sometimes, PA2407 is referred to herein as 'PSE41-5' or 'PSE41'.

Useful 'PSE41-5' antigens can elicit an antibody (e.g. when administered to a human) that recognises SEQ ID NO: 5 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 5; and/or (b) comprising a fragment of at least 'n' consecutive amino acids of SEQ ID NO: 5, wherein 'n' is 7 or more (e.g. 8, 10, 12, 14, 16, 18, 20, 25, 30, 35, 40, 50, 60, 70, 80, 90, 100, 150, 200, 250 or more). These 'PSE41-5' proteins include variants of SEQ ID NO: 5. Preferred fragments of (b) comprise an epitope from SEQ ID NO: 5. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 5 while retaining at least one epitope of SEQ ID NO: 5. The final 40 C-terminal amino acids of SEQ ID NO: 5 can usefully be omitted. The first 37 N-terminal amino acids of SEQ ID NO: 5 can usefully be omitted. Other fragments omit one or more protein domains. 'PSE41-5' is naturally a long protein and so the use of fragments is helpful e.g. for purification, handling, fusion, expression, etc.

SEQ ID NO: 40 is a useful fragment of SEQ ID NO: 5 ("PSE41-5'$_{38-317}$). This fragment includes the most exposed domain of 'PSE41-5' and is more easily used at an industrial scale. It also reduces the antigen's similarity with human proteins.

PA3526 or PSE44-4

The PSE44-4 antigen is annotated as 'probable outer membrane protein precursor'. In the PAO1 strain PSE44-4 is PA3526 and has amino acid sequence SEQ ID NO: 6 (GI: 15598722). See Ref 37. Sometimes, PA3526 is referred to herein as 'PSE44-4 or 'PSE44'.

Useful PSE44-4 antigens can elicit an antibody (e.g. when administered to a human) that recognises SEQ ID NO: 6 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 6; and/or (b) comprising a fragment of at least 'n' consecutive amino acids of SEQ ID NO: 6, wherein 'n' is 7 or more (e.g. 8, 10, 12, 14, 16, 18, 20, 25, 30, 35, 40, 50, 60, 70, 80, 90, 100, 150, 200, 250 or more). These PSE44-4 proteins include variants of SEQ ID NO: 6. Preferred fragments of (b) comprise an epitope from SEQ ID NO: 6. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 6 while retaining at least one epitope of SEQ ID NO: 6. The first 19 N-terminal amino acids of SEQ ID NO: 6 can usefully be omitted. Other fragments omit one or more protein domains. PSE44-4 is naturally a long protein and so the use of fragments is helpful e.g. for purification, handling, fusion, expression, etc.

SEQ ID NO: 41 is a useful fragment of SEQ ID NO: 6 ('PSE44-4$_{20-321}$'). This fragment includes the most exposed domain of PSE44-4 and is more easily used at an industrial scale. It also reduces the antigen's similarity with human proteins.

PA4082 or PSE47A-2

The PSE47A-2 antigen is annotated as 'adhesive protein CupB5' or as "Serine protease". In the PAO1 strain PSE47A-2 is named PA4082 and has amino acid sequence SEQ ID NO: 7 (GI: 15599277). See Ref 37. Sometimes, PA4082 is referred to herein as 'PSE47A' or 'PSE47A-2' (fragment).

Useful PSE47A-2 antigens can elicit an antibody (e.g. when administered to a human) that recognises SEQ ID NO: 7 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 7; and/or (b) comprising a fragment of at least 'n' consecutive amino acids of SEQ ID NO: 7, wherein 'n' is 7 or more (e.g. 8, 10, 12, 14, 16, 18, 20, 25, 30, 35, 40, 50, 60, 70, 80, 90, 100, 150, 200, 250 or more). These PSE47A-2 proteins include variants of SEQ ID NO: 7. Preferred fragments of (b) comprise an epitope from SEQ ID NO: 7. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 7 while retaining at least one epitope of SEQ ID NO: 7. Since the C-terminal portion of this protein is corresponding to the translocator domain, which is totally embedded in the outer membrane and therefore totally inaccessible to antibodies can be useful omitted. Hence, the final 435 C-terminal amino acids of SEQ ID NO: 7 can usefully be omitted. The first 53 N-terminal amino acids of SEQ ID NO: 7 can usefully be omitted. Other fragments omit one or more protein domains. PSE47A-2 is naturally a long protein and so the use of fragments is helpful e.g. for purification, handling, fusion, expression, etc.

SEQ ID NO: 42 is a useful fragment of SEQ ID NO: 7 ('PSE47A-2$_{54-583}$'). This fragment includes the most exposed domain of PSE47A-2 and is more easily used at an industrial scale. It also reduces the antigen's similarity with human proteins.

PA5047 or PSE53-1

The PSE53-1 antigen is annotated as 'hypothetical protein'. In the PAO1 strain PSE53-1 is PA5047 and has amino acid sequence SEQ ID NO: 9 (GI: 15600240). See Ref. 37. Sometimes, PA5047 is referred to herein as 'PSE53-1 or 'PSE53'.

Useful PSE53-1 antigens can elicit an antibody (e.g. when administered to a human) that recognises SEQ ID NO: 9 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 9; and/or (b) comprising a fragment of at least 'n' consecutive amino acids of SEQ ID NO: 9, wherein 'n' is 7 or more (e.g. 8, 10, 12, 14, 16, 18, 20, 25, 30, 35, 40, 50, 60, 70, 80, 90, 100, 150, 200, 250 or more). These PSE53-1 proteins include variants of SEQ ID NO: 9. Preferred fragments of (b) comprise an epitope from SEQ ID NO: 9. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 9 while retaining at least one epitope of SEQ ID NO: 9. The final 40 C-terminal amino acids of SEQ ID NO: 9 can usefully be omitted. The first 18 N-terminal amino acids of SEQ ID NO: 9 can usefully be omitted. Other fragments omit one or more protein domains. PSE53-1 is naturally a long protein and so the use of fragments is helpful e.g. for purification, handling, fusion, expression, etc.

SEQ ID NO: 44 is a useful fragment of SEQ ID NO: 9 ('PSE53-1$_{19-479}$'). This fragment includes the most exposed domain of PSE53-1 and is more easily used at an industrial scale. It also reduces the antigen's similarity with human proteins.

PA5340 or PSE54

The PSE54 antigen is annotated as 'probable outer membrane protein precursor' and as 'hypothetical protein'. In the PAO1 strain PSE54 is PA5340 and has amino acid sequence SEQ ID NO: 10 (GI:15598722). See Ref. 37. Sometimes, PA5340 is referred to herein as 'PSE54'.

Useful PSE54 antigens can elicit an antibody (e.g. when administered to a human) that recognises SEQ ID NO: 10 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 10; and/or (b) comprising a fragment of at least 'n' consecutive amino acids of SEQ ID NO: 10, wherein 'n' is 7 or more (e.g. 8, 10, 12, 14, 16, 18, 20, 25, 30, 35, 40, 50, 60, 70, 80, 90, 100, 150, 200, 250 or more). These PSE54 proteins include variants of SEQ ID NO: 10. Preferred fragments of (b) comprise an epitope from SEQ ID NO: 10. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 10 while retaining at least one epitope of SEQ ID NO: 10. The final 40 C-terminal amino acids of SEQ ID NO: 10 can usefully be omitted. The first 16 N-terminal amino acids of SEQ ID NO: 10 can usefully be omitted. Other fragments omit one or more protein domains. PSE54 is naturally a long protein and so the use of fragments is helpful e.g. for purification, handling, fusion, expression, etc.

SEQ ID NO: 45 is a useful fragment of SEQ ID NO: 10 ('PSE54$_{17-243}$'). This fragment includes the most exposed domain of PSE54 and is more easily used at an industrial scale. It also reduces the antigen's similarity with human proteins.

PA0595 or PSE5-1

The PSE5-1 antigen is annotated as 'organic solvent tolerance protein OstA precursor'. In the PAO1 strain PSE5-1 is PA0595 and has amino acid sequence SEQ ID NO: 11 (GI: 15595792). See Ref. 37. Sometimes, PA0595 is referred to herein as 'PSE5-1 or 'PSE5'.

Useful PSE5-1 antigens can elicit an antibody (e.g. when administered to a human) that recognises SEQ ID NO: 11 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 11; and/or (b) comprising a fragment of at least 'n' consecutive amino acids of SEQ ID NO: 11, wherein 'n' is 7 or more (e.g. 8, 10, 12, 14, 16, 18, 20, 25, 30, 35, 40, 50, 60, 70, 80, 90, 100, 150, 200, 250 or more). These PSE5-1 proteins include variants of SEQ ID NO: 11. Preferred fragments of (b) comprise an epitope from SEQ ID NO: 11. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 11 while retaining at least one epitope of SEQ ID NO: 11. The final 40 C-terminal amino acids of SEQ ID NO: 11 can usefully be omitted. The first 33 N-terminal amino acids of SEQ ID NO: 11 can usefully be omitted. Other fragments omit one or more protein domains. PSE5-1 is naturally a long protein and so the use of fragments is helpful e.g. for purification, handling, fusion, expression, etc.

SEQ ID NO: 46 is a useful fragment of SEQ ID NO: 11 ('PSE5-1$_{34-924}$'). This fragment includes the most exposed domain of PSE5-1 and is more easily used at an industrial scale.

PA1954 or PSE13-2

The PSE13-2 antigen is annotated as 'hypothetical protein'. In the PAO1 strain PSE13-2 is PA1954 and has amino acid sequence SEQ ID NO: 12 (GI: 15597150). See Ref. 37. Sometimes, PA1954 is referred to herein as 'PSE13-2' or 'PSE13'.

Useful PSE13-2 antigens can elicit an antibody (e.g. when administered to a human) that recognises SEQ ID NO: 12 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 12; and/or (b) comprising a fragment of at least 'n' consecutive amino acids of SEQ ID NO: 12, wherein 'n' is 7 or more (e.g. 8, 10, 12, 14, 16, 18, 20, 25, 30, 35, 40, 50, 60, 70, 80, 90, 100, 150, 200, 250 or more). These PSE13-2 proteins include variants of SEQ ID NO: 12. Preferred fragments of (b) comprise an epitope from SEQ ID NO: 12. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 12 while retaining at least one epitope of SEQ ID NO: 12. The final 40 C-terminal amino acids of SEQ ID NO: 12 can usefully be omitted. The first 24 N-terminal amino acids of SEQ ID NO: 12 can usefully be omitted. Other fragments omit one or more protein domains. PSE13-2 is naturally a long protein and so the use of fragments is helpful e.g. for purification, handling, fusion, expression, etc.

SEQ ID NO: 47 is a useful fragment of SEQ ID NO: 12 ('PSE13-2$_{25-340}$'). This fragment includes the most exposed domain of PSE13-2 and is more easily used at an industrial scale.

PA3692 or PSE17-1

The PSE17-1 antigen is annotated as 'Lipotoxin F, LptF'. In the PAO1 strain PSE17-1 is PA3692 and has amino acid sequence SEQ ID NO: 13 (GI: 15598888). See Ref. 37. It has been described as belonging to Outer membrane protein and related peptidoglycan-associated (lipo) proteins as shown in reference 39. Sometimes, PA3692 is referred to herein as 'PSE17-1' or 'PSE17'.

Useful PSE17-1 antigens can elicit an antibody (e.g. when administered to a human) that recognises SEQ ID NO: 13 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 13; and/or (b) comprising a fragment of at least 'n' consecutive amino acids of SEQ ID NO: 13, wherein 'n' is 7 or more (e.g. 8, 10, 12, 14, 16, 18, 20, 25, 30, 35, 40, 50, 60, 70, 80, 90, 100, 150, 200, 250 or more). These PSE17-1 proteins include variants of SEQ ID NO: 13. Preferred fragments of (b) comprise an epitope from SEQ ID NO: 13. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 13 while retaining at least one epitope of SEQ ID NO: 13. The final 40 C-terminal amino acids of SEQ ID NO: 13 can usefully be omitted. The first 19 N-terminal amino acids of SEQ ID NO: 13 can usefully be omitted. Other fragments omit one or more protein domains. PSE17-1 is naturally a long protein and so the use of fragments is helpful e.g. for purification, handling, fusion, expression, etc.

SEQ ID NO: 48 is a useful fragment of SEQ ID NO: 13 ('PSE17-1$_{20-261}$'). This fragment includes the most exposed domain of PSE17-1 and is more easily used at an industrial scale.

PA4370 or PSE18-2

The PSE18-2 antigen is annotated as 'Insulin-cleaving metalloproteinase outer membrane protein precursor'. In the PAO1 strain PSE18-2 is PA4370 and has amino acid sequence SEQ ID NO: 14 (GI: 15599566). See Ref 37. It has been described as belonging to Outer membrane protein and in particular as insulin-cleaving metalloproteinase outer membrane protein (IcmP) as shown in reference 40. Sometimes, PA4370 is referred to herein as 'PSE18-2' or 'PSE18'.

Useful PSE18-2 antigens can elicit an antibody (e.g. when administered to a human) that recognises SEQ ID NO: 14 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 14; and/or (b) comprising a fragment of at least 'n' consecutive amino acids of SEQ ID NO: 14, wherein 'n' is 7 or more (e.g. 8, 10, 12, 14, 16, 18, 20, 25, 30, 35, 40, 50, 60, 70, 80, 90, 100, 150, 200, 250 or more). These PSE18-2 proteins include variants of SEQ ID NO: 14. Preferred fragments of (b) comprise an epitope from SEQ ID NO: 14. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 14 while retaining at least one epitope of SEQ ID NO: 14. The final 40 C-terminal amino acids of SEQ ID NO: 14 can usefully be omitted. The first 20 N-terminal amino acids of SEQ ID NO: 14 can usefully be omitted. Other fragments omit one or more protein domains. PSE18-2 is naturally a long protein and so the use of fragments is helpful e.g. for purification, handling, fusion, expression, etc.

SEQ ID NO: 49 is a useful fragment of SEQ ID NO: 14 ('PSE18-2$_{21-446}$'). This fragment includes the most exposed domain of PSE18-2 and is more easily used at an industrial scale.

PA4735 or PSE20-1

The PSE20-1 antigen is annotated as 'hypothetical protein'. In the PAO1 strain PSE20-1 is PA4735 and has amino acid sequence SEQ ID NO: 16 (GI: 15599929). See Ref 37. Sometimes, PA4735 is referred to herein as 'PSE20-1' or 'PSE20'.

Useful PSE20-1 antigens can elicit an antibody (e.g. when administered to a human) that recognises SEQ ID NO: 16 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 16; and/or (b) comprising a fragment of at least 'n' consecutive amino acids of SEQ ID NO: 16, wherein 'n' is 7 or more (e.g. 8, 10, 12, 14, 16, 18, 20, 25, 30, 35, 40, 50, 60, 70, 80, 90, 100, 150, 200, 250 or more). These PSE20-1 proteins include variants of SEQ ID NO: 16. Preferred fragments of (b) comprise an epitope from SEQ ID NO: 16. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 16 while retaining at least one epitope of SEQ ID NO: 16. The final 40 C-terminal amino acids of SEQ ID NO: 16 can usefully be omitted. The first 19 N-terminal amino acids of SEQ ID NO: 16 can usefully be omitted. Other fragments omit one or more protein domains. PSE20-1 is naturally a long protein and so the use of fragments is helpful e.g. for purification, handling, fusion, expression, etc.

SEQ ID NO: 51 is a useful fragment of SEQ ID NO: 16 ('PSE20-1$_{20-1088}$'). This fragment includes the most exposed domain of PSE20-1 and is more easily used at an industrial scale.

PA3647 or PSE23-1

The PSE23-1 antigen is annotated as 'hypothetical protein'. In the PAO1 strain PSE23-1 is PA3647 and has amino acid sequence SEQ ID NO: 17 (GI: 15598843). See Ref 37. It has been described as probable outer membrane protein precursor or as OmpH gene and it was described as contaminant during the purification process of OprI as shown in reference 41. Sometimes, PA3647 is referred to herein as 'PSE23-1' or 'PSE23'.

Useful PSE20-1 antigens can elicit an antibody (e.g. when administered to a human) that recognises SEQ ID NO: 17 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 17; and/or (b) comprising a fragment of at least 'n' consecutive amino acids of SEQ ID NO: 17, wherein 'n' is 7 or more (e.g. 8, 10, 12, 14, 16, 18, 20, 25, 30, 35, 40, 50, 60, 70, 80, 90, 100, 150, 200, 250 or more). These PSE20-1 proteins include variants of SEQ ID NO: 17. Preferred fragments of (b) comprise an epitope from SEQ ID NO: 17. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 17 while retaining at least one epitope of SEQ ID NO: 17. The final 40 C-terminal amino acids of SEQ ID NO: 17 can usefully be omitted. The first 22 N-terminal amino acids of SEQ ID NO: 17 can usefully be omitted. Other fragments omit one or more protein domains. PSE23-1 is naturally a long protein and so the use of fragments is helpful e.g. for purification, handling, fusion, expression, etc.

SEQ ID NO: 52 is a useful fragment of SEQ ID NO: 17 ('PSE20-1$_{23-168}$'). This fragment includes the most exposed domain of PSE23-1 and is more easily used at an industrial scale.

PA0126 or PSE24-1

The PSE24-1 antigen is annotated as 'hypothetical protein'. In the PAO1 strain PSE24-1 is PA0126 and has amino acid sequence SEQ ID NO: 18 (GI: 15595324). See Ref 37. Sometimes, PA0126 is referred to herein as 'PSE24-1' or 'PSE24'.

Useful PSE24-1 antigens can elicit an antibody (e.g. when administered to a human) that recognises SEQ ID NO: 18 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 18; and/or (b) comprising a fragment of at least 'n' consecutive amino acids of SEQ ID NO: 18, wherein 'n' is 7 or more (e.g. 8, 10, 12, 14, 16, 18, 20, 25, 30, 35, 40, 50, 60, 70, 80, 90, 100, 150, 200, 250 or more). These PSE24-1 proteins include variants of SEQ ID NO: 18. Preferred fragments of (b) comprise an epitope from SEQ ID NO: 18. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 18 while retaining at least one epitope of SEQ ID NO: 18. The first 19 N-terminal amino acids of SEQ ID NO: 18 can usefully be omitted. Other fragments omit one or more protein domains. PSE24-1 is naturally a long protein and so the use of fragments is helpful e.g. for purification, handling, fusion, expression, etc.

SEQ ID NO: 53 is a useful fragment of SEQ ID NO: 18 ('PSE24-1$_{20-206}$'). This fragment includes the most exposed domain of PSE24-1 and is more easily used at an industrial scale.

PA0189 or PSE25-1

The PSE25-1 antigen is annotated as 'probable porin'. In the PAO1 strain PSE25-1 is PA0189 and has amino acid sequence SEQ ID NO: 19 (GI: 15595387). See Ref 37. Sometimes, PA0189 is referred to herein as 'PSE25-1' or 'PSE25'.

Useful PSE25-1 antigens can elicit an antibody (e.g. when administered to a human) that recognises SEQ ID NO: 19 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 19; and/or (b) comprising a fragment of at least 'n' consecutive amino acids of SEQ ID NO: 19, wherein 'n' is 7 or more (e.g. 8, 10, 12, 14, 16, 18, 20, 25, 30, 35, 40, 50, 60, 70, 80, 90, 100, 150, 200, 250 or more). These PSE25-1 proteins include variants of SEQ ID NO: 19. Preferred fragments of (b) comprise an epitope from SEQ ID NO: 19. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 19 while retaining at least one epitope of SEQ ID NO: 19. The first 25 N-terminal amino acids of SEQ ID NO: 19 can usefully be omitted. Other fragments omit one or more protein domains. PSE25-1 is naturally a long protein and so the use of fragments is helpful e.g. for purification, handling, fusion, expression, etc.

SEQ ID NO: 54 is a useful fragment of SEQ ID NO: 19 ('PSE25-1$_{26-452}$'). This fragment includes the most exposed domain of PSE25-1 and is more easily used at an industrial scale.

PA0274 or PSE26-1

The PSE26-1 antigen is annotated as 'hypothetical protein'. In the PAO1 strain PSE26-1 is PA0274 and has amino acid sequence SEQ ID NO: 20 (GI: 15595471). See Ref 37. Sometimes, PA0274 is referred to herein as 'PSE26-1' or 'PSE26'.

Useful PSE26-1 antigens can elicit an antibody (e.g. when administered to a human) that recognises SEQ ID NO: 20 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 20; and/or (b)

comprising a fragment of at least 'n' consecutive amino acids of SEQ ID NO: 20, wherein 'n' is 7 or more (e.g. 8, 10, 12, 14, 16, 18, 20, 25, 30, 35, 40, 50, 60, 70, 80, 90, 100, 150, 200, 250 or more). These PSE26-1 proteins include variants of SEQ ID NO: 20. Preferred fragments of (b) comprise an epitope from SEQ ID NO: 20. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 20 while retaining at least one epitope of SEQ ID NO: 20. The first 23 N-terminal amino acids of SEQ ID NO: 20 can usefully be omitted. Other fragments omit one or more protein domains. PSE26-1 is naturally a long protein and so the use of fragments is helpful e.g. for purification, handling, fusion, expression, etc.

SEQ ID NO: 55 is a useful fragment of SEQ ID NO: 20 ('PSE26-1$_{24-256}$'). This fragment includes the most exposed domain of PSE26-1 and is more easily used at an industrial scale.

PA0537 or PSE28-2

The PSE28-1 antigen is annotated as 'conserved hypothetical protein'. In the PAO1 strain PSE28-1 is PA0537 and has amino acid sequence SEQ ID NO: 21 (GI: 15595734). See Ref 37. Sometimes, PA0537 is referred to herein as 'PSE28-1' or 'PSE28'.

Useful PSE28-1 antigens can elicit an antibody (e.g. when administered to a human) that recognises SEQ ID NO: 21 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 21; and/or (b) comprising a fragment of at least 'n' consecutive amino acids of SEQ ID NO: 21, wherein 'n' is 7 or more (e.g. 8, 10, 12, 14, 16, 18, 20, 25, 30, 35, 40, 50, 60, 70, 80, 90, 100, 150, 200, 250 or more). These PSE28-1 proteins include variants of SEQ ID NO: 21. Preferred fragments of (b) comprise an epitope from SEQ ID NO: 21. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 21 while retaining at least one epitope of SEQ ID NO: 21. The first 19 N-terminal amino acids of SEQ ID NO: 21 can usefully be omitted. Other fragments omit one or more protein domains. PSE28-1 is naturally a long protein and so the use of fragments is helpful e.g. for purification, handling, fusion, expression, etc.

SEQ ID NO: 56 is a useful fragment of SEQ ID NO: 21 ('PSE28-1$_{\cdot 20\text{-}202}$'). This fragment includes the most exposed domain of PSE28-1 and is more easily used at an industrial scale.

PA0737 or PSE31-2

The PSE31-2 antigen is annotated as 'conserved hypothetical protein'. In the PAO1 strain PSE31-2 is PA0737 and has amino acid sequence SEQ ID NO: 22 (GI: 15595934). See Ref 37. It has been described as up-regulated lipoproteins. See Ref 42. Sometimes, PA0737 is referred to herein as 'PSE31-2' or 'PSE31'.

Useful PSE31-2 antigens can elicit an antibody (e.g. when administered to a human) that recognises SEQ ID NO: 22 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 22; and/or (b) comprising a fragment of at least 'n' consecutive amino acids of SEQ ID NO: 22, wherein 'n' is 7 or more (e.g. 8, 10, 12, 14, 16, 18, 20, 25, 30, 35, 40, 50, 60, 70, 80, 90, 100, 150, 200, 250 or more). These PSE31-2 proteins include variants of SEQ ID NO: 22. Preferred fragments of (b) comprise an epitope from SEQ ID NO: 22. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 22 while retaining at least one epitope of SEQ ID NO: 22. The first 19 N-terminal amino acids of SEQ ID NO: 22 can usefully be omitted. Other fragments omit one or more protein domains. PSE31-2 is naturally a long protein and so the use of fragments is helpful e.g. for purification, handling, fusion, expression, etc.

SEQ ID NO: 57 is a useful fragment of SEQ ID NO: 22 ('PSE31-2$_{\cdot 20\text{-}151}$'). This fragment includes the most exposed domain of PSE31-2 and is more easily used at an industrial scale.

PA1086 or PSE33-2

The PSE33-2 antigen is annotated as 'flagellar hook-associated protein 1 FlgK'. In the PAO1 strain PSE33-2 is PA1086 and has amino acid sequence SEQ ID NO: 23 (GI: 15596283). See Ref 37. Sometimes, PA1086 is referred to herein as 'PSE33-2' or 'PSE33'.

Useful PSE33-2 antigens can elicit an antibody (e.g. when administered to a human) that recognises SEQ ID NO: 23 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 23; and/or (b) comprising a fragment of at least 'n' consecutive amino acids of SEQ ID NO: 23, wherein 'n' is 7 or more (e.g. 8, 10, 12, 14, 16, 18, 20, 25, 30, 35, 40, 50, 60, 70, 80, 90, 100, 150, 200, 250 or more). These PSE33-2 proteins include variants of SEQ ID NO: 23. Preferred fragments of (b) comprise an epitope from SEQ ID NO: 23. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 23 while retaining at least one epitope of SEQ ID NO: 23. The first N-terminal amino acid of SEQ ID NO: 23 can usefully be omitted. Other fragments omit one or more protein domains. PSE33-2 is naturally a long protein and so the use of fragments is helpful e.g. for purification, handling, fusion, expression, etc.

SEQ ID NO: 58 is a useful fragment of SEQ ID NO: 23, wherein only the Met at position 1 of the polypeptide has been removed to allow proper cloning and expression in commonly known expression systems i.e. PET vector system. This fragment includes the most exposed domain of PSE31-2 and is more easily used at an industrial scale.

PA2793 or PSE42-1

The PSE42-1 antigen is annotated as 'hypothetical protein'. In the PAO1 strain PSE42-1 is PA2793 and has amino acid sequence SEQ ID NO: 27 (GI: 15597989). See Ref 37. Sometimes, PA2793 is referred to herein as 'PSE42-1' or 'PSE42'.

PSORT available program has predicted this protein as lipoprotein and a Type II (lipoprotein) export signal predicted by LipoP by a cleavage after residue 20. See Ref 37.

Useful PSE42-1 antigens can elicit an antibody (e.g. when administered to a human) that recognises SEQ ID NO: 27 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 27; and/or (b)

comprising a fragment of at least 'n' consecutive amino acids of SEQ ID NO: 27, wherein 'n' is 7 or more (e.g. 8, 10, 12, 14, 16, 18, 20, 25, 30, 35, 40, 50, 60, 70, 80, 90, 100, 150, 200, 250 or more). These PSE42-1 proteins include variants of SEQ ID NO: 27. Preferred fragments of (b) comprise an epitope from SEQ ID NO: 27. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 27 while retaining at least one epitope of SEQ ID NO: 27. The first 20 N-terminal amino acids of SEQ ID NO: 27 can usefully be omitted. Other fragments omit one or more protein domains. PSE42-1 is naturally a long protein and so the use of fragments is helpful e.g. for purification, handling, fusion, expression, etc.

SEQ ID NO: 62 is a useful fragment of SEQ ID NO: 27 ('PSE42-1$_{21-344}$'). This fragment includes the most exposed domain of PSE42-1 and is more easily used at an industrial scale.

PA3535 or PSE45-2

The PSE45-2 antigen is annotated as 'probable outer membrane protein precursor'. In the PAO1 strain PSE45-2 is PA3535 and has amino acid sequence SEQ ID NO: 28 (GI: 15598731). See Ref 37. Sometimes, PA3535 is referred to herein as 'PSE45-2' or 'PSE45'.

Useful PSE45-2 antigens can elicit an antibody (e.g. when administered to a human) that recognises SEQ ID NO: 28 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 28; and/or (b) comprising a fragment of at least 'n' consecutive amino acids of SEQ ID NO: 28, wherein 'n' is 7 or more (e.g. 8, 10, 12, 14, 16, 18, 20, 25, 30, 35, 40, 50, 60, 70, 80, 90, 100, 150, 200, 250 or more). These PSE45-2 proteins include variants of SEQ ID NO: 28. Preferred fragments of (b) comprise an epitope from SEQ ID NO: 28. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 28 while retaining at least one epitope of SEQ ID NO: 28. The first 30 N-terminal amino acids of SEQ ID NO: 28 can usefully be omitted. Other fragments omit one or more protein domains. PSE45-2 is naturally a long protein and so the use of fragments is helpful e.g. for purification, handling, fusion, expression, etc.

SEQ ID NO: 63 is a useful fragment of SEQ ID NO: 28 ('PSE45-2$_{31-995}$'). This fragment includes the most exposed domain of PSE45-2 and is more easily used at an industrial scale.

PA4578 or PSE50-1

The PSE50-1 antigen is annotated as 'hypothetical protein'. In the PAO1 strain PSE50-1 is PA4578 and has amino acid sequence SEQ ID NO: 29 (GI: 15599774). See Ref 37. Sometimes, PA4578 is referred to herein as 'PSE50-1' or 'PSE50'.

Useful PSE50-1 antigens can elicit an antibody (e.g. when administered to a human) that recognises SEQ ID NO: 29 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 29; and/or (b) comprising a fragment of at least 'n' consecutive amino acids of SEQ ID NO: 29, wherein 'n' is 7 or more (e.g. 8, 10, 12, 14, 16, 18, 20, 25, 30, 35, 40, 50, 60, 70, 80, 90, 100, 150, 200, 250 or more). These PSE50-1 proteins include variants of SEQ ID NO: 29. Preferred fragments of (b) comprise an epitope from SEQ ID NO: 29. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 19, 20, 25 or more) from the N-terminus of SEQ ID NO: 29 while retaining at least one epitope of SEQ ID NO: 29. The first 19 N-terminal amino acids of SEQ ID NO: 29 can usefully be omitted. Other fragments omit one or more protein domains. PSE45-2 is naturally a long protein and so the use of fragments is helpful e.g. for purification, handling, fusion, expression, etc.

SEQ ID NO: 64 is a useful fragment of SEQ ID NO: 29 ('PSE50-1$_{20-162}$'). This fragment includes the most exposed domain of PSE50-1 and is more easily used at an industrial scale.

PA4667 or PSE51-4

The PSE51-4 antigen is annotated as 'hypothetical protein'. In the PAO1 strain PSE51-4 is PA4667 and has amino acid sequence SEQ ID NO: 30 (GI: 15599862). See Ref 37. Sometimes, PA4667 is referred to herein as 'PSE51-4' or 'PSE51'.

Useful PSE51-4 antigens can elicit an antibody (e.g. when administered to a human) that recognises SEQ ID NO: 30 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 30; and/or (b) comprising a fragment of at least 'n' consecutive amino acids of SEQ ID NO: 30, wherein 'n' is 7 or more (e.g. 8, 10, 12, 14, 16, 18, 20, 25, 30, 35, 40, 50, 60, 70, 80, 90, 100, 150, 200, 250 or more). These PSE51-4 proteins include variants of SEQ ID NO: 30. Preferred fragments of (b) comprise an epitope from SEQ ID NO: 30. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 19, 20, 25, 30 or more) from the N-terminus of SEQ ID NO: 30 while retaining at least one epitope of SEQ ID NO: 30. The first 31 N-terminal amino acids of SEQ ID NO: 30 can usefully be omitted. Other fragments omit one or more protein domains. PSE51-4 is naturally a long protein and so the use of fragments is helpful e.g. for purification, handling, fusion, expression, etc.

SEQ ID NO: 65 is a useful fragment of SEQ ID NO: 30 ('PSE51-4$_{32-590}$'). This fragment includes the most exposed domain of PSE51-4 and is more easily used at an industrial scale.

PA1106 or PSE34-1

The PSE34-1 antigen is annotated as 'hypothetical protein'. In the PAO1 strain PSE34-1 is PA1106 and has amino acid sequence SEQ ID NO: 24 (GI: 15596303). See Ref 37. Sometimes, PA1106 is referred to herein as 'PSE34-1' or 'PSE34'.

Useful PSE34-1 antigens can elicit an antibody (e.g. when administered to a human) that recognises SEQ ID NO: 24 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 24; and/or (b) comprising a fragment of at least 'n' consecutive amino acids of SEQ ID NO: 24, wherein 'n' is 7 or more (e.g. 8, 10, 12, 14, 16, 18, 20, 25, 30, 35, 40, 50, 60, 70, 80, 90, 100, 150, 200, 250 or more). These PSE34-1 proteins include variants of SEQ ID NO: 24. Preferred fragments of (b) comprise an epitope from SEQ ID NO: 24. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 24 while retaining at least one epitope of SEQ ID NO: 24. The first 20 N-terminal amino acids of SEQ ID NO: 24 can usefully be omitted. Other fragments omit one or more protein domains. PSE34-1 is naturally a long protein and so the use of fragments is helpful e.g. for purification, handling, fusion, expression, etc.

SEQ ID NO: 59 is a useful fragment of SEQ ID NO: 24 ('PSE34-1$_{21-237}$'). This fragment includes the most exposed domain of PSE34-1 and is more easily used at an industrial scale.

PA1324 or PSE36-3

The PSE36-3 antigen is annotated as 'hypothetical protein'. In the PAO1 strain PSE36-3 is PA1324 and has amino acid sequence SEQ ID NO: 25 (GI: 15596521). See Ref 37. Sometimes, PA1324 is referred to herein as 'PSE36-3' or 'PSE36'.

PA1324 is postulated to be involved in the binding and transport of sugars or polysaccharides associated with the peptidoglycan matrix during biofilm formation. [43]

Useful PSE36-3 antigens can elicit an antibody (e.g. when administered to a human) that recognises SEQ ID NO: 25 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 25; and/or (b) comprising a fragment of at least 'n' consecutive amino acids of SEQ ID NO: 25, wherein 'n' is 7 or more (e.g. 8, 10, 12, 14, 16, 18, 20, 25, 30, 35, 40, 50, 60, 70, 80, 90, 100, 150, 200, 250 or more). These PSE36-3 proteins include variants of SEQ ID NO: 25. Preferred fragments of (b) comprise an epitope from SEQ ID NO: 25. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 25 while retaining at least one epitope of SEQ ID NO: 25. The first 19 N-terminal amino acids of SEQ ID NO: 25 can usefully be omitted. Other fragments omit one or more protein domains. PSE36-3 is naturally a long protein and so the use of fragments is helpful e.g. for purification, handling, fusion, expression, etc.

SEQ ID NO: 60 is a useful fragment of SEQ ID NO: 25 ('PSE36-3$_{'20-170'}$'). This fragment includes the most exposed domain of PSE36-3 and is more easily used at an industrial scale.

Second Antigen Group

PA1178 or PSE10

The 'PSE10' antigen is annotated as 'PhoP/Q and low Mg2+ inducible outer membrane protein'. In the PAO1 strain PSE10 is called also as OprH [44] and has amino acid sequence SEQ ID NO: 2. In the PAO1 strain PSE10 is annotated as PA1178 and its NCBI identifier is GI: 15596375. See Ref 37. Sometimes, PA1178 is referred to herein as 'PSE10-1' or 'PSE10'.

Useful PSE10 antigens can elicit an antibody (e.g. when administered to a human) that recognises SEQ ID NO: 2 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 2; and/or (b) comprising a fragment of at least 'n' consecutive amino acids of SEQ ID NO: 2, wherein 'n' is 7 or more (e.g. 8, 10, 12, 14, 16, 18, 20, 25, 30, 35, 40, 50, 60, 70, 80, 90, 100, 150, 200, 250 or more). These PSE10 proteins include variants of SEQ ID NO: 2. Preferred fragments of (b) comprise an epitope from SEQ ID NO: 2. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25, 30, 35, 40, 45, 50 or more) from the N-terminus of SEQ ID NO: 2 while retaining at least one epitope of SEQ ID NO: 2. The first 21 N-terminal amino acids of SEQ ID NO: 2 can usefully be omitted. Other fragments omit one or more protein domains. The use of fragments is helpful e.g. for purification, handling, fusion, expression, etc.

SEQ ID NO: 37 is a useful fragment of SEQ ID NO: 2 ('PSE10$_{22-200}$'). This fragment includes the most exposed domain of PSE10 and is more easily used at an industrial scale.

PA1248 or PSE11-3

The 'PSE11-3' antigen is annotated as 'Alkaline protease secretion outer membrane protein AprF precursor'. In the PAO1 strain PSE11-3 is PA1248 and has amino acid sequence SEQ ID NO: 4. In the PAO1 strain the NCBI identifier is GI: 15596445. See reference 37 and 45.

Sometimes, PA1248 is referred to herein as 'PSE11-3' or 'PSE11'.

Useful PSE11-3 antigens can elicit an antibody (e.g. when administered to a human) that recognises SEQ ID NO: 4 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 4; and/or (b) comprising a fragment of at least 'n' consecutive amino acids of SEQ ID NO: 4, wherein 'n' is 7 or more (e.g. 8, 10, 12, 14, 16, 18, 20, 25, 30, 35, 40, 50, 60, 70, 80, 90, 100, 150, 200, 250 or more). These PSE11-3 proteins include variants of SEQ ID NO: 4. Preferred fragments of (b) comprise an epitope from SEQ ID NO: 4. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 4 while retaining at least one epitope of SEQ ID NO: 4. The first 18 N-terminal amino acids of SEQ ID NO: 4 can usefully be omitted. Other fragments omit one or more protein domains. PSE11-3 is naturally a long protein and so the use of fragments is helpful e.g. for purification, handling, fusion, expression, etc. In reference 45 this antigen is described as a known virulence factor and tested as antigen.

SEQ ID NO: 39 is a useful fragment of SEQ ID NO: 4 ('PSE11-3$_{19-481}$'). This fragment includes the most exposed domain of PSE11-3 and is more easily used at an industrial scale.

PA4765 or PSE52-1

The PSE52-1 antigen is annotated as 'Outer membrane lipoprotein OmlA precursor'. In the PAO1 strain PSE52-1 is PA4765 and has amino acid sequence SEQ ID NO: 8 (GI: 15599959). See Ref 37. Sometimes, PA4765 is referred to herein as 'PSE52-1' or 'PSE52'.

It has been described since 1999 as belonging to outer membrane protein family as in reference 46.

Useful PSE52-1 antigens can elicit an antibody (e.g. when administered to a human) that recognises SEQ ID NO: 8 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 8; and/or (b) comprising a fragment of at least 'n' consecutive amino acids of SEQ ID NO: 8, wherein 'n' is 7 or more (e.g. 8, 10, 12, 14, 16, 18, 20, 25, 30, 35, 40, 50, 60, 70, 80, 90, 100, 150, 200, 250 or more). These PSE52-1 proteins include variants of SEQ ID NO: 8. Preferred fragments of (b) comprise an epitope from SEQ ID NO: 8. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 8 while retaining at least one epitope of SEQ ID NO: 8. The final 40 C-terminal amino acids of SEQ ID NO: 8 can usefully be omitted. The first 21 N-terminal amino acids of SEQ ID NO: 8 can usefully be omitted. Other fragments omit one or more protein domains. PSE52-1 is naturally a long protein and so the use of fragments is helpful e.g. for purification, handling, fusion, expression, etc.

SEQ ID NO: 43 is a useful fragment of SEQ ID NO: 8 ('PSE52-1$_{22-176}$'). This fragment includes the most exposed domain of PSE52-1 and is more easily used at an industrial scale.

PA4710 or PSE19-1

The PSE19-1 antigen is annotated as 'Heme/Hemoglobin uptake outer membrane receptor PhuR precursor'. In the PAO1 strain PSE19-1 is PA4710 and has amino acid sequence SEQ ID NO: 15 (GI: 15599904). See Ref 37. Short peptides derived from said antigen have been proposed to show certain immunogenicity, however this antigen has not been tested as vaccine antigen in combination [47]. Sometimes, PA4710 is referred to herein as 'PSE19-1' or 'PSE19'.

Useful PSE19-1 antigens can elicit an antibody (e.g. when administered to a human) that recognises SEQ ID NO: 15 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 15; and/or (b) comprising a fragment of at least 'n' consecutive amino acids of SEQ ID NO: 15, wherein 'n' is 7 or more (e.g. 8, 10, 12, 14, 16, 18, 20, 25, 30, 35, 40, 50, 60, 70, 80, 90, 100, 150, 200, 250 or more). These PSE19-2 proteins include variants of SEQ ID NO: 15. Preferred fragments of (b) comprise an epitope from SEQ ID NO: 15. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 15 while retaining at least one epitope of SEQ ID NO: 15. The final 40 C-terminal amino acids of SEQ ID NO: 15 can usefully be omitted. The first 25 N-terminal amino acids of SEQ ID NO: 15 can usefully be omitted. Other fragments omit one or more protein domains. PSE19-1 is naturally a long protein and so the use of fragments is helpful e.g. for purification, handling, fusion, expression, etc.

SEQ ID NO: 50 is a useful fragment of SEQ ID NO: 15 ('PSE19-1$_{26-764}$'). This fragment includes the most exposed domain of PSE19-1 and is more easily used at an industrial scale.

PA1777 or PSE38-1

The PSE38-1 antigen is annotated as 'Major porin and structural outer membrane porin OprF precursor'. In the PAO1 strain PSE38-1 is PA1777 and has amino acid sequence SEQ ID NO: 26 (GI: 15596974). See Ref 37 and 48. EP0297291 described for the first time this protein as useful antigen. Sometimes, PA1777 is referred to herein as 'PSE38-1' or 'PSE38'.

Useful PSE38-1 antigens can elicit an antibody (e.g. when administered to a human) that recognises SEQ ID NO: 26 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 26; and/or (b) comprising a fragment of at least 'n' consecutive amino acids of SEQ ID NO: 26, wherein 'n' is 7 or more (e.g. 8, 10, 12, 14, 16, 18, 20, 25, 30, 35, 40, 50, 60, 70, 80, 90, 100, 150, 200, 250 or more). These PSE38-1 proteins include variants of SEQ ID NO: 26. Preferred fragments of (b) comprise an epitope from SEQ ID NO: 26. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 26 while retaining at least one epitope of SEQ ID NO: 26. The first 24 N-terminal amino acids of SEQ ID NO: 26 can usefully be omitted. Other fragments omit one or more protein domains. PSE38-1 is naturally a long protein and so the use of fragments is helpful e.g. for purification, handling, fusion, expression, etc.

SEQ ID NO: 61 is a useful fragment of SEQ ID NO: 26 ('PSE38-1$_{25-350}$'). This fragment includes the most exposed domain of PSE38-1 and is more easily used at an industrial scale.

Further Antigenic Polypeptides

PA4525 or PilA

The PilA antigen is annotated as 'type 4 fimbrial precursor PilA'. In the PAO1 strain PilA is PA4525 and has amino acid sequence SEQ ID NO: 31 (GI: 15599721). See Ref 37. Useful PilA antigens can elicit an antibody (e.g. when administered to a human) that recognises SEQ ID NO: 31 and/or may comprise an amino acid sequence: (a) having 50% or more identity (e.g. 60%, 65%, 70%, 75%, 80%, 85%, 90%, 91%, 92%, 93%, 94%, 95%, 96%, 97%, 98%, 99%, 99.5% or more) to SEQ ID NO: 31; and/or (b) comprising a fragment of at least 'n' consecutive amino acids of SEQ ID NO: 31, wherein 'n' is 7 or more (e.g. 8, 10, 12, 14, 16, 18, 20, 25, 30, 35, 40, 50, 60, 70, 80, 90, 100, 150, 200, 250 or more). These PilA proteins include variants of SEQ ID NO: 31. Preferred fragments of (b) comprise an epitope from SEQ ID NO: 31. Other preferred fragments lack one or more amino acids (e.g. 1, 2, 3, 4, 5, 6, 7, 8, 9, 10, 15, 20, 25 or more) from the C-terminus and/or one or more amino acids (e.g. 1, 2, 3, 4, 5, 6, 7, 8, 9, 10, 15, 20, 25 or more) from the N-terminus of SEQ ID NO: 31 while retaining at least one epitope of SEQ ID NO: 31. Other fragments omit one or more protein domains. PilA is naturally a long protein and so the use of fragments is helpful e.g. for purification, handling, fusion, expression, etc.

Useful fragment include the most exposed domain of PilA and is more easily used at an industrial scale. It also reduces the antigen's similarity with human proteins. Vaccines and immunotherapy using this antigen have been attempted as shown in reference 49, and in reference 50.

OprF-OprI

The OmpF/I antigen is a fusion protein consisting of a hybrid protein [Met-Ala-(His)$_6$OprF (190-342)-OprI (21-83)], ("(His)$_6$" disclosed as SEQ ID NO: 70), resulting by the fusion of the mature outer membrane protein I (OprI) and amino acids 190 to 342 of OprF of *Pseudomonas aeruginosa* expressed in *Escherichia coli* and purified.

The fusion protein has been described in reference 4 as SEQ ID NO 006. For reference purposes, a full-length amino acid sequence of the fusion protein described herein is given as SEQ ID NO: 32. This antigen can be usefully used as positive control as single antigen, or showing a surprising positive effect increasing vaccine efficacy in in vivo experiments when used in combination with specific *pseudomonas* antigens.

PA1092 or FliC (Flagellar Protein)

Flagella and main flagella proteins like FliC (PA1092) or FliD (PA1094) have been extensively characterized and used as single vaccine antigens in the past as shown in reference 51. For reference purposes, a full-length amino acid sequence of FliC is given as SEQ ID NO: 33 herein.

PA1092 antigen and/or PA1094 antigen may be usefully combined with any of the "first antigen group" or the "second antigen group".

PA1094 or FliD (Flagellar Protein)

Flagella and main flagella proteins like FliD (PA1094) have been extensively characterized and used as vaccine antigens in the past as shown in reference 51. For reference purposes, a full-length amino acid sequence of FliD is given as SEQ ID NO: 34 herein.

PA1094 may be usefully combined with any of the "first antigen group" or any of the "second antigen group".

PA1148 or Exoprotein A or Exotoxin A

The Exoprotein A known also as Exotoxin A is an exoprotein which has been extensively characterized and used primarily as carrier protein in polysaccharide conjugate vaccine approach, e.g. reference 22. It is known as PA1148 in the PAO1PAO1 strain. See Ref 37.

PA1148 antigen may be usefully combined with any of the "first antigen group" or any of the "second antigen group".

Hybrid Polypeptides

Antigens used in the invention may be present in the composition as individual separate polypeptides. Where more than one antigen is used, however, they do not have to be present as separate polypeptides. Instead, at least two (e.g. 2, 3, 4, 5, or more) antigens can be expressed as a single polypeptide chain (a 'hybrid' polypeptide). Hybrid polypeptides offer two main advantages: first, a polypeptide that may be unstable or poorly expressed on its own can be assisted by adding a suitable hybrid partner that overcomes the problem; second, commercial manufacture is simplified as only one expression and purification need be employed in order to produce two polypeptides which are both antigenically useful.

The hybrid polypeptide may comprise two or more polypeptide sequences from the first antigen group. The hybrid polypeptide may comprise one or more polypeptide sequences from the first antigen group and one or more polypeptide sequences from the second antigen group. Moreover, the hybrid polypeptide may comprise two or more polypeptide sequences from each of the antigens listed above, or two or more variants of the same antigen in the cases in which the sequence has partial variability across strains.

Hybrids consisting of amino acid sequences from two, three, four, five, six, seven, eight, nine, or ten antigens are useful. In particular, hybrids consisting of amino acid sequences from two, three, four, or five antigens are preferred, such as two or three antigens.

Different hybrid polypeptides may be mixed together in a single formulation. Hybrids may be combined with non-hybrid antigens selected from the first, second or third antigen groups. Within such combinations, an antigen may be present in more than one hybrid polypeptide and/or as a non-hybrid polypeptide. It is preferred, however, that an antigen is present either as a hybrid or as a non-hybrid, but not as both.

The hybrid polypeptides can also be combined with conjugates or non-*P. aeruginosa* antigens as described above.

Hybrid polypeptides can be represented by the formula $NH_2$-A-$\{$-X-L-$\}_n$-B—COOH, wherein: X is an amino acid sequence of a *P. aeruginosa* antigen, as described above; L is an optional linker amino acid sequence; A is an optional N-terminal amino acid sequence; B is an optional C-terminal amino acid sequence; n is an integer of 2 or more (e.g. 2, 3, 4, 5, 6, etc.). Usually n is 2 or 3.

If a —X— moiety has a leader peptide sequence in its wild-type form, this may be included or omitted in the hybrid protein. In some embodiments, the leader peptides will be deleted except for that of the —X— moiety located at the N-terminus of the hybrid protein i.e. the leader peptide of $X_1$ will be retained, but the leader peptides of $X_2 \ldots X_n$ will be omitted. This is equivalent to deleting all leader peptides and using the leader peptide of $X_1$ as moiety -A-.

For each n instances of $\{$—X-L-$\}$, linker amino acid sequence -L- may be present or absent. For instance, when n=2 the hybrid may be $NH_2$—$X_1$-$L_1$-$X_2$-$L_2$-COOH, $NH_2$—$X_1$—$X_2$—COOH, $NH_2$—$X_1$-$L_1$-$X_2$—COOH, $NH_2$—$X_1$—$X_2$-$L_2$-COOH, etc. Linker amino acid sequence(s) -L- will typically be short (e.g. 20 or fewer amino acids i.e. 20, 19, 18, 17, 16, 15, 14, 13, 12, 11, 10, 9, 8, 7, 6, 5, 4, 3, 2, 1). Examples comprise short peptide sequences which facilitate cloning, poly-glycine linkers (i.e. comprising $Gly_n$ where n=2, 3, 4, 5, 6, 7, 8, 9, 10 or more) (SEQ ID NO: 71), and histidine tags (i.e. $His_n$ where n=3, 4, 5, 6, 7, 8, 9, 10 or more) (SEQ ID NO: 72). Other suitable linker amino acid sequences will be apparent to those skilled in the art. A useful linker is GSGGGG (SEQ ID NO: 67) or GSGSGGGG (SEQ ID NO: 68), with the Gly-Ser dipeptide being formed from a BamHI restriction site, thus aiding cloning and manipulation, and the $(Gly)_4$ (SEQ ID NO: 73) tetrapeptide being a typical poly-glycine linker. Other suitable linkers, particularly for use as the final $L_n$ are ASGGGS (SEQ ID NO: 69) or a Leu-Glu dipeptide.

-A- is an optional N-terminal amino acid sequence. This will typically be short (e.g. 40 or fewer amino acids i.e. 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1). Examples include leader sequences to direct protein trafficking, or short peptide sequences which facilitate cloning or purification (e.g. histidine tags i.e. $His_n$ where n=3, 4, 5, 6, 7, 8, 9, 10 or more) (SEQ ID NO: 72). A useful tag contains a sequence of 6 consecutive Histidine (SEQ ID NO: 70), having at its start a homologue or heterologous start Methionine and/or an Alanine, i.e. SEQ ID NO 66. Other suitable N-terminal amino acid sequences will be apparent to those skilled in the art. If $X_1$ lacks its own N-terminus methionine, -A- is preferably an oligopeptide (e.g. with 1, 2, 3, 4, 5, 6, 7 or 8 amino acids) which provides a N-terminus methionine e.g. Met-Ala-Ser, or a single Met residue.

—B— is an optional C-terminal amino acid sequence. This will typically be short (e.g. 40 or fewer amino acids i.e. 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1).

Polypeptides Used with the Invention

Polypeptides used with the invention can take various forms (e.g. native, fusions, glycosylated, non-glycosylated, lipidated, non-lipidated, phosphorylated, non-phosphorylated, myristoylated, non-myristoylated, monomeric, multimeric, particulate, denatured, etc.).

Polypeptides used with the invention can be prepared by various means (e.g. recombinant expression, purification from cell culture, chemical synthesis, isolated from a natural biological source etc.). Recombinantly-expressed proteins are preferred, particularly for hybrid polypeptides.

Polypeptides used with the invention are preferably provided in purified or substantially purified form i.e. substantially free from other polypeptides (e.g. free from naturally-occurring polypeptides), particularly from other *pseudomonas* or host cell polypeptides, and are generally at least about 50% pure (by weight), and usually at least about 90% pure i.e. less than about 50%, and more preferably less than about 10% (e.g. 5%) of a composition is made up of other expressed polypeptides. Thus the antigens in the compositions are separated from the whole organism with which the molecule is expressed.

Polypeptides used with the invention are preferably *pseudomonas* polypeptides.

The term "polypeptide" refers to amino acid polymers of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labelling component. Also included are, for example, polypeptides containing one or more analogs of an amino acid (including, for example, unnatural amino acids, etc.), as well as other modifications known in the art. Polypeptides can occur as single chains or associated chains.

The invention provides polypeptides comprising a sequence —P-Q- or -Q-P—, wherein: —P— is an amino acid sequence as defined above and -Q- is not a sequence as defined above i.e. the invention provides fusion proteins. Where the N-terminus codon of —P— is not ATG, but this codon is not present at the N-terminus of a polypeptide, it will be translated as the standard amino acid for that codon rather than as a Met. Where this codon is at the N-terminus of a polypeptide, however, it will be translated as Met. Examples of -Q- moieties include, but are not limited to, histidine tags (i.e. $His_n$ where n=3, 4, 5, 6, 7, 8, 9, 10 or more) (SEQ ID NO: 72), maltose-binding protein, or glutathione-S-transferase (GST).

The invention also provides a process for producing a polypeptide of the invention, comprising the step of culturing a host cell transformed with nucleic acid of the invention under conditions which induce polypeptide expression.

Although expression of the polypeptides of the invention may take place in a *Pseudomonas*, the invention will usually use a heterologous host for expression (recombinant expression). The heterologous host may be prokaryotic (e.g. a bacterium) or eukaryotic. It may be *E. coli*, but other suitable hosts include *Bacillus subtilis, Vibrio cholerae, Salmonella typhi, Salmonella typhimurium, Neisseria lactamica, Neisseria cinerea, Mycobacteria* (e.g. *M. tuberculosis*), yeasts, etc. Compared to the wild-type *P. aeruginosa* genes encoding polypeptides of the invention, it is helpful to change codons to optimise expression efficiency in such hosts without affecting the encoded amino acids.

The invention provides a process for producing a polypeptide of the invention, comprising the step of synthesising at least part of the polypeptide by chemical means.

Nucleic Acids

The invention also provides nucleic acid encoding polypeptides and hybrid polypeptides of the invention. It also provides nucleic acid comprising a nucleotide sequence that encodes one or more polypeptides or hybrid polypeptides of the invention.

The invention also provides nucleic acid comprising nucleotide sequences having sequence identity to such nucleotide sequences. Identity between sequences is preferably determined by the Smith-Waterman homology search algorithm as described above. Such nucleic acids include those using alternative codons to encode the same amino acid.

The invention also provides nucleic acid which can hybridize to these nucleic acids. Hybridization reactions can be performed under conditions of different "stringency". Conditions that increase stringency of a hybridization reaction are widely known and published in the art. Examples of relevant conditions include (in order of increasing stringency): incubation temperatures of 25° C., 37° C., 50° C., 55° C. and 68° C.; buffer concentrations of 10×SSC, 6×SSC, 1×SSC, 0.1×SSC (where SSC is 0.15 M NaCl and 15 mM citrate buffer) and their equivalents using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6×SSC, 1×SSC, 0.1×SSC, or de-ionized water. Hybridization techniques and their optimization are well known in the art.

In some embodiments, nucleic acid of the invention hybridizes to a target under low stringency conditions; in other embodiments it hybridizes under intermediate stringency conditions; in preferred embodiments, it hybridizes under high stringency conditions. An exemplary set of low stringency hybridization conditions is 50° C. and 10×SSC. An exemplary set of intermediate stringency hybridization conditions is 55° C. and 1×SSC. An exemplary set of high stringency hybridization conditions is 68° C. and 0.1×SSC.

The invention includes nucleic acid comprising sequences complementary to these sequences (e.g. for antisense or probing, or for use as primers).

Nucleic acids of the invention can be used in hybridisation reactions (e.g. Northern or Southern blots, or in nucleic acid microarrays or 'gene chips') and amplification reactions (e.g. PCR, SDA, SSSR, LCR, TMA, NASBA, etc.) and other nucleic acid techniques.

Nucleic acid according to the invention can take various forms (e.g. single-stranded, double-stranded, vectors, primers, probes, labelled etc.). Nucleic acids of the invention may be circular or branched, but will generally be linear. Unless otherwise specified or required, any embodiment of the invention that utilizes a nucleic acid may utilize both the double-stranded form and each of two complementary single-stranded forms which make up the double-stranded form. Primers and probes are generally single-stranded, as are antisense nucleic acids.

Nucleic acids of the invention are preferably provided in purified or substantially purified form i.e. substantially free from other nucleic acids (e.g. free from naturally-occurring nucleic acids), particularly from other *pseudomonas* or host cell nucleic acids, generally being at least about 50% pure (by weight), and usually at least about 90% pure. Nucleic acids of the invention are preferably *pseudomonas* nucleic acids.

Nucleic acids of the invention may be prepared in many ways e.g. by chemical synthesis (e.g. phosphoramidite synthesis of DNA) in whole or in part, by digesting longer nucleic acids using nucleases (e.g. restriction enzymes), by joining shorter nucleic acids or nucleotides (e.g. using ligases or polymerases), from genomic or cDNA libraries, etc.

Nucleic acid of the invention may be attached to a solid support (e.g. a bead, plate, filter, film, slide, microarray support, resin, etc.). Nucleic acid of the invention may be labelled e.g. with a radioactive or fluorescent label, or a biotin label. This is particularly useful where the nucleic acid is to be used in detection techniques e.g. where the nucleic acid is a primer or as a probe.

The term "nucleic acid" includes in general means a polymeric form of nucleotides of any length, which contain deoxyribonucleotides, ribonucleotides, and/or their analogs. It includes DNA, RNA, DNA/RNA hybrids. It also includes DNA or RNA analogs, such as those containing modified backbones (e.g. peptide nucleic acids (PNAs) or phosphorothioates) or modified bases. Thus the invention includes mRNA, tRNA, rRNA, ribozymes, DNA, cDNA, recombinant nucleic acids, branched nucleic acids, plasmids, vectors, probes, primers, etc. Where nucleic acid of the invention takes the form of RNA, it may or may not have a 5' cap.

Nucleic acids of the invention may be part of a vector i.e. part of a nucleic acid construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, "viral vectors" which is designed to result in the production of a recombinant virus or virus-like particle, or "shuttle vectors", which comprise the attributes of more than one type of vector. Preferred vectors are plasmids. A "host cell" includes an individual cell or cell culture which can be or has been a recipient of exogenous nucleic acid. Host cells include progeny of a single host cell, and the progeny may not necessarily be completely identical (in morphology or in total DNA complement) to the original parent cell due to natural, accidental, or deliberate mutation and/or change. Host cells include cells transfected or infected in vivo or in vitro with nucleic acid of the invention.

Where a nucleic acid is DNA, it will be appreciated that "U" in a RNA sequence will be replaced by "T" in the DNA. Similarly, where a nucleic acid is RNA, it will be appreciated that "T" in a DNA sequence will be replaced by "U" in the RNA.

The term "complement" or "complementary" when used in relation to nucleic acids refers to Watson-Crick base pairing. Thus the complement of C is G, the complement of G is C, the complement of A is T (or U), and the complement of T (or U) is A. It is also possible to use bases such as I (the purine inosine) e.g. to complement pyrimidines (C or T).

Nucleic acids of the invention can be used, for example: to produce polypeptides; as hybridization probes for the detection of nucleic acid in biological samples; to generate additional copies of the nucleic acids; to generate ribozymes or antisense oligonucleotides; as single-stranded DNA primers or probes; or as triple-strand forming oligonucleotides.

The invention provides a process for producing nucleic acid of the invention, wherein the nucleic acid is synthesised in part or in whole using chemical means.

The invention provides vectors comprising nucleotide sequences of the invention (e.g. cloning or expression vectors) and host cells transformed with such vectors.

Nucleic acid amplification according to the invention may be quantitative and/or real-time.

For certain embodiments of the invention, nucleic acids are preferably at least 7 nucleotides in length (e.g. 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 90, 100, 110, 120, 130, 140, 150, 160, 170, 180, 190, 200, 225, 250, 275, 300 nucleotides or longer).

For certain embodiments of the invention, nucleic acids are preferably at most 500 nucleotides in length (e.g. 450, 400, 350, 300, 250, 200, 150, 140, 130, 120, 110, 100, 90, 80, 75, 70, 65, 60, 55, 50, 45, 40, 39, 38, 37, 36, 35, 34, 33, 32, 31, 30, 29, 28, 27, 26, 25, 24, 23, 22, 21, 20, 19, 18, 17, 16, 15 nucleotides or shorter).

Primers and probes of the invention, and other nucleic acids used for hybridization, are preferably between 10 and 30 nucleotides in length (e.g. 10, 11, 12, 13, 14, 15, 16, 17, 18, 19, 20, 21, 22, 23, 24, 25, 26, 27, 28, 29, 30, 40 or more nucleotides).

Strains and Variants

Antigens are defined above by reference to existing nomenclature (e.g. "PA0328"), to "PSE52" or to "PSE followed by a natural number, indicating the clone number, i.e. PSE52-1, etc" or to the respective SEQ ID NOs numbers.

Table 1 below associates these three naming/numbering systems to existing PAO1 public available numbering.

PAO1 numbering refers to the genome of *P. aeruginosa* strain PAO1 which is extensively described in terms of genomic analysis in reference 37.

Functional annotations for each antigen are also given in the databases.

Thus an exemplary amino acid and nucleotide sequence for any of these antigens can easily be found in public sequence databases from the PAO1 strain, but the invention is not limited to sequences from the PAO1 strains. Standard search and alignment techniques can be used to identify in any of these (or other) further genome sequences the homolog of any particular sequence from the PAO1 strain. Moreover, the available sequences from the PAO1 strain can be used to design primers for amplification of homologous sequences from other strains. Thus the invention is not limited to this strain, but rather encompasses such variants and homologs from other strains of *P. aeruginosa*, as well as non-natural variants. In general, suitable variants of a particular SEQ ID NO include its allelic variants, its polymorphic forms, its homologs, its orthologs, its paralogs, its mutants, etc.

Thus, for instance, polypeptides used with the invention may, compared to the SEQ ID NO herein, include one or more (e.g. 1, 2, 3, 4, 5, 6, 7, 8, 9, etc.) amino acid substitutions, such as conservative substitutions (i.e. substitutions of one amino acid with another which has a related side chain). Genetically-encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity. The polypeptides may also include one or more (e.g. 1, 2, 3, 4, 5, 6, 7, 8, 9, etc.) single amino acid deletions relative to the SEQ ID NO sequences. The polypeptides may also include one or more (e.g. 1, 2, 3, 4, 5, 6, 7, 8, 9, etc.) insertions (e.g. each of 1, 2, 3, 4 or 5 amino acids) relative to the SEQ ID NO sequences.

Similarly, a polypeptide used with the invention may comprise an amino acid sequence that:
- is identical (i.e. 100% identical) to a sequence disclosed in the sequence listing;
- shares sequence identity (e.g. 80%, 85%, 90%, 91%, 92%, 93%, 94%, 95%, 96%, 97%, 98%, 99%, 99.5% or more) with a sequence disclosed in the sequence listing;
- has 1, 2, 3, 4, 5, 6, 7, 8, 9 or 10 (or more) single amino acid alterations (deletions, insertions, substitutions), which may be at separate locations or may be contiguous, as compared to the sequences of (a) or (b);

when aligned with a particular sequence from the sequence listing using a pairwise alignment algorithm, each moving window of x amino acids from N-terminus to C-terminus (such that for an alignment that extends to p amino acids, where p>x, there are p−x+1 such windows) has at least x·y identical aligned amino acids, where: x is selected from 20, 25, 30, 35, 40, 45, 50, 60, 70, 80, 90, 100, 150, 200; y is selected from 0.50, 0.60, 0.70, 0.75, 0.80, 0.85, 0.90, 0.91, 0.92, 0.93, 0.94, 0.95, 0.96, 0.97, 0.98, 0.99; and if x·y is not an integer then it is rounded up to the nearest integer. The preferred pairwise alignment algorithm is the Needleman-Wunsch global alignment algorithm [52], using default parameters (e.g. with Gap opening penalty=10.0, and with Gap extension penalty=0.5, using the EBLOSUM62 scoring matrix). This algorithm is conveniently implemented in the needle tool in the EMBOSS package [53].

Where hybrid polypeptides are used, the individual antigens within the hybrid (i.e. individual —X— moieties) may be from one or more strains. Where n=2, for instance, $X_2$ may be from the same strain as $X_1$ or from a different strain. Where n=3, the strains might be (i) $X_1=X_2=X_3$ (ii) $X_1=X_2\neq X_3$ (iii) $X_1\neq X_2=X_3$ (iv) $X_1\neq X_2\neq X_3$ or (v) $X_1=X_3\neq X_2$, etc.

Within group (c), deletions or substitutions may be at the N-terminus and/or C-terminus, or may be between the two termini. Thus a truncation is an example of a deletion. Truncations may involve deletion of up to 40 (or more) amino acids at the N-terminus and/or C-terminus. N-terminus truncation can remove leader peptides e.g. to facilitate recombinant expression in a heterologous host. C-terminus truncation can remove anchor sequences e.g. to facilitate recombinant expression in a heterologous host.

In general, when an antigen comprises a sequence that is not identical to a complete *P. aeruginosa* sequence from the sequence listing (e.g. when it comprises a sequence listing with <100% sequence identity thereto, or when it comprises a fragment thereof) it is preferred in each individual instance that the antigen can elicit an antibody which recognises the respective complete *P. aeruginosa* sequence.

Mutant Bacteria

Present invention, also provides a *P. aeruginosa* bacterium in which one or more of the antigens from the various antigen groups of the invention has/have been knocked out (see Ref 46). Techniques for producing knockout bacteria are well known, and knockout of genes from *P. aeruginosa* strains have been reported i.e. in Ref 54. A knockout mutation may be situated in the coding region of the gene or may lie within its transcriptional control regions (e.g. within its promoter). A knockout mutation will reduce the level of mRNA encoding the antigen to <1% of that produced by the wild-type bacterium, preferably <0.5%, more preferably <0.1%, and most preferably to 0%.

The invention also provides a *P. aeruginosa* in which one or more of the antigens from the various antigen groups of the invention has a mutation which inhibits its activity. The gene encoding the antigen will have a mutation that changes the encoded amino acid sequence. Mutation may involve deletion, substitution, and/or insertion, any of which may be involve one or more amino acids.

The invention also provides a bacterium, such as a *P. aeruginosa* bacterium, which hyper-expresses an antigen of the invention.

The invention also provides a bacterium, such as a *P. aeruginosa* bacterium, that constitutively expresses an antigen of the invention. The invention also provides a *E. coli* comprising a gene encoding an antigen of the invention, wherein the gene is under the control of an inducible promoter.

Mutant bacteria are particularly useful for preparing bacterial outer membrane vesicles which include *P. aeruginosa* antigens (e.g. antigens of the invention), which can be used as immunogens [55-57].

Immunogenic Compositions and Medicaments

Immunogenic compositions of the invention may be useful as vaccines. Vaccines according to the invention may either be prophylactic (i.e. to prevent infection) or therapeutic (i.e. to treat infection), but will typically be prophylactic.

Compositions may thus be pharmaceutically acceptable. They will usually include components in addition to the antigens e.g. they typically include one or more pharmaceutical carrier(s) and/or excipient(s).

Compositions will generally be administered to a mammal in aqueous form. Prior to administration, however, the composition may have been in a non-aqueous form. For instance, although some vaccines are manufactured in aqueous form, then filled and distributed and administered also in aqueous form, other vaccines are lyophilised during manufacture and are reconstituted into an aqueous form at the time of use. Thus a composition of the invention may be dried, such as a lyophilised formulation.

The composition may include preservatives such as thiomersal or 2-phenoxyethanol. It is preferred, however, that the vaccine should be substantially free from (i.e. less than 5 µg/ml) mercurial material e.g. thiomersal-free. Vaccines containing no mercury are more preferred. Preservative-free vaccines are particularly preferred.

To improve thermal stability, a composition may include a temperature protective agent. Further details of such agents are provided below.

To control tonicity, it is preferred to include a physiological salt, such as a sodium salt. Sodium chloride (NaCl) is preferred, which may be present at between 1 and 20 mg/ml e.g. about 10±2 mg/ml NaCl. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a composition will generally be between 5.0 and 8.1, and more typically between 6.0 and 8.0 e.g. 6.5 and 7.5, or between 7.0 and 7.8.

The composition is preferably sterile. The composition is preferably non-pyrogenic e.g. containing <1 EU (endotoxin unit, a standard measure) per dose, and preferably <0.1 EU per dose. The composition is preferably gluten free.

The composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Human vaccines are typically administered in a dosage volume of about 0.5 ml, although a half dose (i.e. about 0.25 ml) may be administered to children.

Immunogenic compositions of the invention may also comprise one or more immunoregulatory agents. Preferably, one or more of the immunoregulatory agents include one or more adjuvants. The adjuvants may include a TH1 adjuvant and/or a TH2 adjuvant, or a TLR7 agonist further discussed below.

Thus the invention provides an immunogenic composition comprising a combination of:
(1) one or more antigen(s) selected from the first, second, and further antigen group (as defined above); and
(2) an adjuvant, such as an aluminium hydroxide adjuvant (for example, one or more antigens may be adsorbed to aluminium hydroxide).

For instance, the invention provides an immunogenic composition comprising a combination of a sta006 antigen and an adjuvant, such as an aluminium hydroxide adjuvant. Similarly, the invention provides an immunogenic composition comprising a combination of a sta011 antigen and an adjuvant, such as an aluminium hydroxide adjuvant. These compositions are ideally buffered e.g. with a histidine buffer.

Adjuvants which may be used in compositions of the invention include, but are not limited to:

A. Mineral-Containing Compositions

Mineral containing compositions suitable for use as adjuvants in the invention include mineral salts, such as aluminium salts and calcium salts (or mixtures thereof). Calcium salts include calcium phosphate (e.g. the "CAP" particles disclosed in ref 58). Aluminum salts include hydroxides, phosphates, sulfates, etc., with the salts taking any suitable form (e.g. gel, crystalline, amorphous, etc.). Adsorption to these salts is preferred (e.g. all antigens may be adsorbed). The mineral containing compositions may also be formulated as a particle of metal salt [59].

The adjuvants known as aluminum hydroxide and aluminum phosphate may be used. The invention can use any of the "hydroxide" or "phosphate" adjuvants that are in general use as adjuvants. The adjuvants known as "aluminium hydroxide" are typically aluminium oxyhydroxide salts, which are usually at least partially crystalline. The adjuvants known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt.

A fibrous morphology (e.g. as seen in transmission electron micrographs) is typical for aluminium hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg $Al^{+++}$ at pH 7.4 have been reported for aluminium hydroxide adjuvants.

Aluminium phosphate adjuvants generally have a $PO_4$/Al molar ratio between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with $PO_4$/Al molar ratio between 0.84 and 0.92, included at 0.6 mg $Al^{3+}$/ml. The aluminium phosphate will generally be particulate (e.g. plate-like morphology as seen in transmission electron micrographs). Typical diameters of the particles are in the range 0.5-20 μm (e.g. about 5-10 μm) after any antigen adsorption. Adsorptive capacities of between 0.7-1.5 mg protein per mg $Al^{+++}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

Suspensions of aluminium salts used to prepare compositions of the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

The invention can use a mixture of both an aluminium hydroxide and an aluminium phosphate. In this case there may be more aluminium phosphate than hydroxide e.g. a weight ratio of at least 2:1 e.g. ≥5:1, ≥6:1, ≥7:1, ≥8:1, ≥9:1, etc.

The concentration of $Al^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of 0.85 mg/dose is preferred.

B. Oil Emulsions

Oil emulsion compositions suitable for use as adjuvants in the invention include squalene-water emulsions, such as MF59 [Chapter 10 of ref 63; see also ref 60] (5% Squalene, 0.5% Tween 80, and 0.5% Span 85, formulated into submicron particles using a microfluidizer). Complete Freund's adjuvant (CFA) and incomplete Freund's adjuvant (IFA) may also be used.

Various oil-in-water emulsion adjuvants are known, and they typically include at least one oil and at least one surfactant, with the oil(s) and surfactant(s) being biodegradable (metabolizable) and biocompatible. The oil droplets in the emulsion are generally less than 5 μm in diameter, and ideally have a sub-micron diameter, with these small sizes being achieved with a microfluidiser to provide stable emulsions. Droplets with a size less than 220 nm are preferred as they can be subjected to filter sterilization.

The emulsion can comprise oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Other preferred oils are the tocopherols (see below). Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used e.g. Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Preferred emulsion adjuvants have an average droplets size of <1 μm e.g. ≤750 nm, ≤500 nm, ≤400 nm, ≤300 nm, ≤250 nm, ≤220 nm, ≤200 nm, or smaller. These droplet sizes can conveniently be achieved by techniques such as microfluidisation.

Specific oil-in-water emulsion adjuvants useful with the invention include, but are not limited to:

A submicron emulsion of squalene, Tween 80, and Span 85. The composition of the emulsion by volume can be about 5% squalene, about 0.5% polysorbate 80 and about 0.5% Span 85. In weight terms, these ratios become 4.3% squalene, 0.5% polysorbate 80 and 0.48% Span 85. This adjuvant is known as 'MF59' [61-], as described in more detail in Chapter 10 of ref 63 and chapter 12 of ref 64. The MF59 emulsion advantageously includes citrate ions e.g. 10 mM sodium citrate buffer.

An emulsion of squalene, a tocopherol, and polysorbate 80 (Tween 80). The emulsion may include phosphate buffered saline. It may also include Span 85 (e.g. at 1%) and/or lecithin. These emulsions may have from 2 to 10% squalene, from 2 to 10% tocopherol and from 0.3 to 3% Tween 80, and the weight ratio of squalene: tocopherol is preferably ≤1 as this provides a more stable emulsion. Squalene and Tween 80 may be present volume ratio of about 5:2 or at a weight ratio of about 11:5. One such emulsion can be made by dissolving Tween 80 in PBS to give a 2% solution, then mixing 90 ml of this solution with a mixture of (5 g of DL-α-tocopherol and 5 ml squalene), then microfluidising the mixture. The resulting emulsion may have submicron oil droplets e.g. with an average diameter of between 100 and 250 nm, preferably about 180 nm. The emulsion may also include a 3-de-O-acylated monophosphoryl lipid A (3d-MPL). Another useful emulsion of this type may comprise, per human dose, 0.5-10 mg squalene, 0.5-11 mg tocopherol, and 0.1-4 mg polysorbate 80 [65].

An emulsion of squalene, a tocopherol, and a Triton detergent (e.g. Triton X-100). The emulsion may also include a 3d-MPL (see below). The emulsion may contain a phosphate buffer.

An emulsion comprising a polysorbate (e.g. polysorbate 80), a Triton detergent (e.g. Triton X-100) and a tocopherol (e.g. an α-tocopherol succinate). The emulsion may include these three components at a mass ratio of about 75:11:10 (e.g. 750 μg/ml polysorbate 80, 110 μg/ml Triton X-100 and 100 μg/ml α-tocopherol succinate), and these concentrations should include any contribution of these components from antigens. The emulsion may also include squalene. The emulsion may also include a 3d-MPL (see below). The aqueous phase may contain a phosphate buffer.

An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [66] (0.05-1% Thr-MDP, 5% squalane, 2.5% Pluronic L121 and 0.2% polysorbate 80). It can also be used without the Thr-MDP, as in the "AF" adjuvant [67] (5% squalane, 1.25% Pluronic L121 and 0.2% polysorbate 80). Microfluidisation is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm [68]. The emulsion may also include one or more of: alditol; a cryoprotective agent (e.g. a sugar, such as dodecylmaltoside and/or sucrose); and/or an alkylpolyglycoside. The emulsion may include a TLR4 agonist [69]. Such emulsions may be lyophilized.

An emulsion of squalene, poloxamer 105 and Abil-Care [70]. The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).

An emulsion having from 0.5-50% of an oil, 0.1-10% of a phospholipid, and 0.05-5% of a non-ionic surfactant. As described in reference 71, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolizable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 72, produced by addition of aliphatic amine to desacylsaponin via the carboxyl group of glucuronic acid), dimethyidioctadecylammonium bromide and/or N,N-dioctadecyl-N, N-bis(2-hydroxyethyl)propanediamine.

An emulsion in which a saponin (e.g. QuilA or QS21) and a sterol (e.g. a cholesterol) are associated as helical micelles [73].

An emulsion comprising a mineral oil, a non-ionic lipophilic ethoxylated fatty alcohol, and a non-ionic hydrophilic surfactant (e.g. an ethoxylated fatty alcohol and/or polyoxyethylene-polyoxypropylene block copolymer) [74].

In some embodiments an emulsion may be mixed with antigen extemporaneously, at the time of delivery, and thus the adjuvant and antigen may be kept separately in a packaged or distributed vaccine, ready for final formulation at the time of use. In other embodiments an emulsion is mixed with antigen during manufacture, and thus the composition is packaged in a liquid adjuvanted form. The antigen will generally be in an aqueous form, such that the vaccine is finally prepared by mixing two liquids. The volume ratio of the two liquids for mixing can vary (e.g. between 5:1 and 1:5) but is generally about 1:1. Where concentrations of components are given in the above descriptions of specific emulsions, these concentrations are typically for an undiluted composition, and the concentration after mixing with an antigen solution will thus decrease.

Where a composition includes a tocopherol, any of the α, β, γ, δ, ε or ξ tocopherols can be used, but α-tocopherols are preferred. The tocopherol can take several forms e.g. different salts and/or isomers. Salts include organic salts, such as succinate, acetate, nicotinate, etc. D-α-tocopherol and DL-α-tocopherol can both be used. Tocopherols are advantageously included in vaccines for use in elderly patients (e.g. aged 60 years or older) because vitamin E has been reported to have a positive effect on the immune response in this patient group [75]. They also have antioxidant properties that may help to stabilize the emulsions [76]. A preferred α-tocopherol is DL-α-tocopherol, and the preferred salt of this tocopherol is the succinate. The succinate salt has been found to cooperate with TNF-related ligands in vivo.

C. Saponin Formulations

Saponin formulations may also be used as adjuvants in the invention. Saponins are a heterogeneous group of sterol glycosides and triterpenoid glycosides that are found in the bark, leaves, stems, roots and even flowers of a wide range of plant species. Saponin from the bark of the *Quillaia saponaria* Molina tree has been widely studied as adjuvant. Saponin can also be commercially obtained from *Smilax ornata* (sarsaprilla), *Gypsophilla paniculata* (brides veil), and *Saponaria officianalis* (soap root). Saponin adjuvant formulations include purified formulations, such as QS21, as well as lipid formulations, such as ISCOMs. QS21 is marketed as Stimulon™.

Saponin compositions have been purified using HPLC and RP-HPLC. Specific purified fractions using these techniques have been identified, including QS7, QS17, QS18, QS21, QH-A, QH-B and QH-C. Preferably, the saponin is QS21. A method of production of QS21 is disclosed in ref 77. Saponin formulations may also comprise a sterol, such as cholesterol [78].

Combinations of saponins and cholesterols can be used to form unique particles called immunostimulating complexs (ISCOMs) [chapter 23 of ref 63]. ISCOMs typically also include a phospholipid such as phosphatidylethanolamine or phosphatidylcholine. Any known saponin can be used in ISCOMs. Preferably, the ISCOM includes one or more of QuilA, QHA & QHC. ISCOMs are further described in refs. 78-. Optionally, the ISCOMS may be devoid of additional detergent [80].

A review of the development of saponin based adjuvants can be found in ref 81.

E. Bacterial or Microbial Derivatives

Adjuvants suitable for use in the invention include bacterial or microbial derivatives such as non-toxic derivatives of enterobacterial lipopolysaccharide (LPS), Lipid A derivatives, immunostimulatory oligonucleotides and ADP-ribosylating toxins and detoxified derivatives thereof.

Non-toxic derivatives of LPS include monophosphoryl lipid A (MPL) and 3-O-deacylated MPL (3dMPL). 3dMPL is a mixture of 3 de-O-acylated monophosphoryl lipid A with 4, 5 or 6 acylated chains. A preferred "small particle" form of 3 De-O-acylated monophosphoryl lipid A is disclosed in ref 82. Such "small particles" of 3dMPL are small enough to be sterile filtered through a 0.22 µm membrane [82]. Other non-toxic LPS derivatives include monophosphoryl lipid A mimics, such as aminoalkyl glucosaminide phosphate derivatives e.g. RC-529 [83].

Lipid A derivatives include derivatives of lipid A from *Escherichia coli* such as OM-174. OM-174 is described for example in refs. 84 & 85.

Immunostimulatory oligonucleotides suitable for use as adjuvants in the invention include nucleotide sequences containing a CpG motif (a dinucleotide sequence containing an unmethylated cytosine linked by a phosphate bond to a guanosine). Double-stranded RNAs and oligonucleotides containing palindromic or poly(dG) sequences have also been shown to be immunostimulatory.

The CpG's can include nucleotide modifications/analogs such as phosphorothioate modifications and can be double-stranded or single-stranded. References 86 and 87 disclose possible analog substitutions e.g. replacement of guanosine with 2'-deoxy-7-deazaguanosine. The adjuvant effect of CpG oligonucleotides is further discussed in refs. 88.

The CpG sequence may be directed to TLR9, such as the motif GTCGTT or TTCGTT [89]. The CpG sequence may be specific for inducing a Th1 immune response, such as a CpG-A ODN, or it may be more specific for inducing a B cell response, such a CpG-B ODN. CpG-A and CpG-B ODNs are discussed in refs. 90-. Preferably, the CpG is a CpG-A ODN.

Preferably, the CpG oligonucleotide is constructed so that the 5' end is accessible for receptor recognition. Optionally, two CpG oligonucleotide sequences may be attached at their 3' ends to form "immunomers". See, for example, refs. 92-.

A useful CpG adjuvant is CpG7909, also known as ProMune™ (Coley Pharmaceutical Group, Inc.). Another is CpG1826. As an alternative, or in addition, to using CpG sequences, TpG sequences can be used [94], and these oligonucleotides may be free from unmethylated CpG motifs. The immunostimulatory oligonucleotide may be pyrimidine-rich. For example, it may comprise more than one consecutive thymidine nucleotide (e.g. TTTT, as disclosed in ref 94), and/or it may have a nucleotide composition with >25% thymidine (e.g. >35%, >40%, >50%, >60%, >80%, etc.). For example, it may comprise more than one consecutive cytosine nucleotide (e.g. CCCC, as disclosed in ref 94), and/or it may have a nucleotide composition with >25% cytosine (e.g. >35%, >40%, >50%, >60%, >80%, etc.). These oligonucleotides may be free from unmethylated CpG motifs Immunostimulatory oligonucleotides will typically comprise at least 20 nucleotides. They may comprise fewer than 100 nucleotides.

A particularly useful adjuvant based around immunostimulatory oligonucleotides is known as IC-31™ [95]. Thus an adjuvant used with the invention may comprise a mixture of (i) an oligonucleotide (e.g. between 15-40 nucleotides) including at least one (and preferably multiple) CpI motifs (i.e. a cytosine linked to an inosine to form a dinucleotide), and (ii) a polycationic polymer, such as an oligopeptide (e.g. between 5-20 amino acids) including at least one (and preferably multiple) Lys-Arg-Lys tripeptide sequence(s). The oligonucleotide may be a deoxynucleotide comprising 26-mer sequence 5'-(IC)$_{31}$-3'.

Bacterial ADP-ribosylating toxins and detoxified derivatives thereof may be used as adjuvants in the invention. Preferably, the protein is derived from *E. coli* (*E. coli* heat labile enterotoxin "LT"), cholera ("CT"), or pertussis ("PT"). The use of detoxified ADP-ribosylating toxins as mucosal adjuvants is described in ref 96 and as parenteral adjuvants in ref 97. The toxin or toxoid is preferably in the form of a holotoxin, comprising both A and B subunits. Preferably, the A subunit contains a detoxifying mutation; preferably the B subunit is not mutated. Preferably, the adjuvant is a detoxified LT mutant such as LT-K63, LT-R72, and LT-G192. The use of ADP-ribosylating toxins and detoxified derivatives thereof, particularly LT-K63 and LT-R72, as adjuvants can be found in refs. 98-101. A useful CT mutant is or CT-E29H [102]. Numerical reference for amino acid substitutions is preferably based on the alignments of the A and B subunits of ADP-ribosylating toxins set forth in ref 103, specifically incorporated herein by reference in its entirety.

F. Human Immunomodulators

Human immunomodulators suitable for use as adjuvants in the invention include cytokines, such as interleukins (e.g. IL-1, IL-2, IL-4, IL-5, IL-6, IL-7, IL-12 [104], etc.), interferons (e.g. interferon-γ), macrophage colony stimulating factor, and tumor necrosis factor. A preferred immunomodulator is IL-12.

G. Bioadhesives and Mucoadhesives

Bioadhesives and mucoadhesives may also be used as adjuvants in the invention. Suitable bioadhesives include esterified hyaluronic acid microspheres [105] or mucoadhesives such as cross-linked derivatives of poly(acrylic acid), polyvinyl alcohol, polyvinyl pyrollidone, polysaccharides and carboxymethylcellulose. Chitosan and derivatives thereof may also be used as adjuvants in the invention [106].

H. Microparticles

Microparticles may also be used as adjuvants in the invention. Microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) are preferred, optionally treated to have a negatively-charged surface (e.g. with SDS) or a positively-charged surface (e.g. with a cationic detergent, such as CTAB).

I. Liposomes

Examples of liposome formulations suitable for use as adjuvants are described in refs. 107-.

J. Polyoxyethylene Ether and Polyoxyethylene Ester Formulations

Adjuvants suitable for use in the invention include polyoxyethylene ethers and polyoxyethylene esters [109]. Such formulations further include polyoxyethylene sorbitan ester surfactants in combination with an octoxynol [110] as well as polyoxyethylene alkyl ethers or ester surfactants in combination with at least one additional non-ionic surfactant such as an octoxynol [111]. Preferred polyoxyethylene ethers are selected from the following group: polyoxyethylene-9-lauryl ether (laureth 9), polyoxyethylene-9-steoryl ether, polyoxytheylene-8-steoryl ether, polyoxyethylene-4-lauryl ether, polyoxyethylene-35-lauryl ether, and polyoxyethylene-23-lauryl ether.

K. Phosphazenes

A phosphazene, such as poly[di(carboxylatophenoxy) phosphazene] ("PCPP") as described, for example, in references 112 and 113, may be used.

L. Muramyl Peptides

Examples of muramyl peptides suitable for use as adjuvants in the invention include N-acetyl-muramyl-L-threonyl-D-isoglutamine (thr-MDP), N-acetyl-normuramyl-L-alanyl-D-isoglutamine (nor-MDP), and N-acetylmuramyl-L-alanyl-D-isoglutaminyl-L-alanine-2-(1'-2'-dipalmitoyl-sn-glycero-3-hydroxyphosphoryloxy)-ethylamine MTP-PE).

M. Imidazoquinolone Compounds.

Examples of imidazoquinolone compounds suitable for use adjuvants in the invention include Imiquimod ("R-837") [114], Resiquimod ("R-848") [115], and their analogs; and salts thereof (e.g. the hydrochloride salts).

N. Substituted Ureas

Substituted ureas useful as adjuvants include compounds of formula I, II or III, or salts thereof:

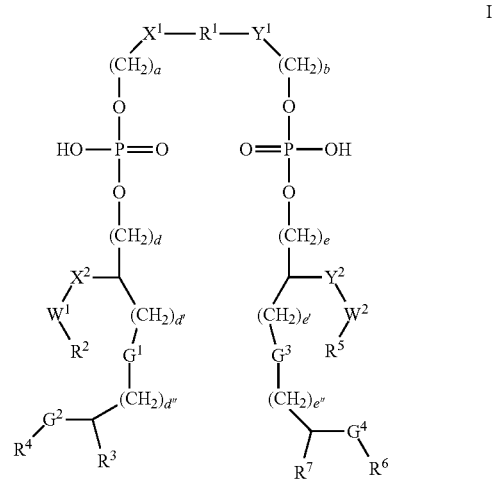

39
-continued
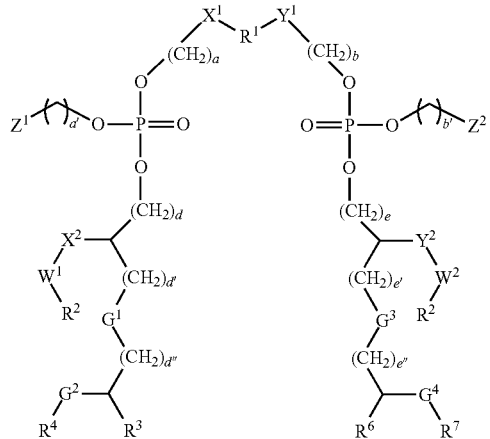
II
40
-continued
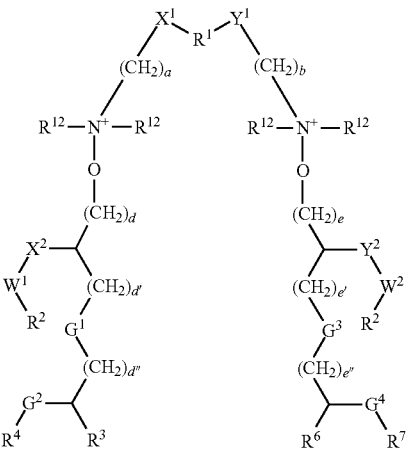
III
as defined in reference 116, such as 'ER 803058', 'ER 803732', 'ER 804053', ER 804058', 'ER 804059', 'ER 804442', 'ER 804680', 'ER 804764', ER 803022 or 'ER 804057' e.g.:
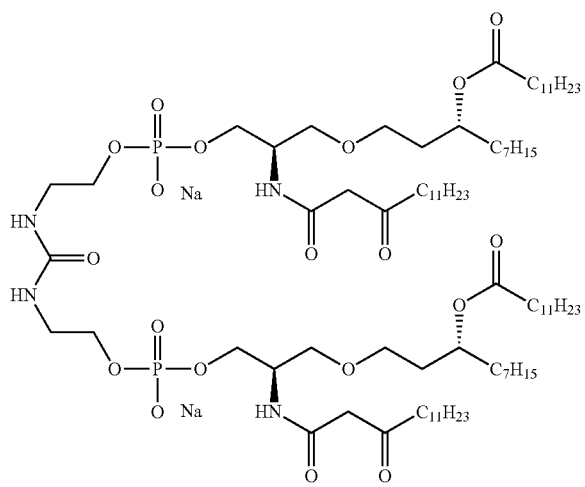
ER804057
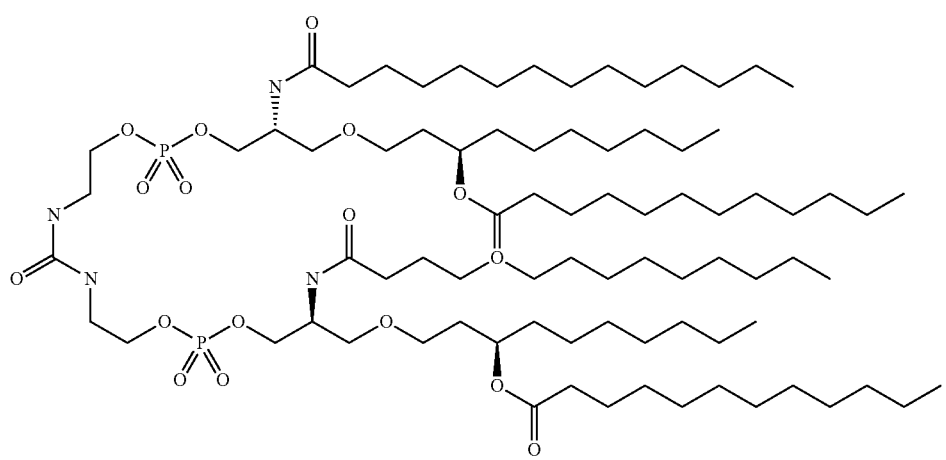
ER-803022

O. Further Adjuvants

Further adjuvants that may be used with the invention include:

An aminoalkyl glucosaminide phosphate derivative, such as RC-529 [117].

A thiosemicarbazone compound, such as those disclosed in reference 118. Methods of formulating, manufacturing, and screening for active compounds are also described in reference 118. The thiosemicarbazones are particularly effective in the stimulation of human peripheral blood mononuclear cells for the production of cytokines, such as TNF-α.

A tryptanthrin compound, such as those disclosed in reference 119. Methods of formulating, manufacturing, and screening for active compounds are also described in reference 119. The thiosemicarbazones are particularly effective in the stimulation of human peripheral blood mononuclear cells for the production of cytokines, such as TNF-α.

A nucleoside analog, such as: (a) Isatorabine (ANA-245; 7-thia-8-oxoguanosine):

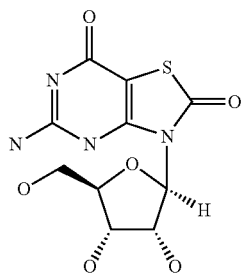 [SMILES: Nc1nc(=O)c2sc(=O)n([C@@H]3O[C@H](CO)[C@@H](O)[C@H]3O)c2[nH]1]

and prodrugs thereof; (b) ANA975; (c) ANA-025-1; (d) ANA380; (e) the compounds disclosed in references 120 to Loxoribine (7-allyl-8-oxoguanosine) [122].

Compounds disclosed in reference 123, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds [124], Hydrapthalamide compounds, Benzophenone compounds, Isoxazole compounds, Sterol compounds, Quinazilinone compounds, Pyrrole compounds [125], Anthraquinone compounds, Quinoxaline compounds, Triazine compounds, Pyrazalopyrimidine compounds, and Benzazole compounds [126].

Compounds containing lipids linked to a phosphate-containing acyclic backbone, such as the TLR4 antagonist E5564 [127:

A polyoxidonium polymer [128] or other N-oxidized polyethylene-piperazine derivative.

Methyl inosine 5'-monophosphate ("MIMP") [129].

A polyhydroxlated pyrrolizidine compound [130], such as one having formula:

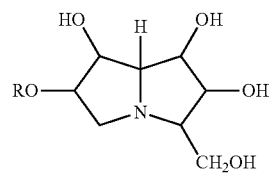

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, etc.

A CD1d ligand, such as an α-glycosylceramide [131-] (e.g. α-galactosylceramide), phytosphingosine-containing α-glycosylceramides, OCH, KRN7000 [(2S,3S,4R)-1-O-(α-D-galactopyranosyl)-2-(N-hexacosanoylamino)-1,3,4-octadecanetriol], CRONY-101, 3"-O-sulfo-galactosylceramide, etc.

A gamma inulin [133] or derivative thereof, such as algammulin.

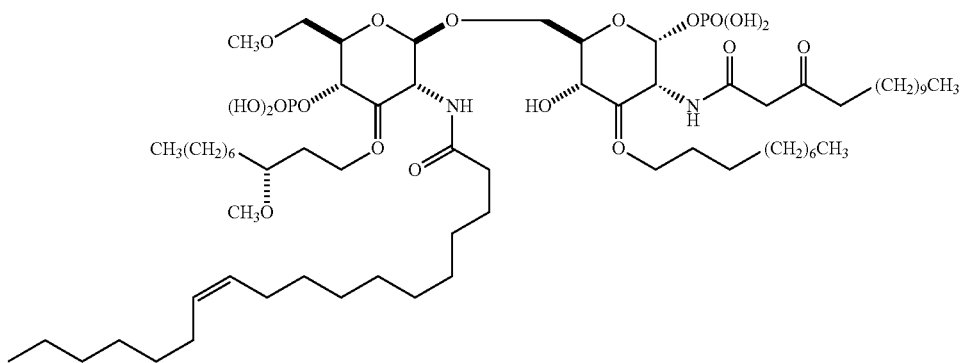

Adjuvant Combinations

The invention may also comprise combinations of one or more of the adjuvants identified above. For example, the following adjuvant compositions may be used in the invention: (1) a saponin and an oil-in-water emulsion [134]; (2) a saponin (e.g. QS21)+a non-toxic LPS derivative (e.g. 3dMPL); (3) a saponin (e.g. QS21)+a non-toxic LPS derivative (e.g. 3dMPL)+a cholesterol; (4) a saponin (e.g. QS21)+3dMPL+IL-12 (optionally+a sterol); (5) combinations of 3dMPL with, for example, QS21 and/or oil-in-water emulsions [135]; (6) SAF, containing 10% squalane, 0.4% Tween 80™, 5% pluronic-block polymer L121, and thr-MDP, either microfluidized into a submicron emulsion or vortexed to generate a larger particle size emulsion. (7) Ribi™ adjuvant system (RAS), (Ribi Immunochem) containing 2% squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™); and (8) one or more mineral salts (such as an aluminum salt)+a non-toxic derivative of LPS (such as 3dMPL).

The use of an aluminium hydroxide and/or aluminium phosphate adjuvant is particularly preferred, and antigens are generally adsorbed to these salts. Calcium phosphate is another preferred adjuvant. Other preferred adjuvant combinations include combinations of Th1 and Th2 adjuvants such as CpG & alum or resiquimod & alum. A combination of aluminium phosphate and 3dMPL may be used.

The compositions of the invention may elicit both a cell mediated immune response as well as a humoral immune response. This immune response will preferably induce long lasting (e.g. neutralising) antibodies and a cell mediated immunity that can quickly respond upon exposure to *pseudomonas*.

Two types of T cells, CD4 and CD8 cells, are generally thought necessary to initiate and/or enhance cell mediated immunity and humoral immunity CD8 T cells can express a CD8 co-receptor and are commonly referred to as Cytotoxic T lymphocytes (CTLs). CD8 T cells are able to recognized or interact with antigens displayed on MHC Class I molecules.

CD4 T cells can express a CD4 co-receptor and are commonly referred to as T helper cells. CD4 T cells are able to recognize antigenic peptides bound to MHC class II molecules. Upon interaction with a MHC class II molecule, the CD4 cells can secrete factors such as cytokines. These secreted cytokines can activate B cells, cytotoxic T cells, macrophages, and other cells that participate in an immune response. Helper T cells or CD4+ cells can be further divided into two functionally distinct subsets: TH1 phenotype and TH2 phenotypes which differ in their cytokine and effector function.

Activated TH1 cells enhance cellular immunity (including an increase in antigen-specific CTL production) and are therefore of particular value in responding to intracellular infections. Activated TH1 cells may secrete one or more of IL-2, IFN-γ, and TNF-β. A TH1 immune response may result in local inflammatory reactions by activating macrophages, NK (natural killer) cells, and CD8 cytotoxic T cells (CTLs). A TH1 immune response may also act to expand the immune response by stimulating growth of B and T cells with IL-12. TH1 stimulated B cells may secrete IgG2a.

Activated TH2 cells enhance antibody production and are therefore of value in responding to extracellular infections. Activated TH2 cells may secrete one or more of IL-4, IL-5, IL-6, and IL-10. A TH2 immune response may result in the production of IgG1, IgE, IgA and memory B cells for future protection.

An enhanced immune response may include one or more of an enhanced TH1 immune response and a TH2 immune response.

A TH1 immune response may include one or more of an increase in CTLs, an increase in one or more of the cytokines associated with a TH1 immune response (such as IL-2, IFN-γ, and TNF-β), an increase in activated macrophages, an increase in NK activity, or an increase in the production of IgG2a. Preferably, the enhanced TH1 immune response will include an increase in IgG2a production.

A TH1 immune response may be elicited using a TH1 adjuvant. A TH1 adjuvant will generally elicit increased levels of IgG2a production relative to immunization of the antigen without adjuvant. TH1 adjuvants suitable for use in the invention may include for example saponin formulations, virosomes and virus like particles, non-toxic derivatives of enterobacterial lipopolysaccharide (LPS), immunostimulatory oligonucleotides. Immunostimulatory oligonucleotides, such as oligonucleotides containing a CpG motif, are preferred TH1 adjuvants for use in the invention.

A TH2 immune response may include one or more of an increase in one or more of the cytokines associated with a TH2 immune response (such as IL-4, IL-5, IL-6 and IL-10), or an increase in the production of IgG1, IgE, IgA and memory B cells. Preferably, the enhanced TH2 immune response will include an increase in IgG1 production.

A TH2 immune response may be elicited using a TH2 adjuvant. A TH2 adjuvant will generally elicit increased levels of IgG1 production relative to immunization of the antigen without adjuvant. TH2 adjuvants suitable for use in the invention include, for example, mineral containing compositions, oil-emulsions, and ADP-ribosylating toxins and detoxified derivatives thereof. Mineral containing compositions, such as aluminium salts are preferred TH2 adjuvants for use in the invention.

Preferably, the invention includes a composition comprising a combination of a TH1 adjuvant and a TH2 adjuvant. Preferably, such a composition elicits an enhanced TH1 and an enhanced TH2 response, i.e., an increase in the production of both IgG1 and IgG2a production relative to immunization without an adjuvant. Still more preferably, the composition comprising a combination of a TH1 and a TH2 adjuvant elicits an increased TH1 and/or an increased TH2 immune response relative to immunization with a single adjuvant (i.e., relative to immunization with a TH1 adjuvant alone or immunization with a TH2 adjuvant alone).

The immune response may be one or both of a TH1 immune response and a TH2 response. Preferably, immune response provides for one or both of an enhanced TH1 response and an enhanced TH2 response.

The enhanced immune response may be one or both of a systemic and a mucosal immune response. Preferably, the immune response provides for one or both of an enhanced systemic and an enhanced mucosal immune response. Preferably the mucosal immune response is a TH2 immune response. Preferably, the mucosal immune response includes an increase in the production of IgA.

*P. aeruginosa* infections can affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition or a spray-freeze dried composition). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops. The composition may be in kit form, designed such that a combined composition is reconstituted just prior to administration to a patient. Such kits may comprise one or more antigens in liquid form and one or more lyophilised antigens.

Where a composition is to be prepared extemporaneously prior to use (e.g. where a component is presented in lyophilised form) and is presented as a kit, the kit may comprise two vials, or it may comprise one ready-filled syringe and one vial, with the contents of the syringe being used to reactivate the contents of the vial prior to injection.

Immunogenic compositions used as vaccines comprise an immunologically effective amount of antigen(s), as well as any other components, as needed. By 'immunologically effective amount', it is meant that the administration of that amount to an individual, either in a single dose or as part of a series, is effective for treatment or prevention. This amount varies depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. It is expected that the amount will fall in a relatively broad range that can be determined through routine trials. Where more than one antigen is included in a composition then two antigens may be present at the same dose as each other or at different doses.

As mentioned above, a composition may include a temperature protective agent, and this component may be particularly useful in adjuvanted compositions (particularly those containing a mineral adjuvant, such as an aluminium salt). As described in reference 136, a liquid temperature protective agent may be added to an aqueous vaccine composition to lower its freezing point e.g. to reduce the freezing point to below 0° C. Thus the composition can be stored below 0° C., but above its freezing point, to inhibit thermal breakdown. The temperature protective agent also permits freezing of the composition while protecting mineral salt adjuvants against agglomeration or sedimentation after freezing and thawing, and may also protect the composition at elevated temperatures e.g. above 40° C. A starting aqueous vaccine and the liquid temperature protective agent may be mixed such that the liquid temperature protective agent forms from 1-80% by volume of the final mixture. Suitable temperature protective agents should be safe for human administration, readily miscible/soluble in water, and should not damage other components (e.g. antigen and adjuvant) in the composition. Examples include glycerin, propylene glycol, and/or polyethylene glycol (PEG). Suitable PEGs may have an average molecular weight ranging from 200-20.000 Da. In a preferred embodiment, the polyethylene glycol can have an average molecular weight of about 300 Da ('PEG-300').

The invention provides an immunogenic composition comprising: (i) one or more antigen(s) selected from the first, second, third or fourth antigen groups; and (ii) a temperature protective agent. This composition may be formed by mixing (i) an aqueous composition comprising one or more antigen(s) selected from the first, second, third or fourth antigen groups, with (ii) a temperature protective agent. The mixture may then be stored e.g. below 0° C., from 0-20° C., from 20-35° C., from 35-55° C., or higher. It may be stored in liquid or frozen form. The mixture may be lyophilised. The composition may alternatively be formed by mixing (i) a dried composition comprising one or more antigen(s) selected from the first, second, third or fourth antigen groups, with (ii) a liquid composition comprising the temperature protective agent. Thus component (ii) can be used to reconstitute component (i).

Methods of Treatment, and Administration of the Vaccine

The invention also provides a method for raising an immune response in a mammal comprising the step of administering an effective amount of a composition of the invention. The immune response is preferably protective and preferably involves antibodies and/or cell-mediated immunity. The method may raise a booster response.

The invention also provides at least two antigens of the invention for combined use as a medicament e.g. for use in raising an immune response in a mammal.

The invention also provides the use of at least two antigens of the invention in the manufacture of a medicament for raising an immune response in a mammal.

By raising an immune response in the mammal by these uses and methods, the mammal can be protected against *P. aeruginosa* infection, including a nosocomial infection. More particularly, the mammal may be protected against a skin infection, including those of burns, trauma wounds and the eyes as shown in reference 137. pneumonia, meningitis and neonatal meningitis, osteomyelitis endocarditis, *pseudomonas* folliculitis, toxic shock syndrome, and/or septicaemia and cystic fibrosis.

The invention also provides a kit comprising a first component and a second component wherein neither the first component nor the second component is a composition of the invention as described above, but wherein the first component and the second component can be combined to provide a composition of the invention as described above. The kit may further include a third component comprising one or more of the following: instructions, syringe or other delivery device, adjuvant, or pharmaceutically acceptable formulating solution.

The invention also provides a delivery device pre-filled with an immunogenic composition of the invention.

The mammal is preferably a human. Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc. Other mammals which can usefully be immunised according to the invention are cows, dogs, horses, and pigs.

One way of checking efficacy of therapeutic treatment involves monitoring *P. aeruginosa* infection after administration of the compositions of the invention. One way of checking efficacy of prophylactic treatment involves monitoring immune responses, systemically (such as monitoring the level of IgG1 and IgG2a production) and/or mucosally (such as monitoring the level of IgA production), against the antigens in the compositions of the invention after administration of the composition. Typically, antigen-specific serum antibody responses are determined post-immunisation but pre-challenge whereas antigen-specific mucosal antibody responses are determined post-immunisation and post-challenge.

Another way of assessing the immunogenicity of the compositions of the present invention is to express the proteins recombinantly for screening patient sera or mucosal secretions by immunoblot and/or microarrays. A positive reaction between the protein and the patient sample indicates that the patient has mounted an immune response to the protein in question. This method may also be used to identify immunodominant antigens and/or epitopes within antigens.

The efficacy of vaccine compositions can also be determined in vivo by challenging animal models of *P. aeruginosa* infection, e.g., guinea pigs or mice, with the vaccine compositions. In particular, there one useful animal model for the study of *P. aeruginosa* infectious disease, described in details in the chapter entitled "efficacy testing" The lethal infection model looks at the number of mice which survive after being infected by a normally-lethal dose of *P. aeruginosa* via intra-tracheal route. Different antigens, and different antigen combinations, may contribute to different aspects of an effective vaccine.

Compositions of the invention will generally be administered directly to a patient. Direct delivery may be accomplished by parenteral injection (e.g. subcutaneously, intraperitoneally, intravenously, intramuscularly, or to the interstitial space of a tissue), or mucosally, such as by rectal, oral (e.g. tablet, spray), vaginal, topical, transdermal or transcutaneous, intranasal, ocular, aural, pulmonary or other mucosal administration.

The invention may be used to elicit systemic and/or mucosal immunity, preferably to elicit an enhanced systemic and/or mucosal immunity.

Preferably the enhanced systemic and/or mucosal immunity is reflected in an enhanced TH1 and/or TH2 immune response. Preferably, the enhanced immune response includes an increase in the production of IgG1 and/or IgG2a and/or IgA.

Th17 cells are a recently described lineage of helper T cells that can enhance antibacterial mucosal defenses and can potentially mediate protective vaccine-induced response. See reference 138

Dosage can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Vaccines prepared according to the invention may be used to treat both children and adults. Thus a human patient may be less than 1 year old, 1-5 years old, 5-15 years old, 15-55 years old, or at least 55 years old. Preferred patients for receiving the vaccines are the elderly (e.g. ≥50 years old, ≥60 years old, and preferably ≥65 years), the young (e.g. ≤5 years old), hospitalised patients, healthcare workers, armed service and military personnel, pregnant women, the chronically ill, or immunodeficient patients. The vaccines are not suitable solely for these groups, however, and may be used more generally in a population.

Vaccines produced by the invention may be administered to patients at substantially the same time as (e.g. during the same medical consultation or visit to a healthcare professional or vaccination centre) other vaccines e.g. at substantially the same time as an influenza vaccine, a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, etc. Further non-*pseudomonas* vaccines suitable for co-administration may include one or more antigens.

Nucleic Acid Immunisation

The immunogenic compositions described above include polypeptide antigens from *P. aeruginosa*. In all cases, however, the polypeptide antigens can be replaced by nucleic acids (typically DNA) encoding those polypeptides, to give compositions, methods and uses based on nucleic acid immunisation. Nucleic acid immunisation is now a developed field.

The nucleic acid encoding the immunogen is expressed in vivo after delivery to a patient and the expressed immunogen then stimulates the immune system. The active ingredient will typically take the form of a nucleic acid vector comprising: (i) a promoter; (ii) a sequence encoding the immunogen, operably linked to the promoter; and optionally (iii) a selectable marker. Preferred vectors may further comprise (iv) an origin of replication; and (v) a transcription terminator downstream of and operably linked to (ii). In general, (i) & (v) will be eukaryotic and (iii) & (iv) will be prokaryotic.

Preferred promoters are viral promoters e.g. from cytomegalovirus (CMV). The vector may also include transcriptional regulatory sequences (e.g. enhancers) in addition to the promoter and which interact functionally with the promoter. Preferred vectors include the immediate-early CMV enhancer/promoter, and more preferred vectors also include CMV intron A. The promoter is operably linked to a downstream sequence encoding an immunogen, such that expression of the immunogen-encoding sequence is under the promoter's control.

Where a marker is used, it preferably functions in a microbial host (e.g. in a prokaryote, in a bacteria, in a yeast). The marker is preferably a prokaryotic selectable marker (e.g. transcribed under the control of a prokaryotic promoter). For convenience, typical markers are antibiotic resistance genes.

The vector of the invention is preferably an autonomously replicating episomal or extrachromosomal vector, such as a plasmid.

The vector of the invention preferably comprises an origin of replication. It is preferred that the origin of replication is active in prokaryotes but not in eukaryotes.

Preferred vectors thus include a prokaryotic marker for selection of the vector, a prokaryotic origin of replication, but a eukaryotic promoter for driving transcription of the immunogen-encoding sequence. The vectors will therefore (a) be amplified and selected in prokaryotic hosts without polypeptide expression, but (b) be expressed in eukaryotic hosts without being amplified. This arrangement is ideal for nucleic acid immunization vectors.

The vector of the invention may comprise a eukaryotic transcriptional terminator sequence downstream of the coding sequence. This can enhance transcription levels. Where the coding sequence does not have its own, the vector of the invention preferably comprises a polyadenylation sequence. A preferred polyadenylation sequence is from bovine growth hormone.

The vector of the invention may comprise a multiple cloning site

In addition to sequences encoding the immunogen and a marker, the vector may comprise a second eukaryotic coding sequence. The vector may also comprise an IRES upstream of said second sequence in order to permit translation of a second eukaryotic polypeptide from the same transcript as the immunogen. Alternatively, the immunogen-coding sequence may be downstream of an IRES.

The vector of the invention may comprise unmethylated CpG motifs e.g. unmethylated DNA sequences which have in common a cytosine preceding a guanosine, flanked by two 5' purines and two 3' pyrimidines. In their unmethylated form these DNA motifs have been demonstrated to be potent stimulators of several types of immune cell.

Vectors may be delivered in a targeted way. Receptor-mediated DNA delivery techniques are described in the known art. Therapeutic compositions containing a nucleic acid are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. Factors such as method of action (e.g. for enhancing or inhibiting levels of the encoded gene product) and efficacy of transformation and expression are considerations which will affect the dosage required for ultimate efficacy. Where greater expression is desired over a larger area of tissue, larger amounts of vector or the same amounts re-administered in a successive protocol of administrations, or several administrations to different adjacent or close tissue portions may be required to effect a positive therapeutic outcome. In all cases, routine experimentation in clinical trials will determine specific ranges for optimal therapeutic effect.

Vectors can be delivered using gene delivery vehicles. The gene delivery vehicle can be of viral or non-viral origin (see generally reference 139).

Viral-based vectors for delivery of a desired nucleic acid and expression in a desired cell are well known in the art. Exemplary viral-based vehicles include, but are not limited to, recombinant retroviruses (e.g. references 140 to), alphavirus-based vectors (e.g. Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532); hybrids or chimeras of these viruses may also be used), poxvirus vectors (e.g. vaccinia, fowlpox, canarypox, modified vaccinia Ankara, etc.), adenovirus vectors, and adeno-associated virus (AAV) vectors (e.g. see refs. 142 to). Administration of DNA linked to killed adenovirus [144] can also be employed.

Non-viral delivery vehicles and methods can also be employed, including, but not limited to, polycationic condensed DNA linked or unlinked to killed adenovirus alone [e.g. 144], ligand-linked DNA [145], eukaryotic cell delivery vehicles cells [e.g. refs. 146 to] and nucleic charge neutralization or fusion with cell membranes. Naked DNA can also be employed. Exemplary naked DNA introduction methods are described in ref 148. Liposomes (e.g. immunoliposomes) that can act as gene delivery vehicles are described in refs. 149 to. Additional approaches are described in references 151-152.

Further non-viral delivery suitable for use includes mechanical delivery systems such as the approach described in ref 152. Moreover, the coding sequence and the product of expression of such can be delivered through deposition of photopolymerized hydrogel materials or use of ionizing radiation (e.g. refs. 153). Other conventional methods for gene delivery that can be used for delivery of the coding sequence include, for example, use of hand-held gene transfer particle gun [154] or use of ionizing radiation for activating transferred genes.

Delivery DNA using PLG {poly(lactide-co-glycolide)} microparticles is a particularly preferred method e.g. by adsorption to the microparticles, which are optionally treated to have a negatively-charged surface (e.g. treated with SDS) or a positively-charged surface (e.g. treated with a cationic detergent, such as CTAB).

Antibodies

Antibodies against *P. aeruginosa* antigens can be used for passive immunisation. Thus the invention provides an antibody which is specific for an antigen in the first, second, third or fourth antigen groups. The invention also provides the use of such antibodies in therapy. The invention also provides the use of such antibodies in the manufacture of a medicament. The invention also provides a method for treating a mammal comprising the step of administering an effective amount of an antibody of the invention. As described above for immunogenic compositions, these methods and uses allow a mammal to be protected against *P. aeruginosa* infection.

The term "antibody" includes intact immunoglobulin molecules, as well as fragments thereof which are capable of binding an antigen. These include hybrid (chimeric) antibody molecules; F(ab')2 and F(ab) fragments and Fv molecules; non-covalent heterodimers; single-chain Fv molecules (sFv); dimeric and trimeric antibody fragment constructs; minibodies; humanized antibody molecules; and any functional fragments obtained from such molecules, as well as antibodies obtained through non-conventional processes such as phage display. Preferably, the antibodies are monoclonal antibodies. Methods of obtaining monoclonal antibodies are well known in the art. Humanised or fully-human antibodies are preferred.

General

The practice of the present invention will employ, unless otherwise indicated, conventional methods of chemistry, biochemistry, molecular biology, immunology and pharmacology, within the skill of the art. Such techniques are explained fully in the literature.

"GI" numbering is used above. A GI number, or "GenInfo Identifier", is a series of digits assigned consecutively to each sequence record processed by NCBI when sequences are added to its databases. The GI number bears no resemblance to the accession number of the sequence record. When a sequence is updated (e.g. for correction, or to add more annotation or information) then it receives a new GI number. Thus the sequence associated with a given GI number is never changed. See also reference 37.

Where the invention concerns an "epitope", this epitope may be a B-cell epitope and/or a T-cell epitope. Such epitopes can be identified empirically (e.g. using PEPSCAN [155] or similar methods), or they can be predicted (e.g. using the Jameson-Wolf antigenic index [156], matrix-based approaches [157], MAPITOPE [158], TEPITOPE [159], OptiMer & EpiMer [160], ADEPT [161], Tsites, hydrophilicity, antigenic index or the methods known in the art. Epitopes are the parts of an antigen that are recognised by and bind to the antigen binding sites of antibodies or T-cell receptors, and they may also be referred to as "antigenic determinants".

Where an antigen "domain" is omitted, this may involve omission of a signal peptide, of a cytoplasmic domain, of a transmembrane domain, of an extracellular domain, etc.

The term "comprising" encompasses "including" as well as "consisting" e.g. a composition "comprising" X may consist exclusively of X or may include something additional e.g. X+Y.

The term "about" in relation to a numerical value x is optional and means, for example, x±10%.

References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of ref 162. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in ref 163.

MODES FOR CARRYING OUT THE INVENTION

Antigen Selection

*P. aeruginosa* proteins have been selected for use as vaccine components based on the combination of various criteria which include the following ones:

Cellular localization prediction, through which priority was attributed to proteins predicted as "outer membrane", "periplasmic", extracellular" and "unknown". In relation to the latest definition proteins predicted as having an "unknown" cellular localization which are often composed of multiple domains, of which one could actually be surface exposed.

Significant homology to known virulence factors, vaccine candidates from other species Lack of significant homology to human proteins encoded by the sequenced human genome, in order to limit the probability of generation of autoimmune response or vaccine induced autoimmunity.

Lack of significant homology to E. coli proteins, considering that proteins having counterparts in many bacterial species, either pathogenic or non-pathogenic have higher probability to have house-keeping functions and therefore are less likely to be good antigens Conservation over a panel of at least 5 out of 7 fully sequenced P. aeruginosa genomes.

Useful aminoacid sequence length which is considered to be of at least 150 aa

Microarray data. In vitro expression of P. aeruginosa PAO1 derived proteins repertoire was tested to analyse changes in gene expression under anaerobic conditions as those found in the mucus of CF (cystic fibrosis) patients compared with aerobic conditions found in the environment. Priority was assigned to proteins whose expression was maintained in both aerobic and anaerobic cell culture conditions.

The protein can also adsorb reasonably well to aluminium hydroxide (see also below), which is useful for stable formulation for delivery to humans Strain Coverage In order to evaluate the conservation of the antigens selected, various P. aeruginosa clinical isolates were used. P. aeruginosa clinical strains were isolated from eight pancreatic-insufficient CF patients attending the CF clinic of the Medizinische Hochschule Hannover. P. aeruginosa strains from the first positive cultures are designated as "early" isolates, whereas intermediate isolates were collected 1 to 5 years thereafter and late isolates were collected 7 to 16 years after colonization or prior to death or lung transplantation. Strains tested are listed in the following Table.

Table on strain coverage

| Strain Genotype | Years of infection |
|---|---|
| SG1 | 0 |
| SG57 | 15.8 |
| SG58 | 15.8 |
| BT2 | 0 |
| BT72 | 15.8 |
| BT73 | 16.3 |
| AA2 | 0.5 |
| AA43° | 7.5 |
| AA44° | 7.5 |
| TR1 | 0 |
| TR66 | 12.8 |
| TR67° | 13.5 |
| MF1 | 0 |
| MF51° | 10.1 |
| KK1 | 0 |
| KK71° | 12.6 |
| KK72° | 12.6 |
| BST2 | 0.9 |
| BST44 | 15.8 |

The symbol ° indicates the last P. aeruginosa strain prior to death or lung transplantation. Genes encoding PSE54, PSE44-4, PSE10-1, PSE21-5, PSE27-1, PSE52-1, PSE53-1, PSE11, PSE41, PSE47-2, were present in all tested strains as confirmed by PCR (polymerase chain reaction).

Thus, considering the vaccine efficacy in terms of a broader cross-strain protection a vaccine based on any of the best combinations/cocktails as tested in table 2, can be a valid solution in order to extend vaccine coverage against pseudomonas derived infections.

Cloning and Expression of P. aeruginosa Recombinant Proteins

Cloning and expression of antigens can be performed by standard methods.

Polypeptides antigens from PA strain PAO1 were PCR-amplified using specific oligonucleotides and PA chromosomal DNA as template. Resulting PCR products were cloned in pET15b (Novagen) using the PIPE method [164], consisting in the PCR amplification of the cloning vector (V-PCR) and in the PCR amplification of the insert (I-PCR). Then, 1 µl of V-PCR and 1 µl of I-PCR are mixed and transformed in chemically competent HK100 cells [165]. I-PCR reactions were set up containing 1 µM each of the forward and reverse primers, 1× Cloned Pfu DNA Polymerase Reaction Buffer, 2.5 units of Pfu Turbo DNA polymerase (Stratagene), 200 µM of each dNTP (Invitrogen) and 50 ng of genomic DNA template. The reactions were conducted as follows: initial denaturation for 2 min at 95° C., then 25 cycles of 95° C. for 30 s, 55° C. for 45 s, and 68° C. for 3 min followed by a final cool down to 4° C. V-PCR reactions were identical to the I-PCR reactions but the steps at 68° C. were lasting 14 min and 2 ng of pET15b plasmid were used as DNA template. Correct transformants where selected by PCR screening and DNA plasmid sequencing of the vector-insert junctions. The correct plasmid were then prepared from selected HK100 clones and used to transform BL21(DE3)T1$^r$ cells (Sigma) in order to allow protein expression.

To express cloned proteins, BL21(DE3)T1$^r$ clones containing pET15b constructs were grown in LB medium containing 100 µg/ml Ampicillin at 37° C. until OD$_{600}$=0.5. Protein expression was then induced by adding 1 mM IPTG and growing at the same temperature for additional 3 hrs. Conventional protein extractions and SDS-Page were performed to check protein expression. Western blot techniques known in the art were used to confirm proper expression of tested P. aeruginosa antigens. Specific antisera from immunized mice were used confirm protein expression Immunofluorescence techniques known in the art were used to confirm surface localization of tested P. aeruginosa antigens using anti-cell wall antibodies as co-localizator and/or a specific anti-antigen serum obtained after mice immunization.

Adjuvant Formulation

Selected P. aeruginosa protein antigen candidates have been formulated with aluminium hydroxide, either individually or as a combination of proteins. The formulations have been optimized for pH and osmolarity.

The antigens were formulated as monovalent antigen or multivalent antigens combinations in Aluminium Hydroxide. Each antigen was used at 10 µg/formulation/animal.

Aluminium hydroxide was used at 2 mg/ml final concentration, in a 10 mM histidine buffer (pH 6.5). Sodium chloride was used to adjust osmolality to physiologic conditions. Formulations were given intratracheal in a final vaccine composition volume of 200 µl/animal.

All monovalent and combination formulations, could be adjusted with respect to a desired pH and osmolality. The formulations had pH in the range 6.2-7.3, and osmolality in the range 248-360 mOsm/kg.

Most of the proteins tested, in various monovalent and combination formulations, adsorbed well to the aluminium hydroxide adjuvant.

The individual PSE54, PSE10-1, PSE21-5, PSE27-1, PSE44-4, PSE52-1, PSE53-1 proteins were completely adsorbed, and could be desorbed without altering their pre-adsorption electrophoretic profile.

Each antigen in a combination of was completely adsorbed, with no inter-antigen competition for the adjuvant. The antigens in a combination of PSE25+PSE54, PSE27-1+PSE44, PSE38-1+PSE11-3, PSE38-1+PSE11-3, PSE41-5+PSE47A-2, PSE41-5+PSE53-1, PSE47A-2+PSE53-1, PSE47A-2+PSE52-1, were also completely adsorbed.

All tested formulations were stable for their pH and osmolality. All antigens remained completely adsorbed to the adjuvant. All antigens maintained their desorption characteristics. There was no evidence of increased degradation or aggregation of antigens after desorption.

Efficacy Testing

Individual antigens as listed in Table 2 were tested for their ability to protect against intra-tracheal (IT) lethal infection challenge by $5\times10^6$ cfu of planktonic PAO1 strain. Results are shown in FIG. 1.

Recombinant proteins were used to immunize mice for protection studies against *P. aeruginosa*, using as reference strain PAO1. Groups of 10 mice (C57BL/6NCrlBR male 5 weeks old, Charles River Laboratories, Italy) were immunized at day 0, 21 and 35 with different antigens and at day 50 challenged with the homologous *P. aeruginosa* PAO1 referent strain by acute infection. In each boost every mouse received 10 µg or 20 µg of recombinant protein/s adsorbed with alum alone or with $10^7$ cfu of heat inactivated PAO1. To obtain antisera mice of all groups were bleeding at day −1, day 34, and day 49. As negative control 10 mice per immunization round were injected with alum alone, while as positive control 10 mice per immunization round were boosted with $10^7$ cfu of heat inactivated PAO1 strain. On day 50, mice were infected with $5\times10^6$ cfu (first lethal dose) of planktonic *P. aeruginosa* PAO1 via intra-tracheal (IT) route. Mice were anesthetized and the trachea directly visualized by a ventral midline incision, exposed and intubated with a sterile, flexible 22-g cannula attached to a 1 ml syringe. A 60 µl inoculum of planktonic bacteria were implanted via the cannula into the lung. Mice were monitored for survival for 120 hrs at intervals of twelve hours and compared with un-vaccinated and PAO1 vaccinated control groups.

Antigens showed to be able to give an incremental shift in the survival curves compared with the control were listed in table 2, and the best results were seen with PSE21-5, PSE47A-2, PSE52-1, PSE53-1 or PSE54, PSE10, PSE 11-3, PSE 27-1, PSE44-4 and PSE 41-5.

Further, individual antigens were tested in combination as reported in Table 2.

Table 2 gives a summary of results obtained with various antigens used alone or in combinations in vivo in the animal mouse model. Survival data are shown in Table 2. In the statistical significance column, the p value in Mantel-Cox test is calculated against negative control group. Survival curve of each protein was compared with the survival curve of the negative control of the same round in which the protein was tested. Survival was measured for 120 hrs at intervals of twelve hours and compared with un-vaccinated and PAO1 vaccinated control groups. Percentage of mice survival after the 36 hours was evidence of positive immunization results in vivo.

Among the different rounds considering the 30 tested recombinant proteins (Table 2), three proteins (PSE10-1 (PA1178), PSE47A-2 (PA4082), and PSE52-1 (PA4765) had also a highly statistical significance different survival curves when compared with the negative control group (p value in Mantel-Cox test against negative control group 0.0261, 0.0364 and 0.0275 respectively).

On the basis of the analysis of the survival curves of seven additional recombinant proteins it can be predicted that results may also be significantly corroborated by increasing the numbers of animal tested in vivo further confirming the preliminary positive and surprising data of PSE11-3 (PA1248), PSE41-5 (PA2407), PSE44-4 (PA3526), PSE53-1 (PA5047), PSE21-5 (PA5112), PSE-54 (PA5340), PSE-27-1 (PA0328).

In addition when a known antigen, namely OprF-OprI, was used alone to immunize mice in the present animal model a 20% of survival, with a statistical significance of 0.0446 was obtained.

In order to further improve the survival in this in vivo model, specific combinations were also tested by combining together the most promising proteins in order to further increase vaccine efficacy.

Comparison of Combinations Versus its Individual Polypeptides

Combinations alias known as cocktails of antigens in a single formulation were also used to immunise mice. The combinations were typically adjuvanted with aluminium hydroxide (see chapter "Adjuvant Formulation) and were administered on days 0, 21 and 35. The immunisations were in C57BL/6NCrlBR male 5 weeks old mice, 10 per group. On day 50 the mice were challenged with a lethal dose of heat inactivated bacteria and survival was then followed for 120 hrs. For comparison, PBS was used as a negative control and PAO1 heat-inactivated as a positive control.

The increase in survival, during monitoring for 120 hrs after the immunization schedule and further infection with lethal dose of the *Pseudomonas* homologous strain, when compared to the negative control group, was surprisingly showing best result when the following combinations were tested (Table 2): PSE47A-2+PSE53-1, PSE47A-2+PSE53-1, PSE54+PSE44-4 and PSE54+PSE21-5 being the most promising; whereas PSE47A-2+PSE52-1 combination was less promising.

Various tests were performed to compare various combinations to its seven individual polypeptides (i.e. PSE54 or PSE21-5 or PSE27-1, PSE44-4, PSE52-1, PSE53-1, PSE47A-2), as well as OprF/I as further positive control or to an antigen-free negative control.

Mice were immunized with cocktails of two different proteins. Eight cocktails had statistically different survival curves when compared to the negative control group (considering also the PSE54+OprF-OprI composition).

In the sixth round, different cocktails of proteins combined with the PSE47A-2 were tested: PSE47A-2+PSE52-1 and PSE47A-2+PSE53-1 were showing a surprising statistical difference respect to the negative control group (p value in Mantel-Cox test against negative control group 0.0374 and 0.0373 respectively).

In particular, vaccination with the cocktail PSE47A-2+PSE53-1 resulted surprisingly in 30% of survival, maintain a good statistical significance.

In the tenth round, different cocktails of proteins combined with the PSE54 were tested. Five cocktails out of eight gave a significantly different mortality curve when compared with negative control group as reported in the Table 2. In particular, vaccination with the cocktails of PSE54+PSE44-4 and PSE54+PSE52-1 antigens gave a very good animal protection resulting in 40% and 33% of animal survival respectively (p value in Mantel-Cox test against negative control group 0.0076 and 0.0142 respectively). When re-tested in the eleventh round, the PSE54+PSE44-4 confirmed the positive result showing an increase of animal survival of 57%. Other cocktails showing better vaccine efficacy when used in combination were: PSE54+PSE21-5, PSE54+PSE53-1 and PSE54+PSE10-1 (p value in Mantel-Cox test against negative control group 0.0332, 0.0085 and 0.0025 respectively).

Furthermore, this last cocktail, PSE54+PSE10-1, had comparable results in two different rounds of immunization corroborating the positive and surprising result, resulting in the same survival rate of animals (20%) in both rounds.

Finally four additional cocktails of different proteins (PSE27-1+PSE44-4, PSE53-1+PSE41-5 and PSE53-1+PSE52-1 and PSE54+PSE27-1) may become even more significant further repeating the experiments in further confirmatory experiments increasing the number of animals.

In order to even further improve the capacity of protection and ultimately the vaccine efficacy of selected antigens, combination of three proteins were tested. Seven groups were tested maintaining two fixed proteins PSE54+PSE44-4 plus one variable protein, while others groups tested were with PSE47A-2+PSE52-1+PSE53-1, PSE54+PSE52-1+PSE53-1 and PSE54+PSE53-1+PSE 27-1. Some of these combination did not gave significant animal protection when compared with negative control group whereas when considering e.g. the PSE54+PSE44-4+PSE47A-2 or PSE54+PSE53-1+PSE 27-1 they may provide significant protection simply through confirmatory experiments, obtained by increasing the number of animals (See table 2). Thus, some of the combination of three proteins did not improve protection rather it seemed worse when considering two proteins.

However, when considering a further combination adding in the cocktail of antigens also the positive control OprF-OprI fusion was included in the further combinations.

When OprF-OprI was used as single fusion protein antigen it showed 20% of survival with a statistical significance of 0.0446, similarly to other single immunization with single promising antigens, whereas when used in combination with PSE54 surprisingly the survival percentage increased to 50% with a similar statistical significance. In addition, the immunization with the following antigens in combination PSE54+PSE27+OprF-OprI showed surprisingly even 60% of survival with a comparable statistical significance, while considering the other combination, namely PSE54+PSE53+OprF-OprI did not show any additive effect or significant immunogenic vaccine efficacy than the single antigens immunization, even in one single immunization using a decrease amount of each single antigen (Table 2). It is reasonable to expect that by increasing the number of animal tested also this specific combination might provide significative increase in immunological protection.

It will be understood that the invention has been described by way of example only and modifications may be made whilst remaining within the scope and spirit of the invention.

TABLE 1

NOMENCLATURE CROSS-REFERENCE

| SEQ ID NOs | Locus Tag PAO1 strain | Internal Name | NCBI definitions |
|---|---|---|---|
| 1 | PA0328 | PSE27 | outer membrane autotransporter |
| 2 | PA1178 | PSE10 | PhoP/Q low Mg2+ inducible outer membrane protein H1 precursor |
| 3 | PA5112 | PSE21 | esterase EstA |
| 4 | PA1248 | PSE11 | alkaline protease secretion outer membrane protein AprF precursor |
| 5 | PA2407 | PSE41-5 | putative adhesion protein |
| 6 | PA3526 | PSE44 | outer membrane protein precursor |
| 7 | PA4082 | PSE47 | adhesive protein CupB5 |
| 8 | PA4765 | PSE52 | Outer membrane lipoprotein OmlA precursor |
| 9 | PA5047 | PSE53 | lipoprotein, putative; peptidase |
| 10 | PA5340 | PSE54 | lipoprotein, putative |
| 11 | PA0595 | PSE5 | OstA precursor |
| 12 | PA1954 | PSE13 | hypothetical protein PA1954 |
| 13 | PA3692 | PSE17 | Lipotoxin F |
| 14 | PA4370 | PSE18 | Metalloproteinase outer membrane protein precursor |
| 15 | PA4710 | PSE19 | receptor PhuR precursor |
| 16 | PA4735 | PSE20 | hypothetical protein PA4735 |
| 17 | PA3647 | PSE23 | hypothetical protein PA3647 |
| 18 | PA0126 | PSE24 | hypothetical protein PA0126 |
| 19 | PA0189 | PSE25 | putative porin |
| 20 | PA0274 | PSE26 | hypothetical protein PA0274 |
| 21 | PA0537 | PSE28 | putative lipoprotein |
| 22 | PA0737 | PSE31 | putative lipoprotein |
| 23 | PA1086 | PSE33 | flagellar hook-associated FlgK |
| 24 | PA1106 | PSE34 | hypothetical protein PA1106 |
| 25 | PA1324 | PSE36 | putative lipoprotein |
| 26 | PA1777 | PSE38 | outer membrane OprF precursor |
| 27 | PA2793 | PSE42 | putative lipoprotein |
| 28 | PA3535 | PSE45 | putative serine protease |
| 29 | PA4578 | PSE50 | hypothetical protein PA4578 |
| 30 | PA4667 | PSE51 | TPR domain protein |
| 31 | PA4525 | PilA | type 4 fimbrial precursor PilA |
| 32 | Fusion | OprF/I | Fusion protein |
| 33 | PA1092 | FliC | Flagellar protein |
| 34 | PA1094 | FliD | Flagellar protein |
| 35 | PA1148 | ExoA | Exotoxin A |
| 36 | PA0328 | PSE27 | Fragment without N-terminus |
| 37 | PA1178 | PSE10 | Fragment without N-terminus |
| 38 | PA5112 | PSE21 | Fragment without N-terminus |
| 39 | PA1248 | PSE11 | Fragment without N-terminus |
| 40 | PA2407 | PSE41-5 | Fragment without N-terminus |
| 41 | PA3526 | PSE44 | Fragment without N-terminus |
| 42 | PA4082 | PSE47-A2 | without N-term and translocator domain |
| 43 | PA4765 | PSE52 | Fragment without N-terminus |
| 44 | PA5047 | PSE53 | Fragment without N-terminus |
| 45 | PA5340 | PSE54 | Fragment without N-terminus |
| 46 | PA0595 | PSE5 | Fragment without N-terminus |
| 47 | PA1954 | PSE13 | Fragment without N-terminus |
| 48 | PA3692 | PSE17 | Fragment without N-terminus |
| 49 | PA4370 | PSE18 | Fragment without N-terminus |
| 50 | PA4710 | PSE19 | Fragment without N-terminus |
| 51 | PA4735 | PSE20 | Fragment without N-terminus |
| 52 | PA3647 | PSE23 | Fragment without N-terminus |
| 53 | PA0126 | PSE24 | Fragment without N-terminus |
| 54 | PA0189 | PSE25 | Fragment without N-terminus |
| 55 | PA0274 | PSE26 | Fragment without N-terminus |
| 56 | PA0537 | PSE28 | Fragment without N-terminus |
| 57 | PA0737 | PSE31 | Fragment without N-terminus |
| 58 | PA1086 | PSE33 | Fragment without N-terminus |
| 59 | PA1106 | PSE34 | Fragment without N-terminus |
| 60 | PA1324 | PSE36 | Fragment without N-terminus |
| 61 | PA1777 | PSE38 | Fragment without N-terminus |
| 62 | PA2793 | PSE42 | Fragment without N-terminus |
| 63 | PA3535 | PSE45 | Fragment without N-terminus |
| 64 | PA4578 | PSE50 | Fragment without N-terminus |
| 65 | PA4667 | PSE51 | Fragment without N-terminus |
| 66 | Histidine-Tag | N.A. | N.A. |

TABLE 1-continued

NOMENCLATURE CROSS-REFERENCE

| SEQ ID NOs | Locus Tag PAO1 strain | Internal Name | NCBI definitions |
|---|---|---|---|
| 67 | Linker | N.A. | N.A. |
| 68 | Linker | N.A. | N.A. |
| 69 | Linker | N.A. | N.A. |
| 70 | His6 | N.A. | Synthetic 6xHis tag |
| 71 | Glyn | N.A. | Synthetic peptide encompassing 2 to 10 residues, wherein some positions may be absent |
| 72 | $His_n$ | N.A. | Synthetic peptide $His_n$ where n = 3, 4, 5, 6, 7, 8, 9, 10 or more |
| 73 | $(Gly)_4$ | N.A. | Synthetic peptide |

TABLE 2

MOUSE ANIMAL MODEL RESULTS SUMMARY

| Ags | Round | ug Ags | Statistical significance £ | Survival % |
|---|---|---|---|---|
| PSE5 | 11 | 10 | 0.10 | 0 (0/5) |
| PSE10 | 1 | 10 | 0.026 | 0 (0/9) |
| PSE10-1 | 8 | 20 | 0.56 | 0 (0/10) |
| PSE11-3 | 2 | 10 | 0.47* | 14 (1/7) |
|  | 7 | 20 | 0.28* | 22 (2/9) |
| PSE13 | 4 | 10 | 0.55 | 0 (0/10) |
| PSE17 | 11 | 10 | 0.35 | 0 (0/8) |
| PSE18-2 | 1 | 10 | 0.73 | 0 (0/8) |
| PSE19-1 | 4 | 10 | 0.17 | 0 (0/6) |
| PSE20 | 11 | 10 | 0.91 | 12.5 (1/8) |
| PSE21-5 | 2 | 10 | 0.08* | 0 (0/10) |
| PSE21 | 11 | 10 | 0.19* | 50 (5/10) |
| PSE23-1 | 1 | 10 | 0.61 | 0 (0/9) |
| PSE24-1 | 1 | 10 | 0.19 | 0 (0/8) |
| PSE25-1 | 4 | 10 | 0.10 | 0 (0/10) |
|  | 8 | 20 | 0.90 | 0 (0/10) |
| PSE26 | 3 | 10 | 0.32 | 0 (0/9) |
| PSE27-1 | 2 | 10 | 0.91 | 0 (0/10) |
|  | 4 | 10 | 0.21* | 0 (0/10) |
|  | 7 | 20 | 0.80 | 11 (1/9) |
| PSE28-2 | 2 | 10 | 0.37 | 0 (0/10) |
| PSE31-2 | 2 | 10 | 1 | 0 (0/10) |
|  | 11 | 10 | 0.76 | 10 (1/10) |
| PSE33 | 11 | 10 | 0.61 | 0 (0/9) |
| PSE34 | 1 | 10 | 0.17 | 0 (0/9) |
| PSE36-3 | 1 | 10 | 1 | 0 (0/10) |
| PSE38-1 | 2 | 10 | 0.53 | 22 (2/9) |
| PSE41-5 | 1 | 10 | 0.34* | 0 (0/10) |
|  | 6 | 20 | 0.25 | 0 (0/9) |
|  | 7 | 20 | 0.65* | 0 (0/10) |
| PSE42-1 | 4 | 10 | 0.55 | 13 (1/8) |
| PSE44-4 | 2 | 10 | 0.08* | 0 (0/9) |
|  | 7 | 20 | 0.28* | 22 (2/9) |
| PSE45-2 | 4 | 10 | 0.32 | 0 (0/8) |
| PSE47-3 | 4 | 10 | 0.06 | 0 (0/5) |
| PSE47A-2 | 2 | 10 | 0.0364 | 10 (1/10) |
|  | 4 | 10 | 0.55 | 0 (0/10) |
|  | 6 | 20 | 0.26 | 20 (2/10) |
|  | 9 | 20 | 0.27 | 20 (2/10) |
| PSE50 | 3 | 10 | 0.96 | 0 (0/9) |
| PSE51 | 3 | 10 | 1 | 0 (0/8) |
| PSE52 | 3 | 10 | 0.0275 | 0 (0/9) |
| PSE52-1 | 6 | 20 | 0.0208 | 10 (1/10) |
| PSE53 | 3 | 10 | 0.07* | 0 (0/9) |
| PSE53-1 | 6 | 20 | 0.22* | 0 (0/8) |
|  | 7 | 20 | 0.25* | 22 (2/9) |
| PSE54 | 3 | 10 | 0.17* | 10 (1/10) |
|  | 8 | 20 | 0.88 | 0 (0/10) |
|  | 9 | 20 | 0.16* | 0 (0/8) |
|  | 14 | 10 | 0.19* | 60 (6/10) |
| PSE25 + PSE54 | 8 | 10 + 10 | 0.49 | 0 (0/10) |
| PSE27-1 + PSE44 | 7 | 10 + 10 | 0.38* | 0 (0/10) |
| PSE38-1 + PSE11-3 | 9 | 10 + 10 | 0.004# | 0 (0/9) |
| PSE41-5 + PSE52-1 | 6 | 10 + 10 | 0.27 | 11 (1/9) |
| PSE41-5 + PSE47A-2 | 6 | 10 + 10 | 0.98 | 0 (0/4) |
| PSE41-5 + PSE53-1 | 7 | 10 + 10 | 0.55* | 10 (1/10) |
| PSE47A-2 + PSE53-1 | 6 | 10 + 10 | 0.0373 | 30 (3/10) |

TABLE 2-continued

MOUSE ANIMAL MODEL RESULTS SUMMARY

| Ags | Round | ug Ags | Statistical significance [£] | Survival % |
|---|---|---|---|---|
| PSE47A-2 + PSE53-1 | 9 | 10 + 10 | 0.09 | 0 (0/10) |
| PSE47A-2 + PSE52-1 | 6 | 10 + 10 | 0.0374 | 0 (0/7) |
| PSE47A-2 + PSE52-1 | 9 | 10 + 10 | 0.06 | 0 (0/9) |
| PAE47A-2 + PSE21-5 | 9 | 10 + 10 | 0.28 | 11 (1/9) |
| PSE47A-2 + PSE44-4 | 9 | 10 + 10 | 0.34 | 0 (0/9) |
| PSE47A-2 + PSE38-1 | 9 | 10 + 10 | 0.003[#] | 0 (0/10) |
| PSE47A-2 + PSE11-3 | 9 | 10 + 10 | 0.01 | 0 (0/10) |
| PSE53-1 + PSE52-1 | 6 | 10 + 10 | 0.20* | 0 (0/9) |
| PSE54 + PSE10-1 | 8 | 10 + 10 | 0.0154 | 20 (2/10) |
|  | 10 | 10 + 10 | 0.0025 | 20 (2/10) |
| PSE54 + PSE47A-2 | 10 | 10 + 10 | 0.55 | 10 (1/10) |
| PSE54 + PSE11-3 | 10 | 10 + 10 | 0.31 | 10 (1/10) |
| PSE54 + PSE52-1 | 10 | 10 + 10 | 0.0142 | 33 (3/9) |
|  | 11 | 10 + 10 | 0.96 | 0 (0/3) |
| PSE54 + PSE53-1 | 10 | 10 + 10 | 0.0085 | 12.5 (1/8) |
| PSE54 + PSE53 | 13 | 10 + 10 | 0.61 | 22 (2/9) |
| PSE54 + PSE21-5 | 7 | 10 + 10 | 0.0332 | 14 (1/7) |
| PSE54 + PSE21 | 13 | 10 + 10 | 0.0213 | 40 (4/10) |
|  | 14 | 10 + 10 | 0.13* | 70 (7/10) |
| PSE54 + PSE27-1 | 10 | 10 + 10 | 0.20* | 22 (2/9) |
| PSE54 + PSE27 | 13 | 10 + 10 | 0.16* | 10 (1/10) |
|  | 14 | 10 + 10 | 0.052* | 80 (8/10) |
| PSE54 + PSE44-4 | 10 | 10 + 10 | 0.0076 | 40 (4/10) |
|  | 11 | 10 + 10 | 0.14* | 57.1 (4/7) |
| PSE54 + OprF-OprI | 13 | 10 + 10 | 0.0403 | 50 (5/10) |
| PSE10-1 + PSE25-1 | 8 | 10 + 10 | 0.44 | 0 (0/7) |
| PSE47A-2 + PSE52-1 + PSE53-1 | 9 | 10 + 10 + 10 | 0.06 | 0 (0/8) |
| PSE54 + PSE44-4 + PSE10-1 | 12 | 10 + 10 + 10 | 0.69 | 0 (0/10) |
| PSE54 + PSE44-4 + PSE21-5 | 12 | 10 + 10 + 10 | 0.34 | 0 (0/10) |
| PSE54 + PSE44-4 + PSE27 | 12 | 10 + 10 + 10 | 0.32 | 0 (0/10) |
| PSE54 + PSE44-4 + PSE52 | 12 | 10 + 10 + 10 | 0.61 | 0 (0/5) |
| PSE54 + PSE44-4 + PSE53-1 | 12 | 10 + 10 + 10 | 0.25 | 0 (0/7) |
| PSE54 + PSE44-4 + PSE47A-2 | 12 | 10 + 10 + 10 | 0.17* | 16.6 (1/6) |
| PSE54 + PSE44-4 + PSE11 | 12 | 10 + 10 + 10 | 0.46 | 0 (0/10) |
| PSE54 + PSE52-1 + PSE53-1 | 12 | 10 + 10 + 10 | 0.68 | 0 (0/4) |
| PSE54 + PSE27 + OprF-OprI | 13 | 10 + 10 + 10 | 0.0021 | 60 (6/10) |
| PSE54 + PSE53 + OprF-OprI | 13 | 10 + 10 + 10 | 0.17* | 20 (2/10) |
| PSE54 + PSE53 + PSE27 | 13 | 10 + 10 + 10 | 0.08* | 20 (2/10) |
| PSE54 + PSE53 + PSE27 | 13 | 6.7 + 6.7 + 6.7 | 0.17* | 20 (2/10) |
| OprF-OprI | 11 | 10 | 0.28 | 0 (0/8) |
|  | 12 | 10 | 0.43 | 10 (1/10) |
|  | 13 | 10 | 0.0446 | 20 (2/10) |

Legend of table 2:
[#] p value in Mantel-Cox test against negative control group: Survival curve of each protein was compared with the survival curve of the negative control of the same round in which the protein was tested. Survival was measured for 120 hrs at intervals of twelve hours and compared with un-vaccinated and PAO1 vaccinated control groups. Percentage of mice survival after the 36 hours was evidence of positive immunization results in vivo.
*t-test significant with increased animal number: antigen vs negative control.
[#]t-test significant: antigen vs. negative control significant but mice immunized with the antigens dead before the negative controls. Nd: not done

REFERENCES

[1] FEMS Microbiol Lett. 2009 November; 300(2):153-64.
[2] J Antimicrob Chemother. 2009 August; 64(2):229-38.
[3] Clin Microbiol Rev. 2009 October; 22(4):582-610.
[4] EP0717106B1
[5] Mansouri et al., *Infect. Immun.* 1999, 67(3):1461
[6] WO2012/084272.
[7] WO2010107778
[8] *Research Disclosure*, 453077 (January 2002).
[9] EP-A-0372501.
[10] EP-A-0378881.
[11] WO93/17712.
[12] WO98/58668.
[13] WO91/01146.
[14] Falugi et al. (2001) *Eur J Immunol* 31:3816-3824.
[15] Baraldo et al. (2004) *Infect Immun* 72(8):4884-7.
[16] EP-A-0594610.
[17] Kuo et al. (1995) *Infect Immun* 63:2706-13.
[18] Michon et al. (1998) *Vaccine.* 16:1732-41.
[19] WO02/091998.
[20] WO01/72337.
[21] WO00/61761.
[22] WO00/33882
[23] U.S. Pat. No. 4,761,283.
[24] U.S. Pat. No. 4,356,170.
[25] U.S. Pat. No. 4,882,317.
[26] U.S. Pat. No. 4,695,624.
[27] *Mol. Immunol.*, 1985, 22, 907-919
[28] Bethell G. S. et al., *J. Biol. Chem.*, 1979, 254, 2572-4
[29] WO00/10599.
[30] Gever et al., Med. Microbiol. Immunol., 165: 171-288 (1979).
[31] U.S. Pat. No. 4,057,685.
[32] U.S. Pat. Nos. 4,673,574; 4,761,283; 4,808,700.
[33] U.S. Pat. No. 4,459,286.
[34] U.S. Pat. No. 4,965,338.
[35] U.S. Pat. No. 4,663,160.

[36] WO2007/000343.
[37] Winsor G L, et al. Nucleic Acids Res. 2011 January; 39(Database issue):D596-600
[38] Luckett et al., (2012) Activity. PLoS Pathog 8(8): e1002854.
[39] Damron et al., (2009) Microbiology 155, 1028-1038
[40] Choi et al., Proteomics 2011, 11, 3424-3429
[41] Finke et al., (1990) Infection and Imunity, July p. 2241-2244
[42] Remans et al., (2010) Microbiology, 156, 2597-2607
[43] Mercier et al., (2009) Protein Science, 18, 606-618
[44] Bell et al., (1989) Journal of bacteriology, 171(6), 3211-3217
[45] Montor et al., Infect. Immun. 2009, 77(11):4877.
[46] Ochsner et al., J. Bacteriol. 1999, 181(4):1099
[47] WO2009005040
[48] EP0297291B
[49] Doring et al., (2008) Vaccine 26, 1011-1024
[50] Kao et al., Chem Biol Drug Des 2009; 74: 33-42
[51] Campodonico et al., INFECTION AND IMMUNITY, February 2010, p. 746-755
[52] Needleman & Wunsch (1970) *J. Mol. Biol.* 48, 443-453.
[53] Rice et al. (2000) *Trends Genet* 16:276-277.
[54] Taniyama et al., J. Bacteriol.—2012-1447-56
[55] Bauman & Kuehn (2006) *Microbes Infect.* 8:2400-8.
[56] Ellis et al. (2010) *Infect Immun.* 78(9):3822-31.
[57] Tashiro et al. (2012) *Environmental Microbiology* 14:1349-62.
[58] U.S. Pat. No. 6,355,271.
[59] WO00/23105.
[60] WO90/14837.
[61] WO90/14837.
[62] Podda & Del Giudice (2003) *Expert Rev Vaccines* 2:197-203.
[63] *Vaccine Design: The Subunit and Adjuvant Approach* (eds. Powell & Newman) Plenum Press 1995 (ISBN 0-306-44867-X).
[64] *Vaccine Adjuvants: Preparation Methods and Research Protocols* (Volume 42 of *Methods in Molecular Medicine* series). ISBN: 1-59259-083-7. Ed. O'Hagan.
[65] WO2008/043774.
[66] Allison & Byars (1992) *Res Immunol* 143:519-25.
[67] Hariharan et al. (1995) *Cancer Res* 55:3486-9.
[68] US-2007/014805.
[69] US-2007/0191314.
[70] Suli et al. (2004) *Vaccine* 22(25-26):3464-9.
[71] WO95/11700.
[72] U.S. Pat. No. 6,080,725.
[73] WO2005/097181.
[74] WO2006/113373.
[75] Han et al. (2005) *Impact of Vitamin E on Immune Function and Infectious Diseases in the Aged at Nutrition, Immune functions and Health* EuroConference, Paris, 9-10 Jun. 2005.
[76] U.S. Pat. No. 6,630,161.
[77] U.S. Pat. No. 5,057,540.
[78] WO96/33739.
[79] EP-A-0109942.
[80] WO00/07621.
[81] Barr et al. (1998) *Advanced Drug Delivery Reviews* 32:247-271.
[82] EP-A-0689454.
[83] Johnson et al. (1999) *Bioorg Med Chem Lett* 9:2273-2278.
[84] Meraldi et al. (2003) *Vaccine* 21:2485-2491.
[85] Pajak et al. (2003) *Vaccine* 21:836-842.
[86] WO02/26757.
[87] WO99/62923.
[88] Krieg (2003) *Nature Medicine* 9:831-835.
[89] Kandimalla et al. (2003) *Biochemical Society Transactions* 31 (part 3):654-658.
[90] Blackwell et al. (2003) *J Immunol* 170:4061-4068.
[91] Krieg (2002) *Trends Immunol* 23:64-65.
[92] Kandimalla et al. (2003) *BBRC* 306:948-953.
[93] Bhagat et al. (2003) *BBRC* 300:853-861.
[94] WO01/22972.
[95] Schellack et al. (2006) *Vaccine* 24:5461-72.
[96] WO95/17211.
[97] WO98/42375.
[98] Beignon et al. (2002) *Infect Immun* 70:3012-3019.
[99] Pizza et al. (2001) *Vaccine* 19:2534-2541.
[100] Scharton-Kersten et al. (2000) *Infect Immun* 68:5306-5313.
[101] Pine et al. (2002) *J Control Release* 85:263-270.
[102] Tebbey et al. (2000) *Vaccine* 18:2723-34.
[103] Domenighini et al. (1995) *Mol Microbiol* 15:1165-1167.
[104] WO99/40936.
[105] Singh et al] (2001) *J Cont Release* 70:267-276.
[106] WO99/27960.
[107] U.S. Pat. No. 6,090,406.
[108] U.S. Pat. No. 5,916,588.
[109] WO99/52549.
[110] WO01/21207.
[111] WO01/21152.
[112] Andrianov et al. (1998) *Biomaterials* 19:109-115.
[113] Payne et al. (1998) *Adv Drug Delivery Review* 31:185-196.
[114] U.S. Pat. No. 4,680,338.
[115] WO92/15582.
[116] WO03/011223.
[117] Johnson et al. (1999) *Bioorg Med Chem Lett* 9:2273-2278.
[118] WO2004/060308.
[119] WO2004/064759.
[120] U.S. Pat. No. 6,924,271.
[121] US2005/0070556.
[122] U.S. Pat. No. 5,011,828.
[123] WO2004/87153.
[124] U.S. Pat. No. 6,605,617.
[125] WO2004/018455.
[126] WO03/082272.
[127] Wong et al. (2003) *J Clin Pharmacol* 43(7):735-42.
[128] Dyakonova et al. (2004) Int Immunopharmacol 4(13): 1615-23.
[129] Signorelli & Hadden (2003) *Int Immunopharmacol* 3(8):1177-86.
[130] WO2004/064715.
[131] De Libero et al, *Nature Reviews Immunology*, 2005, 5: 485-496
[132] U.S. Pat. No. 5,936,076.
[133] Cooper (1995) *Pharm Biotechnol* 6:559-80.
[134] WO99/11241.
[135] European patent applications 0835318, 0735898 and 0761231.
[136] WO2006/110603.
[137] Molina et al., Bol Asoc Med P R. 1991 April; 83(4):160-3.
[138] Weihui et al., Am J Respir Crit Care Med Vol 186, Iss. 5, pp 420-427, Sep. 1, 2012
[139] Jolly, *Cancer Gene Therapy* (1994) 1:51
[140] WO 90/07936.
[141] WO 94/03622.
[142] WO 94/12649.

[143] WO 93/03769.
[144] Curiel, *Hum. Gene Ther.* (1992) 3:147
[145] Wu, *J. Biol. Chem.* (1989) 264:16985
[146] U.S. Pat. No. 5,814,482.
[147] WO 95/07994.
[148] U.S. Pat. No. 5,580,859
[149] U.S. Pat. No. 5,422,120
[150] WO 95/13796.
[151] Philip, *Mol. Cell Biol.* (1994) 14:2411
[152] Woffendin, *Proc. Natl. Acad. Sci.* (1994) 91:11581
[153] U.S. Pat. No. 5,206,152.
[154] U.S. Pat. No. 5,149,655.
[155] Geysen et al. (1984) *PNAS USA* 81:3998-4002.
[156] Jameson, B A et al. 1988, *CABIOS* 4(1):181-186.
[157] Raddrizzani & Hammer (2000) *Brief Bioinform* 1(2): 179-89.
[158] Bublil et al. (2007) *Proteins* 68(1):294-304.
[159] De Lalla et al. (1999) *J. Immunol.* 163:1725-29.
[160] Meister et al. (1995) *Vaccine* 13(6):581-91.
[161] Maksyutov & Zagrebelnaya (1993) *Comput Appl Biosci* 9(3):291-7.
[162] *Current Protocols in Molecular Biology* (F. M. Ausubel et al., eds., 1987) Supplement 30
[163] Smith & Waterman (1981) *Adv. Appl. Math.* 2: 482-489.
[164] Klock, H. E., et al. (2008). *Proteins* 71:982-994
[165] Klock, H. E., et al. (2005) *J. Struct. Funct. Genomics* 6, 89-94

---

The invention claimed is:

1. A composition comprising an immunologically effective amount of an isolated *Pseudomonas* PSE54 (PA5340) antigen comprising a polypeptide having 90% or more sequence identity with SEQ ID NO:10, wherein the composition further comprises (i) an immunologically effective amount of an adjuvant, and (ii) an immunologically effective amount of at least one other antigen selected from any of: a PSE10-1 (PA1178) antigen comprising a polypeptide having 90% or more sequence identity with SEQ ID NO:37; a PSE47A-2 (PA4082) antigen comprising a polypeptide having 90% or more sequence identity with SEQ ID NO:7; a PSE11-3 (PA1248) comprising a polypeptide having 90% or more sequence identity with SEQ ID NO:4; a PSE52-1 (PA4765) antigen comprising a polypeptide having 90% or more sequence identity with SEQ ID NO:8; a PSE53-1 (PA5047) antigen comprising a polypeptide having 90% or more sequence identity with SEQ ID NO:9; a PSE21-5 (PA5112) antigen comprising a polypeptide having 90% or more sequence identity with SEQ ID NO:3; a PSE27-1 (PA0328) antigen comprising a polypeptide having 90% or more sequence identity with SEQ ID NO:42; a PSE44-4 (PA3526) antigen comprising a polypeptide having 90% or more sequence identity with SEQ ID NO:6; and a OprF-OprI antigen comprising a polypeptide having 90% or more sequence identity with SEQ ID NO:32.

2. An immunogenic composition according to claim 1, further comprising at least one other antigen selected from any of: a PSE41-5 (PA2407) antigen comprising a polypeptide having 90% or more sequence identity with SEQ ID NO:5; a PSE5-1 (PA0595) antigen comprising a polypeptide having 90% or more sequence identity with SEQ ID NO:11; a PSE13-2 (PA1954) antigen comprising a polypeptide having 90% or more sequence identity with SEQ ID NO:12; a PSE17-1 (PA3692) antigen comprising a polypeptide having 90% or more sequence identity with SEQ ID NO:13; a PSE18-2 (PA4370) antigen comprising a polypeptide having 90% or more sequence identity with SEQ ID NO:14;

a PSE20-1 (PA4735) antigen comprising a polypeptide having 90% or more sequence identity with SEQ ID NO:16; a PSE23-1 (PA3647) antigen comprising a polypeptide having 90% or more sequence identity with SEQ ID NO:17; a PSE24-1 (PA0126) antigen comprising a polypeptide having 90% or more sequence identity with SEQ ID NO:18; a PSE25-1 (PA0189) antigen comprising a polypeptide having 90% or more sequence identity with SEQ ID NO:19; a PSE26-1 (PA0274) antigen comprising a polypeptide having 90% or more sequence identity with SEQ ID NO:20; a PSE28-2 (PA0537) antigen comprising a polypeptide having 90% or more sequence identity with SEQ ID NO:21; a PSE31-2 (PA0737) antigen comprising a polypeptide having 90% or more sequence identity with SEQ ID NO:22; a PSE33-2 (PA1086) antigen comprising a polypeptide having 90% or more sequence identity with SEQ ID NO:23; a PSE42-1 (PA2793) antigen comprising a polypeptide having 90% or more sequence identity with SEQ ID NO:27; a PSE45-2 (PA3535) antigen comprising a polypeptide having 90% or more sequence identity with SEQ ID NO:28; a PSE50-1 (PA4578) antigen comprising a polypeptide having 90% or more sequence identity with SEQ ID NO:29; a PSE51-4 (PA4667) antigen comprising a polypeptide having 90% or more sequence identity with SEQ ID NO:30; a PSE34-1 (PA1106) antigen comprising a polypeptide having 90% or more sequence identity with SEQ ID NO:24; and a PSE36-3 (PA1324) antigen comprising a polypeptide having 90% or more sequence identity with SEQ ID NO:25.

3. The composition of claim 1, further comprising at least one other antigen is selected from: a PSE21-5 (PA5112) antigen comprising a polypeptide having 90% or more sequence identity with SEQ ID NO:38 and PSE41-5 (PA2407) comprising a polypeptide having 90% or more sequence identity with SEQ ID NO:40.

4. The composition of claim 1, further comprising at least one other antigen is selected from the list: a PSE41 (PA2407) antigen comprising a polypeptide having 90% or more sequence identity with SEQ ID NO:5; a PSE5-1 (PA0595) antigen comprising a polypeptide having 90% or more sequence identity with SEQ ID NO:11; a PSE13-2 (PA1954) antigen comprising a polypeptide having 90% or more sequence identity with SEQ ID NO:12; a PSE17-1 (PA3692) antigen comprising a polypeptide having 90% or more sequence identity with SEQ ID NO:13; a PSE18-2 (PA4370) antigen comprising a polypeptide having 90% or more sequence identity with SEQ ID NO:14; a PSE20-1 (PA4735) antigen comprising a polypeptide having 90% or more sequence identity with SEQ ID NO:16; a PSE23-1 (PA3647) antigen comprising a polypeptide having 90% or more sequence identity with SEQ ID NO:17; a PSE24-1 (PA0126) antigen comprising a polypeptide having 90% or more sequence identity with SEQ ID NO:18; a PSE25-1 (PA0189) antigen comprising a polypeptide having 90% or more sequence identity with SEQ ID NO:19; a PSE26-1 (PA0274) antigen comprising a polypeptide having 90% or more sequence identity with SEQ ID NO:20; a PSE28-2 (PA0537) antigen comprising a polypeptide having 90% or more sequence identity with SEQ ID NO:21; a PSE31-2 (PA0737) antigen comprising a polypeptide having 90% or more sequence identity with SEQ ID NO:22; a PSE33-2 (PA1086) antigen comprising a polypeptide having 90% or more sequence identity with SEQ ID NO:23; a PSE42-1 (PA2793) antigen comprising a polypeptide having 90% or more sequence identity with SEQ ID NO:27; a PSE45-2 (PA3535) antigen comprising a polypeptide having 90% or more sequence identity with SEQ ID NO:28; a PSE50-1 (PA4578) antigen comprising a polypeptide having 90% or more sequence identity with SEQ ID NO:29; a PSE51-4 (PA4667) antigen comprising a polypeptide having 90% or more sequence identity with SEQ ID NO:30; a PSE19-1 (PA4710) antigen comprising a polypeptide having 90% or more sequence identity with SEQ ID NO:15; a PSE34-1 (PA1106) antigen comprising a polypeptide having 90% or more sequence identity with SEQ ID NO:24; a PSE36-3 (PA1324) antigen comprising a polypeptide having 90% or more sequence identity with SEQ ID NO:25; and a PSE38-1 (PA1777) antigen comprising a polypeptide having 90% or more sequence identity with SEQ ID NO:26.

5. The composition of claim 4, further comprising one or more antigens selected from the list: PilA comprising a polypeptide having 90% or more sequence identity with SEQ ID NO:31, FliC comprising a polypeptide having 90% or more sequence identity with SEQ ID NO:33, FliD comprising a polypeptide having 90% or more sequence identity with SEQ ID NO:34, and ExoA4 comprising a polypeptide having 90% or more sequence identity with SEQ ID NO:35.

6. The composition of claim 4, further comprising PSE21-5 (PA4765) comprising a polypeptide having 90% or more sequence identity with SEQ ID NO:38.

7. The composition of claim 1, wherein the *Pseudomonas* PSE54 (PA5340) antigen is adsorbed to an aluminum hydroxide adjuvant.

8. The composition of claim 1, further comprising: one or more conjugates of (i) a *P. aeruginosa* exopolysaccharide and (ii) a carrier protein.

9. An immunogenic composition comprising the composition of claim 1, and further comprising one or more of:
(A) one or more conjugates of (i) a *S. aureus* exopolysaccharide;
(B) one or more protein antigens of (i) a *S. aureus*;
(C) one or more pathogenic *E. coli* antigens; and
(D) one or more pathogenic *B. cenocepacia* antigens.

10. The immunogenic composition of claim 1, further comprising one or more of (i) a FliC antigen comprising a polypeptide having 90% or more sequence identity with SEQ ID NO:33; (ii) a FliD antigen comprising a polypeptide having 90% or more sequence identity with SEQ ID NO:34 and/or (iii) a PilA antigen comprising a polypeptide having 90% or more sequence identity with SEQ ID NO:31.

11. A composition comprising an isolated polypeptide comprising an amino acid sequence having 90% or more identity to an amino acid sequence selected from SEQ ID NO: 10 and SEQ ID NO: 45 and at least one other isolated *Pseudomonas* polypeptide, wherein the composition further comprises an immunologically effective amount of an adjuvant.

12. A method for raising an immune response in a mammal comprising the step of administering to the mammal an effective amount of the composition of claim 1.

13. The composition according to claim 1 wherein the at least one other antigen is a OprF-OprI antigen comprising a polypeptide having 90% or more sequence identity with SEQ ID NO:32.

14. The composition of claim 1, wherein the polypeptide of the isolated *Pseudomonas* PSE54 (PA5340) antigen has 95% or more sequence identity with SEQ ID NO:10.

15. The composition of claim 2, wherein the polypeptide of the isolated *Pseudomonas* PSE54 (PA5340) antigen has 95% or more sequence identity with SEQ ID NO:10.

16. The composition of claim 3, wherein the polypeptide of the isolated *Pseudomonas* PSE54 (PA5340) antigen has 95% or more sequence identity with SEQ ID NO:10.

17. The composition of claim 4, wherein the polypeptide of the isolated *Pseudomonas* PSE54 (PA5340) antigen has 95% or more sequence identity with SEQ ID NO:10.

18. The composition of claim 5, wherein the polypeptide of the isolated *Pseudomonas* PSE54 (PA5340) antigen has 95% or more sequence identity with SEQ ID NO:10.

\* \* \* \* \*